(12) United States Patent
Berger et al.

(10) Patent No.: US 7,105,531 B2
(45) Date of Patent: Sep. 12, 2006

(54) TRICYCLIC PROTEIN KINASE INHIBITORS

(75) Inventors: Dan M. Berger, New City, NY (US); Minu D. Dutia, West Nyack, NY (US); Frenel F. DeMorin, Nanuet, NY (US); Diane H. Boschelli, New City, NY (US); Dennis W. Powell, Westchester, NY (US); Hwei-Ru Tsou, New City, NY (US); Allan Wissner, Ardsley, NY (US); Nan Zhang, Eastchester, NY (US); Fei Ye, Nanuet, NY (US); Biqi Wu, Nanuet, NY (US)

(73) Assignee: WYETH, Madison, NJ (US)

( * ) Notice: Subject to any disclaimer, the term of this patent is extended or adjusted under 35 U.S.C. 154(b) by 20 days.

(21) Appl. No.: 10/618,044

(22) Filed: Jul. 10, 2003

(65) Prior Publication Data

US 2004/0110762 A1    Jun. 10, 2004

Related U.S. Application Data

(62) Division of application No. 09/751,274, filed on Dec. 29, 2000, now Pat. No. 6,638,929.

(60) Provisional application No. 60/240,905, filed on Dec. 29, 1999.

(51) Int. Cl.
    *A61K 31/44*      (2006.01)
    *C07D 471/04*      (2006.01)

(52) U.S. Cl. ................................. 514/292; 546/81

(58) Field of Classification Search ............. 548/302.1; 514/276, 292; 546/81
See application file for complete search history.

(56) References Cited

U.S. PATENT DOCUMENTS

| | | | |
|---|---|---|---|
| 4,139,704 A | 2/1979 | Borror et al. | 540/467 |
| 4,332,952 A | 6/1982 | Schnur | 548/226 |
| 4,952,584 A | 8/1990 | Thompson et al. | 514/292 |
| 5,480,883 A | 1/1996 | Spada et al. | 514/249 |
| 5,597,832 A | 1/1997 | Michaelides et al. | 514/285 |
| 5,679,683 A | 10/1997 | Bridges et al. | 514/53 |
| 5,955,464 A | 9/1999 | Barker | 514/233.8 |

FOREIGN PATENT DOCUMENTS

| | | |
|---|---|---|
| EP | 0755934 A1 | 7/1996 |
| EP | 0837063 A1 | 10/1997 |
| WO | 95/19970 | 7/1995 |
| WO | 96/09294 | 3/1996 |
| WO | 97/05137 | 2/1997 |
| WO | 97/13760 | 4/1997 |
| WO | 97/30044 | 8/1997 |
| WO | 97/49688 | 12/1997 |
| WO | 98/02434 | 1/1998 |
| WO | 98/13350 | 4/1998 |
| WO | 98/43960 | 10/1998 |

OTHER PUBLICATIONS

Theodoridis et al., "Synthesis and Structure-Activity Relationships of 1-Aryl-4-substituted-1,4-dihydro-5H-tetrazol-5-ones, a Novel Class of Pre- and Post-emergence Herbicides," Pestic. Sci. 30: 259-274 (1990).
Ross et al., "Inhibitors of Dopamine β-Hydroxylase. 3. Some 1-(Pyridylmethyl)imidazole-2-thiones," J. Med. Chem. 30:1309-1313 (1987).
Denat et al., "Pyrrolyl Compounds of Main Group Elements. Synthesis of Group 14 5-Metallated Pyrrole-2-Carbaldehydes," J. Organometallic Chem. 423:173-182 (1992).

*Primary Examiner*—Johann Richter
*Assistant Examiner*—Ebenezer Sackey
(74) *Attorney, Agent, or Firm*—John W. Hogan, Jr.; Anne M. Rosenblum

(57) ABSTRACT

This invention provides compounds of formula 1, having the structure

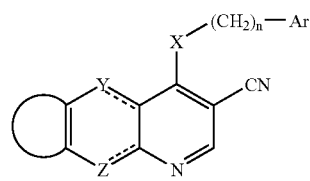

which are useful as inhibitors of protein tyrosine kinase and are antiproliferative agents.

17 Claims, No Drawings

TRICYCLIC PROTEIN KINASE INHIBITORS

The application is a division of prior application Ser. No. 09/751,274, filed on Dec. 29, 2000 now U.S. Pat. No. 6,638,929, which claims the benefit under 35 U.S.C § 119(e) of U.S. Provisional Application No 60/240,905 filed Dec. 29, 1999 abandoned.

BACKGROUND OF THE INVENTION

This invention relates to substituted aromatic tricyclic compounds containing nicotinonitrile rings as well as the pharmaceutically acceptable salts thereof. The compounds of the present invention inhibit the action of certain protein kinases, thereby inhibiting the abnormal growth of particular cell types. The compounds of this invention are therefore useful for the treatment or inhibition of certain diseases that are the result of deregulation of these protein kinases. The compounds of this invention are anti-cancer agents and are useful for the treatment or inhibition of cancer in mammals. In addition, the compounds of this invention are useful for the treatment and inhibition of polycystic kidney disease and colonic polyps.

Protein kinases are a class of enzymes that catalyze the transfer of a phosphate group from ATP to a tyrosine, serine, threonine, or histidine residue located on a protein substrate. Protein kinases clearly play a role in normal cell growth. Many of the growth factor receptor proteins function as kinases and it is by this process that they effect signaling. The interaction of growth factors with these receptors is a necessary event in normal regulation of cell growth. However, under certain conditions, as a result of either mutation or over expression, these receptors can become deregulated; the result of which is uncontrolled cell proliferation which can lead to tumor growth and ultimately to the disease known as cancer [Wilks, A. F., *Adv. Cancer Res.,* 60, 43 (1993) and Parsons, J. T.; Parsons, S. J., *Important Advances in Oncology*, DeVita, V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, over expression of the receptor kinase product of the erbB-2 oncogene has been associated with human breast and ovarian cancers [Slamon, D. J. et al., *Science,* 244, 707 (1989) and *Science,* 235, 177 (1987)]. Deregulation of EGF-R kinase has been associated with epidermoid tumors [Reiss, M., et al., *Cancer Res.,* 51, 6254 (1991)], breast tumors [Macias, A. et al., *Anticancer Res.,* 7, 459 (1987)], and tumors involving other major organs [Gullick, W. J., *Brit. Med. Bull.,* 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Traxler, P., *Exp. Opin. Ther. Patents,* 8, 1599 (1998) and Bridges, A. J., *Emerging Drugs,* 3, 279 (1998)].

It is also known that deregulation of EGF receptors is a factor in the growth of epithelial cysts in the disease described as polycystic kidney disease [Du, J., Wilson, P. D., *Amer. J. Physiol.,* 269 (2 Pt 1), 487 (1995); Nauta, J., et al., *Pediatric Research,* 37(6), 755 (1995); Gattone, V. H. et al., *Developmental. Biology,* 169(2), 504 (1995); Wilson, P. D. et al., *Eur. J. Cell Biol.,* 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP kinases (MAPK). There are different isoforms in the MAP kinase family. (For review, see Seger, R.; Krebs, E. G., *FASEB,* 9, 726, (1995).) The compounds of this invention can inhibit the action of two of these kinases: MEK, a MAP kinase kinase, and its substrate ERK, a MAP kinase. MEK is activated by phosphorylation on two serine residues by upstream kinases such as members of the raf family. When activated, MEK catalyzes phosphorylation on a threonine and a tyrosine residue of ERK. The activated ERK then phosphorylates and activates transcription factors in the nucleus, such as fos and jun, or other cellular targets with PXT/SP sequences. ERK, a p42 MAPK, is found to be essential for cell proliferation and differentiation. Over-expression and/or over-activation of MEK or ERK has been found to be associated with various human cancers [For example, Sivaraman, V. S.; Wang, H-Y.; Nuovo, G. J. Malbon, C. C. *J. Clin. Invest.,* 99, 1478 (1997)]. It has been demonstrated that inhibition of MEK prevents activation of ERK and subsequent activation of ERK substrates in cells, resulting in inhibition of cell growth stimulation and reversal of the phenotype of ras-transformed cells [Dudley, D. T.; Pang, L.; Decker, S. J.; Bridges, A. J.; Saltiel, A. R., *Proc. Nat. Acad. Sci.,* 92, 7686, (1995)]. Since, as demonstrated below, the compounds of this invention can inhibit the coupled action of MEK and ERK, they are useful for the treatment of diseases such as cancer which are characterized by uncontrolled cell proliferation and which, at least in part, depend on the MAPK pathway.

As mentioned above, members of the raf family of kinases phosphorylate serine residues on MEK. There are three serine/threonine kinase members of the raf family known as a-raf, b-raf and c-raf. While mutations in the raf genes are rare in human cancers, c-raf is activated by the ras oncogene which is mutated in a wide number of human tumors. Therefore inhibition of the kinase activity of c-raf may provide a way to prevent ras mediated tumor growth [Campbell, S. L., *Oncogene,* 17, 1395 (1998)].

The Src family of cytoplasmic protein tyrosine kinases consists of at least eight members (Src, Fyn, Lyn, Yes, Lck, Fgr, lck and Bik) that participate in a variety of signaling pathways [Schwartzberg, P. L., *Oncogene,* 17, 1463–1468, (1998)]. The prototypical member of this tyrosine kinase family is p60$^{src}$ (Src). Src is involved in proliferation and migration responses in many cell types. In limited studies, Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley et al., *Cell Growth & Differentiation.,* 8, 269–74, (1997)], suggesting that Src inhibitors should slow tumor growth. In addition to its role in cell proliferation, Src also acts in stress response pathways, including the hypoxia response, and nude mice studies with colon tumor cells expressing antisense Src message have reduced vascularization [Ellis, et al., *J. Biol. Chem.*, 273, 1052–7 (1998)], which suggests that Src inhibitors would be anti-angiogenic as well as anti-proliferative.

In addition to its role in cancer, Src also appears to play a role in osteoporosis. Mice genetically engineered to be deficient in src production were found to exhibit osteopetrosis, the failure to resorb bone [Soriano, P., *Cell*, 64, 693 (1991); Boyce, B. F., *J. Clin., Invest.*, 90, 1622 (1992)]. This defect was characterized by a lack of osteoclast activity. Since osteoclasts normally express high levels of Src, inhibition of Src kinase activity may be useful in the treatment of osteoporosis [Missbach, M., *Bone*, 24, 437 (1999)].

In addition to EGFr, there are several other RTKs including FGFr, the receptor for fibroblast growth factor (FGF); flk-1, also known as KDR, and flt-1, the receptors for vascular endothelial growth factor (VEGF); and PDGFr, the receptor for platelet derived growth factor (PDGF). The formation of new blood vessels, a process known as angiogenesis, is essential for tumor growth. Two natural angiogenesis inhibitors, angiostatin and endostatin, dramatically inhibited the growth of a variety of solid tumors. [O'Reilly, M. S., *Cell*, 79, 315 (1994); O'Reilly, M. S., *Nature Medicine*, 2, 689 (1996); O'Reilly, M. S., *Cell*, 88, 277 (1997)]. Since FGF and VEGF are known to stimulate angiogenesis, inhibition of the kinase activity of their receptors should block the angiogenic effects of these growth factors. In addition, the receptor tyrosine kinases tie-1 and tie-2 also play a key role in angiogenesis [Sato, T. N., *Nature*, 376, 70 (1995)]. Compounds of the invention that inhibit the kinase activity of FGFr, flk-1, flt-1, tie-1 or tie-2 may inhibit tumor growth by their effect on angiogenesis. Normal angiogenesis is required in many physiological conditions such as wound healing, female reproduction and fetal development. Abnormal or pathological angiogenesis has been implicated in neoplastic diseases including solid tumor growth, metastasis, and Karposi's sarcoma; various eye diseases including diabetic retinopathy, and macular degeneration; inflammatory conditions including rheumatoid arthritis, and osteoarthritis; skin diseases including psoriasis, eczema and scleroderma; as well as ulcerative colitis and childhood haemangiomas [Toi, M. et al., *Breast Cancer Res. And Treat.*, 36, 192–204 (1995); Folkman, J., *Nature Medicine*, 1, 27–31 (1995); Jackson, J. R. et al., *FASEB J.*, 11, 457–465 (1997)]. Inhibition of VEGF function has been shown to inhibit disease progression in tumors [Borgstrom, P. et al., *Cancer Res.*, 56, 4032–4039 (1996); Kim, J. K. et al., *Nature*, 362, 841–844 (1993)] and retinal neovascularization [Aiello, L. P. et al., *Proc. Nat. Acad. Sci.*, 92, 10457–10461 (1995)] as well as vascular dysfunction mediated by glucose in models of diabetes [Tilton, R. G. et al., *J. Clin. Invest.*, 99, 2192–2202 (1997)].

PDGF is a potent growth factor and chemoattractant for smooth muscle cells (SMCs) and the renarrowing of coronary arteries following angioplasty is due in part to the enhanced proliferation of SMCs in response to increased levels of PDGF. Therefore, compounds that inhibit the kinase activity of PDGFr may be useful in the treatment of restenosis. In addition, since PDGF and PDGFr are overexpressed in several types of human gliomas, small molecules capable of suppressing PDGFr activity, have potential utility as anticancer therapeutics [Nister, M., *J. Biol. Chem.* 266, 16755 (1991); Strawn, L. M., *J. Biol. Chem.* 269, 21215 (1994)].

In accordance with the present invention, the tricyclic ring systems described herein will be numbered as indicated in the representative formulas below (where U=N or O or S):

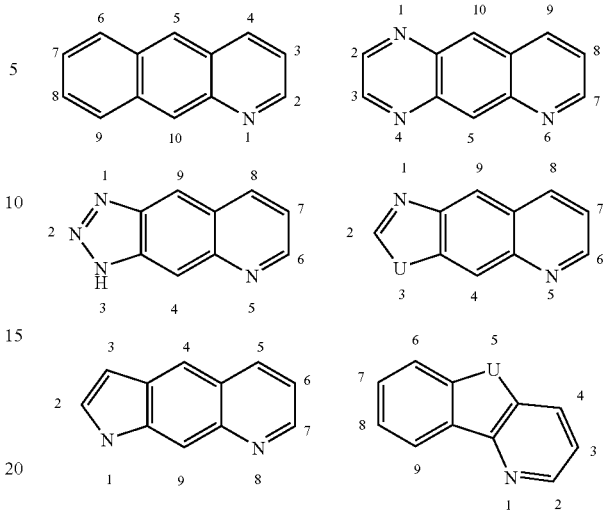

No fully aromatic fused tricyclic compounds containing nicotinonitrile rings have been reported that have biological activity as inhibitors of protein tyrosine kinases. 3-Cyanoquinoline derivatives described in WO-9843960 have been disclosed as inhibitors of tyrosine kinase. A 3-cyanoquinoline with a 4-(2-methyl anilino) substituent having gastric ($H^+/K^+$)-ATPase inhibitory activity at high concentrations has been described [Ife R. J., et al., *J. Med. Chem.*, 35(18), 3413 (1992)]. However, there are no references to any fully aromatic tricyclic compounds containing nicotinonitrile rings in the above publications.

In WO-9713760, a series of fused tricyclic compounds containing pyridine rings (and pyrimidines) that are reported to be inhibitors of protein tyrosine kinases is disclosed. However, it is specified that the position meta to the pyridine nitrogen bears a hydrogen atom only. No compounds possessing cyano substituents at this position are claimed. In two patents: AU 8767450 and U.S. Pat. No. 4,952,584, 4-amino-9H-pyrido-(2,3-b)-indole-3-carboxylic acid derivatives are disclosed as anxiolytic and antidepressant agents. No corresponding 3-cyano substituents are claimed. In EP 755934, fused tricyclic compounds containing nicotinonitrile rings are disclosed as endothelin receptor antagonists. However, these derivatives do not have the unique combination of substituents contained in the compounds of the present invention. In particular, it is specified that these compounds possess aromatic substituents directly attached to the position para to the pyridine nitrogen. Such substituents are not claimed in the present invention. Similarly, a series of compounds claimed in WO 9705137 do include tricyclics containing nicotinonitrile rings, but with hydrogen or simple alkyl chains attached to the position para to the pyridine nitrogen. Such substituents are not claimed in the present invention. Several patents exist which disclose substituted quinoline compounds as tyrosine kinase inhibitors, none of which possess the 3-cyano substituent: 1. An international patent WO-9813350 describing 3-fluoroquinoline and quinoline tyrosine kinase inhibitors. 2. WO-9609294 discloses inhibitors of protein tyrosine kinases that include 4-anilino quinolines with a large variety of substituents on positions 5–8 but which must also have a hydrogen atom at position 3. 3. U.S. Pat. No. 5,480,883 discloses quinoline derivatives that are inhibitors of protein tyrosine kinases but these derivatives do not have the unique combination of substituents, including the 3-cyano group, contained in the compounds of the present invention.

In addition to the above-mentioned compounds, certain tricyclics containing pyrimidine rings are known to be inhibitors of protein tyrosine kinases. WO-9749688, WO-9519970, U.S. Pat. No. 5,679,683 and the previously-mentioned WO-9713760 disclose a variety of tricyclic heterocycles which are tyrosine kinase inhibitors. Other patent applications WO-9802434, WO-9730044 and EP-837063 describe quinazolines substituted at positions 5 to 8 with one or more optionally substituted 5- or 6-membered heterocyclic rings.

In addition to the aforementioned patent applications, a number of publications describe fused tricyclics containing 4-anilinopyrimidine rings: Rewcastle G. W., et. al., *J. Med. Chem.*, 39, 918 (1996); Bencteux, E., et. al., *J. Heterocycl. Chem.*, 34, 1375, (1997); Palmer B. D., et. al. *J. Med Chem.*, 40, 1519 (1997); and Zhou, H., et. al., *Book of Abstracts*, 210$^{th}$ ACS National Meeting, Chicago, Ill., August 20–24 (1995), Issue Pt. 2, MEDI-017. There are no publications that describe fused tricyclic tricyclic compounds containing nicotinonitrile rings as PTK inhibitors.

SUMMARY OF THE INVENTION

The present invention relates to certain protein kinase inhibitors of formula 1 having the structure:

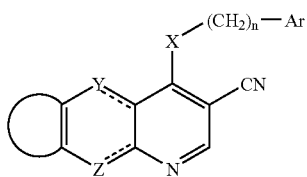

wherein:

Ar is cycloalkyl of 3 to 7 carbon atoms, which may be optionally substituted with one or more alkyl of 1 to 6 carbon atoms; or Ar is a pyridinyl, pyrimidinyl, or phenyl ring; wherein the pyridinyl, pyrimidinyl, or phenyl ring may be optionally mono-, di-, or tri-substituted with substituents selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8; carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoallyl of 3–10 carbon atoms, N-alkylaminoalkoxy of 3–9 carbon atoms, N,N-dialkylaminoalkoxy of 4–10 carbon atoms, mercapto, methylmercapto and benzoylamino; or Ar is a bicyclic aryl or bicyclic heteroaryl ring system of 8 to 12 atoms where the bicyclic heteroaryl ring may contain 1 to 4 heteroatoms selected from N, O, and S wherein the bicyclic aryl or bicyclic heteroaryl ring may be optionally mono- di-, tri, or tetra-substituted with substituent(s) independently selected from the group consisting of halogen, oxo, thiocarbonyl, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

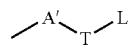

A' is a pyridinyl, pyrimidinyl, or phenyl ring; wherein the pyridinyl, pyrimidinyl, or phenyl ring may be optionally mono- or di-substituted with a substituent(s) independently selected from the group consisting of alkyl of 1–6 carbon atoms, alkenyl of 2–6 carbon atoms, alkynyl of 2–6 carbon atoms, azido, hydroxyalkyl of 1–6 carbon atoms, halogen, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino;

T is substituted on A' at carbon and is —NH(CH$_2$)$_m$—, —O(CH$_2$)$_m$—, —S(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S—, —SO(CH$_2$)$_m$—, —SO$_2$(CH$_2$)$_m$—, —CO(CH$_2$)$_m$—, —(CH$_2$)$_m$CO—, —(CH$_2$)$_m$SO—, —(CH$_2$)$_m$SO$_2$— or —(CH$_2$)$_m$NR—;

L is a phenyl ring that is optionally substituted with one, two, or three substituent(s) independently selected from the group consisting of alkyl of 1–6 carbon atoms, alkenyl of 2–6 carbon atoms, alkynyl of 2–6 carbon atoms, azido, hydroxyalkyl of 1–6 carbon atoms, halogen, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or L is a 5- or 6-membered heteroaryl ring where the heteroaryl ring contains 1 to 3 heteroatoms selected from N, O, and S and where the heteroaryl ring may be optionally mono- or di-substituted with substituent(s) selected from the group consisting of halogen, oxo, thiocarbonyl, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino;

m is 0–3;

n is 0–1;

X is NH O, S, or NR;

R is alkyl of 1–6 carbon atoms;

Y and Z are both carbon or N; the ring structure of formula 1 then being a fused 5,6,6 or 6,6,6 tricycle; or one of Y and Z is N, O or S, and the other is a bond between the two end rings; the ring structure of formula 1 then being a fused 5,5,6 or 6,5,6 tricycle; or one of Y or Z is N with the other being carbon; the ring structure of formula 1 then being a fused 5,6,6 or 6,6,6 tricycle;

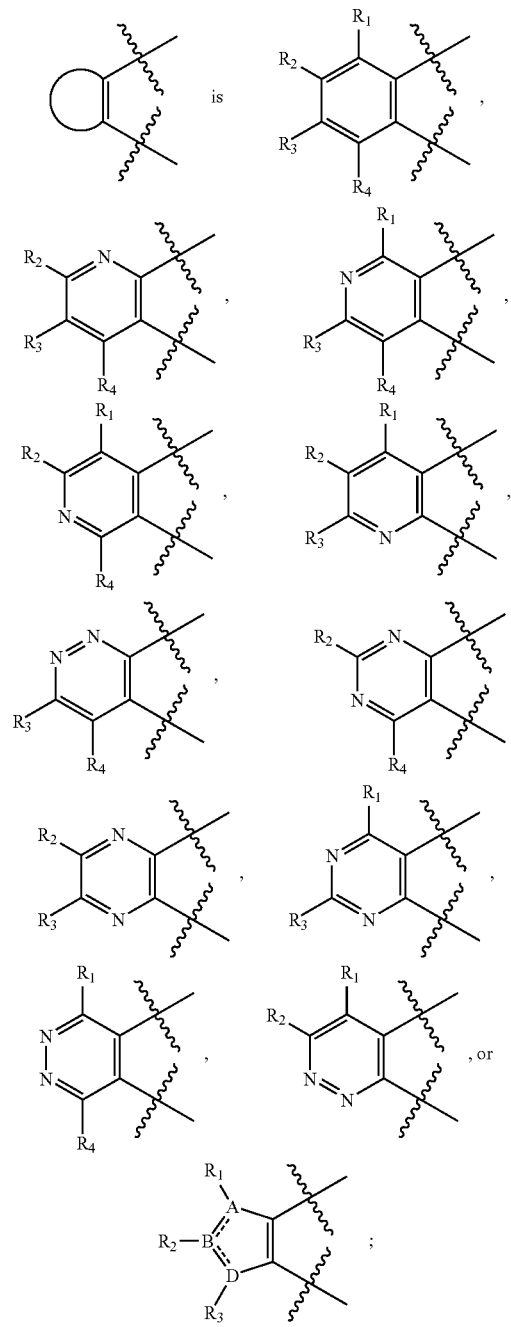

A and D are each, independently, carbon, N, O, or S;

B is carbon or N;

the dashed line indicates an optional double bond;

$R_1$, $R_2$, $R_3$, and $R_4$ are each, independently, not present, hydrogen, halogen, hydroxy, amino, hydroxyamino, trifluoromethyl, trifluoromethoxy, mercapto, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, alkynyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, nitro, carboxy, alkoxycarbonyl of 2–7 carbon atoms, alkanoyl of 2–7 carbon atoms, alkenoyl of 3–7 carbon atoms, N-alkyl-N-alkenylamino of 4 to 12 carbon atoms, N,N-dialkenylamino of 6–12 carbon atoms, phenylamino, benzylamino, phenoxy, phenyl, thiophenoxy, benzyl, alkylamino of 1–6 carbon atoms, alkanoyloxy of 2–7 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms, alkanoyloxymethyl group of 2–7 carbon atoms, alkenoyloxymethyl group of 2–7 carbon atoms, alkynoyloxymethyl group of 2–7 carbon atoms, azido, benzoyl, carboxyalkyl of 2–7 carbons, carboalkoxyalkyl of 3–8 carbon atoms,

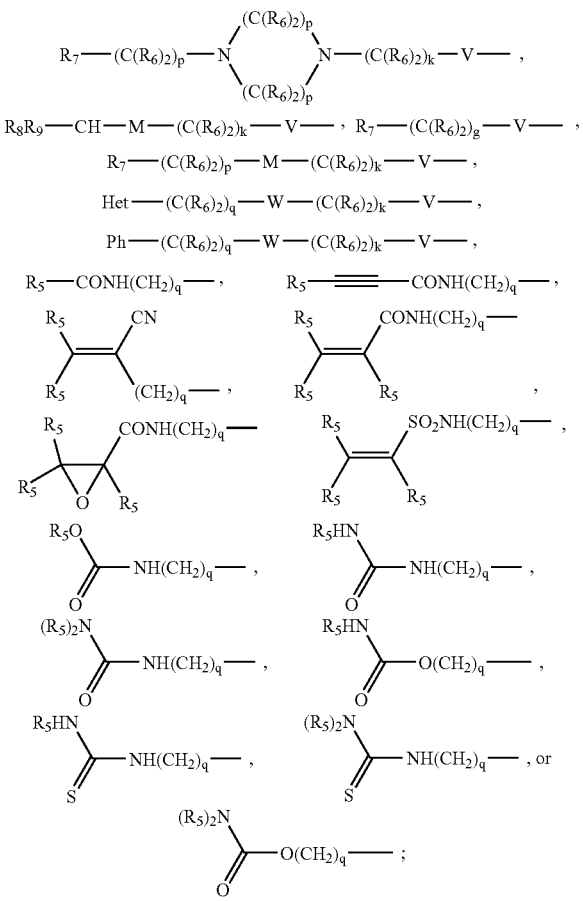

$R_5$ is independently hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperazino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, or phenyl;

V is $(CH_2)_m$, O, S, or $NR_6$;

$R_7$ is $NR_6R_6$, $OR_6$, J, $N(R_6)_3^+$, or $NR_6(OR_6)$;

M is $NR_6$, O, S, N-$[(C(R_6)_2)_p NR_6R_6]$, or N-$[(C(R_6)_2)_p$—$OR_6]$;

W is $NR_6$, O, S, or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane pyrrole, and tetrahydropyran; wherein the heterocycle is optionally mono- or di-substituted on carbon or nitrogen with $R_6$; optionally mono- or di-substituted on carbon with hydroxy, —$N(R_6)_2$, or —$OR_6$; optionally mono or di-substituted on carbon with the mono-valent radicals —$(C(R_6)_2)_s OR_6$ or —$[(C(R_6)_2)_s N(R_6)_2]$; or optionally mono or di-substituted on a saturated carbon with divalent radicals =O or —$O(C(R_6)_2)_s O$—;

Ph is a phenyl ring optionally mono-, di- or tri-substituted with halogen, alkyl of 1–6 carbon atoms, trifluoromethyl, nitro, cyano, azido, halomethyl, carboxyl, alkoxycarbonyl, alkylthio, mercapto, mercaptomethyl, —$N(R_6)_2$, —$OR_6$, —$(C(R_6)_2)_s OR_6$, —$[(C(R_6)_2)_s N(R_6)_2]$, or —$(C(R_6)_2)_k$Het;

$R_6$ is hydrogen, alkyl of 1–6 carbon atoms, alkenyl of 2–6 carbon atoms, alkynyl of 2–6 carbon atoms, cycloalkyl of 1–6 carbon atoms, alkanoyl of 2–7 carbon atoms, carbamoylalkyl of 2–7 carbon atoms, hydroxyalkyl of 1–6 carbon atoms, hydroxycycloalkyl of 3–6 carbon atoms, or carboxyalkyl of 2–7 carbon atoms; or $R_6$ is phenyl optionally mono-, di-, or tri-substituted with substituent(s) independently selected from halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, alkoxycarbonyl of 2–7 carbon atoms, phenoxy, phenyl, thiophenoxy, benzoyl, benzyl, phenylamino, benzylamino; alkanoylamino of 1–6 carbon atoms or alkyl of 1–6 carbon atoms;

$R_8$ and $R_9$ are each, independently, —$[(C(R_6)_2)_r NR_6R_6]$, and —$[(C(R_6)_2)_r OR_6]$;

J is independently hydrogen, chlorine, fluorine, or bromine;

g=1–6;
k=0–4;
p=2–4;
q=0–4;
r=1–4;
s=1–6;

or a pharmaceutically acceptable salt thereof;
provided that when

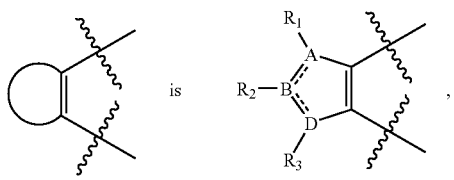

at least one of the bonds between A and B or B and D must be a double bond, with the other being a single bond;
at least one of A, B, and D are not carbon;
only one of A, B, or D can be O or S;
when A, B, or D is O or S, the adjacent atoms must be carbon;
provided that when $R_5$ is bound to a nitrogen atom, the resulting structures do not include —N—C—N— or —O—C—N— radicals; and when $R_5$ is bound to an oxygen atom, the resulting structures do not include an —N—C—O— radical;
provided that when $R_6$ is alkenyl of 2–7 carbon atoms or alkynyl of 2–7 carbon atoms, the alkenyl or alkynyl moieties are bound to a nitrogen or oxygen atom through a saturated carbon atom in the alkenyl or alkynyl chain;
provided that when V is $NR_6$ and $R_7$ is $NR_6R_6$, $N(R_6)_3^+$, or $NR_6(OR_6)$, then g=2–6;
provided that when M is O or S and $R_7$ is $OR_6$, then p=1–4;
provided that when V is $NR_6$, O, S, then k=2–4;
provided that when V is O or S and M or W is O or S, then k=1–4
provided that when W is not a bond with Het bonded through a nitrogen atom then q=2–4; and
finally provided when W is a bond with Het bonded through a nitrogen atom and V is O or $NR_6$ or S, then k=2–4.

The present invention also relates to a method for making compounds of formula 1 and methods of using the compounds of formula 1.

DESCRIPTION OF THE INVENTION

The present invention relates to substituted aromatic tricyclic compounds containing nicotinonitrile rings of formula 1 above as well as the pharmaceutically acceptable salts thereof. The compounds of the present invention inhibit the action of certain protein kinases, thereby inhibiting the abnormal growth of particular cell types.

The compounds of this invention are therefore useful for the treatment or inhibition of certain diseases that are the result of deregulation of these protein kinases. The compounds of this invention are anti-cancer agents and are useful for the treatment or inhibition of cancer in mammals. In addition, the compounds of this invention are useful for the treatment and inhbition of polycystic kidney disease and colonic polyps.

The pharmaceutically acceptable salts are any conventionally known salts useful in the pharmaceutical industry including those derived from such organic and inorganic acids such as: acetic, lactic, citric, tartaric, succinic, maleic, malonic, gluconic, hydrochloric, hydrobromic, phosphoric, nitric, sulfuric, methanesulfonic, and similarly known acceptable acids.

In the present application in those cases in which a substituent, moiety, or group is di-, tri-, and/or tetra-substituted, it is understood that the 2, 3, and/or 4 substituents on the substituent, moiety, or group may be the same or different.

It is understood by one skilled in the art that the heteroaryl or bicyclic heteroaryl rings of the compounds of Formula I do not contain O—O, S—S, or S—O bonds, as they would be unstable. Preferred bicyclic aryl or bicyclic heteroaryl ring systems include naphthalene, tetralin, indan, 1-indanone, 1,2,3,4-tetrahydroquinoline, naphthyridine, benzofuran, 3-oxo-1,3-dihydroisobenzofuran, benzothiophene, 1,1-dioxo-benzothiophene, indole, indoline 1,3-dioxo-2,3-dihydro-1H-isoindole, benzotriazole, 1H-indazole, indoline, indazole, 1,3-benzodioxole, benzoxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)-isoquinolone, 2-oxo-2,3-dihydrobenzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydrophthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring; preferred heteroaryl rings are pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. A thiocarbonyl substituent on the bicyclic aryl or bicyclic heteroaryl moiety means that one of the carbon atoms has a thiocarbonyl group When L is a 5 or 6-membered heteroaryl ring, it may be fully unsaturated, partially saturated, or fully saturated. The heteroaryl ring can be bound to A' via carbon or nitrogen. An oxo substituent on the heteroaryl ring means that one of the carbon atoms has a carbonyl group. A thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulfonyl, alkylsulfonamido, alkoxycarbonyl, carboxyalkyl, carboalkoxyalkyl, alkanoylamino, N-alkylcarbamoyl, N,N-dialkylcarbamoyl, N-alkylaminoalkoxy and N,N-dialkylaminoalkoxy include both straight chain as well as branched carbon chains. The cycloalkyl portions of cycloalkyl, N-cycloalkylamino, N-cycloalkyl-N-alkylaminoalkyl, N,N-dicycloalkylaminoalkyl, cycloalkylthio and azacycloalkyl substituents include both simple carbocycles as well as carbocycles containing alkyl substituents. The alkenyl portion of the alkenyl, alkenyloxy, alkenylsulfonamido, substituents include both straight chain as well as branched carbon chains and one or more sites of unsaturation and all possible configurational isomers. The alkynyl portion of the alkynyl, alkynylsulfonamido, alkynyloxy, substituents include both straight chain as well as branched carbon chains and one or more sites of unsaturation. Carboxy is defined as a —$CO_2H$ radical. Alkoxycarbonyl of 2–7 carbon atoms is defined as a —$CO_2R''$ radical, where R" is an alkyl radical of 1–6 carbon atoms. Carboxyalkyl is defined as a $HO_2C$—R'''— radical where R''' is a divalent alkyl radical of 1–6 carbon atoms. Carboalkoxyalkyl is defined as a $R''O_2C$—R'''— radical where R''' is a divalent alkyl radical and where R" and R''' may be the same or different, and together have 2–7 carbon atoms. Alkanoyl is defined as a —COR" radical, where R" is an alkyl radical of 1–6 carbon atoms. Alkenoyl is defined as a —COR" radical, where R" is an alkenyl radical of 2–6 carbon atoms. Alkanoyloxy is defined as a —OCOR" radical, where R" is an alkyl radical of 1–6 carbon atoms. Alkanoyloxymethyl is defined as $R''CO_2CH_2$— radical, where R" is an alkyl radical of 1–6 carbon atoms. Alkoxymethyl is defined as $R''OCH_2$— radical, where R" is an alkyl radical of 1–6 carbon atoms. Alkylsulphinyl is defined as R"SO— radical, where R" is an alkyl radical of 1–6 carbon atoms. Alkylsulfonyl is defined as R"SO$_2$— radical, where R" is an alkyl radical of 1–6 carbon atoms. Alkylsulfonamido, alkenylsulfonamido, alkynylsulfonamido are defined as R"SO$_2$NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R"R'NCO— radical, where R" is an alkyl radical of 1–6 carbon atoms, R' is an alkyl radical of 1–6 carbon atoms and R' and R" may be the same or different.

Het is a heterocycle, as defined above which in some cases when Het is substituted with =O (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with R$_6$, such substitution may be on a ring carbon, or in the case of a nitrogen containing heterocycle, which also contains a saturated carbon-nitrogen, such nitrogen may be substituted with R$_6$ or in the case of a nitrogen containing heterocycle, which also contains an unsaturated carbon-nitrogen, such nitrogen may be substituted with R$_6$ in which case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-subsitituted 1,4-piperazine, N-subsitituted piperidine, and N-substituted pyrrolidine.

The compounds of this invention may contain one or more asymmetric carbons atoms; in such cases, the compounds of this invention include the individual diasteromers, the racemates, and the individual R and S enantiomers thereof. Some of the compounds of this invention may contain one or more double bonds; in such cases, the compounds of this invention include each of the possible configurational isomers as well as mixtures of these isomers.

Preferred compounds of the invention are selected from:

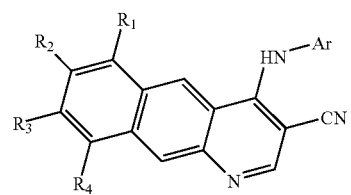

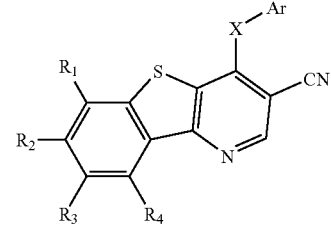

-continued

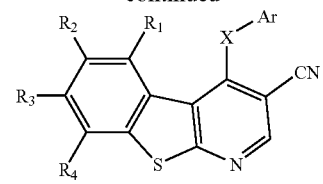

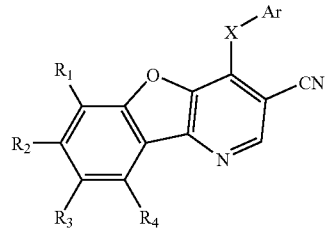

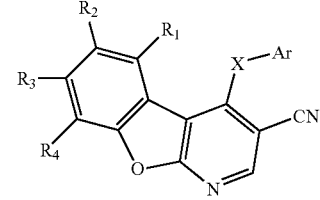

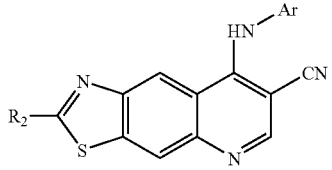

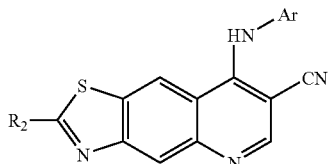

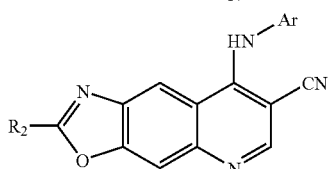

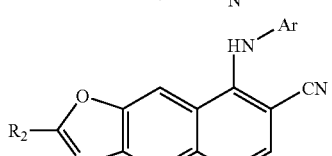

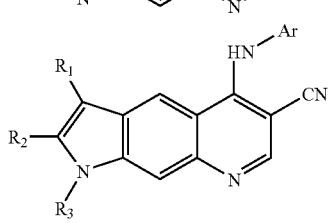

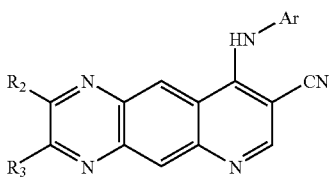

-continued

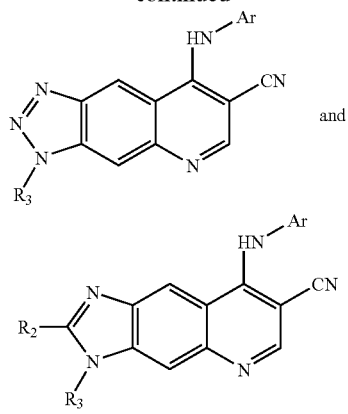

and

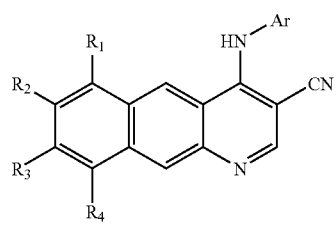

wherein Ar, $R_1$, $R_2$, $R_3$ and $R_4$ are as defined above.

More preferred compounds of this invention are described below. Except as otherwise indicated below, the substituents are as defined above.

A. Compounds according to the formula 1, having the structure

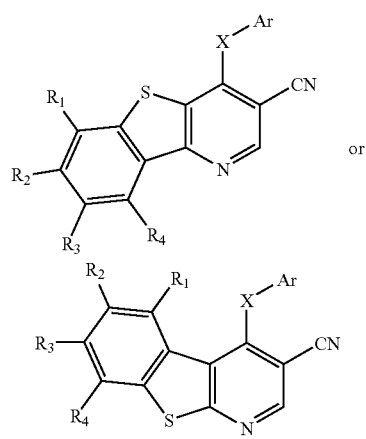

or a pharmaceutically acceptable salt thereof.

B. Compounds according to formula 1, having the structure

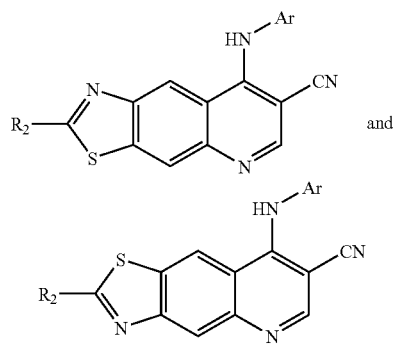

X is selected from NH, sulfur or oxygen;

or a pharmaceutically acceptable salt thereof.

C. Compounds according to formula 1, having the structure

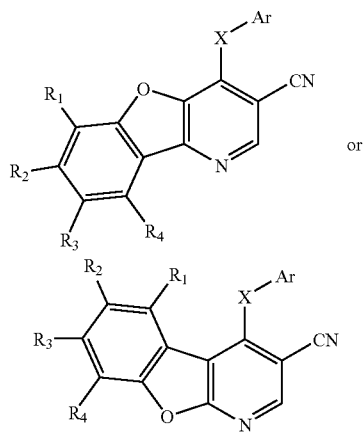

X is selected from NH, sulfur, or oxygen;

or a pharmaceutically acceptable salt thereof.

D. Compounds according to formula 1, having the structure

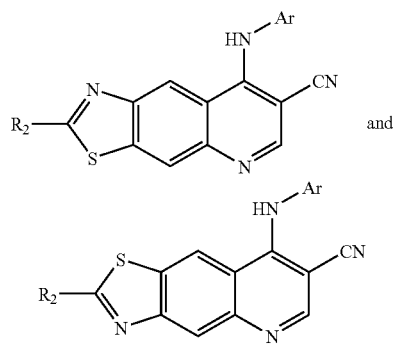

wherein
$R_2$ is hydrogen, amino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, cyano, carboxy, alkoxycarbonyl of 2–7 carbon atoms, alkanoyl of 2–7 carbon atoms, phenylamino, benzylamino, phenoxy, phenyl, thiophenoxy, benzyl, alkylamino of 1–6 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms,

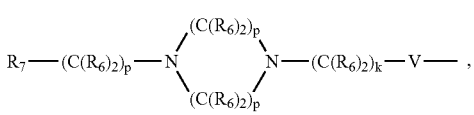

-continued

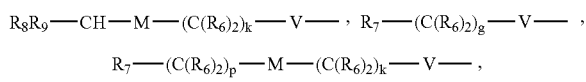
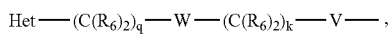
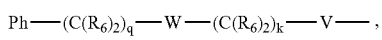
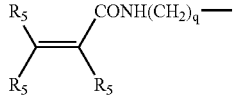
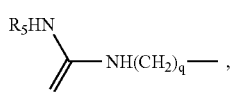
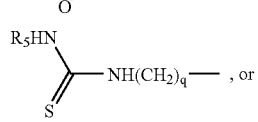

or a pharmaceutically acceptable salt thereof,

E. Compounds according to formula 1, having the structure

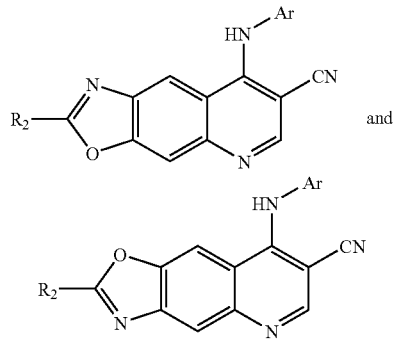

and $R_2$ is hydrogen, amino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, cyano, carboxy, alkoxycarbonyl of 2–7 carbon atoms, alkanoyl of 2–7 carbon atoms, phenylamino, benzylamino, phenoxy, phenyl, thiophenoxy, benzyl, alkylamino of 1–6 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms, F. Compounds according to formula 1 having the structure

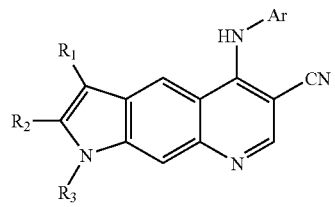

$R_1$ is hydrogen, hydroxymethyl, aminomethyl, N-alkylaminomethyl of 2–6 carbon atoms, N,N-dialkylaminomethyl of 3–12 carbon atoms, N-cycloalkylaminomethyl of 4–9 carbon atoms, N-cycloalkyl-N-alkylaminoalkyl of 5–16 carbon atoms, N,N-dicycloalkylaminomethyl of 7–18 carbon atoms, morpholino-N-methyl, piperidino-N-methyl, N-alkyl-piperazino-N-methyl wherein the alkyl group is 1–6 carbon atoms, azacycloalkyl-N-methyl of 3–6 carbon atoms, N-(hydroxyalkyl)aminomethyl of 3–7 carbon atoms, N,N-di(hydroxyalkyl)aminomethyl of 5–12 carbon atoms, N-(hydroxycycloalkyl)aminomethyl of 4–9 carbon atoms, N-(hydroxycycloalkyl)-N-(hydroxyalkyl)aminoalkyl of 6–16 carbon atoms, or N,N-di(hydroxycycloalkyl)aminomethyl of 7–18 carbon atoms;

$R_2$ is hydrogen;

$R_3$ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

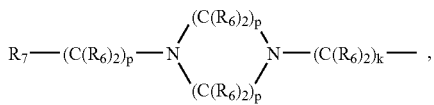

-continued

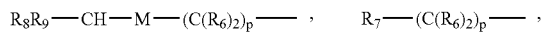

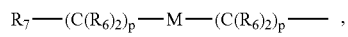

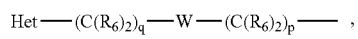

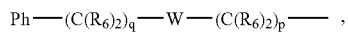

or a pharmaceutically acceptable salt thereof

G. Compounds according to formula 1, having the structure

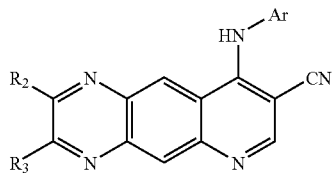

$R_2$ and $R_3$ are hydrogen;

or a pharmaceutically acceptable salt thereof.

H. Compounds according to formula 1, having the structure

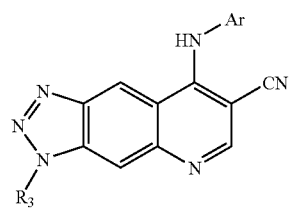

$R_3$ is hydrogen;

or a pharmaceutically acceptable salt thereof.

I. Compounds according to formula 1, having the structure

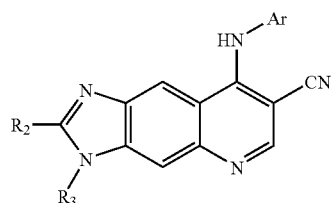

$R_2$ is hydrogen, amino, hydroxyamino, trifluoromethyl; alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, carboxy, alkoxycarbonyl of 2–7 carbon atoms, alkanoyl of 2–7 carbon atoms, N-alkyl-N-alkenylamino of 4 to 12 carbon atoms, N,N-dialkenylamino of 6–12 carbon atoms, phenylamino, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, benzylamino, phenoxy, phenyl, thiophenoxy, benzyl, alkylamino of 1–6 carbon atoms, dialkylamino of 2 to 12 carbon atoms,

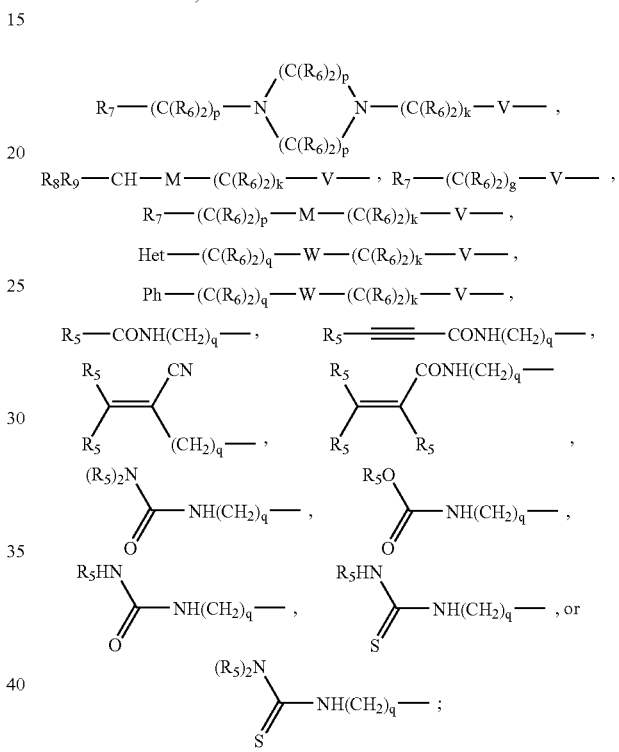

$R_3$ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

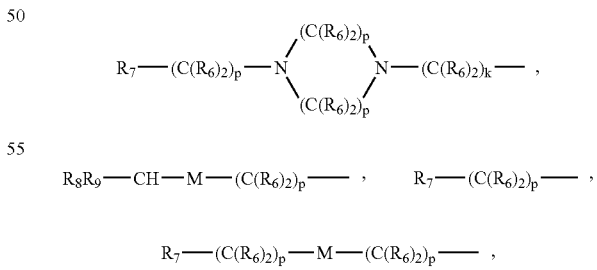

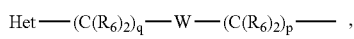

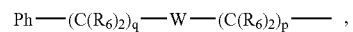

or a pharmaceutically acceptable salt thereof.

J. Compounds according to the formula 1, having the structure

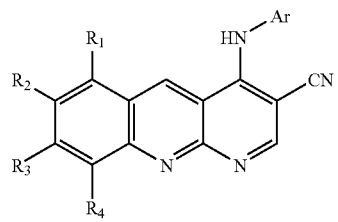

or a pharmaceutically acceptable salt thereof.

K. Compounds according to formula 1, having the structure

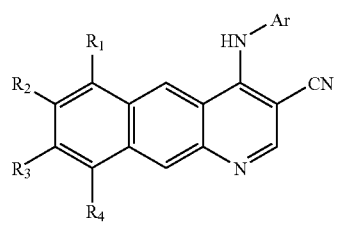

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or
Ar is the radical:

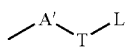

$R_1$ and $R_4$ are hydrogen;

or a pharmaceutically acceptable salt thereof.

L. Compounds according to formula 1, having the structure

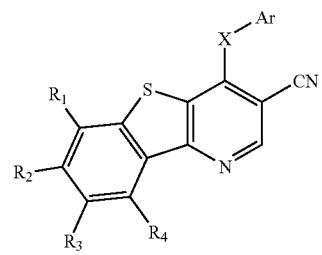

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or
Ar is the radical:

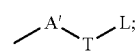

$R_4$ is hydrogen and
one or two of the substituents $R_1$, $R_2$ and $R_3$ are as defined above, the remaining being hydrogen;

or a pharmaceutically acceptable salt thereof.

M. Compounds according to formula 1, having the structure

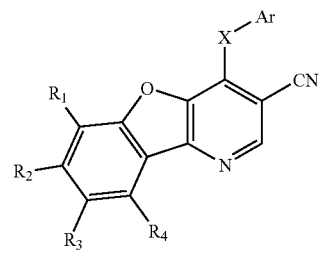

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

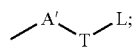

$R_4$ is hydrogen and
one or two of the substituents $R_1$, $R_2$ and $R_3$ are as herein above described, the remaining being hydrogen;

or a pharmaceutically acceptable salt thereof.

N. Compounds according to formula 1, having the structure

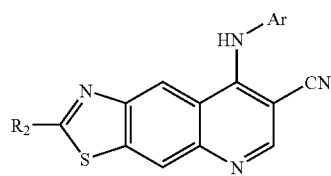

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

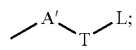

$R_2$ is hydrogen, amino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, cyano, carboxy, alkoxycarbonyl of 2–7 carbon atoms, alkanoyl of 2–7 carbon atoms, phenylamino, benzylamino, phenoxy, phenyl, thiophenoxy, benzyl, alkylamino of 1–6 carbon atoms, alkanoyloxy of 1–6 carbon atoms, alkenoyloxy of 3–8 carbon atoms, alkynyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms,

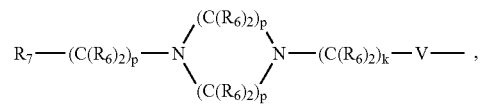

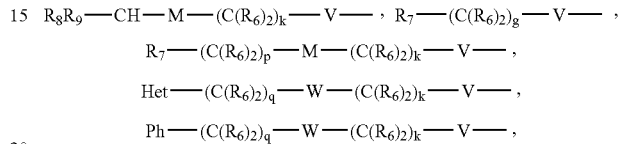

or a pharmaceutically acceptable salt thereof.

O. Compounds according to formula 1, having the structure

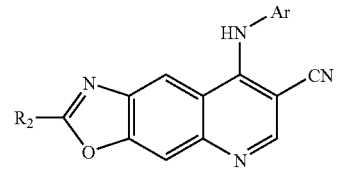

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

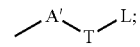

$R_2$ is hydrogen, amino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, cyano, carboxy, alkoxycarbonyl of 2–7 carbon atoms, alkanoyl of 2–7 carbon atoms, phenylamino, benzylamino, phenoxy, phenyl, thiophenoxy, benzyl, alkylamino of 1–6 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms,

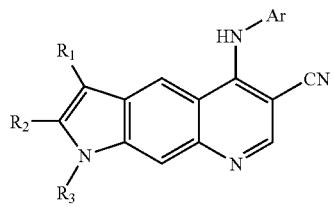

or a pharmaceutically acceptable salt thereof.

P. Compounds according to formula 1, having the structure

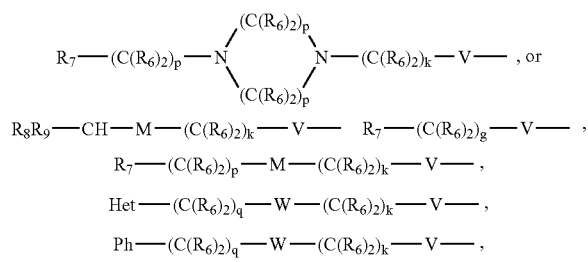

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

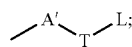

R₁ is hydrogen, hydroxymethyl, aminomethyl, N-alkylaminomethyl of 2–6 carbon atoms, N,N-dialkylaminomethyl of 3–12 carbon atoms, N-cycloalkylaminomethyl of 4–9 carbon atoms, N-cycloalkyl-N-alkylaminoalkyl of 5–16 carbon atoms, N,N-dicycloalkylaminomethyl of 7–18 carbon atoms, morpholino-N-methyl, piperidino-N-methyl, N-alkyl-piperazino-N-methyl wherein the alkyl group is 1–6 carbon atoms, azacycloalkyl-N-methyl of 3–6 carbon atoms, N-(hydroxyalkyl)aminomethyl of 3–7 carbon atoms, N,N-di(hydroxyalkyl)aminomethyl of 5–12 carbon atoms, N-(hydroxycycloalkyl)aminomethyl of 4–9 carbon atoms, N-(hydroxycycloalkyl)-N-(hydroxyalkyl)aminoalkyl of 6–16 carbon atoms, or N,N-di(hydroxycycloalkyl)aminomethyl of 7–18 carbon atoms;

R₂ is hydrogen;

R₃ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

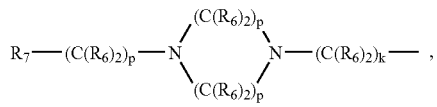

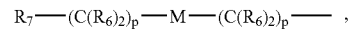

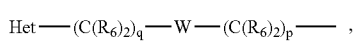

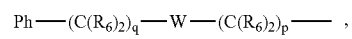

or a pharmaceutically acceptable salt thereof.

Q. Compounds according to formula 1, having the structure

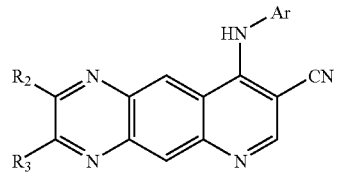

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

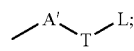

R₂ and R₃ are hydrogen;

or a pharmaceutically acceptable salt thereof.

R. Compounds according to formula 1, having the structure

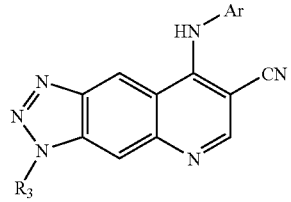

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

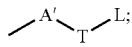

R₃ is hydrogen;

or a pharmaceutically acceptable salt thereof.

S. Compounds according to formula 1, having the structure

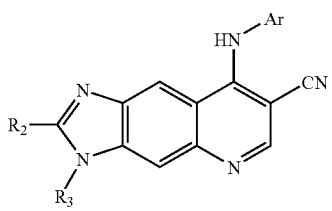

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

R₂ is hydrogen, amino, hydroxyamino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, carboxy, alkoxycarbonyl of 2–7 carbon atoms, alkanoyl of 2–7 carbon atoms, N-alkyl-N-alkenylamino of 4 to 12 carbon atoms, N,N-dialkenylamino of 6–12 carbon atoms, phenylamino, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, benzylamino, phenoxy, phenyl, thiophenoxy, benzyl, alkylamino of 1–6 carbon atoms, dialkylamino of 2 to 12 carbon atoms,

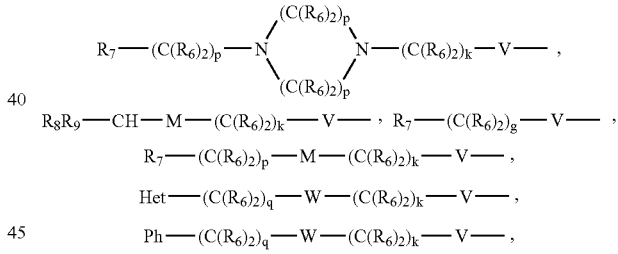

R₃ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

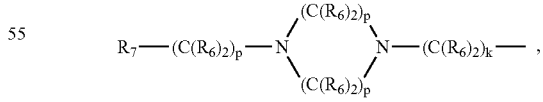
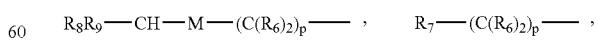
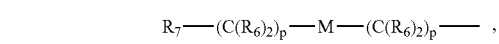
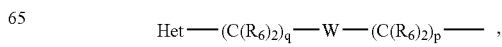

-continued $$Ph-(C(R_6)_2)_q-W-(C(R_6)_2)_p-,$$

or a pharmaceutically acceptable salt thereof.

T. Compounds according to formula 1, having the structure

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or
Ar is the radical:

$R_1$ and $R_4$ are hydrogen;

or a pharmaceutically acceptable salt thereof.

Another group of preferred compounds of the present invention are those in which:
1) Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or
Ar is the radical:

2) X is N, S, or O;
3) $R_2$ is hydrogen, amino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, cyano, carboxy, alkoxycarbonyl of 2–7 carbon atoms, alkanoyl of 2–7 carbon atoms, phenylamino, benzylamino, phenoxy, phenyl, thiophenoxy, benzyl, alkylamino of 1–6 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms, It being especially preferred when $R_2$ is H;
4) $R_1$ is hydrogen, hydroxymethyl, aminomethyl, N-alkylaminomethyl of 2–6 carbon atoms, N,N-dialkylaminomethyl of 3–12 carbon atoms, N-cycloalkylaminomethyl of 4–9 carbon atoms, N-cycloalkyl-N-alkylaminoalkyl of 5–16 carbon atoms, N,N- dicycloalkylaminomethyl of 7–18 carbon atoms, morpholino-N-methyl, piperidino-N-methyl, N-alkyl-piperazino-N-methyl wherein the alkyl group is 1–6 carbon atoms, azacycloalkyl-N-methyl of 3–6 carbon atoms, N-(hydroxyalkyl)aminomethyl of 3–7 carbon atoms, N,N-di(hydroxyalkyl)aminomethyl of 5–12 carbon atoms, N-(hydroxycycloalkyl)aminomethyl of 4–9 carbon atoms, N-(hydroxycycloalkyl)-N-(hydroxyalkyl)aminoalkyl of 6–16 carbon atoms, or N,N-di(hydroxycycloalkyl)aminomethyl of 7–18 carbon atoms; and/or 5) $R_3$ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

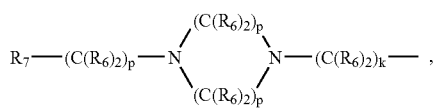

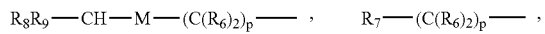

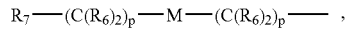

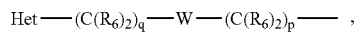

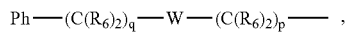

it being especially preferred when $R_3$ is hydrogen;

Specifically preferred compounds of this invention include:

a) 4-(4-phenoxyanilino)benzo[g]quinoline-3-carbonitrile,
b) 4-(3-chloro-4-fluoroanilino)benzo[g]quinoline-3-carbonitrile,
c) 4-(4-chloro-5-methoxy-2-methylanilino)benzo[g]quinoline-3-carbonitrile,
d) 7,8-dimethoxy-4-(4-phenoxyanilino)benzo[g]quinoline-3-carbonitrile,
e) 4-(4-chloro-5-methoxy-2-methylanilino)-7,8-dimethoxybenzo[g]quinoline-3-carbonitrile,
f) 4-(3-chloro-4-fluoroanilino)-7,8-dimethoxybenzo[g]quinoline-3-carbonitrile,
g) 4-(2,4-dichloroanilino)-7,8-dimethoxybenzo[g]quinoline-3-carbonitrile,
h) 4-(2,4-dichloroanilino)-7,8-dihydroxybenzo[g]quinoline-3-carbonitrile,
i) 9-(3,4,5-trimethoxyanilino)-3H-[1,2,3]triazolo[4,5-g]quinoline-7-carbonitrile,
j) 9-(4-chloro-5-methoxy-2-methylanilino)pyrido[2,3-g]quinoxaline-8-carbonitrile,
k) 8-(5-methoxy-2-methylanilino)-2-{[2-(4-morpholinyl)ethyl]ammo}imidazo[4,5-g]quinoline-7-carbonitrile,
l) 2-{[2-(4-morpholinyl)ethyl]amino}-8-(3,4,5-trimethoxyanilino)imidazo[4,5-g]quinoline-7-carbonitrile,
m) 2-amino-8-(4-phenoxyanilino)imidazo[4,5-g]quinoline-7-carbonitrile,
n) 8-(3-bromo-phenylamino)imidazo[4,5-g]quinoline-7-carbonitrile,
o) 8-(2-bromo-4-chlorophenylamino)imidazo[4,5-g]quinoline-7-carbonitrile,
p) 8-(2-bromo-4-chloro-5-methoxyphenylamino)imidazo[4,5-g]quinoline-7-carbonitrile,
q) 8-(2-chloro-5-methoxyphenylamino)imidazo[4,5-g]quinoline-7-carbonitrile,
r) 8-(3-hydroxy-4-methylphenylamino)imidazo[4,5-g]quinoline-7-carbonitrile,
s) 8-(3,4,5-trimethoxyanilino)imidazo[4,5-g]quinoline-7-carbonitrile,
t) 8-(4-phenoxyanilino)imidazo[4,5-g]quinoline-7-carbonitrile,
u) 2-(chloromethyl)-8-(3,4,5-trimethoxyanilino)imidazo[4,5-g]quinoline-7-carbonitrile,
v) 2-(4-morpholinylmethyl)-8-(3,4,5-trimethoxyanilino)imidazo[4,5-g]quinoline-7-carbonitrile,
w) 8-(4-chloro-5-methoxy-2-methylanilino)-3-[2-(4-morpholinyl)ethyl]-3H-imidazo[4,5-g]quinoline-7-carbonitrile,
x) 3-[2-(4-morpholinyl)ethyl]-8-(4-phenoxyanilino)-3H-imidazo[4,5-g]quinoline-7-carbonitrile,
y) 8-[(4-chloro-5-methoxy-2-methylphenyl)amino]-thiazolo[4,5-g]quinoline-7-carbonitrile,
z) 4-(3-bromophenylamino)benzo[4,5]thieno[3,2-b]pyridine-3-carbonitrile,
aa) 4-(4-chloro-2-fluorophenylamino)benzo[4,5]thieno[3,2-b]pyridine-3-carbonitrile,
bb) 4-(2,4-dichlorophenylamino)benzo[4,5]thieno[3,2-b]pyridine-3-carbonitrile,
cc) 4-(2,4-dichloro-5-methoxyphenylamino)benzo[4,5]thieno[3,2-b]pyridine-3-carbonitrile,
dd) 4-(4-phenoxyphenylamino)benzo[4,5]thieno[3,2-b]pyridine-3-carbonitrile,
ee) 4-(3-hydroxy-4-methylphenylamino)benzo[4,5]thieno[3,2-b]pyridine-3-carbonitrile,
ff) 4-(4-chloro-2-fluorophenoxy)benzo[4,5]thieno[3,2-b]pyridine-3-carbonitrile,
gg) 4-(4-chloro-5-methoxy-2-methylphenylamino)-8-nitrobenzo[4,5]thieno[3,2-b]pyridine-3-carbonitrile,
hh) 8-amino-4-(4-chloro-5-methoxy-2-methylanilino)[1]benzothieno[3,2-b]pyridine-3-carbonitrile,
ii) 4-(3-bromoanilino)-6-nitro[1]benzothieno[3,2-b]pyridine-3-carbonitrile,
jj) 6-amino-4-(3-bromoanilino)[1]benzothieno[3,2-b]pyridine-3-carbonitrile,
kk) 4-(3-bromophenylamino)benzo[4,5]furo[3,2-b]pyridine-3-carbonitrile,
ll) 4-(4-chloro-2-fluorophenylamino)benzo[4,5]furo[3,2-b]pyridine-3-carbonitrile,
mm) 4-(3-hydroxy-4-methylphenylamino)benzo[4,5]furo[3,2-b]pyridine-3-carbonitrile,
nn) 4-(4-phenoxyphenylamino)benzo[4,5]furo[3,2-b]pyridine-3-carbonitrile,
oo) 4-(4-chloro-2-fluorophenoxy)benzo[4,5]furo[3,2-b]pyridine-3-carbonitrile,
pp) 4-(2,4-dichloroanilino)-8-nitro[1]benzothieno[3,2-b]pyridine-3-carbonitrile,
qq) 4-(3-bromoanilino)-8-nitro[1]benzothieno[3,2-b]pyridine-3-carbonitrile,
rr) 8-amino-4-(3-bromoanilino)[1]benzothieno[3,2-b]pyridine-3-carbonitrile,
ss) N-[4-(3-bromoanilino)-3-cyano[1]benzothieno[3,2-b]pyridin-8-yl]acrylamide,
tt) N-[4-(3-bromoanilino)-3-cyano[1]benzothieno[3,2-b]pyridin-6-yl]acrylamide,
uu) 4-(2,4-dichloroanilino)-7-methoxybenzo[g]quinoline-3-carbonitrile,
vv) 4-(2,4-dichloroanilino)-8-methoxybenzo[g]quinoline-3-carbonitrile, ww) 4-(2,4-dichloroanilino)-7-hydroxybenzo[g]quinoline-3-carbonitrile,
xx) 4-(2,4-dichloroanilino)-8-hydroxybenzo[g]quinoline-3-carbonitrile,
yy) 4-(2,4-dichloroanilino)-7-[2-(dimethylamino)ethoxy]benzo[g]quinoline-3-carbonitrile,
zz) 4-(4-chloro-5-methoxy-2-methylanilino)-7-methoxy-8-(chloroethoxy)benzo[g]quinoline-3-carbonitrile,
aaa) 4-(4-chloro-5-methoxy-2-methylanilino)-8-methoxy-7-(chloroethoxy)benzo[g]quinoline-3-carbonitrile,
bbb) 4-(4-chloro-5-methoxy-2-methylanilino)-7-methoxy-8-[2-(4-morpholinyl)ethoxy]benzo[g]quinoline-3-carbonitrile,
ccc) 4-(4-chloro-5-methoxy-2-methylanilino)-8-methoxy-7-[2-(4-morpholinyl)ethoxy]benzo[g]quinoline-3-carbonitrile,
ddd) 4-(2,4-dichloro-5-methoxyanilino)-7-methoxy-8-(chloroethoxy)benzo[g]quinoline-3-carbonitrile,
eee) 4-(2,4-dichloro-5-methoxyanilino)-8-methoxy-7-(chloroethoxy)benzo[g]quinoline-3-carbonitrile,
fff) 4-(2,4-dichloro-5-methoxyanilino)-8-methoxy-7-[2-(4-morpholinyl)ethoxy]benzo[g]quinoline-3-carbonitrile,
ggg) 4-(2,4-dichloro-5-methoxyanilino)-7-methoxy-8-[2-(4-morpholinyl)ethoxy]benzo[g]quinoline-3-carbonitrile,
hhh) 4-(2,4-dichloro-5-methoxyanilino)-8-methoxy-7-[2-(4-methyl 1-piperazinyl)ethoxy]benzo[g]quinoline-3-carbonitrile,
iii) 4-(2,4-dichloro-5-methoxyanilino)-7-methoxy-8-[2-(4-methyl-1-piperazinyl)ethoxy]benzo[g]quinoline-3-carbonitrile,
jjj) 4-(4-chloro-5-methoxy-2-methylanilino)-8-methoxy-7-[2-(4-methyl-1-piperazinyl)ethoxy]benzo[g]quinoline-3-carbonitrile,
kkk) 4-(4-chloro-5-methoxy-2-methylanilino)-7-methoxy-8-[2-(4-methyl 1-piperazinyl)ethoxy]benzo[g]quinoline-3-carbonitrile,
lll) 4-[3-Chloro-4-(1-methyl-1H-imidazol-2-ylsulfanyl)phenylamino]-8-hydroxy-7-methoxybenzo[g]quinoline-3-carbonitrile,
mmm) 8-(2-Chloroethoxy)-4-[3-chloro-4-(1-methyl-1H-imidazol-2-ylsulfanyl)phenylamino]-7-methoxybenzo[g]quinoline-3-carbonitrile,
nnn) 4-[3-Chloro-4-(1-methyl-1H-imidazol-2-ylsulfanyl)phenylamino]-7-methoxy-8-(2-morpholin-4-yl-ethoxy)benzo[g]quinoline-3-carbonitrile,
ooo) 4-[3-Chloro-4-(1-methyl-1H-imidazol-2-ylsulfanyl)phenylamino]-8-(3-chloropropoxy)-7-methoxybenzo[g]quinoline-3-carbonitrile,
ppp) 4-[3-Chloro-4-(1-methyl-1H-imidazol-2-ylsulfanyl)phenylamino]-7-methoxy-8-(3-morpholin-4-yl-propoxy)benzo[g]quinoline-3-carbonitrile,
qqq) 4-[3-Chloro-4-(1-methyl-1H-imidazol-2-ylsulfanyl)phenylamino]-7-methoxy-8-[2-(4-methylpiperazin-1-yl)ethoxy]-benzo[g]quinoline-3-carbonitrile,
rrr) 4-[3-Chloro-4-(1-methyl-1H-imidazol-2-ylsulfanyl)phenylamino]-7-methoxy-8-(2-[1,2,3]triazol-2-yl-ethoxy)benzo[g]quinoline-3-carbonitrile,
sss) 4-[3-Chloro-4-(1-methyl-1H-imidazol-2-ylsulfanyl)phenylamino]-7-methoxy-8-(2-[1,2,3]triazol-1-yl-ethoxy)benzo[g]quinoline-3-carbonitrile,
ttt) 4-(2,4-Dichloro-5-methoxyphenylamino)-8-hydroxy-7-methoxybenzo[g]quinoline-3-carbonitrile,
uuu) 8-(3-Chloropropoxy)-4-(2,4-dichloro-5-methoxyphenylamino)-7-methoxybenzo[g]quinoline-3-carbonitrile,
vvv) 4-(2,4-Dichloro-5-methoxyphenylamino)-7-methoxy-8-(3-morpholin-4-yl-propoxy)benzo[g]quinoline-3-carbonitrile,
www) 4-(2,4-Dichloro-5-methoxyphenylamino)-7-methoxy-8-(2-[1,2,3]triazol-2-yl-ethoxy)benzo[g]quinoline-3-carbonitrile,
xxx) 4-(2,4-Dichloro-5-methoxyphenylamino)-7-methoxy-8-(2-[1,2,3]triazol-1-yl-ethoxy)benzo[g]quinoline-3-carbonitrile,
yyy) 4-(2,4-Dichloro-5-methoxyanilino)-7,8-dimethoxybenzo[b][1,8]naphthyridine-3-carbonitrile,
zzz) 8-(2-Chloroethoxy)-4-(2,4-dichloro-5-methoxyanilino)-7-methoxybenzo[b][1,8]naphthyridine-3-carbonitrile,
aaaa) 4-(2,4-Dichloro-5-methoxyanilino)-7-methoxy-8-[2-(4-morpholinyl)ethoxy]benzo[b][1,8]naphthyridine-3-carbonitrile,
bbbb) 8-(2-Chloroethoxy)-4-{3-chloro-4-[(1-methyl-1H-imidazol-2-yl)sulfanyl]anilino}-7-methoxybenzo[b][1,8]naphthyridine-3-carbonitrile,
cccc) 4-(2,4-Dichloro-5-methoxyanilino)-7-methoxy-8-[2-(4-methyl-1-piperazinyl)ethoxy]benzo[b][1,8]naphthyridine-3-carbonitrile,
dddd) 4-{3-Chloro-4-[(1-methyl-1H-imidazol-2-yl)sulfanyl]anilino}-7-methoxy-8-[2-(4-morpholinyl)ethoxy]benzo[b][1,8]naphthyridine-3-carbonitrile,
eeee) 4-(2,4-Dichloroanilino)-7,8-dimethoxybenzo[b][1,8]naphthyridine-3-carbonitrile,
ffff) 8-(2-Chloroethoxy)-4-(4-chloro-5-methoxy-2-methylanilino)-7-ethoxybenzo[g]quinoline-3-carbonitrile,
gggg) 8-(2-Chloroethoxy)-4-(2-chloro-4-fluoro-5-methoxyanilino)-7-methoxybenzo[g]quinoline-3-carbonitrile,
hhhh) 7-(2-Chloroethoxy)-4-(2-chloro-4-fluoro-5-methoxyanilino)-8-methoxybenzo[g]quinoline-3-carbonitrile,
iiii) 8-(2-Chloroethoxy)-4-(2-chloro-5-methoxy-4-methylphenylamino)-7-methoxybenzo[g]quinoline-3-carbonitrile,
jjjj) 7-(2-Chloroethoxy)-4-(2-chloro-5-methoxy-4-methylphenylamino)-8-methoxybenzo[g]quinoline-3-carbonitrile,
kkkk) 7-(2-Chloroethoxy)-4-(3-chloro-4-fluoroanilino)-8-methoxybenzo[g]quinoline-3-carbonitrile,
llll) 8-(2-Chloroethoxy)-4-(3-chloro-4-fluoroanilino)-7-methoxybenzo[g]quinoline-3-carbonitrile,
mmmm) 4-(4-Benzyloxy-3-chlorophenylamino)-7-(2-chloroethoxy)-8-methoxybenzo[g]quinoline-3-carbonitrile,
nnnn) 4-(4-Benzyloxy-3-chlorophenylamino)-8-(2-chloroethoxy)-7-methoxybenzo[g]quinoline-3-carbonitrile,
oooo) 7-(2-Chloroethoxy)-4-(3-chloro-4-phenoxyphenylamino)-8-methoxybenzo[g]quinoline-3-carbonitrile,
pppp) 8-(2-Chloroethoxy)-4-(3-chloro-4-phenoxyphenylamino)-7-methoxybenzo[g]quinoline-3-carbonitrile,
qqqq) 4-(4-Chloro-5-methoxy-2-methylanilino)-8-ethoxy-7-[2-(4-morpholinyl)ethoxy]benzo[g]quinoline-3-carbonitrile,
rrrr) 4-(4-Chloro-5-methoxy-2-methylanilino)-7-ethoxy-8-[2-(4-morpholinyl)ethoxy]benzo[g]quinoline-3-carbonitrile,
ssss) ({2[4-(4-Chloro-5-methoxy-2-methylphenylamino)-3-cyano-8-ethoxybenzo[g]quinoline-7-yloxy]-ethyl}-ethoxycarbonylmethylamino)-acetic acid ethyl ester, tttt) ({2-[4-(4-Chloro-5-methoxy-2-methylphenylamino)-3-cyano-7-ethoxybenzo[g]quinoline-8-yloxy]-ethyl}-ethoxycarbonylmethylamino)-acetic acid ethyl ester, uuuu) 2-(Carbamoylmethyl-{2-[4-(4-chloro-5-methoxy-2-methylphenylamino)-3-cyano-7-ethoxybenzo[g]quinolin-8-yloxy]-ethyl}-amino)-acetamide, vvvv) 4-(2,4-Dichloroanilino)-7-methoxy-8-[2-(4-morpholinyl)ethoxy]benzo[g]quinoline-3-carbonitrile, wwww) 4-(2,4-Dichloroanilino)-8-methoxy-7-[2-(4-morpholinyl)ethoxy]benzo[g]quinoline-3-carbonitrile, xxxx) 8-Methoxy-7-[2-(4-methyl-1-piperazinyl)ethoxy]-4-(3,4,5-trimethoxyanilino)benzo[g]quinoline-3-carbonitrile, yyyy) 7-Methoxy-8-[2-(4-methyl-1-piperazinyl)ethoxy]-4-(3,4,5-trimethoxyanilino)benzo[g]quinoline-3-carbonitrile, zzzz) 7-Methoxy-8-[2-(4-morpholinyl)ethoxy]4-(3,4,5-trimethoxyanilino)benzo[g]quinoline-3-carbonitrile, aaaaa) 8-Methoxy-7-[2-(4-morpholinyl)ethoxy]-4-(3,4,5-trimethoxyanilino)benzo[g]quinoline-3-carbonitrile, bbbbb) 4-(2-Chloro-4-fluoro-5-methoxyanilino)-8-methoxy-7-[2(4-methyl 1-piperazinyl)ethoxy]benzo[g]quinoline-3-carbonitrile, ccccc) 4-(2-Chloro-5-methoxy-4-methylamino)-8-methoxy-7-[2-(4-methyl-1-piperazinyl)ethoxy]benzo[g]quinoline-3-carbonitrile, ddddd) 4-(2-Chloro-5-methoxy-4-methylanilino)-7-methoxy-8-[2-(4-methyl-1-piperazinyl)ethoxy]benzo[g]quinoline-3-carbonitrile, eeeee) 4-(2,4-Dichloro-5-methoxyanilino)-7-[2-(4-hydroxy-1-piperidinyl)ethoxy]-8-methoxybenzo[g]quinoline-3-carbonitrile, fffff) 4-(3-Chloro-4-fluoroanilino)-7-methoxy-8-[2-(4-morpholinyl)ethoxy]benzo[g]quinoline-3-carbonitrile, ggggg) 4-(2,4-Dichloro-5-methoxyanilino)-8-[2-(4-hydroxy-1-piperidinyl)ethoxy]-7-methoxybenzo[g]quinoline-3-carbonitrile, hhhhh) 4-(2-Chloro-5-methoxy-4-methylanilino)-8-methoxy-7-[2-(4-hydroxy-1-piperidinyl)ethoxy]benzo[g]quinoline-3-carbonitrile, iiiii) 4-(2-Chloro-5-methoxy-4-methylanilino)-7-methoxy-8-[2-(4-hydroxy-1-piperidinyl)ethoxy]benzo[g]quinoline-3-carbonitrile, jjjjj) 4-(2-Chloro-4-fluoro-5-methoxyanilino)-8-methoxy-7-[2-(4-morpholinyl)ethoxy]benzo[g]quinoline-3-carbonitrile, kkkkk) 4-(2-Chloro-4-fluoro-5-methoxyanilino)-7-methoxy-8-[2-(4-morpholinyl)ethoxy]benzo[g]quinoline-3-carbonitrile, lllll) 4-(2-Chloro-4-fluoro-5-methoxyanilino)-7-methoxy-8-[2-(4-methyl-1-piperazinyl)ethoxy]benzo[g]quinoline-3-carbonitrile, mmmmm) 4-(3-Chloro-4-fluoroanilino)-8-methoxy-7-[2-(4-morpholinyl)ethoxy]benzo[g]quinoline-3-carbonitrile, nnnnn) 4-(3-Chloro-4-phenoxyphenylamino)-7-methoxy-8-(2-morpholin-4-yl-ethoxy)benzo[g]quinoline-3-carbonitrile, ooooo) 4-(3-Chloro-4-phenoxyphenylamino)-8-methoxy-7-(2-morpholin-4-yl-ethoxy)benzo[g]quinoline-3-carbonitrile, ppppp) 4-(2-Chloro-5-methoxy-4-methylphenylamino)-8-methoxy-7-(2-morpholin-4-yl-ethoxy)benzo[g]quinoline-3-carbonitrile, qqqqq) 4-(2-Chloro-5-methoxy-4-methylphenylamino)-7-methoxy-8-(2-morpholin-4-yl-ethoxy)benzo[g]quinoline-3-carbonitrile, rrrrr) 4-(4-Benzyloxy-3-chlorophenylamino)-8-methoxy-7-(2-morpholin-4-yl-ethoxy)benzo[g]quinoline-3-carbonitrile, sssss) 4-(4-Benzyloxy-3-chlorophenylamino)-7-methoxy-8-(2-morpholin-4-yl-ethoxy)benzo[g]quinoline-3-carbonitrile, ttttt) 8-(Benzyloxy)-4-[(2-chloro-4-fluoro-5-methoxyphenyl)amino]-7-methoxybenzo[g]quinoline-3-carbonitrile, and uuuuu) 4-[(2-Chloro-4-fluoro-5-methoxyphenyl)amino]-8-hydroxy-7-methoxybenzo[g]quinoline-3-carbonitrile, or a pharmaceutically acceptable salt thereof.

Also included in the present invention are compounds useful as intermediates for producing the above compounds of formula 1. Such intermediates specifically include the following:

a) 4-oxo-1,4-dihydrobenzo[g]quinoline-3-carbonitrile,
b) 4-chlorobenzo[g]quinoline-3-carbonitrile,
c) 3-(dimethylaminomethyleneamino)-6,7-dimethoxynaphthalene-2-carboxylic acid methyl ester,
d) 7,8-dimethoxy-4-oxo-1,4-dihydrobenzo[g]quinoline-3-carbonitrile,
e) 4-chloro-7,8-dimethoxybenzo[g]quinoline-3-carbonitrile,
f) 7-chloro-6-nitro-4-oxo-1-([2-(trimethylsilyl)ethoxy]methyl)-1,4-dihydro-3-quinolinecarbonitrile,
g) 6,7-diamino-4-oxo-1-(2-trimethylsilanyl-ethoxymethyl)-1,4-dihydro-quinoline-3-carbonitrile,
h) 8-oxo-5-{[2-(trimethylsilyl)ethoxy]methyl}-5,8-dihydro[1,2,3]triazolo[4,5-g]quinoline-7-carbonitrile,
i) 8-oxo-5,8-dihydro[1,2,3]triazolo[4,5-g]quinoline-7-carbonitrile,
j) 8-chloro[1,2,3]triazolo[4,5-g]quinoline-7-carbonitrile,
k) 2-amino-8-oxo-5-([2-(trimethylsilyl)ethoxy]methyl-5,8-dihydroimidazo[4,5-g]quinoline-7-carbonitrile,
l) 2-amino-8-oxo-5,8-dihydroimidazo[4,5-g]quinoline-7-carbonitrile,
m) 2-amino-8-chloroimidazo[4,5-g]quinoline-7-carbonitrile,
n) 8-oxo-5,8-dihydroimidazo[4,5-g]quinoline-7-carbonitrile,
o) 8-chloroimidazo[4,5-g]quinoline-7-carbonitrile,
p) 7-cyanoimidazo[4,5-g]quinolin-8-yl(3,4,5-trimethoxyphenyl)formamide,
q) 7-cyanoimidazo[4,5-g]quinolin-8-yl(4-phenoxyphenyl)formamide,
r) 7-{[2-(4-morpholinyl)ethyl]amino}-6-nitro-4-oxo-1-{[2-(trimethylsilyl)ethoxy]methyl}-1,4-dihydro-3-quinolinecarbonitrile,
s) 6-amino-7-{[2-(4-morpholinyl)ethyl]amino}-4-oxo 1-{[2-(trimethylsilyl)ethoxy]methyl}-1,4-dihydro-3-quinolinecarbonitrile,
t) 3-[2-(4-morpholinyl)ethyl]-8-oxo-5,8-dihydro-3H-imidazo[4,5-g]quinoline-7-carbonitrile,
u) 8-chloro-3-[2-(4-morpholinyl)ethyl]-3H-imidazo[4,5-g]quinoline-7-carbonitrile,
v) 1,4-dihydro-7-mercapto-6-nitro-4-oxo-1-[[2-(trimethylsilyl)ethoxy]methyl]-3-quinolinecarbonitrile,
w) 8-hydroxy[1,3]thiazolo[4,5-g]quinoline-7-carbonitrile,
x) 3-(dimethylaminomethyleneamino)benzo[b]thiophene-2-carboxylic acid methyl ester,
y) 4-hydroxybenzo[4,5]thieno[3,2-b]pyridine-3-carbonitrile, z) 4-chlorobenzo[4,5]thieno[3,2-b]pyridine-3-carbonitrile,
aa) 4-hydroxy-8-nitrobenzo[4,5]thieno[3,2-b]pyridine-3-carbonitrile,
bb) 4-chloro-8-nitrobenzo[4,5]thieno[3,2-b]pyridine-3-carbonitrile,
cc) 4-chloro-6-nitro[1]benzothieno[3,2-b]pyridine-3-carbonitrile,
dd) 3-(dimethylaminomethyleneamino)benzofuran-2-carboxylic acid ethyl ester,
ee) 4-hydroxybenzo[4,5]furo[3,2-b]pyridine-3-carbonitrile,
ff) 4-chlorobenzo[4, 5]furo[3,2-b]pyridine-3-carbonitrile,
gg) 7-methoxy-4-oxo-1,4-dihydrobenzo[g]quinoline-3-carbonitrile,
hh) 8-methoxy-4-oxo-1,4-dihydrobenzo[g]quinoline-3-carbonitrile,
ii) 4-chloro-7-methoxybenzo[g]quinoline-3-carbonitrile,
jj) 4-chloro-8-methoxybenzo[g]quinoline-3-carbonitrile,
kk) ethyl 7-(2-chloroethoxy)-6-methoxy-3-nitro-2-naphthoate,
ll) ethyl 6-(2-chloroethoxy)-7-methoxy-3-nitro-2-naphthoate,
mm) ethyl 3-amino-7-(2-chloroethoxy)-6-methoxy-2-naphthoate,
nn) ethyl 3-amino-6-(2-chloroethoxy)-7-methoxy-2-naphthoate,
oo) 8-(2-chloroethoxy)-7-methoxy-4-oxo-1,4-dihydrobenzo[g]quinoline-3-carbonitrile,
pp) 7-(2-chloroethoxy)-8-methoxy-4-oxo-1,4-dihydrobenzo[g]quinoline-3-carbonitrile,
qq) 4-chloro-7-methoxy-8-(2-chloroethoxy)benzo[g]quinoline-3-carbonitrile,
rr) 4-chloro-8-methoxy-7-(2-chloroethoxy)benzo[g]quinoline-3-carbonitrile,
ss) 7,8-dimethoxy-4-oxo-1,4-dihydrobenzo[b][1,8] naphthyridine-3-carbonitrile,
tt) 4-chloro-7,8-dimethoxybenzo[b][1,8]naphthyridine-3-carbonitrile,
uu) 8-(2-chloroethoxy)-7-methoxy-4-oxo-1,4-dihydrobenzo[b][1,8]naphthyridine-3-carbonitrile, and
vv) 4-chloro-8-(2-chloroethoxy)-7-methoxybenzo[b][1,8]naphthyridine-3-carbonitrile.

The compounds and intermediates of this invention encompassed by Formula 6 may be prepared as described below and in Flowsheet 1 wherein Ar, X and n are hereinbefore defined. $R_1'$, $R_2'$, $R_3'$ and $R_4'$ are each, independently, hydrogen, halogen, hydroxy, amino, hydroxyamino, trifluoromethyl, trifluoromethoxy, mercapto, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, alkynyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, nitro, carboxy, alkoxycarbonyl of 2–7 carbon atoms, alkanoyl of 2–7 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, phenoxy, phenyl, thiophenoxy, benzyl, alkylamino of 1–6 carbon atoms, or dialkylamino of 2 to 12 carbon atoms;

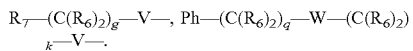

where V, $R_6$, $R_7$, W; Ph, g, k and q are as hereinabove defined.

Reaction of 3-amino-2-naphthoic acids (Formula 2) with dimethylformamide dimethyl acetal, with or without a solvent, gives intermediates of Formula 3. The reaction of 3 with the lithium anion of acetonitrile prepared by using a base such as n-butyllithium or the like in an inert solvent gives 3-cyano-4-oxo-1,4-dihydrobenzo[g]quinolines 4 or the 3-cyano-4-hydroxybenzo[g]quinoline tautomers thereof. Heating 4, with or without solvent, with a chlorinating agent such as phosphorus oxychloride or oxalyl chloride provides the corresponding 4-chloro-3-cyanobenzo[g]quinolines. Condensation of 4-chloro-3-cyanobenzo[g]quinolines with a nucleophilic amine, aniline, mercaptan, thiophenol, phenol, or alcohol reagent of Formula 5, $HX-(CH_2)_n-Ar$, wherein Ar, X and n are as hereinbefore defined, give the 3-cyanobenzo[g]quinolines of Formula 6. The condensation can be accelerated by heating the reaction mixture together with one equivalent of pyridine hydrochloride or by using bases such as trialkylamines, sodium hydride in an inert solvent, sodium or potassium alkoxides in an alcohol solvent, or by using transition metal catalysts such as tris(dibenzylideneacetone)dipalladium(0) or the like, together with ligands such as, but not limited to 2-dicyclohexylphosphino-2'-(N,N-dimethylamino)biphenyl, and potassium phosphate or the like in an inert solvent. In those cases where the substituents may contain an asymmetric carbon atom, the intermediates can be used as the racemate or as the individual R or S enantiomers in which case the compounds of this invention will be in the racemic or the R and S optically active forms, respectively. In cases where the substituents may contain more than one asymmetric carbon atoms, diastereomers may be present; these can be separated by methods well known in the art including, but not limited to, fractional crystallization and chromatographic methods. When Ar contains primary or secondary amino groups or hydroxyl groups, it may be necessary to protect these groups prior to the reaction with the substituted 4-chloro-3-cyanobenzo[g]quinolines. Suitable protecting groups include, but are not limited to tert-butoxycarbonyl (BOC), β-trimethylsilylethanesulfonamide (SES), benzyloxycarbonyl (CBZ) and benzyl (Bn) protecting groups. The first protecting group listed above can be removed from the final products of Formula 6 by treatment with an acid such as trifluoroactic acid, the second protecting group with a fluoride salt, such as cesium fluoride or tetrabutylammonium fluoride. The latter two protecting groups can be removed by catalytic hydrogenation or sodium in ammonia. In those cases where the Ar contains hydroxyl groups, the hydroxyl groups may first have to be protected prior to final product formation. Suitable protecting groups include, but are not limited to, t-butyldimethylsilyl, tetrahydropyranyl, or benzyl protecting groups. The first two protecting groups listed above can be removed from the final products of Formula 6 by treatment with an acid such as acetic acid or hydrochloric acid while the latter protecting group can be removed by catalytic hydrogenation. The 3-amino-2-naphthoic acids of Formula 2 are commercially available or can be prepared by procedures known in the art from compounds detailed by the following references: Zhu, Z.; Drach, J. C.; Townsend, L. B. *J. Org. Chem.*, 63, 977–983, (1998); Kienzle, F. *Helv. Chim. Acta.*, 63, 2364–2369, (1980), Kobayashi, K.; Kanno, C.; Seko, S.; Suginome, H. *J. Chem. Soc., Perkin Trans.* 1., 3111–317, (1992), Levy, L. A. *Synth. Commun.*, 13, 639–48 (1983) and Moder, K. P.; Leonard, N. J. *J. Am. Chem. Soc.,* 104, 2613–24 (1982).

It will be recognized by those skilled in the art that the 4-hydroxy substituent of the benzoquinoline tautomer may be converted to a leaving group such as halogen, tosyl, mesyl, aryl- or alkyl-sulfonate, preferably trifluoromethanesulfonate and the like.

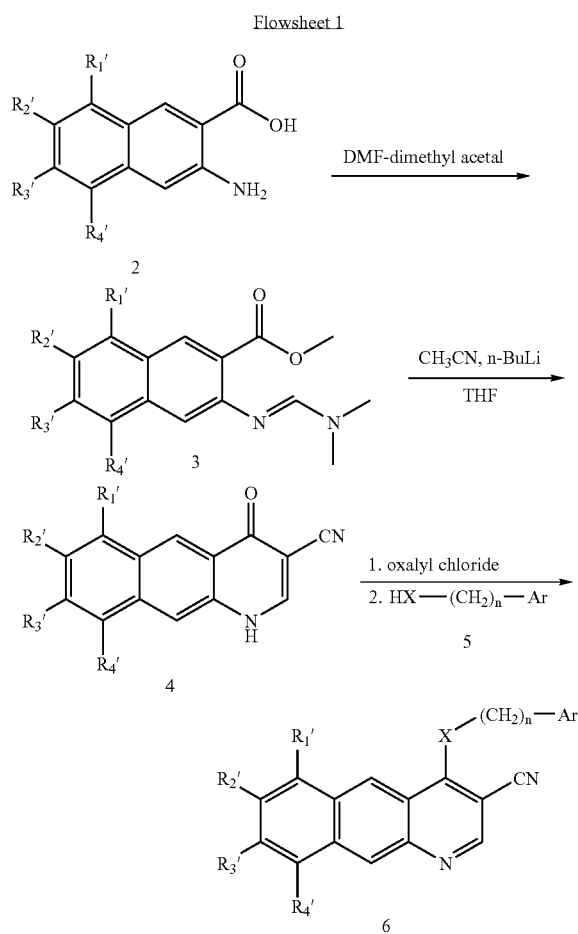

Intermediate 3 can also be prepared as described below and in Flowsheet 1'.

The reaction of substituted naphtho[2,3-c]furan-1,3-dione compounds (McOmie, John F. W.; Perry, David H. Synthesis (1973), Issue 7, 416–417) with an alcohol such as methanol, with or without a base such as sodium hydride, provides substituted 3-(methoxycarbonyl)-2-naphthoic acids as a mixture of geometric isomers if $R_1'$ differs from $R_4'$ and/or $R_2'$ differs from $R_3'$. Treatment of the 3-(methoxycarbonyl)-2-naphthoic acids with diphenylphosphoryl azide and a base such as triethylamine in an inert solvent, followed by workup with an aqueous acetone solution or the like, provides the corresponding substituted methyl 3-amino-2-naphthoates, which when reacted with dimethylformamide dimethyl acetal, with or without a solvent, provides intermediates of Formula 3 (and the geometric isomer 3' if $R_1'$ differs from $R_4'$ and/or $R_2'$ differs from $R_3'$). Separation of the geometric isomers can be carried out by silica gel chromatography or other purification methods at any step in the preparation of intermediate of Formula 3. The above-mentioned chemical transformations can be carried out separately on each isomer. If a mixture of geometric isomers of Formula 3 and 3' is converted to compounds of Formula 6, a chromatographic separation can be carried out on the mixture of products of Formula 6 or any of the intermediates formed in this sequence.

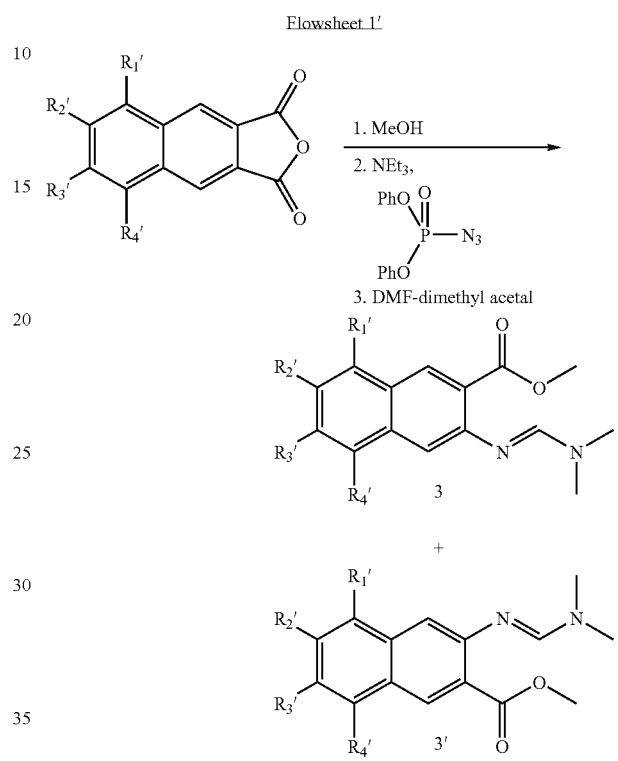

Intermediate 4 can also be prepared as described below and in Flowsheet 1".

The reaction of phenyl compounds with electron-rich $R_2'$ and $R_3'$ substituents, such as alkoxy of 1 to 6 carbons or, for example, a haloalkoxy moiety of the formula $R_7$—$(C(R_6)_2)_g$—V— where $R_6$ is hydrogen, $R_7$ is a halogen, V is oxygen and g=2–6, with a solution of formalin and hydrochloric acid provides substituted 1,2-bis(chloromethyl)benzene intermediates. Heating these substituted 1,2-bis(chloromethyl)benzene intermediates with sodium acetate in acetic acid provides the corresponding substituted 1,2-bis (acetyloxymethyl)benzene compounds which can be converted to the corresponding 1,2-bis(hydroxymethyl)benzene intermediates by reaction with a ammonia-saturated methanol or aqueous sodium hydroxide. Oxidation of the substituted 1,2-bis(hydroxymethyl)benzene intermediates by oxalyl chloride, dimethyl sulfoxide and triethylamine in an inert solvent such as methylene chloride provides the substituted phthalaldehyde intermediates. Reaction of the substituted phthalaldehyde intermediates with an excess of a 3-nitropropanoate ester such as ethyl 3-nitropropanoate (as described by Kienzle, F. *Helv. Chim. Acta,* 63, 2364–2369, (1980)), and sodium ethoxide in ethanol provides the corresponding ethyl 3-nitro-2-naphthoate intermediates as a mixture of geometric isomers if $R_2'$ differs from $R_3'$. Reduction of the substituted ethyl 3-nitro-2-naphthoate intermediates by catalytic hydrogenation over palladium-on-carbon or platinum-on-carbon in tetrahydrofuran provides the substituted ethyl 3-amino-2-naphthoate intermediates as a mixture of geometric isomers if R$_2$' differs from R$_3$'. Reaction of the substituted ethyl 3-amino-2-naphthoate intermediates with dimethylformamide dimethyl acetal, with or without a solvent, followed by reaction with the lithium anion of acetonitrile prepared by using a base such as n-butyllithium or the like, in an inert solvent, gives 3-cyano-4-oxo-1,4-dihydrobenzo[g]quinolines 4 (and the geometric isomer 4' if R$_2$' differs from R$_3$') or the 3-cyano-4-hydroxybenzo[g] quinoline tautomers thereof. Separation of the geometric isomers can be carried out by silica gel chromatography or other purification methods at any step in the preparation of intermediate of Formula 4. The above-mentioned chemical transformations can be carried out separately on each isomer. If a mixture of geometric isomers of Formula 4 and 4' is converted to compounds of Formula 6, a chromatographic separation can be carried out on the mixture of products of Formula 6 or any of the intermediates formed in this sequence.

Flowsheet 1'''

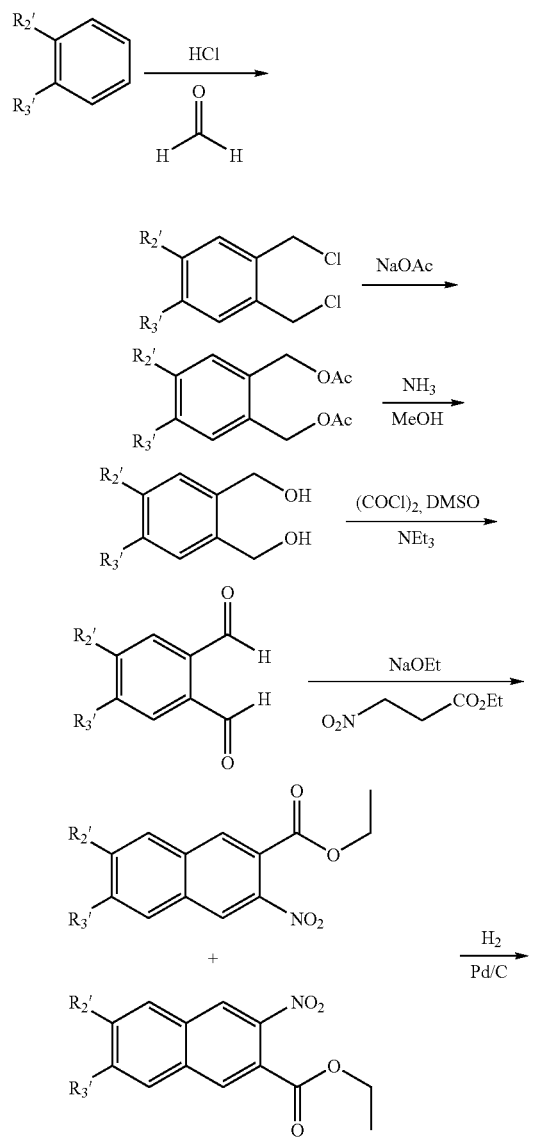

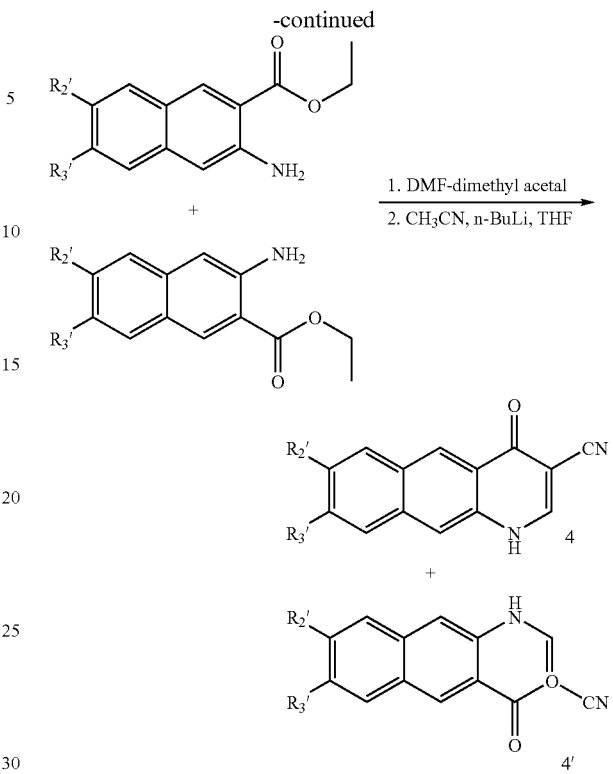

Intermediate 4 can also be prepared as described below and in Flowsheet 1'''.

Bicyclo[4.2.0]octa-1(6),2,4-triene-7-carbonitriles with R$_1$', R$_2$' and R$_3$' substituents being alkoxy of 1 to 6 carbon atoms, alkyl of 1 to 6 carbon atoms, or benzyloxy moiety of the formula Ph—(C(R$_6$)$_2$)$_q$—W—(C(R$_6$)$_2$)$_k$—V— where R$_6$ is hydrogen, W is a bond, V is oxygen and k=0, q=1, can be synthesized in regioisomerically pure form by procedures known in the art as detailed by the following references: Kametani, T. et al *J. Het. Chem,* 11, 179, (1974), Kametani, T.; kondoh, H.; Tsubuki, M.; Honda, T. *J. Chem. Soc Perkin Trans.* 1, 5 (1990), Kametani, T.; Kato, Honda, T. Fukumoto, K. *J. Chem. Soc Perkin* 1, 2001 (1990), Kametani, T.; Kajiwara, M.; Takahashi, T.; Fukumoto, K. *Tetrahedron,* 31, 949 (1975) and Honda, T. Toya, T. *Heterocycles,* 33, 291 (1992). The reaction of the substituted bicyclo[4.2.0]octa-1 (6),2,4-triene-7-carbonitriles with a base such as sodium (bistrimethylsilyl)amide or n-butyllithium at −78° C. and the like provides the corresponding anion α to the cyano group which is then reacted with a suitable electrophile such as a substituted diphenyl disulfide PhSSPh (where Ph is as hereinabove defined) to provide substituted 7-phenylsulfanylbicyclo[4.2.0]octa-1,3,5-triene-7-carbonitriles after warming to room temperature. Reaction of these intermediates with the magnesium bromide salt of an ester such as, but not limited to t-butyl acetate at 0° C. in an inert solvent such as ether or tetrahydrofuran and the like provides the corresponding substituted 3-amino-3-(7-phenylsulfanyl-bicyclo[4.2.0]octa-1,3,5-trien-7-yl)-acrylic acid tert-butyl esters. Refluxing these adducts in a high boiling solvent such as dichlorobenzene or the like for 0.5 to 3 hours provides the substituted 3-amino-naphthalene-2-carboxylic acid tert-butyl esters. Reaction of the substituted 3-amino-2-naphthoate tert-butyl ester intermediates with dimethylformamide dimethyl acetal, with or without a solvent, followed by reaction with the lithium anion of acetonitrile prepared by using a base such as n-butyllithium or the like, in an inert solvent, gives 3-cyano-4-oxo-1,4-dihydrobenzo[g]quinolines 4 or the 3-cyano-4-hydroxybenzo[g]quinoline tautomers thereof.

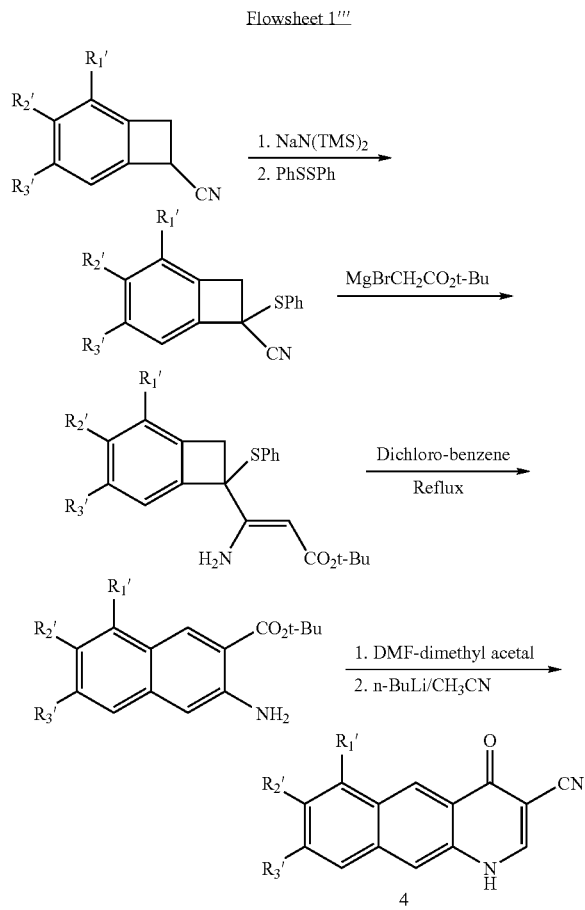

Converting the $R_1'$, $R_2'$, $R_3'$ and $R_4'$ groups to $R_1$, $R_2$, $R_3$ and $R_4$ groups can be accomplished through any conventionally known techniques, for example:

where one or more of $R_1'$, $R_2'$, $R_3'$ and $R_4'$ of Formula 6 or an intermediate is a methoxy group, it can be converted to the corresponding hydroxy group by reaction with a demethylating agent such as boron tribromide in an inert solvent or by heating with pyridinium chloride with or without solvent;

where one or more of $R_1'$, $R_2'$, $R_3'$ and $R_4'$ of Formula 6 is a benzyloxy group of the formula Ph—$(C(R_6)_2)_q$—W—$(C(R_6)_2)_k$—V— where $R_6$ is hydrogen, W is a bond, V is oxygen and k=0, q=1, it can be converted to the corresponding hydroxy group by reaction with a debenzylating agent such as boron tribromide in an inert solvent, trifluoroacetic acid or catalytic hydrogenation with a catalyst such as palladium-on-carbon;

where one or more of $R_1'$, $R_2'$, $R_3'$ and $R_4'$ of Formula 6 or an intermediate is a hydroxy group, it can be converted to the corresponding alkanoyloxy group of 1–6 carbon atoms by reaction with an appropriate carboxylic acid chloride, anhydride, or mixed anhydride in a inert solvent using pyridine or a trialkylamine as a base;

where one or more of $R_1'$, $R_2'$, $R_3'$ and $R_4'$ of Formula 6 or an intermediate is a hydroxy group, it can be converted to the corresponding alkenoyloxy group of 1–6 carbon atoms by reaction with an appropriate carboxylic acid chloride, anhydride, or mixed anhydride in an inert solvent using pyridine or a trialkylamine as a base;

where one or more of $R_1'$, $R_2'$, $R_3'$ and $R_4'$ of Formula 6 or an intermediate is a hydroxy group, it can be converted to the corresponding alkynoyloxy group of 1–6 carbon atoms by reaction with an appropriate carboxylic acid chloride, anhydride, or mixed anhydride in a inert solvent using pyridine or a trialkylamine as a base;

where one or more of $R_1'$, $R_2'$, $R_3'$ and $R_4'$ of Formula 6 or an intermediate is a hydroxy group, it can be converted to the corresponding groups:

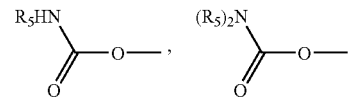

wherein $R_5$ is as defined hereinabove, by the reaction in an inert solvent with an alkyl or phenyl substituted isocyanate, $R_5$—N=C=O, or using a base such as pyridine, with a reagent $(R_5)_2NCOCl$;

where one or more of $R_1'$, $R_2'$, $R_3'$ and $R_4'$ of Formula 6 or an intermediate is a hydroxy group, it can be converted to the corresponding groups:

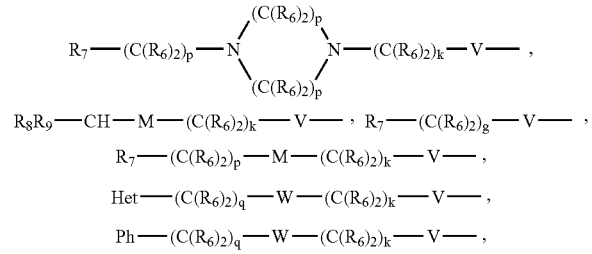

wherein V is oxygen, $R_6$, $R_7$, $R_8$, $R_9$, M, W, Het, Ph, p and q are as defined hereinabove and g=2–6 and k=2–4 by reacting with an appropriately substituted alcohol using triphenyl phosphine and diethyl azodicarboxylate in an inert solvent, or alternatively by first reacting with a reagent such as, but not limited to, a bromoalkyl chloride or chloroalkyl tosylate to provide an intermediate haloalkoxy group which can be converted to the above described groups by subsequent reaction with an appropriately substituted nucleophile;

where one or more of $R_1'$, $R_2'$, $R_3'$ and $R_4'$ of Formula 6 or an intermediate is a hydroxy group, it can be converted to a alkoxycarbonyl group of 2–7 carbon atoms by first converting to a trifluoromethanesulfonate using trifluoromethanesulfonate anhydride or N-phenyltrifluoromethylsulfonamide and a base such as triethylamine in an inert solvent, then reacting with carbon monoxide in an alcoholic solvent of 1–6 carbons in the presence of a palladium (0) catalyst such as palladium tetrakis triphenylphosphine;

where one or more of $R_1'$, $R_2'$, $R_3'$ and $R_4'$ of Formula 6 or an intermediate is an alkoxycarbonyl group of 2–7 carbon atoms, it can be converted to the corresponding hydroxymethyl group by reduction with an appropriate reducing agent such as lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorus pentachloride to give a chloromethyl group. The hydroxymethyl group can be acylated with an appropriate acid chloride, anhydride, or mixed anhydride in an inert solvent using pyridine or a trialkylamine as a base to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms;

where one or more of $R_1'$, $R_2'$, $R_3'$ and $R_4'$ of Formula 6 or an intermediate is a halomethyl group, it can be converted to the corresponding groups:

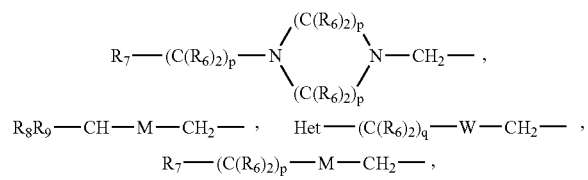

wherein $R_6$, $R_7$, $R_8$, $R_9$, M, W, Het, p and q are as defined hereinabove by reacting with the appropriately substituted alcohol, amine or mercaptan in an inert solvent such as dioxane or acetonitrile and a base such as triethylamine or potassium carbonate;

where one or more of $R_1'$, $R_2'$, $R_3'$ and $R_4'$ of Formula 6 or an intermediate is a alkoxycarbonyl group of 2–7 carbon atoms, it can be converted to the corresponding carboxy group by reaction with a strong base such as aqueous sodium hydroxide in an alcoholic solvent such as ethanol;

where one or more of $R_1'$, $R_2'$, $R_3'$ and $R_4'$ of Formula 6 or an intermediate is a carboxy group, it can be converted to a carbamoyl, N-alkylcarbamoyl or N,N-dialkylcarbamoyl of 4–12 carbon atoms by reaction in an inert solvent with a halogenating agent such as phosphorus oxychloride or oxalyl chloride, or alternatively activating by reaction with a coupling agent such as, but not limited to carbonyl diimidazole in an inert solvent such as dimethylformamide, followed by reaction with the appropriate amine;

where one or more of $R_1'$, $R_2'$, $R_3'$ and $R_4'$ of Formula 6 or an intermediate is a carboxy group, it can be converted to an amino group by heating with diphenyl phosphoryl azide and t-butanol in an inert solvent such as dioxane, followed by treatment with a strong acid such as hydrochloric or trifluoroacetic acid;

where one or more of $R_1'$, $R_2'$, $R_3'$ and $R_4'$ of Formula 6 or an intermediate is an amino group, it can be converted to the corresponding dialkylamino group of 2 to 12 carbon atoms by alkylation with at least two equivalents of an alkyl halide of 1 to 6 carbon atoms by heating in an inert solvent;

where one or more of $R_1'$, $R_2'$, $R_3'$ and $R_4'$ of Formula 6 or an intermediate is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a base such as triethylamine or pyridine;

where one or more of $R_1'$, $R_2'$, $R_3'$ and $R_4'$ of Formula 6 or an intermediate is an amino group, it can be converted to the corresponding alkylamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof;

where one or more of $R_1'$, $R_2'$, $R_3'$ and $R_4'$ of Formula 6 or an intermediate is an amino group, it can be converted to the corresponding groups:

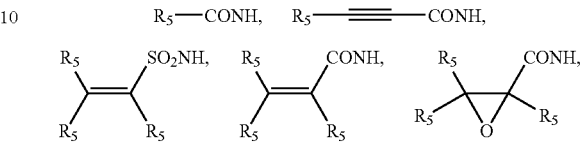

wherein $R_5$ is as defined hereinabove by reacting with the appropriately substituted carboxylic acid chloride or sulfonyl chloride or mixed anhydride (which is prepared from the corresponding carboxylic acid) in an inert solvent such as tetrahydrofuran (THF) in the presence of an organic base such as pyridine, triethylamine or N-methyl morpholine;

where one or more of $R_1'$, $R_2'$, $R_3'$ and $R_4'$ of Formula 6 or an intermediate is an amino group, it can be converted to the corresponding groups:

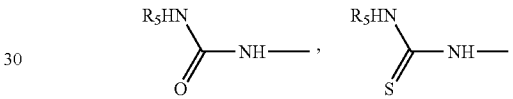

wherein $R_5$ is as defined hereinabove, by the reaction in an inert solvent with an alkyl or phenyl substituted isocyanate, $R_5-N=C=O$, or an alkyl or phenyl substituted isothiocyanate, $R_5-N=C=S$;

where one or more of $R_1'$, $R_2'$, $R_3'$ and $R_4'$ of Formula 6 or an intermediate is an amino group, it can be converted to the corresponding groups:

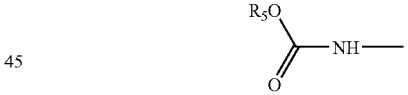

wherein $R_5$ is as defined hereinabove, by reacting with phosgene in an inert solvent such as toluene in the presence of a base such as pyridine to give an isocyanate which, in turn, is treated with an excess of the alcohol $R_5-OH$.

In those cases when the $R_1'$, $R_2'$, $R_3'$ and $R_4'$ substituents of Formula 6 or an intermediate may contain an asymmetric carbon atom, the intermediates can be used as the racemate or as the individual R or S enantiomers in which case the compounds of this invention will be in the racemic or R and S optically active forms, respectively. In cases where the substituents may contain more than one asymmetric carbon atom, diastereomers may be present; these can be separated by methods well known in the art including, but not limited to, fractional crystallization and chromatographic methods. In those cases where the $R_1'$, $R_2'$, $R_3'$, $R_4'$, $R_5$, $R_6$ $R_7$, $R_8$, $R_9$ and Het substituents of Formula 6 or an intermediate contains primary or secondary amino groups or hydroxyl groups, it may be necessary to protect these groups during the reaction sequence The same amine or alcohol protecting groups described hereinabove can be used and they can be removed from the products of Formula 6 as previously described.

The preparation of the compounds and intermediates of this invention encompassed by Formula 13 is described below and in Flowsheet 2 where Ar, X and n are as hereinabove defined.

According to the sequence of reaction outlined in Flowsheet 2, a quinoline-3-carboxylic acid ester of Formula 7 is hydrolyzed with base to furnish a carboxylic acid of Formula 8. The carboxylic acid group of 8 is converted to an acyl imidazole by heating it with carbonyldiimidazole in an inert solvent such as dimethylformamide (DMF) followed by the addition of ammonia to give the amide 9. Dehydration of the amide functional group with the dehydrating agent, cyanuric chloride in dimethylformamide (DMF), gives the 3-cyano-4-quinolone of Formula 10. Deprotonation of 10 with sodium hydride in anhydrous dimethylformamide (DMF), followed by reaction with 2-(trimethylsilyl)ethoxymethyl (SEM) chloride provides a 4-quinolone of Formula 11. By heating 11 with sodium azide in dimethylsulfoxide (DMSO), it can be converted to an azide, which is reduced to the diamine of Formula 12 by catalytic hydrogenation over palladium-on-carbon or platinum-on-carbon in tetrahydrofuran. Reaction of 12 with nitrous acid provides 13. Refluxing 13 in formic acid provides the 7-cyano-8-oxo-5,8-dihydrotriazolo[4,5-g]quinoline 14 or the 7-cyano-8-hydroxytriazolo[4,5-g]quinoline tautomer thereof. Heating 14 with or without solvent with a chlorinating agent such as phosphorus oxychloride or oxalyl chloride provides the corresponding 7-cyano-8-chlorotriazolo[4,5-g]quinoline. Condensation of 7-cyano-8-chlorotriazolo[4,5-g]quinoline with a nucleophilic amine, aniline, mercaptan, thiophenol, phenol, or alcohol reagent of Formula 5 gives the 7-cyano-triazolo[4,5-g]quinolines of Formula 15; this condensation can be accelerated by heating the reaction mixture together with one equivalent of pyridine hydrochloride or by using bases such as trialkylamines, sodium hydride in an inert solvent, sodium or potassium alkoxides in alcohol solvents, and the like. In those cases where the Ar substituents may contain an asymmetric carbon atom, the intermediates can be used as the racemate or as the individual R or S enantiomers in which case the compounds of this invention will be in the racemic or R and S optically active forms, respectively. In cases where the Ar substituents may contain more than one asymmetric carbon atoms, diastereomers may be present; these can be separated by methods well known in the art including, but not limited to, fractional crystallization and chromatographic methods. In those cases, in intermediates 5 where Ar contains primary or secondary amino groups or hydroxyl groups, it may be necessary to protect these groups prior to the reaction with 7-cyano-8-chlorotriazolo[4,5-g]quinoline. The same amine or alcohol protecting groups described hereinabove can be used and they can be removed from the products 15 as previously described.

The quinoline-3-carboxylic acid ester of Formula 7 needed to prepare the compounds of this invention are either already known in the art or can be prepared by procedures known in the art as detailed in the following reference: Koga, Hiroshi; Itoh, Akira; Murayama, Satoshi; Suzue, Seigo; kikura, Tsutomu, *J. Med. Chem.,* 23, 1358 (1980).

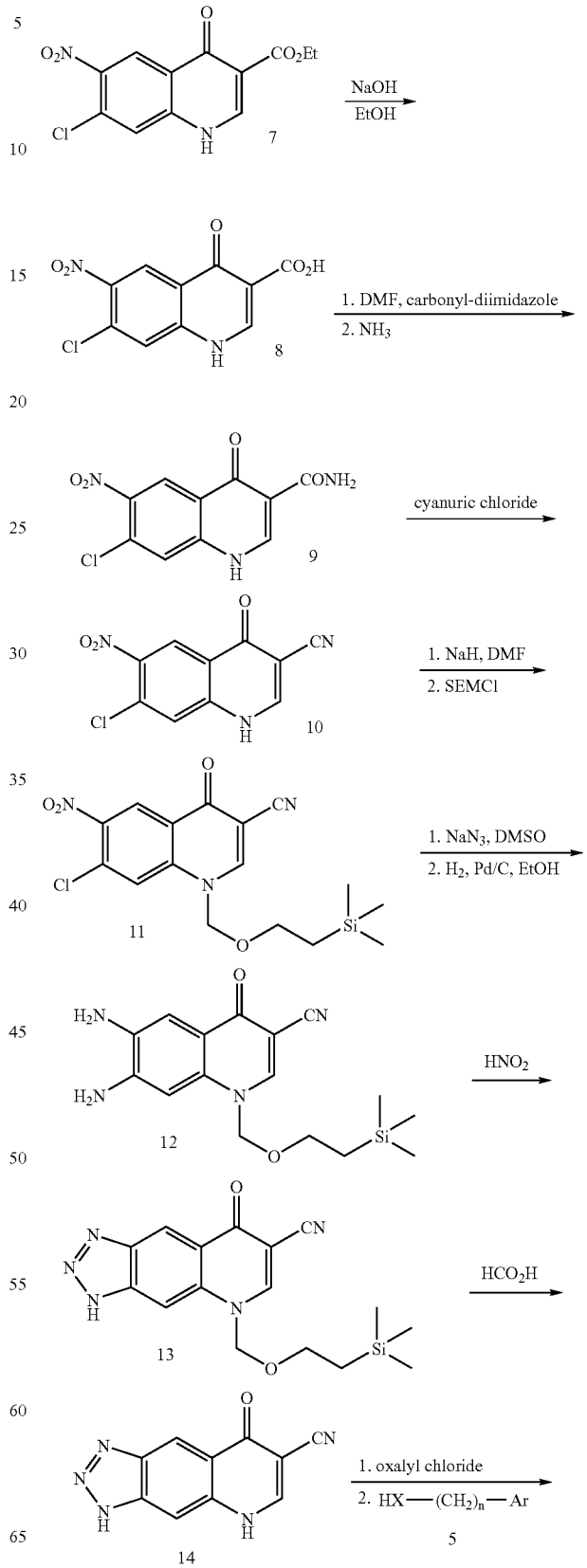

Flowsheet 2

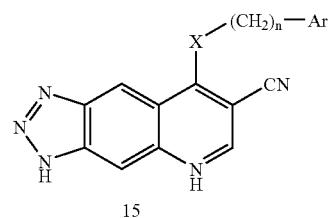

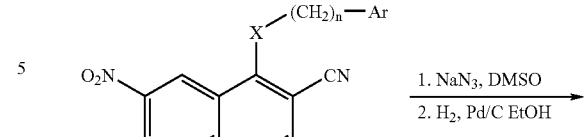

The preparation of the compounds and intermediates of this invention encompassed by Formula 19 is described below and in Flowsheet 3 where Ar, X and n are as hereinabove defined.

Heating 10 with or without solvent with a chlorinating agent such as phosphorus oxychloride or oxalyl chloride provides the intermediate 4,7-dichloro-6-nitro-3-quinolinecarbonitrile. Condensation of 4,7-dichloro-6-nitro-3-quinolinecarbonitrile with a nucleophilic amine, aniline, mercaptan, thiophenol, phenol, or alcohol reagent of Formula 5 gives the 7-cyano-triazolo[4,5-g]quinolines of Formula 16; this condensation can be accelerated by heating the reaction mixture together with one equivalent of pyridine hydrochloride or by using bases such as trialkylamines, sodium hydride in an inert solvent, sodium or potassium alkoxides in an alcohol solvents, and the like. Heating 16 with sodium azide in dimethylsulfoxide (DMSO), provides the corresponding azides, which are reduced to the diamines of Formula 17 by catalytic hydrogenation over palladium-on-carbon or platinum-on-carbon in tetrahydrofuran. Reaction of 17 with 2,3-dihydroxy-1,4-dioxane of Formula 18 in an inert solvent such as methanol provides the pyrido[2,3-g]quinoxaline-8-carbonitriles of Formula 19. In those cases where the Ar substituents may contain an asymmetric carbon atom, the intermediates can be used as the racemate or as the individual R or S enantiomers in which case the compounds of this invention will be in the racemic or R and S optically active forms, respectively. In cases where the Ar substituents may contain more than one asymmetric carbon atoms, diastereomers may be present; these can be separated by methods well known in the art including, but not limited to, fractional crystallization and chromatographic methods. In those cases, in intermediates 5 where Ar contains primary or secondary amino groups or hydroxyl groups, it may be necessary to protect these groups prior to the reaction with 4,7-dichloro-6-nitro-3-quinoline carbonitrile. The same amine or alcohol protecting groups hereinabove can be used and they can be removed from the products 19 as previously described.

Flowsheet 3

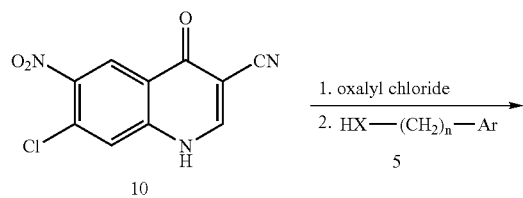

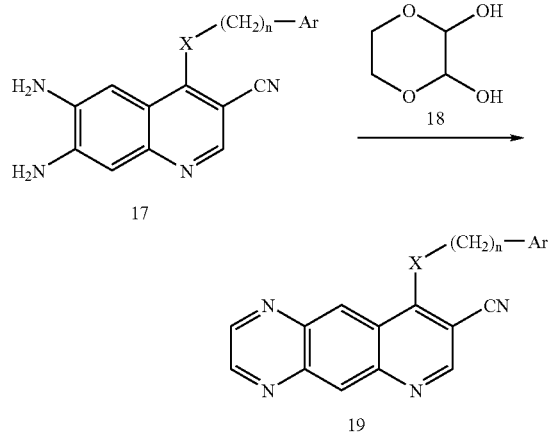

The preparation of the compounds and intermediates of this invention encompassed by Formula 23 is described below and in Flowsheet 4 where Ar, X and n are as hereinabove defined. G is selected from the group consisting of: alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

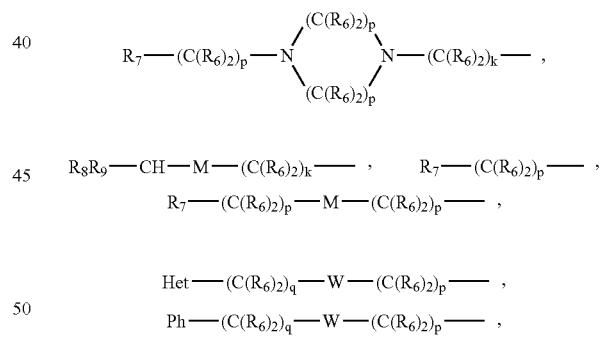

where $R_6$, $R_7$, $R_8$, $R_9$, M, W, Het, Ph, p and q are as defined hereinabove, g 2–6 and k=2–4.

Reaction of 17 with an isothiocyanate 20 provides a mixture of thioureas of Formulas 21 and 22. Heating the mixture of Formulas 21 and 22 with mercury (II) oxide and a catalytic amount of sulfur in an inert solvent such as dioxane provides the corresponding substituted 2-amino-7-cyanoimidazo[4,5-g]quinolines of Formula 23. In those cases where the Ar and/or G substituents may contain an asymmetric carbon atom, the intermediates can be used as the racemate or as the individual R or S enantiomers in which case the compounds of this invention will be in the racemic or R and S optically active forms, respectively. In cases where the Ar and/or G substituents may contain more than one asymmetric carbon atoms, diastereomers may be present; these can be separated by methods well known in the art including, but not limited to, fractional crystallization and chromatographic methods. In those cases, in intermediates 20 where G contains primary or secondary amino groups or hydroxyl groups, it may be necessary to protect these groups prior to the reaction with 17. The same amine or alcohol protecting groups defined hereinabove can be used and they can be removed from the products 23 as previously described.

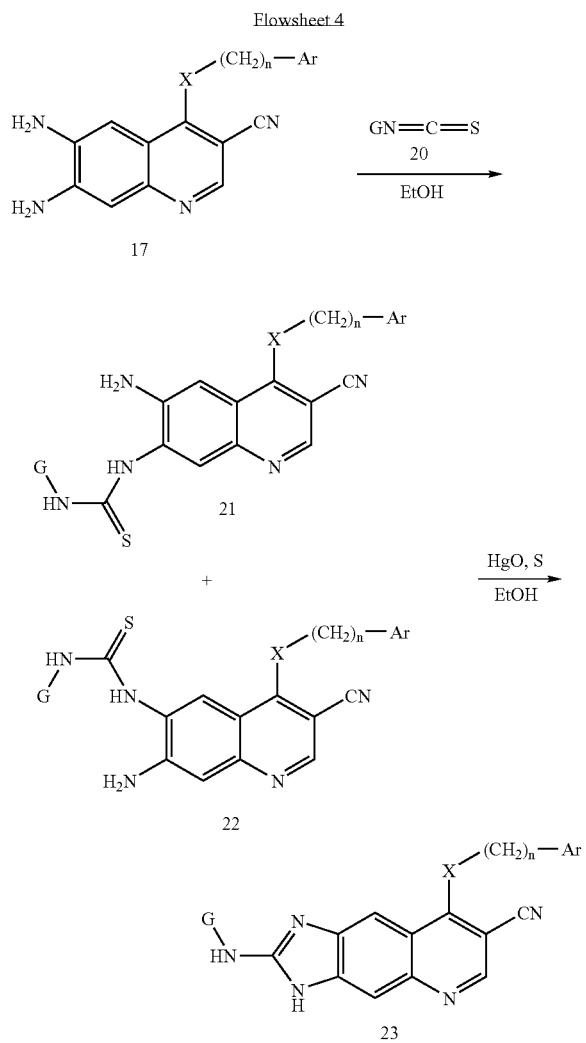

The preparation of the compounds and intermediates of this invention encompassed by Formula 26 is described below and in Flowsheet 5 where Ar, X and n are as hereinabove defined.

Reaction of 12 with cyanogen bromide in an inert solvent such as methanol provides a compound of Formula 24. Refluxing 24 in formic acid with 4 equivalents of imidazole provides a compound of formula 25. Heating 25 with or without solvent with a chlorinating agent such as phosphorus oxychloride or oxalyl chloride provides the corresponding 2-amino-8-chloroimidazo[4,5-g]quinoline-7-carbonitrile. Condensation of 2-amino-8-chloroimidazo[4,5-g] quinoline-7-carbonitrile with a nucleophilic amine, aniline, mercaptan, thiophenol, phenol, or alcohol reagent of Formula 5 gives the 7-cyano imidazo[4,5-g]quinolines of Formula 26; this condensation can be accelerated by heating the reaction mire together with one equivalent of pyridine hydrochloride or by using bases such as trialkylamines, sodium hydride in an inert solvent, sodium or potassium alkoxides in an alcohol solvents, and the like. In those cases where the Ar substituents may contain an asymmetric carbon atom, the intermediates can be used as the racemate or as the individual R or S enantiomers in which case the compounds of this invention will be in the racemic or R and S optically active forms, respectively. In cases where the Ar substituents may contain more than one asymmetric carbon atoms, diastereomers may be present; these can be separated by methods well known in the art including, but not limited to, fractional crystallization and chromatographic methods. In those cases, in intermediates 5 where Ar contains primary or secondary amino groups or hydroxyl groups, it may be necessary to protect these groups prior to the reaction with 2-amino-8-chloro-imidazo[4,5-g]quinoline-7-carbonitrile. The same amine or alcohol protecting groups described hereinabove can be used and they can be removed from the products 26 as previously described.

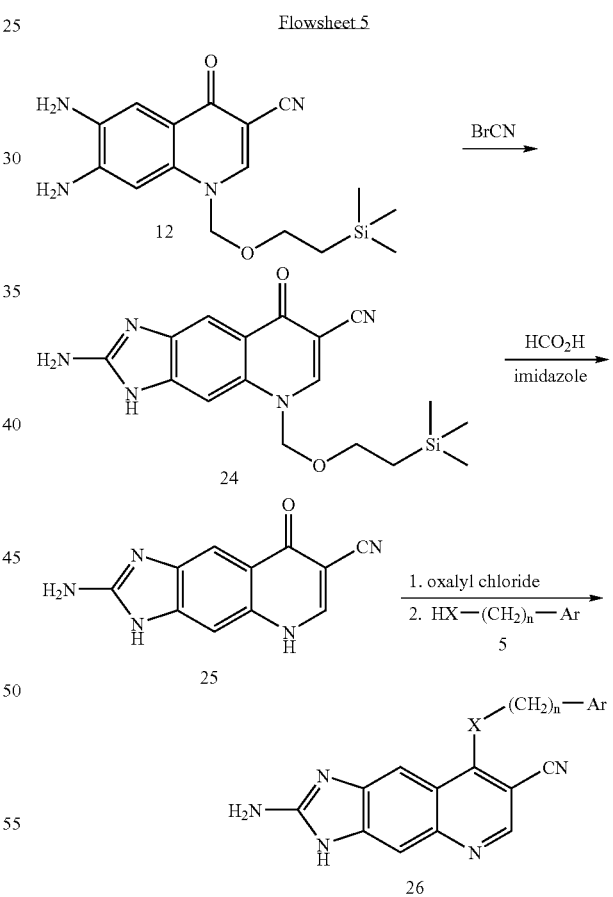

The preparation of the compounds and intermediates of this invention encompassed by Formula 28 is described below and in Flowsheet 6 where Ar, X and n are as hereinabove defined.

Refluxing 12 in formic acid with 4 equivalents of imidazole provides a compound of formula 27. Heating 27 with or without solvent with a chlorinating agent such as phosphorus oxychloride or oxalyl chloride provides the corresponding 8-chloroimidazo[4,5-g]quinoline-7-carbonitrile. Condensation of 8-chloroimidazo[4,5-g]quinoline-7-carbonitrile with a nucleophilic amine, aniline, mercaptan, thiophenol, phenol, or alcohol reagent of Formula 5 gives the 7-cyano-imidazo[4,5-g]quinolines of Formula 28; this condensation can be accelerated by heating the reaction mixture together with one equivalent of pyridine hydrochloride or by using bases such as trialkylamines, sodium hydride in an inert solvent, sodium or potassium alkoxides in an alcohol solvents, and the like. In those cases where the Ar substituents may contain an asymmetric carbon atom, the intermediates can be used as the racemate or as the individual R or S enantiomers in which case the compounds of this invention will be in the racemic or R and S optically active forms, respectively. In cases where the Ar substituents may contain more than one asymmetric carbon atoms, diastereomers may be present; these can be separated by methods well known in the art including, but not limited to, fractional crystallization and chromatographic methods. In those cases, in intermediates 5 where Ar contains primary or secondary amino groups or hydroxyl groups, it may be necessary to protect these groups prior to the reaction with 8-chloroimidazo[4,5-g]quinoline-7-carbonitrile. The same amine or alcohol protecting groups described hereinabove can be used and they can be removed from the products 28 as previously described.

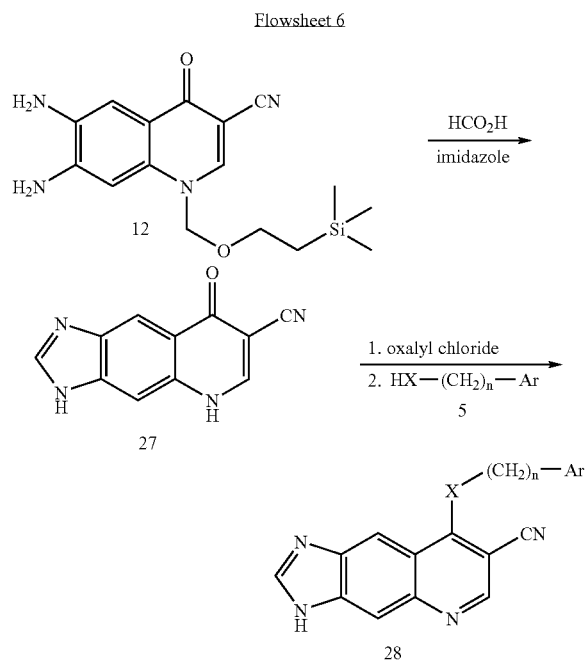

An alternative preparation of the compounds and intermediates of this invention encompassed by Formula 28 is described below and in Flowsheet 7 where Ar, X and n are as hereinabove defined.

Refluxing intermediates of Formula 17 in diethoxymethyl acetate provides the 7-cyano-imidazo[4,5-g]quinolines of Formula 28 when X is oxygen or sulfur. When X is nitrogen with a hydrogen substituent, the corresponding 7-cyanoimidazo[4,5-g]quinolin-8-ylformamides are formed. Heating the 7-cyanoimidazo[4,5-g]quinolin-8-ylformamides with potassium carbonate in a solvent such as methanol or ethanol provides the compounds of Formula 28. In those cases where the Ar substituents may contain an asymmetric carbon atom, the intermediates can be used as the racemate or as the individual R or S enantiomers in which case the compounds of this invention will be in the racemic or R and S optically active forms, respectively. In cases where the Ar substituents may contain more than one asymmetric carbon atoms, diastereomers may be present; these can be separated by methods well known in the art including, but not limited to, fractional crystallization and chromatographic methods. In those cases, in intermediates 17 where Ar contains primary or secondary amino groups or hydroxyl groups, it may be necessary to protect these groups prior to the reaction with diethoxymethyl acetate. The same amine or alcohol protecting groups described hereinabove can be used and they can be removed from the products 28 as previously described.

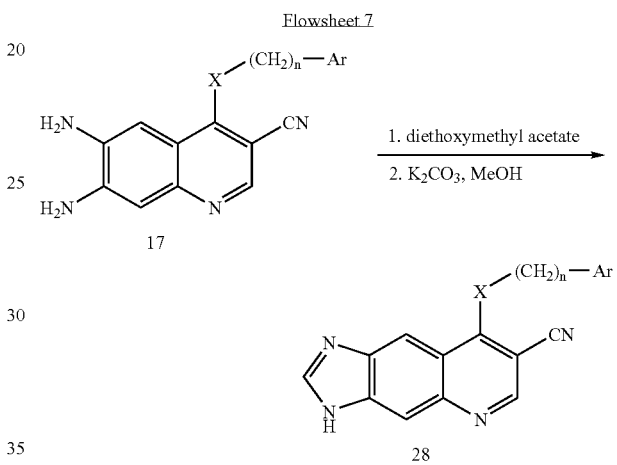

The preparation of the compounds and intermediates of this invention encompassed by Formula 32 is described below and in Flowsheet 8 where Ar, X and n are as hereinabove defined; and G' is selected from the group consisting of hydrogen, alkyl of 1–6 carbon atoms, trifluoromethyl, cycloalkyl of 3–8 carbon atoms, alkenyl of 2–6 carbon atoms, alkynyl of 2–6 carbon atoms, thiol, hydroxyalkyl of 1–6 carbon atoms; mercaptoalkyl of 1–6 carbon atoms; halomethyl, alkoxycarbonyl of 2–7 carbon atoms, phenyl, benzyl, phenoxy;

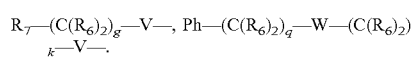

where g, k, q, $R_6$, $R_7$, V, W and Ph are as defined hereinabove.

Reaction of 17 with a carboxylic acid chloride of Formula 29 with a base such as pyridine, diethylaniline or triethylamine with or without an inert solvent such as tetrahydrofuran (THF) provides mixtures of compounds of Formula 30 and 31. Heating the mixture of Formulas 30 and 31 in formic acid or acetic acid provides the corresponding substituted 7-cyano-imidazo[4,5-g]quinolines of Formula 32. Alternatively, intermediates 17 can be directly converted to substituted 7-cyano-imidazo[4,5-g]quinolines of Formula 32 by reaction with G'-C(L')$_3$, where L' is chloro, hydroxy, alkoxy, alkylthio, phenoxy, thiophenoxy or dimethylamine, or two L' groups can be taken together to form =S, =NH, =O or =Se substituents, using acidic conditions (Hagen, H; Kohler, R.-D.; Fleig, H. Liebigs Ann. Chem., 1216 (1980), or basic reaction conditions (Webb, R. L. et al, J. Heterocycl.

*Chem.*, 24, 275 (1987), McKee, R. L.; Mckee, M. K.; Bost, R. W. *J. Am. Chem. Soc.*, 68, 1904 (1946), Allen, J. A.; Deacon, B. D. *Org. Synth.*, 30, 56 (1950)) or by using a strongly dehydrating solvent such as polyphosphoric acid (Hein, D. W.; Leavitt, J. J. *J. Am. Chem. Soc.*, 79, 427 (1957), or by using agents such as 2-ethoxy-1-ethoxycarbonyl-1,2-dihydroquinoline (Corrol, F. I.; Coleman, M. C. *J. Med. Chem.*, 18, 318 (1975)) or by heating in an inert solvent (Cohen, V. I.; Pourabass, *J. Heterocycl. Chem.*, 14, 1321 (1977)). In those cases, in intermediates 29 or GE-C (L')$_3$ where G' contains primary or secondary amino groups or hydroxyl groups, it may be necessary to protect these groups prior to the reaction with 17. The same amine or alcohol protecting groups as defined hereinabove can be used and they can be removed from the products 32 as previously described. In those cases where the Ar and/or G' substituents may contain an asymmetric carbon atom, the intermediates can be used as the racemate or as the individual R or S enantiomers in which case the compounds of this invention will be in the racemic or R and S optically active forms, respectively. In cases where the substituents may contain more than one asymmetric carbon atoms, diastereomers may be present; these can be separated by methods well known in the art including, but not limited to, fractional crystallization and chromatographic methods.

Converting the G' groups of Formula 32 to R$_2$ groups can be accomplished through any conventionally known techniques.

The preparation of the compounds and intermediates of this invention encompassed by Formula 36 is described below and in Flowsheet 9 where Ar, X, G' and n are as hereinabove defined; and G" is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

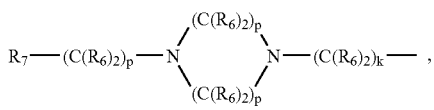

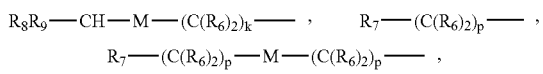

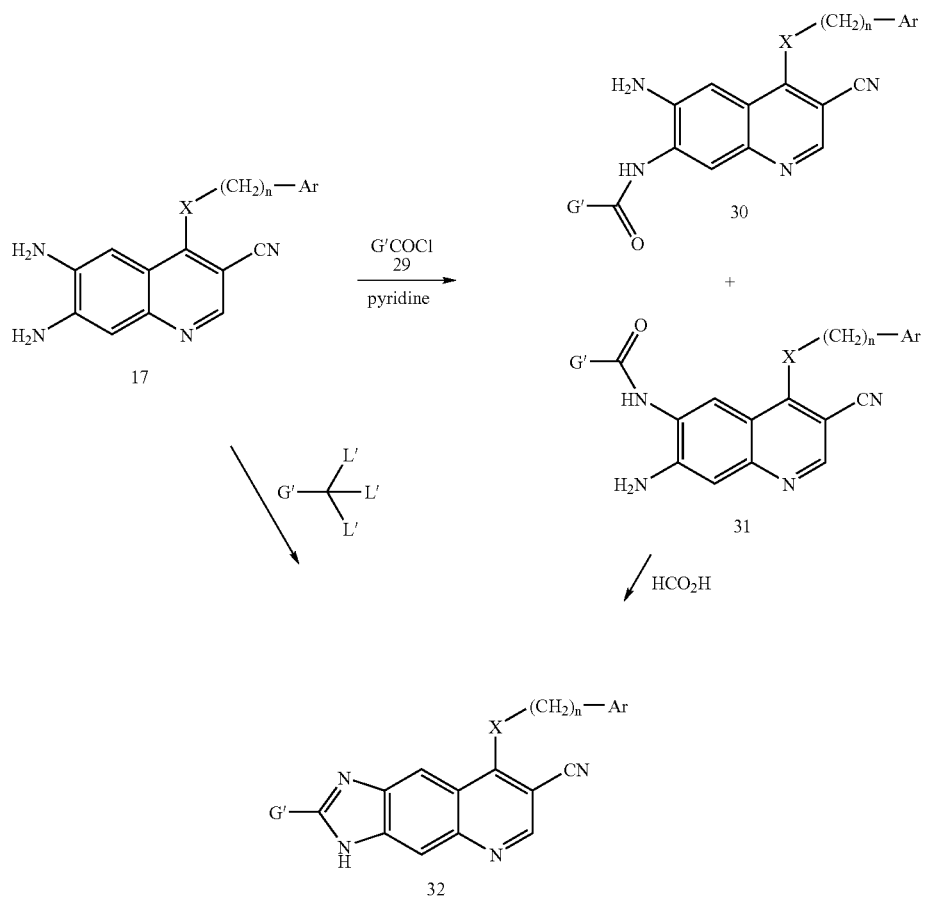

Flowsheet 8

-continued

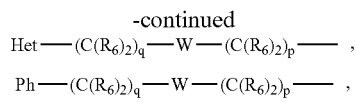

where $R_6$, $R_7$, $R_8$, $R_9$, M, W, Het, Ph, p and q are as hereinabove defined and g=2–6 and k=2–4.

By heating 11 with amines of Formula 33 in an inert solvent such as acetonitrile or dimethyl sulfoxide (DMSO), followed by catalytic hydrogenation over palladium on carbon in tetrahydrofuran and ethanol, it can be converted to compounds of Formula 34. The compounds of Formula 34 can be converted to compounds of Formula 35 by reaction with G'-C(L')$_3$, where L' is chloro, hydroxy, alkoxy, alkylthio, phenoxy, thiophenoxy or dimethylamine, or two L' groups can be taken together to form =S, =NH, =O or =Se substituents, using acidic conditions (Hagen, H; Kohler, R.-D.; Fleig, H. Liebigs Ann. Chem., 1216 (1980), or basic reaction conditions (Webb, R. L. et al, J. Heterocycl. Chem., 24, 275 (1987), McKee, R. L.; Mckee, M. K.; Bost, R. W. J. Am. Chem. Soc., 68, 1904 (1946), Allen, J. A.; Deacon, B. D. Org. Synth., 30, 56 (1950)) or by using a strongly dehydrating solvent such as polyphosphoric acid (Hein, D. W.; Leavitt, J. J. J. Am. Chem. Soc., 79, 427 (1957), or by using agents such as 2-ethoxy-1-ethoxycarbonyl-1,2-dihydroquinoline (Corrol, F. I.; Coleman, M. C. J. Med. Chem., 18, 318 (1975)) or by heating in an inert solvent (Cohen, V. I.; Pourabass, J. Heterocycl. Chem., 14, 1321 (1977)). Heating 35 with or without solvent with a chlorinating agent such as phosphorus oxychloride or oxalyl chloride provides the corresponding 8-chloroimidazo[4,5-g]quinoline-7-carbonitriles. Condensation of 8-chloroimidazo[4,5-g]quinoline-7-carbonitriles with a nucleophilic amine, aniline, mercaptan, thiophenol, phenol, or alcohol reagent of Formula 5 gives the 7-cyano-imidazo[4,5-g]quinolines of Formula 36; this condensation can be accelerated by heating the reaction mixture together with one equivalent of pyridine hydrochloride or by using bases such as trialkylamines, sodium hydride in an inert solvent, sodium or potassium alkoxides in an alcohol solvent, and the like. In those cases where the Ar and/or G' and/or G" substituents may contain an asymmetric carbon atom, the intermediates can be used as the racemate or as the individual R or S enantiomers in which case the compounds of this invention will be in the racemic or R and S optically active forms, respectively. In cases where the Ar and/or G' and/or G" substituents may contain more than one asymmetric carbon atoms, diastereomers may be present; these can be separated by methods well known in the art including, but not limited to, fractional crystallization and chromatographic methods. In those cases, in intermediates 33 where G" contains primary or secondary amino groups or hydroxyl groups, it may be necessary to protect these groups prior to the reaction with 11. In those cases, in intermediates 5 where Ar contains primary or secondary amino groups or hydroxyl groups, it may be necessary to protect these groups prior to the reaction with 8-chloroimidazo[4,5-g]quinoline-7-carbonitriles. The same amine or alcohol protecting groups described hereinabove can be used and they can be removed from the products 36 as previously described.

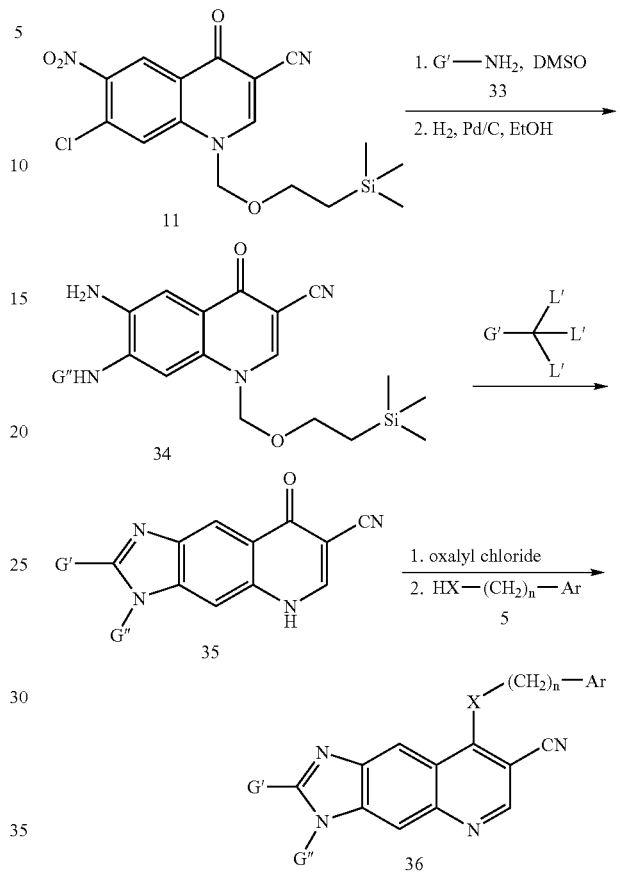

Flowsheet 9

Converting the G' groups of Formula 36 or Formula 35 to $R_2$ groups and the G" groups of Formula 36 or Formula 35 to $R_3$ groups can be accomplished through any conventionally known techniques.

The preparation of the compounds and intermediates of this invention encompassed by Formula 39 is described below and in Flowsheet 10 where Ar, x, G' and n are as hereinabove defined.

By heating 11 with sodium sulfide in dimethylsulfoxide (DMSO), followed by catalytic hydrogenation over palladium on carbon in tetrahydrofuran and ethanol, it can be converted to a compound of Formula 37. Refluxing 37 in formic acid with 4 equivalents of imidazole provides a compound of formula 38. The compounds of Formula 37 can be converted to compounds of Formula 38 by reaction with G'—C(L')$_3$, where L' is chloro, hydroxy, alkoxy, alkylthio, phenoxy, thiophenoxy or dimethylamine, or two L' groups can be taken together to form =S, =NH, =O or =Se substituents, using acidic conditions (Hagen, H; Kohler, R.-D.; Fleig, H. Liebigs Ann. Chem., 1216 (1980), or basic reaction conditions (Tawins, A; Hsiu, R. K.-C. Can. J. Chem., 49, 4054 (1971)) or by using a strongly dehydrating solvent such as polyphosphoric acid (Hein, D. W.; Leavitt, J. J. J. Am. Chem. Soc., 79, 427 (1957), or by using agents such as phosphorus oxychloride (Davis, C. S. J. Pharm. Sci., 51, 1111 (1962)) or by heating in an inert solvent (Campaigne, E.; Van Verth, J. E. J. Org. Chem., 23, 1344 (1958), George, B.; Papadopoulos, E. P. J. Org. Chem., 42, 2530 (1977). Heating 38 with or without solvent with a chlorinating agent such as phosphorus oxychloride or oxalyl chloride provides the corresponding 7-cyano-8-chlorothiazolo[4,5-g]quinoline. Condensation of a substituted 7-cyano-8-chlorothiazolo[4,5-g]quinoline with a nucleophilic amine, aniline, mercaptan, thiophenol, phenol, or alcohol reagent of Formula 5 gives the 7-cyanothiazolo[4,5-g]quinolines of Formula 39; this condensation can be accelerated by heating the reaction mixture together with one equivalent of pyridine hydrochloride or by using bases such as trialkylamines, sodium hydride in an inert solvent, sodium or potassium alkoxides in an alcohol solvent, and the like. In those cases where Ar and/or G' may contain an asymmetric carbon atom, the intermediates can be used as the racemate or as the individual R or S enantiomers in which case the compounds of this invention will be in the racemic or R and S optically active forms, respectively. In cases where the substituents may contain more than one asymmetric carbon atoms, diastereomers may be present; these can be separated by methods well known in the art including, but not limited to, fractional crystallization and chromatographic methods. In those cases, in intermediates 5 where Ar contains primary or secondary amino groups or hydroxyl groups, it may be necessary to protect these groups prior to the reaction with 7-cyano-8-chlorothiazolo[4,5-g]quinoline. The same amine or alcohol protecting groups described hereinabove can be used and they can be removed from the products 39 as previously described.

Converting the G' groups of Formula 39 to $R_2$ groups can be accomplished through any conventionally known techniques.

The preparation of the compounds and intermediates of this invention encompassed by Formula 44 is described below and in Flowsheet 11 where Ar, X and n are as hereinabove defined.

$Q_1$, $Q_2$, $Q_3$ and $Q_4$ are each, independently, hydrogen, halogen, hydroxy, amino, hydroxyamino, trifluoromethyl, trifluoromethoxy, mercapto, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, alkynyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, nitro, carboxy, alkoxycarbonyl of 2–7 carbon atoms, alkanoyl of 2–7 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, phenoxy, phenyl, thiophenoxy, benzyl, alkylamino of 1–6 carbon atoms, dialkylamino of 2 to 12 carbon atoms,

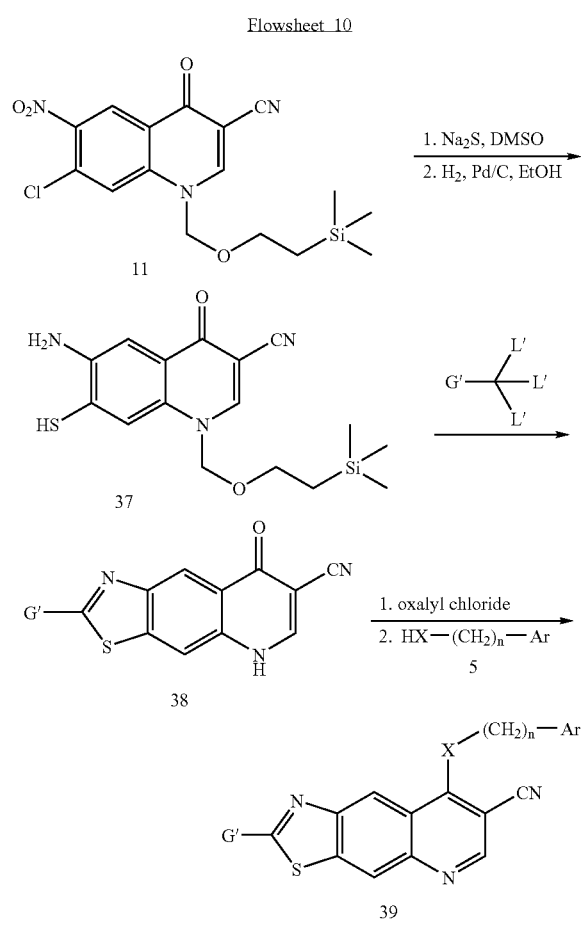

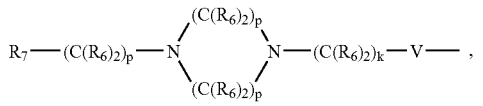

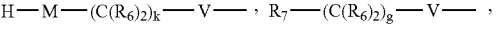

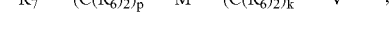

where V, $R_6$, $R_7$, $R_8$, $R_9$, M, W, Het, Ph, g, k, p and q are as hereinabove defined.

By reacting substituted 2-nitrobenzonitriles of Formula 40 with methyl thioglycolate and a base such as potassium hydroxide or triethylamine in an inert solvent such as dimethyl sulfoxide (DMSO) or aqueous dimethyl formamide (DMF) with or without heating provides compounds of Formula 41. Heating the substituted aniline of Formula 41 with dimethylformamide dimethyl acetal with or without a solvent gives intermediates of Formula 42. The reaction of 42 with from one to ten equivalents of acetonitrile using a base such as n-butyllithium, sodium methoxide or the like in an inert solvent gives the 4-oxo-1,4-dihydro[1]benzothieno [3,2-b]pyridine-3-carbonitrile 43, or the 4-hydroxy[1]benzothieno[3,2-b]pyridine-3-carbonitriles tautomers thereof. Heating 43 with or without solvent with a chlorinating agent such as phosphorus oxychloride or oxalyl chloride provides the corresponding 4-chloro[1]benzothieno[3,2-b]pyridine-3-carbonitriles. Condensation of 4-chloro[1]benzothieno[3,2-b]pyridine-3-carbonitriles with a nucleophilic amine, aniline, mercaptan, thiophenol, phenol, or alcohol reagent of Formula 5 gives the benzothieno[3,2-b]pyridine-3-carbonitriles of Formula 44; this condensation can be accelerated by heating the reaction mixture together with one equivalent of pyridine hydrochloride or by using bases such as trialkylamines, sodium hydride in an inert solvent, sodium or potassium alkoxides in an alcohol solvents, and the like. In those cases where the Ar and/or $Q_1$, $Q_2$, $Q_3$ and $Q_4$ substituents may contain an asymmetric carbon atom, the intermediates can be used as the racemate or as the individual R or S enantiomers in which case the compounds of this invention will be in the racemic or R and S optically active forms, respectively. In cases where the Ar and/or $Q_1$, $Q_2$, $Q_3$ and $Q_4$ substituents may contain more than one asymmetric carbon atoms, diastereomers may be present; these can be separated by methods well known in the art including, but not limited to, fractional crystallization and chromatographic methods. In those cases, in intermediates 40 where $Q_1$, $Q_2$, $Q_3$ and $Q_4$ contain primary or secondary amino groups or hydroxyl groups, it may be necessary to protect these groups prior to the reaction with methyl thioglycolate. In those cases, in intermediates 5 where Ar contains primary or secondary amino groups or hydroxyl groups, it may be necessary to protect these groups prior to the reaction with the 4-chloro [1]benzothieno[3,2-b]pyridine-3-carbonitriles. The same amine or alcohol protecting groups described hereinabove can be used and they can be removed from the products 44 as previously described.

The 2-nitrobenzonitriles of Formula 40 are either commercially available, or are already known to the art or can be prepared by procedures known in the art.

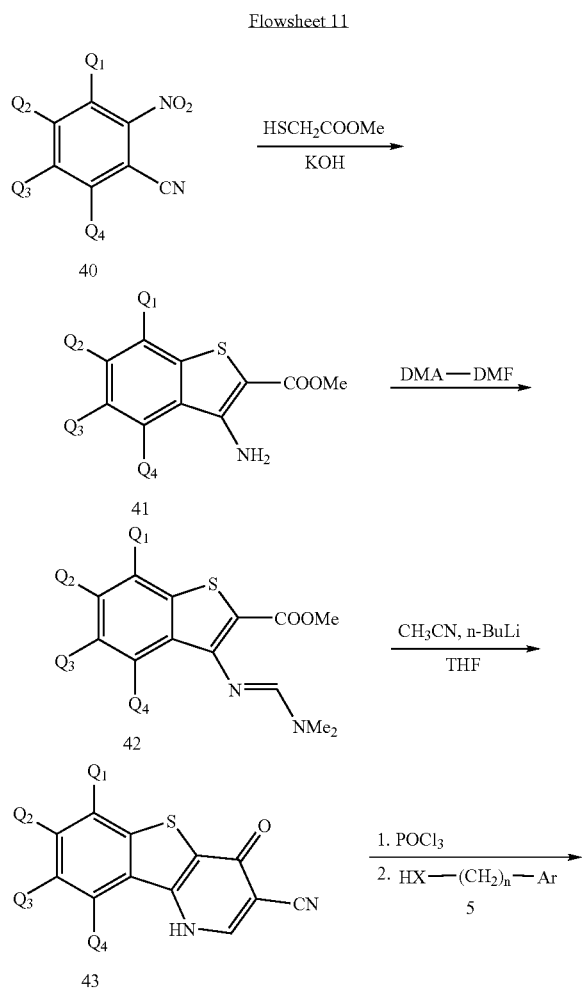

Flowsheet 11

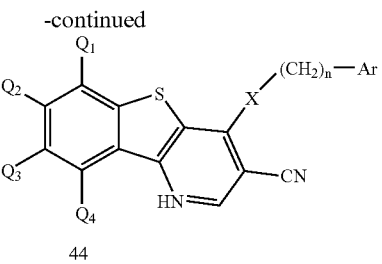

44

Converting the $Q_1$, $Q_2$, $Q_3$ and $Q_4$ groups to $R_1$, $R_2$, $R_3$ and $R_4$ groups can be accomplished through any conventionally known techniques, for example:

Where one or more of $Q_1$, $Q_2$, $Q_3$ or $Q_4$ of Formula 44 is a nitro group, it can be converted to the corresponding amino group by reduction using a reducing agent such as iron in acetic acid;

where one or more of $Q_1$, $Q_2$, $Q_3$ or $Q_4$ of Formula 44 is an amino group, it can be converted to the corresponding dialkylamino group of 2 to 12 carbon atoms by alkylation with at least two equivalents of an alkyl halide of 1 to 6 carbon atoms by heating in an inert solvent;

where one or more of $Q_1$, $Q_2$, $Q_3$ or $Q_4$ of Formula 44 is a methoxy group, it can be converted to the corresponding hydroxy group by reaction with a demethylating agent such as boron tribromide in an inert solvent or by heating with pyridinium chloride with or without solvent;

where one or more of $Q_1$, $Q_2$, $Q_3$ or $Q_4$ of Formula 44 is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a base such as triethylamine or pyridine;

where two of $Q_1$, $Q_2$, $Q_3$ or $Q_4$ of Formula 44 are contiguous methoxy groups, the corresponding compound with contiguous hydroxy groups can be prepared by using a demethylating agent such as boron tribromide in an inert solvent or by heating with pyridinium chloride with or without solvent.

Where one or more of $Q_1$, $Q_2$, $Q_3$ or $Q_4$ of Formula 44 is an amino group, it can be converted with or without heating to the corresponding alkylamino group of 1 to 6 carbon atoms by alkylation with one equivalent of an alkyl halide of 1 to 6 carbon atoms or by reductive alkylation using an aldehyde of 1 to 6 carbon atoms and a reducing agent such as sodium cyanoborohydride in a protic solvent such as water or alcohol, or mixtures thereof;

where one or more of $Q_1$, $Q_2$, $Q_3$ or $Q_4$ of Formula 44 is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a base;

where one or more of $Q_1$, $Q_2$, $Q_3$ or $Q_4$ of Formula 44 is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a base;

where one or more of $Q_1$, $Q_2$, $Q_3$ or $Q_4$ of Formula 44 is hydroxy, it can be converted to the corresponding groups:

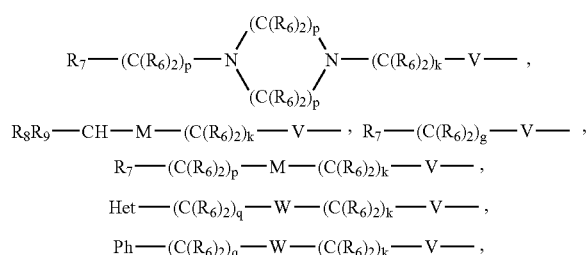

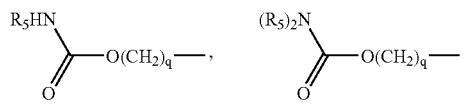

wherein V is oxygen, $R_6$, $R_7$, $R_8$, $R_9$, M, W, Het, Ph, p and q are as hereinabove defined and g=2–6 and k=2–4 by reacting with the appropriately substituted alcohol using triphenyl phosphine and diethyl azodicarboxylate in an inert solvent, or alternatively by first reacting with a reagent such as, but not limited to, a bromoalkyl chloride or chloroalkyl tosylate to provide an intermediate haloalkoxy group which can be converted to the above described groups by subsequent reaction with an appropriately substituted nucleophile;

where one or more of $Q_1$, $Q_2$, $Q_3$ or $Q_4$ of Formula 44 is a HO—$(CH_2)_q$— group, it can be converted to the corresponding groups:

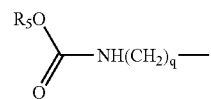

wherein q and $R_5$ are as defined above, by the reaction in an inert solvent with an alkyl or phenyl substituted isocyanate, $R_5$—N=C=O, or using a base such as pyridine, with a reagent $(R_5)_2$NCOCl;

where one or more of $Q_1$, $Q_2$, $Q_3$ or $Q_4$ of Formula 44 is carboxy or a alkoxycarbonyl group of 2–7 carbon atoms, it can be converted to the corresponding hydroxymethyl group by reduction with an appropriate reducing agent such as lithium borohydride, or lithium aluminum hydride in a inert solvent; the hydroxymethyl group, in turn, can be converted to the corresponding halomethyl group by reaction in an inert solvent with a halogenating reagent such as phosphorus tribromide to give a bromomethyl group, or phosphorus pentachloride to give a chloromethyl group. The hydroxymethyl group can be acylated with an appropriate acid chloride, anhydride, or mixed anhydride in an inert solvent using pyridine or a trialkylamine as a base to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms;

where one or more of $Q_1$, $Q_2$, $Q_3$ or $Q_4$ of Formula 44 is a halomethyl group, it can be converted to the corresponding groups:

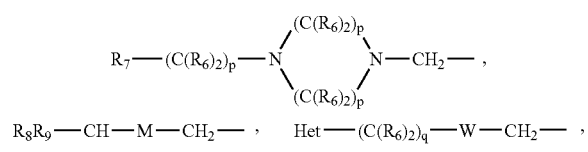

-continued

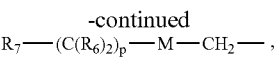

wherein $R_6$, $R_7$, $R_8$, $R_9$, M, W, Het, p and q are as hereinabove defined by reacting with the appropriately substituted alcohol, amine or mercaptan in an inert solvent such as dioxane or acetonitrile and a base such as triethylamine or potassium carbonate;

where one or more of $Q_1$, $Q_2$, $Q_3$ or $Q_4$ of Formula 44 is a $H_2N(CH_2)_q$— -group, it can be converted to the corresponding groups:

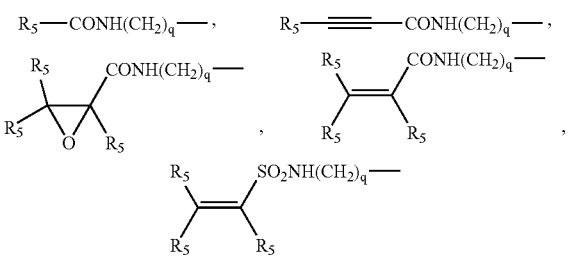

wherein $R_5$ and q are as hereinabove defined, by reacting with the appropriately substituted acid chloride or mixed anhydride (which is prepared from the corresponding carboxylic acid) in an inert solvent such as tetrahydrofuran (THF) in the presence of an organic base such as pyridine, triethylamine or N-methyl morpholine;

where one or more of $Q_1$, $Q_2$, $Q_3$ or $Q_4$ of Formula 44 is a $H_2N(CH_2)_q$— group, it can be converted to the corresponding groups:

$$R_5O\underset{O}{\overset{}{\diagup\!\!\!\diagdown}}NH(CH_2)_q-$$

wherein $R_5$ and q are as hereinabove defined, by reacting with phosgene in an inert solvent such as toluene in the presence of a base such as pyridine to give an isocyanate which, in turn, is treated with an excess of the alcohol $R_5$—OH;

where one or more of $Q_1$, $Q_2$, $Q_3$ or $Q_4$ of Formula 44 is a $H_2N(CH_2)_q$— group, it can be converted to the corresponding groups:

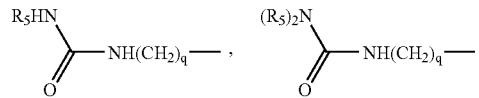

wherein $R_5$ and q are as hereinabove defined, by the reaction in an inert solvent with an alkyl or phenyl substituted isocyanate, $R_5$—N=C=O, or by reacting with phosgene in an inert solvent such as toluene in the presence of a base such as pyridine to give an isocyanate which, in turn, is treated with an excess of amine $(R_5)_2$NH;

where one or more of $Q_1$, $Q_2$, $Q_3$ or $Q_4$ of Formula 44 is a $H_2N(CH_2)_q$— group, it can be converted to the corresponding groups:

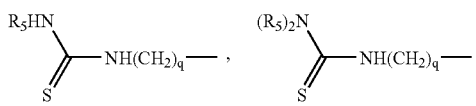

wherein $R_5$ and q are as hereinabove defined, by the reaction in an inert solvent with an alkyl or phenyl substituted isothiocyanate, $R_5$—N=C=S, or by reacting with 1,1'-thiocarbonyldiimidazole in an inert solvent such as toluene in the presence of a base such as pyridine to give an isothiocyanate which, in turn, is treated with an excess of amine $(R_5)_2$NH.

Intermediate 43 can also be prepared as described below and in Flowsheet 12.

By reacting substituted 2-fluorobenzonitriles of Formula 45 with methyl thioglycolate and a base such as potassium hydroxide or triethylamine in an inert solvent such as dimethyl sulfoxide (DMSO) or aqueous dimethyl formamide (DMF) with or without heating provides compounds of Formula 41. Heating the substituted anilines of Formula 41 with N-methyl piperazine in an inert solvent such as N-methyl pyrrolidine (NMP) provides intermediates 46. Treatment of 46 with ethyl (ethoxymethylene)cyanoacetate gives intermediates 47. Cyclization of 47 in refluxing 1:3 biphenyl/diphenyl ether to provide compounds of Formula 43, or the 4-hydroxy[1]benzothieno[3,2-b]pyridine-3-carbonitriles tautomers thereof, which can be converted to the compounds of this invention using the procedures outlined in Flowsheet 11.

The 2-fluorobenzonitriles of Formula 45 are either commercially available, or are already known to the art or can be prepared by procedures known in the art.

Flowsheet 12

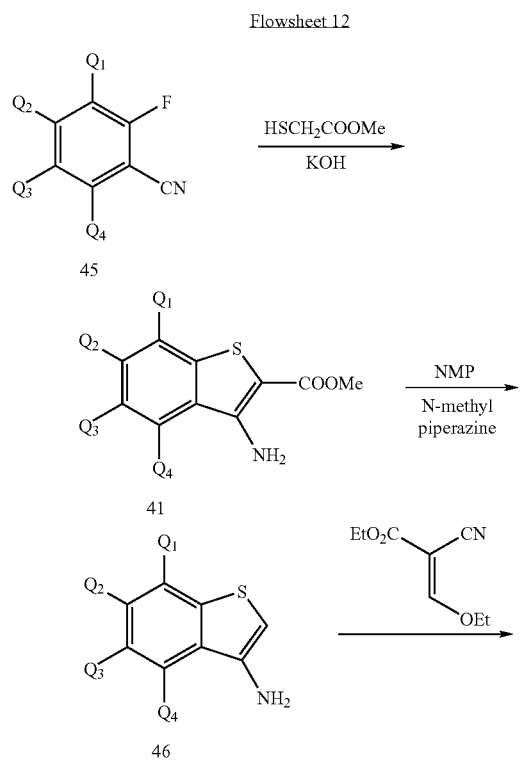

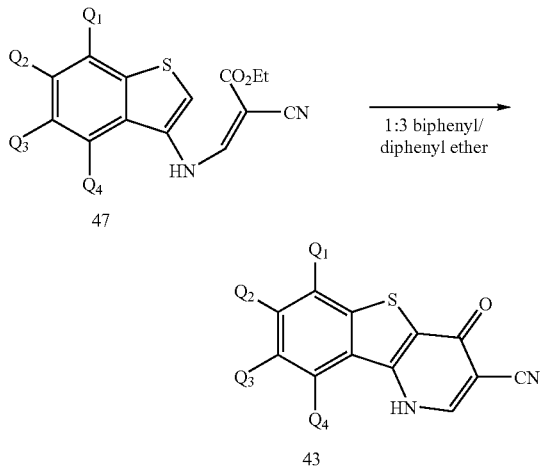

The preparation of the compounds and intermediates of this invention encompassed by Formula 52 is described below and in Flowsheet 13 where Ar, X, $Q_1$, $Q_2$, $Q_3$ and $Q_4$ and n are as hereinabove defined.

Reaction of substituted 2-nitrophenols of Formula 48 with ethyl bromoacetate and a base such as potassium carbonate in an inert solvent such as dimethyl formamide (DMF) with or without heating, followed by further treatment with potassium t-butoxide in an inert solvent such as tetrahydrofuran (THF) provides compounds of Formula 49. Heating the substituted aniline of Formula 49 with dimethylformamide dimethyl acetal with or without a solvent gives intermediates of Formula 50. The reaction of 50 with from one to ten equivalents of acetonitrile using a base such as n-butyllithium, sodium methoxide or the like in an inert solvent gives the 4-oxo-1,4-dihydro[1]benzofuro[3,2-b]pyridine-3-carbonitrile 51, or the 4-hydroxy[1]benzofuro[3,2-b]pyridine-3-carbonitriles tautomers thereof. Heating 51 with or without solvent with a chlorinating agent such as phosphorus oxychloride or oxalyl chloride provides the corresponding 4-chloro[1]benzofuro[3,2-b]pyridine-3-carbonitriles. Condensation of 4-chloro[1]benzofuro[3,2-b]pyridine-3-carbonitriles with a nucleophilic amine, aniline, mercaptan, thiophenol, phenol, or alcohol reagent of Formula 5 gives the benzofuro[3,2-b]pyridine-3-carbonitriles of Formula 52; this condensation can be accelerated by heating the reaction mixture together with one equivalent of pyridine hydrochloride or by using bases such as trialkylamines, sodium hydride in an inert solvent, sodium or potassium alkoxides in alcohol solvents, and the like. In those cases where the Ar and/or $Q_1$, $Q_2$, $Q_3$ and $Q_4$ substituents may contain an asymmetric carbon atom, the intermediates can be used as the racemate or as the individual R or S enantiomers in which case the compounds of this invention will be in the racemic or R and S optically active forms, respectively. In cases where the Ar and/or $Q_1$, $Q_2$, $Q_3$ and $Q_4$ substituents may contain more than one asymmetric carbon atoms, diastereomers may be present; these can be separated by methods well known in the art including, but not limited to, fractional crystallization and chromatographic methods. In those cases, in intermediates 48 where $Q_1$, $Q_2$, $Q_3$ and $Q_4$ contains primary or secondary amino groups or hydroxyl groups, it may be necessary to protect these groups prior to the reaction with ethyl bromoacetate. In those cases, in intermediates 5 where Ar contains primary or secondary amino groups or hydroxyl groups, it may be necessary to protect these groups prior to the reaction with the 4-chloro[1]benzofuro[3,2-b]pyridine-3-carbonitriles. The same amine or alcohol protecting groups hereinabove described can be used and they can be removed from the products 54 as previously described.

The 2-nitrophenols of Formula 48 are either commercially available, or are already known to the art or can be prepared by procedures known in the art

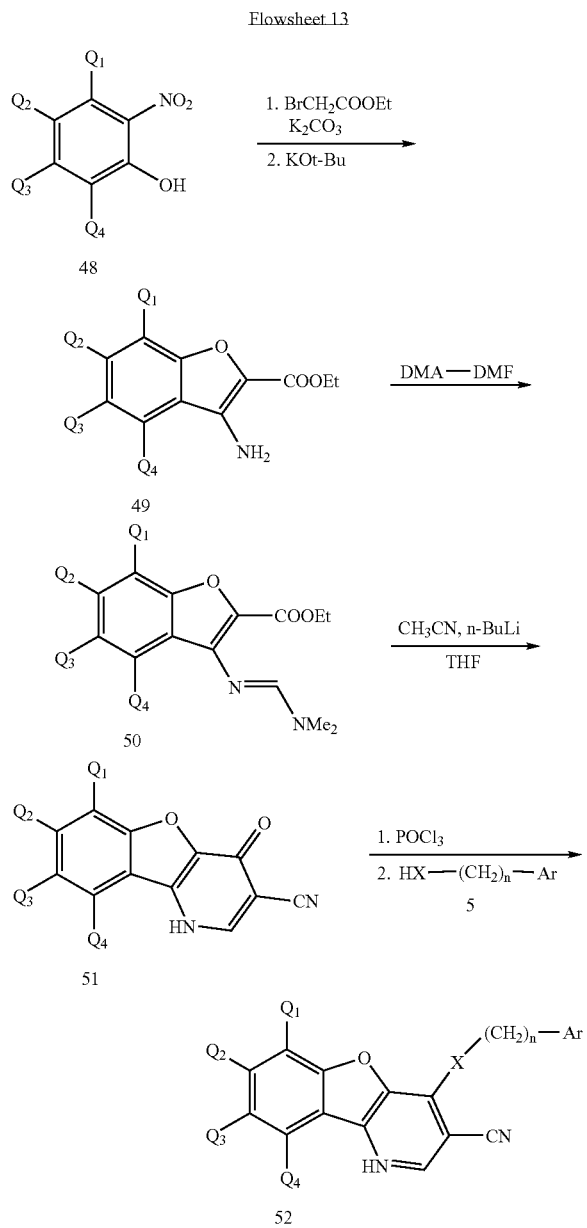

Flowsheet 13

Converting the $Q_1$, $Q_2$, $Q_3$ and $Q_4$ groups to $R_1$, $R_2$, $R_3$ and $R_4$ groups can be accomplished through any conventionally known techniques, for example:

Where one or more of $Q_1$, $Q_2$, $Q_3$, $Q_4$ of Formula 52 is a nitro group, it can be converted to the corresponding amino group by reduction using a reducing agent such as iron in acetic acid;

where one or more of $Q_1$, $Q_2$, $Q_3$ or $Q_4$ of Formula 52 is an amino group, it can be converted to the corresponding dialkylamino group of 2 to 12 carbon atoms by alkylation with at least two equivalents of an alkyl halide of 1 to 6 carbon atoms by heating in an inert solvent;

where one or more of $Q_1$, $Q_2$, $Q_3$ or $Q_4$ of Formula 52 is a methoxy group, it can be converted to the corresponding hydroxy group by reaction with a demethylating agent such as boron tribromide in an inert solvent or by heating with pyridinium chloride with or without solvent;

where one or more of $Q_1$, $Q_2$, $Q_3$ or $Q_4$ of Formula 52 is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a base such as triethylamine or pyridine;

where two of $Q_1$, $Q_2$, $Q_3$ or $Q_4$ of Formula 52 are contiguous methoxy groups, the corresponding compound with contiguous hydroxy groups can be prepared by using a demethylating agent such as boron tribromide in an inert solvent or by heating with pyridinium chloride with or without solvent;

where one or more of $Q_1$, $Q_2$, $Q_3$ or $Q_4$ of Formula 52 is an amino group, it can be converted to the corresponding alkylamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof;

where one or more of $Q_1$, $Q_2$, $Q_3$ or $Q_4$ of Formula 52 is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a base;

where one or more of $Q_1$, $Q_2$, $Q_3$ or $Q_4$ of Formula 52 is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a base;

where one or more of $Q_1$, $Q_2$, $Q_3$ or $Q_4$ of Formula 52 is hydroxy, it can be converted to the corresponding groups:

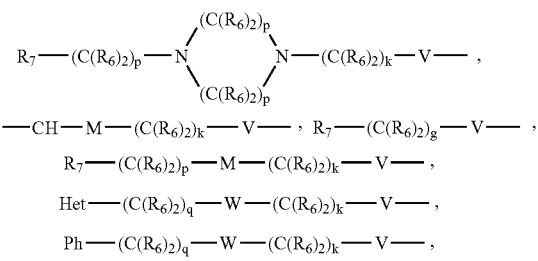

wherein V is oxygen, $R_6$, $R_7$, $R_8$, $R_9$, M, W, Het, Ph, p and q are as hereinabove defined and g=2–6 and k=2–4, by reacting with the appropriately substituted alcohol using triphenyl phosphine and diethyl azodicarboxylate in an inert solvent;

where one or more of $Q_1$, $Q_2$, $Q_3$ or $Q_4$ of Formula 52 is a HO—$(CH_2)_q$— group, it can be converted to the corresponding groups:

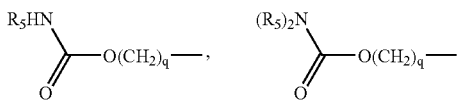

wherein q and $R_5$ are as hereinabove defined, by the reaction in an inert solvent with an alkyl or phenyl substituted isocyanate, $R_5$—N=C=O, or using a base such as pyridine, with a reagent $(R_5)_2$NCOCl;

where one or more of $Q_1$, $Q_2$, $Q_3$ or $Q_4$ of Formula 52 is carboxy or a alkoxycarbonyl group of 2–7 carbon atoms, it can be converted to the corresponding hydroxymethyl group by reduction with an appropriate reducing agent such as lithium borohydride, or lithium aluminum hydride in an inert solvent; the hydroxymethyl group, in turn, can be converted to the corresponding halomethyl group by reaction in an inert solvent with a halogenating reagent such as phosphorus tribromide to give a bromomethyl group, or phosphorus pentachloride to give a chloromethyl group. The hydroxymethyl group can be acylated with an appropriate acid chloride, anhydride, or mixed anhydride in an inert solvent using pyridine or a trialkylamine as a base to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms;

where one or more of $Q_1$, $Q_2$, $Q_3$ or $Q_4$ of Formula 52 is a halomethyl group, it can be converted to the corresponding groups:

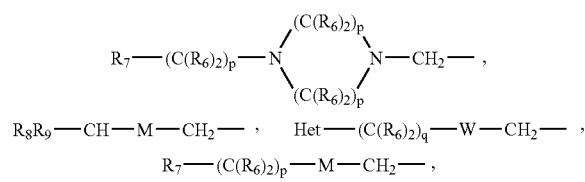

wherein $R_6$, $R_7$, $R_8$, $R_9$, M, W, Het, p and q are as hereinabove defined by reacting with the appropriately substituted alcohol, amine or mercaptan in an inert solvent such as dioxane or acetonitrile and a base such as triethylamine or potassium carbonate;

where one or more of $Q_1$, $Q_2$, $Q_3$ or $Q_4$ of Formula 52 is a $H_2N(CH_2)_q$— group, it can be converted to the corresponding groups:

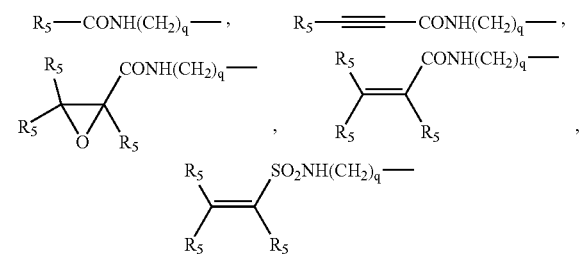

wherein $R_5$ and q are as hereinabove defined by reacting with the appropriately substituted acid chloride or mixed anhydride (which is prepared from the corresponding carboxylic acid) in an inert solvent such as tetrahydrofuran (THF) in the presence of an organic base such as pyridine, triethylamine or N-methylmorpholine;

where one or more of $Q_1$, $Q_2$, $Q_3$ or $Q_4$ of Formula 52 is a $H_2N(CH_2)_q$— group, it can be converted to the corresponding groups:

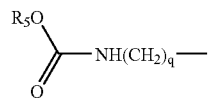

wherein $R_5$ and q are as hereinabove defined, by reacting with phosgene in an inert solvent such as toluene in the presence of a base such as pyridine to give an isocyanate which, in turn, is treated with an excess of the alcohol $R_5$—OH;

where one or more of $Q_1$, $Q_2$, $Q_3$ or $Q_4$ of Formula 52 is a $H_2N(CH_2)_q$— group, it can be converted to the corresponding groups:

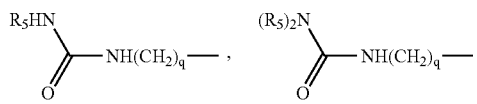

wherein $R_5$ and q are as hereinabove defined, by the reaction in an inert solvent with an alkyl or phenyl substituted isocyanate, $R_5$—N=C=O, or by reacting with phosgene in an inert solvent such as toluene in the presence of a base such as pyridine to give an isocyanate which, in turn, is treated with an excess of amine $(R_5)_2$NH;

where one or more of $Q_1$, $Q_2$, $Q_3$ or $Q_4$ of Formula 52 is a $H_2N(CH_2)_q$— group, it can be converted to the corresponding groups:

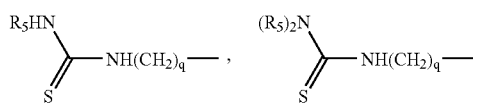

wherein $R_5$ and q are as hereinabove defined, by the reaction in an inert solvent with an alkyl or phenyl substituted isothiocyanate, $R_5$—N=C=S, or by reacting with 1,1'-thiocarbonyldiimidazole in an inert solvent such as toluene in the presence of a base such as pyridine to give an isothiocyanate which, in turn, is treated with an excess of amine $(R_5)_2$NH.

The preparation of the compounds and intermediates of this invention encompassed by Formula 59 is described below and in Flowsheet 14 where Ar, X $Q_1$, $Q_2$, $Q_3$ and $Q_4$ and n are as hereinabove defined.

Reaction of substituted benzaldehydes (Formula 53) with a nitrating agent such as, but not limited to fuming nitric acid, provides substituted nitrobenzaldehyde intermediates of Formula 54. The condensation reaction of the substituted nitrobenzaldehyde intermediates 54 with methyl cyanoacetate and a base such as piperidine in an alcoholic solvent such as methanol, with or without heating, provides the corresponding substituted 2-cyano-3-(2-nitrophenyl)acrylic acid methyl esters 55. Reduction of the substituted 2-cyano-3-(2-nitrophenyl)acrylic acid methyl esters 55 a reducing agent such as, but not limited to, iron (0) in an alcoholic solvent provides the substituted 2-aminoquinoline-3-carboxylic acid methyl ester intermediates of Formula 56. Heating the substituted 2-aminoquinoline-3-carboxylic acid methyl ester intermediates of Formula 56 with dimethylformamide dimethyl acetal with or without a solvent gives intermediates of Formula 57. The reaction of 57 with from one to ten equivalents of acetonitrile using a base such as n-butyllithium, sodium methoxide or the like in an inert solvent gives the 4-oxo-1,4-dihydrobenzo[b][1,8]naphthyridine-3-carbonitriles 58, or the 4-hydroxy-benzo[b][1,8]naphthyridine-3-carbonitrile tautomers thereof. Heating 58 with or without solvent with a chlorinating agent such as phosphorus oxychloride or oxalyl chloride provides the corresponding 4-chlorobenzo[b][1,8]naphthyridine-3-carbonitriles. Condensation of 4-chlorobenzo[b][1,8]naphthyridine-3-carbonitriles with a nucleophilic amine, aniline, mercaptan, thiophenol, phenol, or alcohol reagent of Formula 5 gives the benzo[b][1,8]naphthyridine-3-carbonitriles of Formula 59; this condensation can be accelerated by heating the reaction mixture together with one equivalent of pyridine hydrochloride or by using bases such as trialkylamines, sodium hydride in an inert solvent, sodium or potassium alkoxides in alcohol solvents, and the like. In those cases where the Ar and/or $Q_1$, $Q_2$, $Q_3$ and $Q_4$ substituents may contain an asymmetric carbon atom, the intermediates can be used as the racemate or as the individual R or S enantiomers in which case the compounds of this invention will be in the racemic or R and S optically active forms, respectively. In cases where the Ar and/or $Q_1$, $Q_2$, $Q_3$ and $Q_4$ substituents may contain more than one asymmetric carbon atoms, diastereomers may be present; these can be separated by methods well known in the art including, but not limited to, fractional crystallization and chromatographic methods. In those cases, in intermediates 54 where $Q_1$, $Q_2$, $Q_3$ and $Q_4$ contains primary or secondary amino groups or hydroxyl groups, it may be necessary to protect these groups prior to the reaction with methyl cyanoacetate. In those cases, in intermediates 5 where Ar contains primary or secondary amino groups or hydroxyl groups, it may be necessary to protect these groups prior to the reaction with the 4-chlorobenzo[b][1,8]naphthyridine-3-carbonitriles. The same amine or alcohol protecting groups hereinabove described can be used and they can be removed from the products 59 as previously described.

The benzaldehydes of Formula 53 are either commercially available, or are already known to the art or can be prepared by procedures known in the art.

Flowsheet 14

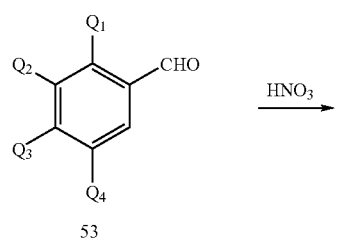

53

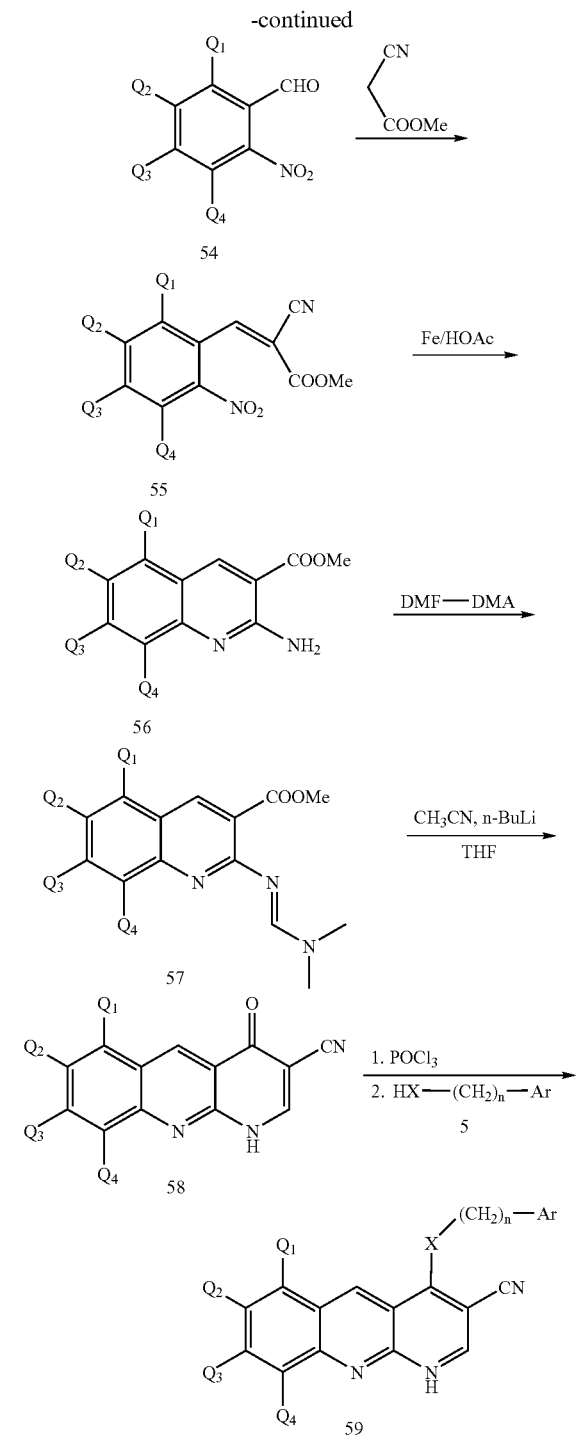

Converting the $Q_1$, $Q_2$, $Q_3$ and $Q_4$ groups to $R_1$, $R_2$, $R_3$ and $R_4$ groups can be accomplished through any conventionally known techniques, for example:

where one or more of $Q_1$, $Q_2$, $Q_3$ or $Q_4$ of Formula 59 is a nitro group, it can be converted to the corresponding amino group by reduction using a reducing agent such as iron in acetic acid;

where one or more of $Q_1$, $Q_2$, $Q_3$ or $Q_4$ of Formula 59 is an amino group, it can be converted to the corresponding dialkylamino group of 2 to 12 carbon atoms by alkylation with at least two equivalents of an alkyl halide of 1 to 6 carbon atoms by heating in an inert solvent;

where one or more of $Q_1$, $Q_2$, $Q_3$ or $Q_4$ of Formula 59 is a methoxy group, it can be converted to the corresponding hydroxy group by reaction with a demethylating agent such as boron tribromide in an inert solvent or by heating with pyridinium chloride with or without solvent;

where one or more of $Q_1$, $Q_2$, $Q_3$ or $Q_4$ of Formula 59 is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a base such as triethylamine or pyridine;

where two of $Q_1$, $Q_2$, $Q_3$ or $Q_4$ of Formula 59 are contiguous methoxy groups, the corresponding compound with contiguous hydroxy groups can be prepared by using a demethylating agent such as boron tribromide in an inert solvent or by heating with pyridinium chloride with or without solvent;

where one or more of $Q_1$, $Q_2$, $Q_3$ or $Q_4$ of Formula 59 is an amino group, it can be converted to the corresponding alkylamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof;

where one or more of $Q_1$, $Q_2$, $Q_3$ or $Q_4$ of Formula 59 is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a base;

where one or more of $Q_1$, $Q_2$, $Q_3$ or $Q_4$ of Formula 59 is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a base;

where one or more of $Q_1$, $Q_2$, $Q_3$ or $Q_4$ of Formula 59 is hydroxy, it can be converted to the corresponding groups:

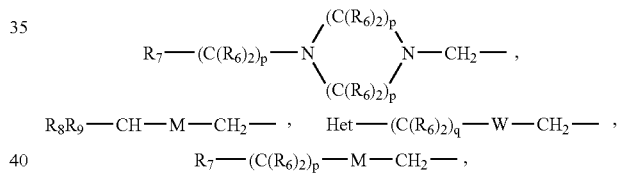

wherein V is oxygen, $R_6$, $R_7$, $R_8$, $R_9$, W, Het, Ph, p and q are as hereinabove defined and g=2–6 and k=2–4, by reacting with the appropriately substituted alcohol using triphenyl phosphine and diethyl azodicarboxylate in an inert solvent;

where one or more of $Q_1$, $Q_2$, $Q_3$ or $Q_4$ of Formula 59 is a $HO-(CH_2)_q-$ group, it can be converted to the corresponding groups:

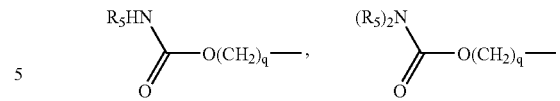

wherein q and $R_5$ are as hereinabove defined, by the reaction in an inert solvent with an alkyl or phenyl substituted isocyanate, $R_5-N=C=O$, or using a base such as pyridine, with a reagent $(R_5)_2NCOCl$;

where one or more of $Q_1$, $Q_2$, $Q_3$ or $Q_4$ of Formula 59 is carboxy or a alkoxycarbonyl group of 2–7 carbon atoms, it can be converted to the corresponding hydroxymethyl group by reduction with an appropriate reducing agent such as lithium borohydride, or lithium aluminum hydride in an inert solvent; the hydroxymethyl group, in turn, can be converted to the corresponding halomethyl group by reaction in an inert solvent with a halogenating reagent such as phosphorus tribromide to give a bromomethyl group, or phosphorus pentachloride to give a chloromethyl group. The hydroxymethyl group can be acylated with an appropriate acid chloride, anhydride, or mixed anhydride in an inert solvent using pyridine or a trialkylamine as a base to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms;

where one or more of $Q_1$, $Q_2$, $Q_3$ or $Q_4$ of Formula 59 is a halomethyl group, it can be converted to the corresponding groups:

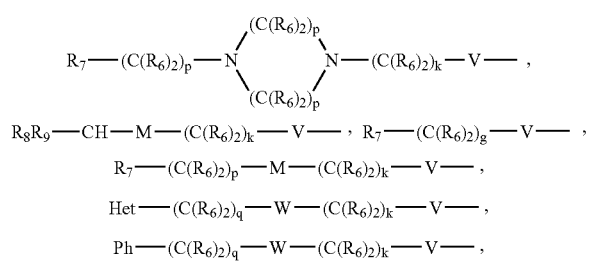

wherein $R_6$, $R_7$, $R_8$, $R_9$, M, W, Het, p and q are as hereinabove defined by reacting with the appropriately substituted alcohol, amine or mercaptan in an inert solvent such as dioxane or acetonitrile and a base such as triethylamine or potassium carbonate;

where one or more of $Q_1$, $Q_2$, $Q_3$ or $Q_4$ of Formula 59 is a $H_2N(CH_2)_q-$ group, it can be converted to the corresponding groups:

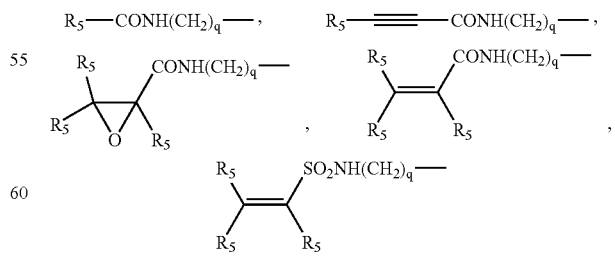

wherein $R_5$ and q are as hereinabove defined by reacting with the appropriately substituted acid chloride or mixed anhydride (which is prepared from the corresponding carboxylic acid) in an inert solvent such as tetrahydrofuran (THF) in the presence of an organic base such as pyridine, triethylamine or N-methylmorpholine;

where one or more of $Q_1$, $Q_2$, $Q_3$ or $Q_4$ of Formula 59 is a $H_2N(CH_2)_q$— group, it can be converted to the corresponding groups:

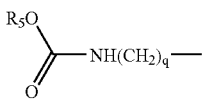

wherein $R_5$ and q are as hereinabove defined, by reacting with phosgene in an inert solvent such as toluene in the presence of a base such as pyridine to give an isocyanate which, in turn, is treated with an excess of the alcohol $R_5$—OH;

where one or more of $Q_1$, $Q_2$, $Q_3$ or $Q_4$ of Formula 59 is a $H_2N(CH_2)_q$— group, it can be converted to the corresponding groups:

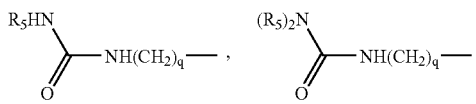

wherein $R_5$ and q are as hereinabove defined, by the reaction in an inert solvent with an alkyl or phenyl substituted isocyanate, $R_5$—N=C=O, or by reacting with phosgene in an inert solvent such as toluene in the presence of a base such as pyridine to give an isocyanate which, in turn, is treated with an excess of amine $(R_5)_2NH$;

where one or more of $Q_1$, $Q_2$, $Q_3$ or $Q_4$ of Formula 59 is a $H_2N(CH_2)_q$— group, it can be converted to the corresponding groups:

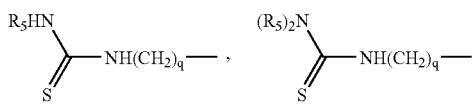

wherein $R_5$ and q are as hereinabove defined, by the reaction in an inert solvent with an alkyl or phenyl substituted isothiocyanate, $R_5$—N=C=S, or by reacting with 1,1'-thiocarbonyldiimidazole in an inert solvent such as toluene in the presence of a base such as pyridine to give an isothiocyanate which, in turn, is treated with an excess of amine $(R_5)_2NH$.

Compounds of this invention are evaluated in several standard pharmacological test procedures that showed that the compounds of this invention possess significant activity as inhibitors of protein kinases and are antiproliferative agents. Among the disease states which can be treated or inhibited by protein kinase inhibitors include those in which the etiology is at least in part caused by a defect upstream in a signaling pathway from a protein kinase (e.g., colon cancer); those in which the etiology is at least in part caused by an overexpressed protein kinase (e.g., lung cancer and colonic polyps); and those in which the etiology is at least in part caused by a dysregulated protein kinase (gene turned on at all times; glioblastoma).

Based on the activity shown in the standard pharmacological test procedures, the compounds of this invention are therefore useful as antineoplastic agents. In particular, these compounds are useful in treating, inhibiting the growth of, or eradicating neoplasms such as those of the breast, kidney, bladder, mouth, larynx, esophagus, stomach, colon, ovary, lung, pancreas, liver, prostate and skin.

In addition to having antineoplastic properties, the compounds of the present invention are useful in treating or inhibiting a variety of protein tyrosine kinase-associated disorders including: polycystic kidney disease, colonic polyps, restenosis; atherosclerosis; angiofibromas; hemangiomas; diabetes; acute and chronic nephropathies; Kaposi's sarcoma; neovascularization associated with macular degeneration; rheumatoid arthritis; osteoarthritis; transplant rejection; psoriasis; lupus; graft versus host disease; glomerulonephritis; respiratory and skin allergies; autoimmune alopecia; Autoimmune Hyperthyroidism; multiple sclerosis; atopic dermatitis; and systemic sclerosis; and are useful as antibacterial and antiviral agents.

As used in accordance with this invention, the term providing an effective amount of a compound means either directly administering such compound, or administering a prodrug, derivative, or analog which will form an effective amount of the compound within the body.

The Test Procedures Used and Results Obtained are Shown Below.

Inhibition of Epidermal Growth Factor Receptor Kinase (EGF-R) Using Recombinant Enzyme Representative test compounds are evaluated in a standard pharmacological test procedure to measure their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this assay is the His-tagged cytoplasmic domain of EGFR A recombinant baculovirus (vH-cEGFR52) is constructed containing the EGFR cDNA encoding amino acids 645–1186 preceded by Met-Ala-(His)$_6$. Sf9 cells in 100 mm plates are infected at a multiplicity of infection of 10 pfu/cell and cells are harvested 48 h post infection. A cytoplasmic extract is prepared using 1% Triton X-100 and applied to Ni-NTA column. After washing the column with 20 mM imidazole, HcEGFR is eluted with 250 mM imidazole (in 50 mM Na$_2$HPO$_4$, pH 8.0, 300 mM NaCl). Fractions collected are dialyzed against 10 mM HEPES, pH 7.0, 50 mM NaCl, 10% glycerol, 1 ug/mL antipain and leupeptin and 0.1 mM Pefabloc SC. The protein is frozen in dry ice/methanol and stored −70° C.

Test compounds are made into 10 mg/mL stock solutions in 100% dimethylsulfoxide (DMSO). Prior to experiment, stock solutions are diluted to 500 uM with 100% DMSO and then serially diluted to the desired concentration with HEPES buffer (30 mM HEPES pH 7.4).

For the enzyme reaction, 10 uL of each inhibitor (at various concentrations) are added to each well of a 96-well plate. To this is added 3 uL of enzyme (1:10 dilution in 10 mM HEPES, pH 7.4 for final conc. of 1:120). This is allowed to sit for 10 min on ice and is followed by the addition of 5 ul peptide (80 uM final conc.), 1out of 4× Buffer containing 50 mM HEPES (pH 7.4), 200 mM Na$_3$VO$_4$, 40 mM MnCl$_2$, 80 uM ATP, 0.25 uL $^{33}$P-ATP (>2500 Ci/mmol; Amersham) and 12 uL H$_2$O. The reaction is allowed to run for 90 min at room temperature and is followed by spotting the entire volume onto precut P81 filter papers. The filter discs are washed 2× with 0.5% phosphoric acid and radioactivity is measured using a liquid scintillation counter.

The inhibition data for representative compounds of the invention are shown below in TABLE 1. The IC$_{50}$ is the concentration of test compound needed to reduce the total amount of phosphorylated substrate by 50%. The % inhibition of the test compound is determined for at least three different concentrations and the IC$_{50}$ value is evaluated from the dose response curve. The % inhibition is evaluated with the following formula:

% inhibition=100−[CPM(drug)/CPM(control)]×100 where CPM(drug) is in units of counts per minute and is a number expressing the amount of radiolabled ATP ($\gamma$-$^{33}$P) incorporated onto the RR-SRC peptide substrate by the enzyme after 90 minutes at room temperature in the presence of test compound as measured by liquid scintillation counting. CPM(control) is in units of counts per minute and is a number expressing the amount of radiolabled ATP ($\gamma$-$^{33}$P) incorporated into the RR-SRC peptide substrate by the enzyme after 90 minutes at room temperature in the absence of test compound as measured by liquid scintillation counting. The CPM values are corrected for the background counts produced by ATP in the absence of the enzymatic reaction.

TABLE 1

Inhibition of EGF-R Kinase (recombinant enzyme)

| Example | IC50 (μM) |
| --- | --- |
| 37 | 0.0015 (a) |
| 4 | 0.005 |
| 85 | 1 |
| 65 | 1 (a) |
| 91 | 10 |
| 92 | 10 |
| 93 | 10 |
| 94 | 0.1 |
| 124 | 3.0 |
| 129 | 1.5 |
| 205 | 0.25 |
| 212 | 1.89 |
| 216 | 0.29 |
| 218 | 0.0053 |

(a) Average of two tests.

Inhibition of Kinase Insert Domain Containing Receptor (KDR; the Catalytic Domain of the VEGF Receptor)

KDR protein is mixed, in the presence or absence of a inhibitor compound, with a substrate peptide to be phosphorylated (a copolymer of glutamic acid and tyrosine, E:Y::4:1) and other cofactors such as Mg$^{++}$ and sodium vanadate (a protein tyrosine phosphatase inhibitor) in an appropriate buffer to maintain pH (7.2). ATP and a radioactive tracer (either P$^{32}$- or P$^{33}$-labeled ATP) is then added to initiate phosphorylation. After incubation, the radioactive phosphate associated with the acid-insoluble fraction of the test procedure mixture is then quantified as reflection of substrate phosphorylation. This radioactive format is used to identify inhibitors of KDR tyrosine kinase activity where the IC$_{50}$ is the concentration of drug that inhibits substrate phosphorylation by 50%. The results obtained for representative compounds of this invention are listed in Table 2.

Mitogen Activated Protein Kinase (MAPK) Test Procedure

To evaluate inhibitors of the MAP (mitogen activated protein) kinase a two component coupled standard pharmacological test procedure, which measures phosphorylation of a serine/threonine residue in an appropriate sequence in the substrate in the presence and absence of a putative inhibitor, is used. Recombinant human MEK 1 (MAPKK) is first used to activate recombinant human ERK2 (MAPK) and the activated MAPK (ERK) is incubated with substrate (myelin basic protein peptide (MBPP) or Myc peptide) in the presence of ATP, Mg$^{+2}$ and radiolabeled $^{33}$P ATP. The phosphorylated peptide is captured on a P 81 phosphocellulose filter (paper filter or embedded in microtiter plate) washed and counted by scintillation methods.

The peptide substrates used in the assay are MBPP, peptide substrate (APRTPGGRR), or synthetic Myc substrate, (KKFELLPTPPLSPSRR.5 TFA). The recombinant enzymes used are prepared as GST fusion proteins of human ERK 2 and human MEK 1. Inhibitor samples are prepared as 10× stocks in 10% DMSO and an appropriate aliquot is used to deliver either 10 ug/ml for a single point screening dose or 100 to 0.0001 uM final concentration for a dose response curve. Final DMSO concentrations are less than or equal to 1%.

The reaction is run as follows in 50 mM Tris kinase buffer, pH 7.4 in a reaction volume of 50 ul. The appropriate volume of kinase buffer and inhibitor sample is added to the tube. Appropriate dilution of enzyme is delivered to give 2–5 ug recombinant MAPK (Erk) per tube. The inhibitor is incubated with MAPK (Erk) for 30 min at 0 deg. C. Recombinant Mek (MAPKK) (0.5–2.5 ug) or fully activated Mek (0.05–0.1 units) is added to activate the Erk and incubated for 30 min at 30° C. Then substrate and $\gamma^{33}$P ATP are added to give a final concentration of 0.5–1 mM MBPP or 250–500 uM Myc; 0.2–0.5 uCi gamma P 33 ATP/tube; 50 μM ATP final concentration. Samples are incubated at 30° C. for 30 minutes and the reaction is stopped by adding 25 μl of ice cold 10% trichloroacetic acid (TCA). After samples are chilled on ice for 30 min. 20 μl of sample is transferred onto P 81 phosphocellulose filter. Filter papers are washed 2 times with a large volume of 1% acetic acid, then 2 times with water. The filters are briefly air dried before addition of scintillant and samples are counted in the appropriate scintillation counter set up for reading $^{33}$P isotope. Samples include a positive control (activated enzyme plus substrate); a no enzyme control; a no substrate control; samples with different concentrations of putative inhibitor, and samples with reference inhibitors (other active compounds or non-specific inhibitors such as staurosporine or K252 B).

The raw data is captured as cpm. Sample replicates are averaged and corrected for background count. Mean cpm data is tabulated by group and % inhibition by a test compound is calculated as (corrected cpm control−corrected. cpm sample/control)×100=% inhibition). If several concentrations of inhibitor are tested, IC$_{50}$ values (the concentration which gives 50% inhibition) are determined graphically. The results obtained for representative compounds of this invention are listed in Table 2.

Src Kinase Test Procedure

Inhibitors of p60$^{c-src}$ (partially purified preparation purchased from Upstate Biotechnologies) tyrosine kinase activity are analyzed in an Elisa format. The Boehringer Mannheim Tyrosine Kinase Assay Kit (Catalog number 1-534505) with a cdc2 substrate peptide containing Tyr15 is used for the assay. HRP-conjugated anti-phosphotyrosine is used to detect phosphorylated peptide via a color reaction. Conditions recommended by the manufacturer are employed.

Reaction conditions: Five microliter aliquots of each compound prepared fresh at the time of the assay are added as a solution in 10 mM HEPES pH 7.5, 10% DMSO to the reaction well. Thirty-five microliters of reaction mix containing Src, buffer and peptide/bovine serum albumin mix are added to the compound wells and incubated at 30° C. for 10 minutes (reaction buffer: 50 mM Tris HCl pH 7.5, 10 mM MgCl$_2$, 0.1 nM EGTA, 0.5 mM Na$_3$VO$_4$). The reaction is started by addition of 10 microliters of ATP, incubated at 30° C. for 1 hour, and stopped by addition of 20 microliters of 0.5M EDTA. The reaction mixture with the phosphorylated peptide is then transferred to a streptavidin-coated microtiter plate (provided in the kit) and allowed to bind for 20 minutes. Unbound peptide and reaction mixture is decanted and the plate is washed with PBS six times. Horseradish peroxidase-conjugated phosphotyrosine antibody supplied in the kit is incubated with the plate for one hour, then decanted. The plate is again washed with PBS six times. Substrate (provided in the kit) is added and absorbance at 405 nm is measured.

Activity is determined as % inhibition as calculated by the formula: (1−Abs/Abs(max))×100=% inhibition. Where multiple concentrations of the test agent are used, an IC$_{50}$ (concentration which gives 50% inhibition) could be determined.

The results obtained for representative compounds of this invention are listed in Table 2.

TABLE 2

Inhibition of Kinase insert Domain containing Receptor (KDR), Mitogen Activated Protein Kinase (Mek-Erk) and p60$^{c\text{-}src}$ (Src)

| Example | KDR % Inh (10 µM) | Mek-Erk IC50 (µM) | Src IC50 (µM) | Src % Inh | Src dose (µM) |
|---|---|---|---|---|---|
| 38 | | 1.3 | 0.075 (a) | | |
| 39 | | 1.3 | 0.016 (a) | | |
| 40 | | 0.5 | 0.03 (a) | | |
| 57 | | | 0.028 (a) | | |
| 58 | | >10 | | | |
| 3 | | 0.2 | | | |
| 5 | | | 0.012 | | |
| 12 | | | 0.0015 (b) | | |
| 14 | | | 0.018 (a) | | |
| 15 | | | | 10 | 0.01 |
| 85 | | | | 53 | 10 |
| | | | | 44 | 10 |
| 86 | | | | 54 | 10 |
| | | | | 46 | 10 |
| 87 | 32 | | | 0 | 10 |
| 88 | | >100 | | | |

| Example | KDR % Inh (10 µM) | Mek-Erk IC50 (µM) | Src IC50 (µM) | Src % Inh | Src dose (µM) |
|---|---|---|---|---|---|
| 69 | | 3 | | | |
| 70 | 22 | | | | |
| 42 | | | 0.012 | | |
| 44 | | 0.03 | | | |
| 61 | | | 0.281 | | |
| 65 | | | | 7 | 10 |
| 67 | | | | 0 | 10 |
| | | | | 7 | 10 |
| 68 | | 4.2 | | | |
| 75 | | | | 0 | 10 |
| 90 | | | | 0 | 1 |
| 103 | | | | 30 | 0.1 |
| 104 | | | | 30 | 0.1 |
| 105 | | | 0.094 | | |
| 106 | | | 0.19 | | |
| 107 | | | 0.40 | | |
| 124 | | | 0.00019(c) | | |
| 125 | | | 0.0021(d) | | |
| 128 | | | 0.0013 | | |
| 129 | | | 0.00035(d) | | |
| 130 | | | 0.0011(d) | | |
| 131 | | | 0.00029(d) | | |
| 132 | | | 0.0014(d) | | |
| 133 | | | 0.00031(d) | | |
| 157 | | | 0.0019(d) | | |
| 158 | | | 0.00049 | | |
| 159 | | | 0.00018 | | |
| 165 | | | 0.22(a) | | |
| 172 | | | 0.053 | | |
| 173 | | | 0.13 | 33 | 0.1 |
| 175 | | | 0.074 | | |
| 177 | | | | 30 | 5 |
| 178 | | | 2.78 | | |
| 179 | | | 0.0029 | | |
| 190 | | | 0.0025 | | |
| 191 | | | 0.00072 | | |
| 192 | | | 0.0062 | | |
| 193 | | | 0.0029 | | |
| 194 | | | 0.0017 | 90 | 0.0015 |
| 195 | | | 0.0018 | | |
| 196 | | | 0.052 | | |
| 197 | | | 0.0027 | | |
| 198 | | | 0.00057 | | |
| 199 | | | 0.00022 | | |
| 200 | | | 0.00051 | | |
| 201 | | | 0.00077 | | |
| 202 | | | 0.00043 | 100 | 0.15 |
| 203 | | | 0.0042 | | |
| 204 | | | 0.0034 | | |
| 205 | | | 0.29 | | |
| 206 | | | 0.0027 | | |
| 207 | | | 0.002 | | |
| 208 | | | 0.00039 | | |
| 209 | | | 0.0049 | | |
| 210 | | | 0.00083 | | |
| 211 | | | 0.0011 | | |
| 212 | | | 0.15 | | |
| 215 | | | 0.0029 | | |
| 216 | | | 0.001(e) | | |

(a)Average of two runs
(b)Average of four runs
(c)Average of six runs
(d)Average of three runs
(e)Average of five runs Cell Proliferation Test Procedure HT-29 cells: Compound effectiveness at inhibiting cell proliferation on plastic is performed in a 96-well format by plating 5000 cells per well in appropriate medium on day one, followed by compound addition on day 2 in serial two-fold dilutions. On day five, compound is washed away and medium containing MTS reagent (Promega) is added. Relative cell number is determined by reading the absorbance at 490 nm of a dye produced by an NAD-dependent cellular enzymatic reaction. These data are shown below in Table 3.

Anchorage Independent Src-transformed Fibroblast Proliferation Test Procedure: Rat2 fibroblasts stably transformed with a plasmid containing CMV promotor controlled v-Src/Hu c-Src fusion gene in which the catalytic domain of human c-Src is inserted in place of the v-Src catalytic domain in the v-Src gene are used for the measurement of src dependent suspension growth. Ultra-low cluster plates (Costar A 3474) are seeded with 10,000 cells per well on Day 1. Compound is added in serial two-fold dilutions from 10 micromolar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an $IC_{50}$ for proliferation (micromolar units) as follows, % inhbition=(Abs490 nm sample−blank)/(Abs490 nm no cmpd control−blank)× 100%. These data are shown below in Table 3.

plots. The test procedure is described in detail by Philip Skehan et. al, *J. Natl. Canc. Inst.,* 82, 1107–1112 (1990). These data are shown below in Table 4. Information about some of the cell lines used in these test procedures is available from the American Type Tissue Collection: Cell Lines and Hybridomas, 1994 Reference Guide, 8th Edition.

TABLE 3

Inhibition of Cancer Cell Growth

| | HT-29 prolif | | | Src TF prolif | | |
|---|---|---|---|---|---|---|
| Example | % Inh | @ dose (µM) | $IC_{50}$ (µM) | % Inh | @ dose (µM) | $IC_{50}$ (µM) |
| 40 | 10 | 10 | | 0 | 10 | |
| 39 | 35 | 10 | | 25 | 10 | |
| 38 | 25 | 10 | | 0 | 10 | |
| 57 | | | | 0 | 10 | |
| 42 | 0 | 10 | | 50 | 0.22 | |
| 124 | | | >10 | | | 0.012(a) |
| 128 | | | | | | 0.23 |
| 129 | | | >10 | | | 0.015(b) |
| 130 | | | | | | 0.26 |
| 131 | | | | | | 0.056(b) |
| 132 | | | | | | 0.30 |
| 133 | | | 8.595 | | | 0.047(b) |
| 157 | | | | | | 0.038(c) |
| 158 | | | | | | 0.067(c) |
| 159 | | | | | | 0.073(c) |
| 165 | | | | | | >10 |
| 172 | | | | | | 1.875 |
| 173 | | | | | | 3.74(d) |
| 190 | | | | | | 0.17 |
| 191 | | | >10 | | | 0.022(b) |
| 194 | | | | | | >10 |
| 195 | | | | | | 0.286 |
| 196 | | | | | | 1.781 |
| 197 | | | | | | 2.071 |
| 198 | | | | | | 0.353 |
| 199 | | | | | | 0.023(c) |
| 200 | | | | | | 0.24 |
| 201 | | | | | | 0.175(b) |
| 202 | | | | | | 0.068 |
| 203 | | | | | | 0.071(b) |
| 204 | | | | | | 1.598(b) |
| 206 | | | | | | 0.307(b) |
| 207 | | | | | | 0.929 |
| 208 | | | | | | 0.096 |
| 209 | | | | | | 0.309 |
| 210 | | | | | | 0.046 |
| 211 | | | | | | 0.128 |
| 212 | | | | | | >10 |
| 215 | | | | | | 0.105 |
| 216 | | | 9.95 | | | 0.004 |

(a)Average of five runs
(b)Average of two runs
(c)Average of three runs
(d)Average of four runs Inhibition of Cancer Cell Growth as Measured by Cell Number Human tumor cell lines are plated in 96-well plates (250 µl/well, 1–6×10$^4$ cells/ml) in RPMI 1640 medium, containing 5% F13S (Fetal Bovine Serum). Twenty four hours after plating, test compounds are added at various concentrations. After 48 hours exposure to test compounds, cells are fixed with trichloroacetic acid, and stained with Sulforhodamine B. After washing with trichloroacetic acid, bound dye is solubilized in 10 mM Tris base and optical density is determined using plate reader. Under conditions of the assay the optical density is proportional to the number of cells in the well. $IC_{50}$s (concentrations causing 50% inhibition of cell growth) are determined from the growth inhibition

TABLE 4

Inhibition of Cancer Cell Growth as Measured by Cell Number ($IC_{50}$ µg/mL)

| Example | MDA-MB-435 | A431 | SK-BR3 | SW620 |
|---|---|---|---|---|
| 4 | 1.65 | 0.332 | 1.01 | 1.08 |
| 15 | 0.85 | 0.58 | >5 | 0.38 |
| 33 | >5 | 4.88 | >5 | >5 |
| 37 | 3.48(a) | 0.58 (a) | 0.6 (a) | 3.72(a) |
| 65 | >5 | >5 | >5 | >5 |
| 85 | >5 | >5 | >5 | >5 |
| 90 | 0.46 | 0.41 | 0.59 | 0.67 |
| 92 | >5 | >5 | >5 | >5 |
| 93 | 1.69 | 0.838 | 0.224 | 1 |

TABLE 4-continued

Inhibition of Cancer Cell Growth as Measured by Cell Number (IC$_{50}$ µg/mL)

| Example | MDA-MB-435 | A431 | SK-BR3 | SW620 |
|---------|------------|------|--------|-------|
| 94      | 3.9        | 1.11 | 1.09   | >5    |
| 129     | 0.88       | 0.62 | 0.93   | 1.3   |
| 212     | —          | 0.76 | 0.04   | 0.36  |
| 218     | 33.5       | 4.7  | 3.5    | 11.6  |

(a) Average of three runs

Raf1 Kinase Cascade Assay Procedure

Raf-1 (c-Raf) is used to phosphorylate and activate inactive GST-MEK1 which then can phosphorylate and activate inactive p42 GST-MAPK, which subsequently is measured for phosphorylation of the TEY sequence (aa's 202–204) by a phospho-specific antibody from Sigma (cat. # 77439219041) Reagents: Sf9 insect cell lysate containing full length 6his-tagged recombinant human c-Raf. (Specific Activity: ~200U/ml). Human Non-active Mek-1-GST and human GST-MAP kinase (recombinant proteins produced in E. coli).

Stock Solutions Raf Assay:
1. Assay Dilution Buffer (ADB): 20 mM MOPS, pH 7.2, 25 mM β-glycerol phosphate, 5 mM EGTA, 1 nM sodium orthovanadate, 1 mM dithiothreitol.
2. Magnesium/ATP Cocktail: 500 µM cold ATP and 75 mM magnesium chloride in ADB.
4. Active Kinase: Human Active c-Raf: Use at 0.4U per assay point.
5. Non-active GST-MEK1: Use at 0.1 µg per assay point.
6. Non-active GST-p42 MAP Kinase: Use at 1.0 µg per assay point.

Stock Solutions ELISA:
1. TBST—Tris (50 mM, pH 7.5), NaCl (150 mM), Tween-20 (0.05%)
2. Superblock (Pierce)
3. Anti-GST Ab (Pharmacia)
4. Anti-Phospho MAPK (Sigma)
5. Anti-Mouse Ab/Europium conjugate (Wallac)

Assay Procedure:

First Stage: c-Raf Dependent Activation of GST-MEK and GST-MAPK
1. Add 20 ml of ADB per assay (i.e. per well of a 96 well plate)
2. Add 10 ml of 0.5 mM cold ATP and 75 mM magnesium chloride in ADB.
3. Add 2 ml of c-Raf (0.4U/assay), in conjunction with 1.6 ml non-active MEK1 (0.4 mg/assay).
4. Add 4 ml of non-active GST-p42 MAP Kinase (1.0 mg/assay).
5. Incubate for 60 minutes at 30° C. in a shaking incubator.
6. Transfer this mixture to an anti-GST Ab coated 96 well plate (Nunc Immunosorb plates coated o/n with a-GST, then blocked with Pierce Superblock).
7. Incubate for 60 minutes at 30° C. in a shaking incubator Wash 3× with TBST, add Anti-Phospho MAPK (Sigma) (1:3000)
6. Incubate for 60 minutes at 30° C. in a shaking incubator
7. Wash 3× with TBST, add Anti-Mouse Ab/Europium conjugate (Wallac) (1:500)
8. Incubate for 60 minutes at 30° C. in a shaking incubator
9. Wash 3× with TBST, Read plates in Wallac Victor model Plate Reader.
10. Collect data analyze in Excel for single point and IC50 determinations.

Single point assay–% inhibition at 10 mg/ml (% Inhibition=1–cpd.treated sample/untreated control). IC$_{50}$ determinations–done on compounds from single point assays with >80% inhibition. Typically Raf-1 assay is run at compound concentrations from 10 µM to 1 nM in half log dilutions. (% inhibition is determined for each compound concentration). The results obtained for representative compounds of this invention are listed in Table 2.

Cell Based Screen for Inhibitors of Raf Kinase.

Materials

Cell Lines: Human adenocarcinoma cell line LoVo which is known to be growth inhibited by low nM concentrations of a reference standard inhibitor of Ras and human adenocarcinoma cell line CaCo-2, which is known to be growth resistant to the same reference compound.

Cell Media: RPMI 1640 with 10% Fetal Bovine Serum supplemented with L-glutamine and Pennicilin/Streptomycin.

Compounds: Supplied usually as a 10 mM stock in 100% DMSO.

Normal Saline: 150 mM NaCl

Trichloroacetic Acid (TCA): 50% (w/v) in water

Sulforhodamine B (SRB): 0.4% (w/v) in 1% Acetic Acid

Tris Base: 10 mM in water

Methods

Cells are plated at 2000 cells per well for cell line LoVo and 1500 cells for cell line CaCo-2 in 96 well plates. Cells are plated in media (200 µl) and allowed to adhere overnight at 37° C. At 24 hours post plating, compounds are added directly at a volume of 0.5 µl. For the qualitative screen (compounds screened at 25 µM) compound is added directly to cells. For the quantitative screen, compound is first diluted in DMSO to generate concentrations of compound or reference standard of 1, 5, 10 and 25 □M. It is advisable to make the dilutions in an identical 96 well plate so that compounds can be added using a multichannel micropipettor set at 0.5 µl. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 µl of normal saline is then added to each well using an 8 well multichannel pipettor, followed by the careful addition of 50 µl of 50% TCA The plates are then incubated for 2 hours at 4° C., after which the supernatant is removed using the same technique as above and the plated washed twice with 200 µl water. The plates are then air dried and 50 µl of SRB stock solution is carefully added so that the entire bottom of each well is covered. This again can be used using an 8 well multichannel pipettor. The SRB is incubated with fixed cells for 15 minutes at room temperature after which the SRB is removed with the manifold as described above and the plates washed twice with 350 µl of 1% acetic acid per well each time. The plates are then air dried after which the bound SRB is released from protein by the addition of 200 µl of Tris base. Resolubilizing the SRB is aided by placing the plates on a rotator for 15–30 minutes.

The absorbance of each well is determined at 550 or 562 nm using a microtiter plate reader.

Each compound or dilution thereof is performed in triplicate. Outliers are identified by visual inspection of the data. Each plate should have a "0" control (vehicle only). Qualitative screen: To calculate % inhibition of a compound at 25 µM, the following formula is used: 1−(experimental absorbance @25 µM compound/"0" control absorbance)×100=% inhibition at 25 µM. Compounds having >50% inhibition at 25 µM are placed in the quantitative assay.

Quantitative Assay: A standard curve is constructed by plotting the concentration of compound against the average absorbance calculated at that concentration. A curve is plotted and the concentration at which the curve passes through the 50% the absorbance mark seen in the "0" control well is the $IC_{50}$ calculated for that compound. Multiple entries for a given compound indicate that it is tested multiple times. The results obtained for representative compounds of this invention are listed in Table 5.

TABLE 5

| Example | raf $IC_{50}$ µM | LoVo $IC_{50}$ µM | BxPC3 $IC_{50}$ µM | LnCAP $IC_{50}$ µM | CaCo-2 $IC_{50}$ µM |
|---|---|---|---|---|---|
| 3 | 0.09 | | | | |
| 39 | 0.9 | | | | |
| 40 | 0.7 | | | | |
| 44 | 0.009 | 0.85 (a) | | | 9.2 (a) |
| 124 | 0.13 | | | | |
| 129 | 0.3 | | | | |
| 149 | 0.004 | 0.006 (c) | 0.037 (b) | 0.053 (b) | 0.9 (c) |
| 151 | 0.007 | 0.0085 | 0.04 | 0.012 | 0.7 |
| 152 | 0.008 | 0.029 | 0.04 | 0.032 | >1 |
| 153 | 0.012 | 0.0094 | 0.038 | 0.019 | >1 |
| 154 | 0.008 | 0.043 | 0.04 | | >1 |
| 174 | >10 | 0.44 | | | 4 |
| 176 | 2.995 | 3.5 | | | 10 |
| 213 | 0.027 | 0.3 | | | 1.4 |
| 214 | 0.31 | 0.25 | | | 8 |
| 217 | >10 | 0.48 | | | 4.8 |
| 218 | 0.66 | 0.43 | | | 6 |

(a) Average of two runs
(b) Average of three runs
(c) Average of five runs

The results shown in tables 1, 2, 3, 4 and 5 demonstrate that the compounds of this Invention are potent inhibitors of protein kinases, and are useful as described above.

The compounds of this invention may be formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

The preparation of representative examples of the compounds of this invention is described below.

EXAMPLE 1

4-Oxo-1,4-dihydrobenzo[g]quinoline-3-carbonitrile

A suspension of 5.6 g (30 mmol) of 3-amino-2-napthoic acid in 30 mL of N,N-dimethylformamide dimethyl acetal is refluxed for 6 hours. Removal of the solvent yields 7.06 g (86.4%) of methyl 3-{[(dimethylamino)methylidene] amino}-2-naphthoate as a dark oil residue. To a solution of 20.8 mL (52 mmol) of n-butyllithium (2.5M in hexane) in 18 mL of tetrahydrofuran (THF) is added dropwise a solution of 5.97 mL (114 mmol) of acetonitrile in 100 mL of THF at −78° C. After completion of addition, the suspension is stirred for 15 minutes. To this is added 7.02 g (26 mmol) of 3-{[(dimethylamino)methylidene]amino}-2-naphthoate in 50 mL of THF dropwise. The resulting reaction mixture is stirred at −78° C. for 1 hour. Then 7.8 g (130 mmol) of acetic acid is added dropwise. The reaction mixture is warmed up to room temperature and diluted with water. The precipitate is collected by filtration and washed with water and ethyl acetate. After drying in vacuo, this yields 3.80 g (67%) of the product as a yellow solid, mp>260° C.

$^1$HNMR(DMSO-$d_6$): δ 7.58 (t, J=6.8, 1H); 7.68 (t, J=6.8, 1H); 8.09 (d, J=8.2, 1H); 8.14 (s, 1H); 8.23 (d, 1H); 8.80 (s, 1H); 8.85 (s, 1); 12.85 (bs, 1H). MS(ES, positive ion mode): m/z calcd for $C_{14}H_8N_2O$: 220.23, found: 221.2 (M+H)$^+$. Analysis for $C_{14}H_8N_2O.0.15H_2O$ Calcd: C 75.42; H 3.75; N 12.56 Found: C 75.38; H 3.68; N 12.52.

EXAMPLE 2

4-Chlorobenzo[g]quinoline-3-carbonitrile

A reaction mixture of 3.5 g (16 mmol) of 4-oxo-1,4-dihydrobenzo[g]quinoline-3-carbonitrile in 35 mL of phosphorus oxychloride and 22 drops of N,N-dimethylformamide (DMF) is heated at 100–110° C. for 5 hours. After cooling, the mixture is concentrated to dryness in vacuo to give a dark residue. The residue is partitioned between methylene chloride and ice-cooled saturated aqueous sodium carbonate solution. The organic layer is washed with ice-cooled brine and dried over sodium sulfate. The organic solvent is passed through a short column of silica gel, and further eluted with additional methylene chloride. Removal of the solvent yields 1.89 g (49.5%) of the product as a bright yellow solid, mp 253–255° C.

$^1$HNMR(DMSO-$d_6$): δ 7.77 (m, 2H); 8.33 (d, J=9.3, 1H); 8.39 (d, J=9.5, 1H); 8.91 (s, 1H); 9.08 (s, 1H); 9.18 (s, 1H). MS (ES, positive ion mode): m/z calcd for $C_{14}H_7ClN_2$: 238.68, found: 239.2 (M+H)$^+$. Analysis for $C_{14}H_7ClN_2$ Calcd: C 70.45; H 2.96; N 11.74 Found: C 70.16; H 3.04; N 11.55.

EXAMPLE 3

4-(4-Phenoxyanilino)benzo[g]quinoline-3-carbonitrile

A reaction mixture of 141.8 mg (0.59 mmol) of 4-chlorobenzo[g]quinoline-3-carbonitrile, 111.1 mg (0.60 mmol) of 4-phenoxyaniline and 57.8 mg (0.50 mmol) of pyridine hydrochloride in 8 ml of 2-ethoxyethanol is heated at 110–120° C. for 1 hour. After cooling, the mixture is diluted with water and made basic by addition of 125.0 mg (1.18 mmol) of sodium carbonate. The precipitate is collected by filtration and washed with water. Drying in vacuo yields the crude product. The crude product is purified by chromatography, eluting with a methylene chloride/methanol gradient from 100:0 to 86:14, to provide 167.8 mg (73.4%) of the pure product as a yellow solid, mp 250–251° C.

$^1$HNMR( )DMSO-$d_6$): δ 7.05 (s, 1H); 7.08 (s, 1H); 7.14 (m, 3H); 7.43 (m, 4H); 7.66 (m, 2H); 8.11 (d, J=8.1, 1H); 8.19 (d, J=7.8, 1H); 8.55 (d, 2H); 9.24 (s, 1H); 10.22 (bs, 1H). MS(ES, positive ion mode): m/z calcd for $C_{26}H_{17}N_3O$: 387.44, found: 388.2 (M+H)$^+$. Analysis for $C_{26}H_{17}N_3O.0.2H_2O$ Calcd: C 79.86; H 4.48; N 10.74 Found: C 79.87; H 4.44; N 10.70.

EXAMPLE 4

4-(3-Chloro-4-fluoroanilino)benzo[g]quinoline-3-carbonitrile

Following the procedure of Example 3, the reaction mixture of 141.8 mg (0.60 mmol) of 4-chlorobenzo[g] quinoline-3-carbonitrile, 87.3 mg (0.60 mmol) of 3-chloro-4-fluoroaniline and 57.8 mg (0.50 mmol) of pyridine hydrochloride in 8.0 mL of 2-ethoxyethanol is heated at 110–120° C. for 1 hour to yield 162.5 mg (77.9%) of the product as a bright yellow solid, mp 257–259° C.

$^1$HNMR(DMSO-$d_6$): δ 7.51 (m, 2H); 7.67 (m, 2H); 8.13 (d, J=8.1, 1H); 8.20 (d, J=8.1, 1H); 8.61 (s, 2H); 9.19 (s, 1H); 10.24 (s, 11); 12.25 (bs, 1H). MS(ES, positive ion mode): m/z calcd for $C_{20}H_{11}ClFN_3$: 347.78, found: 348.3 (M+H)$^+$. Analysis for $C_{20}H_{11}ClFN_3.0.2H_2O$ Calcd: C 68.36; H 3.27; N 11.96 Found: C 68.60; H 3.29; N 11.70.

EXAMPLE 5

4-(4-Chloro-5-methoxy-2-methylanilino)benzo[g] quinoline-3-carbonitrile

Following the procedure of Example 3, the reaction mixture of 141.8 mg (0.60 mmol) of 4-chlorobenzo[g] quinoline-3-carbonitrile, 102.9 mg (0.60 mmol) of 4-chloro-5-methoxy-2-methylaniline (can be prepared by the procedure disclosed in WO 85/01939, which is hereby incorporated by reference) and 57.8 mg (0.50 mmol) of pyridine hydrochloride in 8.0 mL of 2-ethoxyethanol is heated at 130–135° C. for 1.5 hours to yield the crude product. Purification of the crude product on preparative TLC (developing solvent: 95:5 methylene chloride/methanol) yields 159.3 mg (72.2%) of the pure product as a yellow solid, mp 195–197° C.

$^1$HNMR (DMSO-$d_6$): δ 2.16 (s, 3H); 3.82 (s, 3H); 7.22 (s, 1H); 7.46 (s, 1H); 7.67 (m, 2H); 8.12 (d, J=8.1, 1H); 8.19 (d, J=8.1, 1H); 8.54 (d, J=14.7, 2H); 9.29 (s, 1H); 10.11 (s, 1H). MS(ES, positive ion mode): m/z calcd for $C_{22}H_{16}ClN_3O$: 373.84, found: 374.3 (M+H)$^+$. Analysis for $C_{22}H_{16}ClN_3O.0.55H_2O$ Calcd: C 68.86; H 4.49; N 10.95 Found C 68.70; H 4.64; N 10.41.

EXAMPLE 6

6,7-Dimethoxy-3-(methoxycarbonyl)-2-naphthoic acid

To 20 mL of methanol at room temperature is added 200 mg (5.0 mmol) of 60% sodium hydride in mineral oil. The solution is stirred for 5 minutes, and then added to a suspension of 516 mg (2.0 mmol) of 6,7-dimethoxy-2,3- naphthalenedicarboxylic anhydride (McOmie, John F. W.; Perry, David H. Synthesis (1973), Issue 7, 416–417) in 30 mL of methanol. The mixture is stirred at room temperature for 10 minutes, and concentrated. The residue is partitioned between ethyl acetate and saturated sodium carbonate solution. The aqueous layer is separated and neutralized with concentrated hydrochloric acid to pH 1. The product is extracted with ethyl acetate, dried over magnesium sulfate, and concentrated in vacuo. The waxy solid thus obtained is washed with ethyl acetate to yield the product as 406 mg (70%) of an off-white solid, mp 181–183° C.

$^1$HNMR (DMSO-$d_6$): δ 13.10 (s, 1H), 8.21 (s, 1H), 8.07 (s, 1H), 7.54 (s, 1H), 7.51 (s, 1H), 3.91 (s, 6H), 3.81 (s, 3H). MS(ES, positive ion mode): m/z calcd for $C_{15}H_{14}O_6$: 290.3, found: 291.3 (M+H)$^+$. Analysis for $C_{15}H_{14}O_6$.0.1H$_2$O Calcd: C 61.12; H 4.96 Found: C 61.03; H 4.99.

EXAMPLE 7

3-Amino-6,7-dimethoxy-2-naphthalene-2-carboxylic acid methyl ester

A mixture of 290 mg (1.0 mmol) of 6,7-dimethoxy-3-(methoxycarbonyl)-2-naphthoic acid, 1.0 g of diphenylphosphoryl azide, and 1 mL of triethylamine in 10 mL of toluene is refluxed for 15 minutes and added dropwise to a solution of 80 mL of acetone and 10 mL of water at 80° C. The mixture is heated at 80° C. for 1 hour and concentrated. The residue is partitioned between ethyl acetate and saturated sodium chloride solution. The organic layer is dried over magnesium sulfate and concentrated. The residue is chromatographed over silica gel, eluted with 1:1 ethyl acetate/hexanes to yield 105 mg (40%) of a yellow solid, mp 125–127° C.

$^1$HNMR (DMSO): δ 8.25 (s, 1H), 7.19 (s, 1H), 6.91 (s, 2H), 6.25 (brs, 2H), 3.85 (s, 3H), 3.84 (s, 3H), 3.79 (s, 3H). MS(ES, positive ion mode): nm/z calcd for $C_{14}H_{15}NO_4$: 261.3, found: 262.3 (M+H)$^+$. Analysis for $C_{14}H_{15}NO_4$ Calcd: C 64.36; H 5.79; N 5.36. Found: C 64.08; H 5.64; N 5.39.

EXAMPLE 8

3-(Dimethylamino-methyleneamino)-6,7-dimethoxy-naphthalene-2-carboxylic acid methyl ester A suspension of 1.95 g (7.46 mmol) of 3-amino-6,7-dimethoxy-2-naphthalene-2-carboxylic acid methyl ester in 40 mL of N,N-dimethylformamide dimethyl acetal is refluxed for 1.5 hours. Removal of the solvent yields a solid residue which is washed with diethyl ether and ethyl acetate, affording 1.99 g (83.8%) of the product as an off-white solid, mp 180–182° C.

$^1$HNMR (DMSO-$d_6$): δ 3.00 (bs, 6H); 3.77 (s, 3H); 3.84 (s, 3H); 3.86 (s, 3H); 7.12 (s, 1H); 7.17 (s, 1H); 7.29 (s, 1H); 7.65 (s, 1); 7.93(s, 1H). MS(ES, positive ion mode): m/z calcd for $C_{17}H_{20}N_2O_4$: 316.36, found: 317.1 (M+H)$^+$. Analysis for $C_{17}H_{20}N_2O_4$ Calcd: C 64.54; H 6.37; N 8.86 Found: C 64.37; H 6.31; N 8.74.

EXAMPLE 9

7,8-Dimethoxy-4-oxo-1,4-dihydrobenzo[g]quinoline-3-carbonitrile

To a solution of 2.6 mL (6.3 mmol) of n-butyllithium (2.5M in hexane) in 2.0 ml of THF is added dropwise a solution of 0.36 mL (6.9 mmol) of acetonitrile in 6 mL of THF at –78° C. After completion of addition, the suspension is stirred for 15 minutes. To this is added 496.7 mg (1.57 mmol) of 3-(dimethylaminomethyleneamino)-6,7-dimethoxy-naphthalene-2-carboxylic acid methyl ester in 15 mL of THF dropwise. The resulting reaction mixture is stirred at –78° C. for 1.5 hours. Then 942.8 mg (15.7 mmol) of acetic acid is added dropwise. The reaction mixture is warmed to room temperature and is diluted with water. The precipitate is collected by filtration and washed with water and methanol. After drying in vacuo, this yields 406.0 mg (92.3%) of the product as a light brown solid, mp>265° C.

$^1$HNMR (DMSO-$d_6$): δ 3.91 (s, 31); 3.95 (s, 3H); 7.45 (s, 1H); 7.59 (s, 1H); 7.94 (s, 1H); 8.62 (s, 1H); 8.70 (s, 1H); 12.75 (bs,1H). MS(ES, positive ion mode): m/z calcd for $C_{16}H_{12}N_2O_3$: 280.28, found: 279.3 (M+H)$^+$. Analysis for $C_{16}H_{12}N_2O_3$.0.75H$_2$O Calcd: C 65.41; H 4.63; N 9.53 Found: C 65.29; H 4.43; N 9.40.

EXAMPLE 10

4-Chloro-7,8-dimethoxybenzo[g]quinoline-3-carbonitrile

A mixture of 356.2 mg (1.3 mmol) of 7,8-dimethoxy-4-oxo-1,4-dihydrobenzo[g]quinoline-3-carbonitrile in 5 mL of phosphorus oxychloride and 4 drops of DMF is heated at 100–110° C. for 4.5 hours. After cooling, the mixture is concentrated to dryness in vacuo to give a dark residue. The residue is partitioned between methylene chloride and ice-cooled saturated aqueous sodium carbonate solution. The organic layer is washed with cooled brine and dried over sodium sulfate. The organic solvent is passed through a short column of silica gel, and the column is first eluted with additional methylene chloride, then a 99:1 methylene chloride/ethyl acetate solution. Removal of the solvent yields 187.0 mg (49.4%) of the product as a bright yellow solid, mp>265° C.

$^1$HNMR (DMSO-$d_6$): δ 3.99 (s, 3H); 4.00 (s, 3H); 7.65 (s, 1H); 7.74 (s, 1H); 8.63 (s, 1H); 8.80 (s, 1H); 9.06 (s, 1H). MS(ES, positive ion mode): m/z calcd for $C_{16}H_{11}ClN_2O_2$: 298.73, found: 299.2 (M+H)$^+$. Analysis for $C_{16}H_{11}ClN_2O_2$.0.5H$_2$O Calcd: C 62.44; H 3.93; N 9.10 Found: C 62.41; H 3.81; N 8.91.

EXAMPLE 11

7,8-Dimethoxy-4-(4-phenoxyanilino)benzo[g]quinoline-3-carbonitrile

A mixture of 75.5 mg (0.25 mmol) of 4-chloro-7,8-dimethoxybenzo[g]quinoline-3-carbonitrile, 56.2 mg (0.30 mmol) of 4-phenoxyaniline and 28.9 mg (0.25 mmol) of pyridine hydrochloride in 5 mL of 2-ethoxyethanol is heated at 120–125° C. for 2 hours. After cooling, the mixture is diluted with water and neutralized by the addition of 53.0 mg (0.5 mmol) of sodium carbonate. The precipitate is collected by filtration and washed with water, diethyl ether and methanol. Drying in vacuo yields 83.2 mg (63.5%) of the product as a yellow solid, mp>265° C.

$^1$HNMR (DMSO-$d_6$): δ 4.00 (s, 3H); 4.02 (s, 3H); 7.07–7.20 (m, 51); 7.36 (s, 1H); 7.42 (dd, J=8.34, J=11.13, 2H); 7.53 (s, 1H); 7.56 (s, 1H); 7.65 (s, 1H); 8.37 (s, 1H); 9.01 (s, 1H); 9.27 (s, 1H); 11.50 (bs, 1H). MS(ES, positive ion mode): m/z calcd for $C_{28}H_{21}N_3O_3$: 447.49, found: 448.3 (M+H)$^+$. Analysis for $C_{28}H_{21}N_3O_3$.2 HCl Calcd: C 64.62; H 4.46; N 8.07 Found: C 64.55; H 4.75; N 7.95.

EXAMPLE 12

4-(4-Chloro-5-methoxy-2-methylanilino)-7,8-dimethoxybenzo[g]quinoline-3-carbonitrile Following the procedure of Example 11, a mixture of 75.8 mg (0.25 mmol) of 4-chloro-7,8-dimethoxybenzo[g]quinoline-3-carbonitrile, 51.5 mg (0.30 mmol) of 4-chloro-5-methoxy-2-methylaniline and 28.9 mg (0.25 mmol) of pyridine hydrochloride in 5.0 mL of 2-ethoxyethanol is heated at 120–130° C. for 2 hours to yield the crude product. Purification of the crude product on preparative TLC (developing solvent: 95:5 methylene chloride/methanol) yields 88.7 mg (82.1%) of the pure product as a yellow solid, mp 171–173° C.

$^1$HNMR (DMSO-$d_6$): δ 2.13 (s, 3H); 3.80 (s, 31); 3.96 (s, 3H); 3.97 (s, 3H) 7.15 (s, 1H); 7.33 (s, 1H); 7.41 (s, 11); 7.52 (s, 11); 8.32 (s, 1H); 8.43 (s, 1H); 9.01 (s, 1H); 9.94 (bs, 1H).
MS(ES, positive ion mode): m/z cacld for $C_{24}H_{20}ClN_3O_3$: 433.89, found: 434.3 (M+H)$^+$. Analysis for $C_{24}H_{20}ClN_3O_3$ Calcd: C 66.44; H 4.65; N 9.68 Found: C 65.06; H 4.80; N 9.46.

EXAMPLE 13

4-(3-Chloro-4-fluoroanilino)-7,8-dimethoxybenzo[g]quinoline-3-carbonitrile

Following the procedure of Example 11, a mixture of 149.4 mg (0.50 mmol) of 4-chloro-7,8-dimethoxybenzo[g]quinoline-3-carbonitrile, 87.3 mg (0.60 mmol) of 3-chloro-4-fluoroaniline and 57.8 mg (0.50 mmol) of pyridine hydrochloride in 7.0 mL of 2-ethoxyethanol is heated at 100–110° C. for 1.0 hour to yield 184.4 mg (83.0%) of the product as a yellow solid, mp>280° C.

$^1$HNMR (DMSO-$d_6$): δ 3.99 (s, 31); 4.02 (s, 3H); 7.36 (s, 1H); 7.58 (m, 2H); 7.65 (s, 1H); 7.85 (d, J=4.5, 1H); 8.40 (s, 11); 9.05 (s, 11); 9.30 (s, 1H); 11.70 (bs, 1H). MS(ES, positive ion mode): m/z calcd for $C_{22}H_{15}ClFN_3O_2$: 407.83, found: 408.2 (M+H)$^+$. Analysis for $C_{22}H_{15}ClFN_3O_2.1HCl.0.5H_2O$ Calcd: C58.29; H 3.78; N 9.27 Found: C 58.05; H 3.94; N 9.10.

EXAMPLE 14

4-(2,4-Dichloroanilino)-7,8-dimethoxybenzo[g]quinoline-3-carbonitrile

A mixture of 178.2 mg (1.1 mmol) of 2,4-dichloroaniline and 44.0 mg (1.1 mmol) of sodium hydride in anhydrous DMF is stirred at room temperature for 0.5 hours. To the mixture is added 149.4 mg (0.5 mmol) of 4-chloro-7,8-dimethoxybenzo[g]quinoline-3-carbonitrile. The resulting mixture is heated at 50–60° C. for 1 hour. After cooling, the mixture is diluted with water and extracted with ethyl acetate. The organic phase is washed with brine and dried over sodium sulfate. Removal of the solvent yields a dark residue which is purified on preparative TLC (developing solvent: 97:3 methylene chloride/methanol), giving a yellow foam. Trituration of the foam with diethyl ether containing several drops of methanol yields 126.1 mg (59.5%) of the product as a yellow solid, mp 271–273° C.

$^1$HNMR (DMSO-$d_6$): δ 3.95 (s, 6H); 7.54 (m, 5H); 8.34 (s, 1H); 8.84 (s, 1H); 10.05 (bs 1H); 12.40 (bs, 1H). MS(ES, positive ion mode): m/z calcd for $C_{22}H_{15}Cl_2N_3O_2$: 424.3, found: 426.1 (+H)$^+$. Analysis for $C_{22}H_{15}Cl_2N_3O_2.0.6H_2O$ Calcd: C 60.73; H 3.75; N 9.66 Found: C 60.69; H 3.70; N 9.51.

EXAMPLE 15

4-(2,4-Dichloroanilino)-7,8-dihydroxybenzo[g]quinoline-3-carbonitrile

A mixture of 252.6 mg (0.6 mmol) of 4-(2,4-dichloroanilino)-7,8-dimethoxybenzo[g]quinoline-3-carbonitrile and 5.0 g of pyridine hydrochloride is heated at 215–220° C. for 40 minutes under nitrogen. After cooling, the mixture is neutralized with 3% ammonium hydroxide aqueous solution and stirred for 30 minutes. The precipitate is collected, washed with water and dried in vacuo. The crude product is passed through a short column of silica gel, eluting with a gradient of methylene chloride/methanol 90:10 to 50:50, to provide 122.8 mg (51.7%) of the product as a brown solid, mp>260° C.

$^1$HNMR (DMSO-$d_6$+TFA): δ 7.44 (d, J=9, 2H); 7.68 (dd, J=3, J=6, 1H); 7.79 (d, J=6, 1H); 7.95, (s 1H); 8.23 (s, 11); 9.15 (s, 1H); 9.17 (s, 1H). MS (ES, positive ion mode): m/z calcd for $C_{20}H_{11}Cl_2N_3O_2$: 396.2, found: (M+H)$^+$ 396.1. Analysis for $C_{20}H_{11}Cl_2N_3O_2.0.6H_2O$ Calcd: C 59.02; H 3.02; N 10.32 Found: C 59.10; H 3.21; N 10.12.

EXAMPLE 16

7-Chloro-6-nitro-4-oxo-1,4-dihydroquinoline-3-carboxylic acid

A mixture of 12.0 g (40.5 mmol) of 7-chloro-6-nitro-4-oxo-1,4-dihydroquinoline-3-carboxylic acid ethyl ester (J. Med. Chem. 23, 1358 (1980)) and 60.0 mL of 2.5 N sodium hydroxide in 160.0 mL of ethanol is heated at reflux temperature for 1.5 hours. After allowing the reaction mixture to cool to room temperature, it is further cooled in an ice bath, brought to pH 4 with 4.0 N hydrochloric acid and stirred for 0.5 hour. The solid is collected by filtration, washed with water and dried in vacuo to yield 10.1 g of 7-chloro-6-nitro-4-oxo-1,4-dihydroquinoline-3-carboxylic acid as a tan solid, mp 294–297° C.

$^1$HNMR (DMSO-$d_6$): δ 9.71(s, 1H); 8.70 (s, 1H); 8.09 (s, 1H). MS (ES, negative mode): m/z calcd for $C_{10}H_5ClN_2O_5$: 268, found: 266.8 (M–H)$^-$. Analysis for $C_{10}H_5ClN_2O_5$ Calcd: C:44.72; H:1.88; N:10.43 Found: C:44.38; H:2.05; N:10.22.

EXAMPLE 17

7-Chloro-6-nitro-4-oxo-1,4-dihydro-quinoline-3-carboxylic acid amide

A mixture of 10.1 g (37.61 mmol) of 7-chloro-6-nitro-4-oxo-1,4-dihydroquinoline-3-carboxylic acid and 14.0 g (86.34 mmol) of 1–1'-carbonyldamidazole in 110 mL of N,N-dimethylformamide is heated at 60° C. for 50 minutes under nitrogen. The mixture is cooled in an ice bath and ammonia gas is bubbled through the solution for 7 minutes. After further stirring for 0.5 hours, the reaction mixture is poured on to ice. The solid is collected by filtration, washed with water and dried to yield 9.75 g of yellow solid. A 0.17 g sample is purified by silica gel chromatography utilizing a gradient of methylene chloride/methanol (98:2 to 92:8) to yield 0.12 g of 7-chloro-6-nitro-4-oxo-1,4-dihydroquinoline-3-carboxylic acid amide as beige solid, mp 298–300° C.

$^1$HNMR (DMSO-$d_6$): δ 13.0 (br s, 1H); 8.96 (d, 1H, J=3.3 Hz); 8.81 (s, 1H); 8.74 (s, 1H); 7.97 (s, 1H); 7.65 (d, 1H, J=3.6 Hz). MS (ES, positive mode): m/z calcd for $C_{10}H_6ClN_3O_4$: 267, found 268 (M+H)$^+$. Analysis for $C_{10}H_6ClN_3O_4.0.3H_2O$ Calcd: C:43.98; H:2.44; N:15.39 Found: C:44.13; H:2.53; N:14.99.

EXAMPLE 18

7-Chloro-6-nitro-4-oxo-1,4-dihydro-quinoline-3-carbonitrile

To a suspension of 9.58 g (35.77 mmol) of 7-chloro-6-nitro-4-oxo-1,4-dihydro-quinoline-3-carboxylic acid amide in 60.0 mL of N,N-dimethylformamide is added 4.0 g (21.7 mmol) of cyanuric chloride and the resulting clear solution is stirred at room temperature for 0.5 hours under nitrogen. The mixture is heated at 50° C. for 10 minutes, stirred at room temperature for an extra 10 minutes and then poured on to ice. The solid is collected by filtration, washed with water and dried to yield 8.9 g of a brown solid. A 0.17 g sample is purified by silica gel chromatography utilizing a gradient of methylene chloride/methanol (97:3 to 95:5) to yield 0.12 g of 7-chloro-6-nitro-4-oxo-1,4-dihydroquinoline-3-carbonitrile as beige solid, mp>300° C.
$^1$HNMR (DMSO-$d_6$): δ 13.2 (bs, 1H); 8.91(s, 1H); 8.71 (s, 1H); 7.88 (s, 1H). MS (ES, negative mode): m/z calcd for $C_{10}H_4ClN_3O_3$: 249, found: 248 (M−H)$^-$. Analysis for $C_{10}H_4ClN_3O_3.0.2H_2O$ Calcd: C:47.43; H:1.75; N:16.60 Found: C:47.70; H:1.96; N:16.34.

EXAMPLE 19

7-Chloro-6-nitro-4-oxo-1-{[2-(trimethylsilyl)ethoxy]methyl}-1,4-dihydro-3-quinolinecarbonitrile To a cold suspension of 1.67 g (41.75 mmol) of sodium hydride (60% in oil) in 70.0 mL of N,N-dimethylformamide is added 8.73 g (34.98 mmol) of 7-chloro-6-nitro-4-oxo-1, 4-dihydroquinoline-3-carbonitrile in portions over a period of 20 minutes under nitrogen. The resulting mixture is stirred at 5° C. for 20 minutes and then 7.5 mL (42.37 mmol) of 2-(trimethylsilyl)ethoxymethyl chloride is added dropwise. After stirring at 5° C. for 20 minutes, the mixture is poured on to ice. The solid is collected by filtration, washed with water and dried to yield 13.3 g of a brown solid. The solid is purified by silica gel chromatography, utilizing a gradient of methylene chloride/methanol (99.5:0.5 to 98:2) to yield 10.5 g of 7-chloro-6-nitro-4-oxo-1-{[2-(trimethylsilyl)methyl]-1,4-dihydro-3-quinolinecarbonitrile as white solid, mp 200–202° C.
$^1$HNMR (DMSO-$d_6$): δ 9.12(s, 1H); 8.74 (s, 1H); 8.27 (s, 1H); 5.71 (s, 2H); 3.63 (dd, 2H, J=5.2, 10.5 Hz);). 0.88 (dd, 2H, J=5.0, 8.1 Hz); 0.07 (s, 9H). MS (ES, positive mode): m/z calcd for $C_{16}H_{18}ClN_3O_4Si$: 379, found: 380 (M+H)$^+$. Analysis for $C_{16}H_{18}ClN_3O_4Si$ Calcd: C:50.59; H:4.78; N:11.06 Found: C:50.57; H:4.97; N:11.02.

EXAMPLE 20

6,7-Diamino-4-oxo-1-(2-trimethylsilanylethoxymethyl)-1,4-dihydro-quinoline-3-carbonitrile To a solution of 6.0 g (15.8 mmol) of 7-chloro-6-nitro-4-oxo-1-{[2-(trimethylsilyl)ethoxy]methyl}-1,4-dihydro-3-quinolinecarbonitrile in 120 mL of dimethyl sulfoxide is added 5.13 g (79.0 mmol) of sodium azide and the resulting mixture is stirred at room temperature for 3 hours. The mixture is then heated at 60° C. for 10 minutes, room temperature for 1 hour and then poured on to ice. The solid is collected by filtration, washed thoroughly with water and dried in vacuo to yield 6.1 g of 7-azido-6-nitro-4-oxo-1-{[2-(trimethylsilyl)ethoxy]methyl}-1,4-dihydro-3-quinolinecarbonitrile as a yellow solid.

A mixture of 6.1 g (15.8 mmol) of 7-azido-6-nitro-4-oxo-1-{[2-(trimethylsilyl) ethoxy]methyl}-1,4-dihydro-3-quinolinecarbonitrile, 1.2 g of 10% palladium on carbon in 80 mL of ethanol and 150 mL of tetrahydrofuran is reacted in a Parr shaker at 30 psi for 3 hours. The mixture is filtered through a pad of diatomaceous earth, washed with 700 mL of tetrahydrofuran and 300 mL of methanol. The filtrate is evaporated to yield 1.23 g of brown solid. The diatomaceous earth pad is further washed with 300 mL of N,N-dimethylformamide and the filtrate is poured on ice. The crude product is collected by filtration, washed with water and dried to yield 3.36 g of a brown solid. The combined solid (4.59 g) is used directly in the next step. A 0.15 g portion of sample is purified by silica gel chromatography utilizing a gradient of methylen chloride/methanol (99:1 to 96:4) to yield 0.1 g of 6,7-diamino-4-oxo-1-(2-trimethylsilanylethoxymethyl)-1,4-dihydro-quinoline-3-carbonitrile as a pink solid, mp>300° C.
$^1$HNMR (DMSO-$d_6$):δ 8.65 (s, 1H); 7.27 (s, 1H); 6.84 (s, 1H); 5.86 (s, 2H); 5.50 (s, 2H); 5.19 (s, 2H); 3.60 (t, 2H, J=5.1, 10.2 Hz);).0.88 (t, 2H, J=5.0, 8.4 Hz); 0.011 (s, 9H). MS (ES, positive mode): m/z calcd for $C_{16}H_{22}N_4O_2Si$: 330, found: 331 (M+H)$^+$. Analysis for $C_{16}H_{22}N_4O_2Si$ Calcd: C:58.15; H:6.71; N:16.95 Found: C:57.91; H:6.82; N: 16.75.

EXAMPLE 21

8-Oxo-5-{[2-(trimethylsilylethoxy]methyl}-5,8-dihydro[1,2,3]triazolo[4,5-g]quinoline-7-carbonitrile A 0.5 g portion of 6,7-diamino-4-oxo-1-([2-(trimethylsilyl)ethoxy]methyl)-1,4-dihydro-3-quinolinecarbonitrile (1.5 mmol) is dissolved in 130 mL of dioxane and 125 mL of 0.1 N hydrochloric acid and cooled in an ice bath. A solution of 0.11 g (1.6 mmol) of sodium nitrite in 5 mL of water is added in one portion and the mixture stirred at 0° C. for 45 minutes. Solids precipitated out of solution and are collected by filtration and washed with water to yield a brown solid. The solid is dissolved in 50 mL of 0.01 N sodium hydroxide and washed with 3×100 mL of methylene chloride. The aqueous layer is acidified to pH=5 and the solids collected by filtration and washed with water. After drying, 0.4 g of a brown solid is obtained that could be recrystallized from methanol to yield a tan needles, mp 249–251° C. with gas evolution.
$^1$HNMR (DMSO-$d_6$): δ 9.1(s, 1H); 8.78 (br s, 1H); 8.35 (br s, 1H); 5.78 (s, 2H); 3.64 (t, 2H, J=8.0 Hz); 0.87 (t, 2H, J=8.0 Hz). MS (ES, positive mode): m/z calcd for $C_{16}H_{19}N_5O_2Si$: 341, found: 342 (M+H)$^+$. Analysis for $C_{16}H_{19}N_5O_2Si$ Calcd: C:56.28; H:5.61; N:20.51 Found: C:56.14; H:5.54; N:20.41.

EXAMPLE 22

8-Oxo-5,8-dihydro[1,2,3]triazolo[4,5-g]quinoline-7-carbonitrile

A mixture of 0.357 g (1.04 mmol) of 8-oxo-5-{[2-(trimethylsilyl)ethoxy]methyl}-5,8-dihydro[1,2,3]triazolo[4,5-g]quinoline-7-carbonitrile and 0.35 g of imidazole (5.2 mmol) in 10 mL of formic acid is heated to 110° C. for 6 hours. The solution is cooled to room temperature and the volatiles are removed at reduced pressure. The residue is suspended in 20 mL of water, filtered and washed with water. After drying, 0.2 g of a brown solid is obtained, mp>300° C.

$^1$HNMR(DMSO-d$_6$):δ 9.1(s, 1H); 8.78 (br s, 1H); 8.35 (br s, 1H); 5.78 (s, 2H); 3.64 (t, 2H, J=8.0 Hz); 0.87 (t, 2H, J=8.0 Hz). MS (ES, negative mode): m/z calcd for C$_{10}$H$_5$N$_5$O: 211, found (M−H)$^-$210. Analysis for C$_{10}$H$_5$N$_5$O Calcd: C:56.28; H:5.61; N:20.51 Found: C:56.14; H:5.54; N:20.41.

EXAMPLE 23

8-Chloro[1,2,3]triazolo[4,5-g]quinoline-7-carbonitrile

A solution of 0.3 g of 8-oxo-5,8-dihydro[1,2,3]triazolo[4,5-g]quinoline-7-carbonitrile (1.4 mmol), is suspended in 10 mL of 2 M oxalyl chloride (in methylene chloride). One mL of DMF is added dropwise and the solution heated to reflux for 6 hours. The solution is cooled to room temperature and the volatiles are removed at reduced pressure. Ice water is added to the residue, and the solids are filtered and washed with water. After drying a brown solid, 0.2 g, is obtained. MS (ES, negative mode): m/z calcd for C$_{10}$H$_4$ClN$_5$: 229.6, found (M−H)$^-$ 228.2.

EXAMPLE 24

8-(3,4,5-trimethoxyanilino)[1,2,3]triazoto[4,5-g] quinoline-7-carbonitrile

A solution of 0.07 g of 8-chloro[1,2,3]triazolo[4,5-g] quinoline-7-carbonitrile (0.3 mmol), 0.035 g of pyridine hydrochloride (0.3 mmol), and 0.83 g of 3,4,5 trimethoxyaniline (0.45 mmol) are dissolved in 3 mL of 2-ethoxyethanol and heated to 110° C. for 3 hours. The solution is cooled to room temperature, filtered and the orange solids are washed with diethyl ether. This yields 0.07 of pure compound as the hydrochloride salt. This material could be recrystallized from methanol to afford yellow fine needles, mp 280° C. with decomposition.

$^1$HNMR (DMSO-d$_6$):δ 10.2 (br s, 1H); 9.4 (br s, 1H); 8.56 (s, 1H); 8.3 (br s, 1H); 6.7 (s, 2H); 3.78 (s, 6H); 37 (s, 3H). MS (ES, positive mode): m/z calcd for C$_{19}$H$_{16}$N$_6$O$_3$: 376, found: 377 (M+H)$^+$. Analysis for C$_{19}$H$_{16}$N$_6$O$_3$0.7 HCl.0.4 CH$_3$OH Calcd: C:56.19; H:4.45; N:20.27 Found: C:55.80; H:4.8; N:19.94.

EXAMPLE 25

4,7-Dichloro-6-nitro-3-quinolinecarbonitrile

A mixture of 1.18 g (4.74 mmol) of 7-chloro-6-nitro-4-oxo-1,4-dihydroquinoline-3-carbonitrile, 60 mL of 2M oxalyl chloride (in methylene chloride) and 25 drops of N,N-dimethylformamide is refluxed for 5.5 hours. After cooling, the mixture is concentrated to dryness and the residue is taken into ice water. The aqueous suspension is neutralized to pH 7 with an aqueous solution of saturated sodium carbonate. The solid is collected by filtration and washed with ice water, and then dried in vacuo, giving 1.20 g of the product as a light brown solid.

An analytical sample is obtained by column chromatography, eluting with a gradient of hexane/ethyl acetate (from 98:2 to 90:10) to afford a light yellow solid, mp 159–161° C.

$^1$HNMR (DMSO-d$_6$): δ 8.70 (s, 1H); 9.09 (s, 1H); 9.41 (s, 1H). MS (ES, negative ion mode): m/z calcd for C$_{10}$H$_3$Cl$_2$N$_3$O$_2$: 268.1, found: (M−H)$^-$ 267.0. Analysis for C$_{10}$H$_3$Cl$_2$N$_3$O$_2$.0.2 AcOEt Calcd: C 45.40, H 1.62; N 14.70 Found: C 45.76; H 1.68; N 14.59.

EXAMPLE 26

7-Chloro-4-(4-chloro-5-methoxy-2-methylanilino)-6-nitro-3-quinolinecarbonitrile

To a stirred suspension of 0.9 g (3.3 mmol) of 4,7-dichloro-6-nitro-3-quinolinecarbonitrile and pyridine hydrochloride (0.381 g, 3.3 mmol) in 2-ethoxyethanol (10 mL) under nitrogen, is added 0.634 g (3.69 mmol) of 4-chloro-5-methoxy-2-methylaniline (WO 8501939 A1). The reaction is stirred at 120° C. for 4 hours. The mixture is then cooled to room temperature and solid sodium bicarbonate is added until foaming subsided. Water is added to the reaction mixture (40 mL), which is subsequently extracted with 3×30 mL ethyl acetate. After combining the organic portions and drying with sodium sulfate, the solvents are removed in vacuo. The residue obtained is purified by flash chromatography, eluting with 99.5:0.5 methylene chloride/methanol. The solid obtained is recrystallized from hot ethyl acetate to afford 1.1 g of an orange crystalline solid, mp 217–219° C.

$^1$HNMR(DMSO-d$_6$): δ 10.27 (s, 1H); 9.42 (s, H); 8.68 (s, 1H); 8.23 (s, 1H); 7.43 (s, 1H); 7.18 (s, 1H); 3.79 (s, 3H); 2.13 (s, 3H). MS (ES, positive ion mode): m/z calcd for: C$_{18}$H$_{12}$Cl$_2$N$_4$O$_3$ 403.22, found: 403.2 (M+H)$^+$. Elemental analysis calculated for: C$_{18}$H$_{12}$ Cl$_2$N$_4$O$_3$.1CH$_3$CO$_2$C$_2$H$_5$ Calcd: C: 53.77; H: 4.07; N: 11.39 Found: C: 53.79; H: 4.46; N: 11.40

EXAMPLE 27

67-Diamino-4-(4-chloro-5-methoxy-2-methylanilino)-3-quinolinecarbonitrile

To 1.1 g (2.7 mmol) of 7-chloro-4-(4-chloro-5-methoxy-2-methylanilino)-6-nitro-3-quinolinecarbonitrile in 5 mL of anhydrous dimethyl sulfoxide (DMSO) is added 1.77 g (27 mmol) of sodium azide under a flow of nitrogen. The mixture is stirred at 55° C. for 3 hours. The reaction is cooled to room temperature and poured onto 30 g of crushed ice. This mixture is stirred for 30 minutes and the suspended solid collected by filtration. After drying, a 1 g portion of 7-azido-4-(4-chloro-5-methoxy-2-methylanilino)-6-nitro-3-quinolinecarbonitrile is obtained as a dark solid. The solid is dissolved in a 1:1 mixture of ethanol/tetrahydrofuran (50 mL) and to this is added 200 mg of 10% palladium on carbon under a flow of nitrogen. After hydrogenation of the mixture for 1.5 hours using a Parr shaker at 40 psi, the crude product is filtered through diatomaceous earth and the filtrate evaporated in vacuo. The residue obtained is purified by flash chromatography, eluting with 85:15 methylene chloride/methanol to provide a 0.638 g of a brown solid, mp 232–235° C.

$^1$HNMR(DMSO-d$_6$): δ 8.72 (s, 1H); 8.122 (s, 1H); 7.31 (s, 1H); 7.23 (s, 11); 6.90 (s, 1H); 6.83 (s, 1H); 5.76 (s, 2H); 5.20 (s, 2H); 3.73 (s, 3H); 2.07 (s, 3H). MS (positive ion mode): m/z calcd for C$_{18}$H$_{16}$ClN$_5$O: 353.81, found: 354.2 (M−H)$^-$. Elemental analysis calculated for: C$_{18}$H$_{16}$ClN$_5$O.1.5H$_2$O Calcd: C: 56.76; H: 5.04; N: 17.36 Found: C: 56.82; H: 5.04; N: 17.54.

EXAMPLE 28

9-(4-Chloro-5-methoxy-2-methylanilino)pyrido[2,3-quinoxaline-8-carbonitrile

A mixture of 0.120 g (0.34 mmol) of 6,7-diamino-4-(4-chloro-5-methoxy-2-methylanilino)-3-quinolinecarbonitrile and 0.408 g of 1,4-dioxane-2,3-diol (3.4 mmol) in 5 mL of anhydrous methanol is stirred at room temperature under a flow of nitrogen for 2 hours. The reaction is concentrated in vacuo and the residue purified by flash chromatography, eluting with 92:8 $CH_2Cl_2$/MeOH. This yields 0.108 g of a yellow solid, mp 158–160° C.

$^1$HNMR(DMSO-$d_6$): δ 10.34 (s, 1H); 9.53 (s, 1H); 9.11 (s, 1H); 9.08 (s, 1H); 8.64 (s, 1H); 8.61 (s, 1H); 7.46 (s, 2H); 7.26 (s, 2H); 3.82 (s, 3H); 2.27 (s, 3H). MS (positive ion mode): m/z calcd for $C_{20}H_{14}ClN_5O$: 375.8, found: 376.2 (M−H)$^-$. Analysis for $C_{20}H_{14}ClN_5O \cdot 0.2H_2O \cdot 0.8\ CH_3OH$ Calcd: C: 61.67; H:4.38; N:17.27 Found: C:61.35; H:4.11; N:16.88.

EXAMPLE 29

7-Chloro-4-(5-methoxy-2-methylanilino)-6-nitro-3-quinolinecarbonitrile

A mixture of 0.9 g (3.36 mmol) of 4,7-dichloro-6-nitro-3-quinolinecarbonitrile, 0.55 g (4.0 mmol) of 5-methoxy-2-methylaniline, 0.46 g (4.0 mmol) of pyridine hydrochloride in 10.0 mL of 2-ethoxyethanol is heated at 115° C. for 1 hour, cooled and poured into a saturated solution of sodium bicarbonate. The oil is extracted with methylene chloride, dried over anhydrous sodium sulfate and the solvent is evaporated to yield a foam. This is purified by silica gel chromatography, eluting with methylene chloride/methanol (99.5:0.5) to yield 0.77 g of 7-chloro-4-(5-methoxy-2-methylanilino)-6-nitro-3-quinolinecarbonitrile as a yellow solid, mp 180–182° C.

$^1$HNMR (DMSO-$d_6$): δ 10.25 (s, 1H); 9.43 (s 1H); 8.67 (s, 1H); 8.23 (s, 1H); 7.24 (d, 1H, J=8.7 Hz); 6.92 (d, 2H, J=7.5 Hz); 3.73 (s, 3H); 2.13 (s, 3H). MS (ES, positive mode): m/z calcd for $C_{18}H_{13}ClN_4O_3$: 368, found: 369 (M+H)$^+$. Analysis for $C_{18}H_{13}ClN_4O_3$ Calcd: C:58.63; H:3.55; N:15.19 Found: C:58.55; H:3.56; N:15.06.

EXAMPLE 30

6,7-Diamino-4-(5-methoxy-2-methylanilino)-3-quinolinecarbonitrile

A mixture of 0.7 g (1.9 mmol) of 7-chloro-4-(5-methoxy-2-methylanilino)-6-nitro-3-quinolinecarbonitrile and 0.62 g (9.5 mmol) of sodium azide is heated at 60° C. under nitrogen for 24 hours. The mixture is cooled and poured onto ice. The solid is collected by filtration, washed with water and dried to yield 0.65 g of 7-azido-4-(5-methoxy-2-methylanilino)-6-nitro-3-quinolinecarbonitrile as a yellow solid.

A mixture of 0.65 g (1.73 mmol) of 7-azido-4-(5-methoxy-2-methylanilino)-6-nitro-3-quinolinecarbonitrile and 0.12 g of 10% palladium on carbon in a 1:1 mixture of ethanol/tetrahydrofuran is shaken on Parr apparatus with hydrogen gas at 40 psi for 2 hours. The mixture is filtered through a pad of diatomaceous earth, washed with methanol and tetrahydrofuran, then dried to provide a dark solid. The crude product is purified by silica gel chromatography, utilizing a gradient of methylene chloride/methanol (95:5 to 88:12) to yield 0.4 g of 6,7-diamino-4-(5-methoxy-2-methylanilino)-3-quinolinecarbonitrile as a dark solid, mp 245° C. (dec).

$^1$HNMR (DMSO-$d_6$): δ 8.56 (s, 1H); 8.12 (s 1H); 7.22 (s, 1H); 7.13 (d, 1H, J=8.5 Hz); 6.91 (s, 1H); 6.70 (d,d, 1H, J=2.6 Hz, 8.4 Hz), 6.55(d, 1H, J=2.6 Hz); 5.74 (s, 2H); 5.18 (s, 2H); 3.67 (s, 3H); 2.08 (s, 3H). MS (ES, positive mode): m/z calcd for $C_{18}H_{17}N_5O$: 319, found: 320 (M+H)$^+$. Analysis for $C_{18}H_{17}N_5O$ Calcd: C:65.83; H:5.53; N:21.33 Found: C:65.71; H:5.32; N:21.32.

EXAMPLE 31

8-(5-Methoxy-2-methylanilino)-2-{[2-(4-morpholinyl)ethyl]amino}imidazo [4,5-g]quinoline-7-carbonitrile A mixture of 0.1 g (0.3 mmol) of 6,7-diamino-4-(5-methoxy-2-methylanilino)-3-quinolinecarbonitrile and 0.11 g (0.62 mmol) of 2-(4-morpholino)ethylisothiocyanate in 0.3 mL of dioxane is heated at 100° C. for 2 hours under nitrogen. The mixture is cooled and solvent is evaporated to dryness to yield an oil consisting of N-[7-amino-3-cyano-4-(5-methoxy-2-methylanilino)-6-quinolinyl]-N-[2-(4-morpholinyl)-ethyl]thiourea and N-[6-amino-3-cyano-4-(5-methoxy-2-methylanilino)-7-quinolinyl]-N'-[2-(4-morpholinyl)ethyl]thiourea. The oil is dissolved in 3.0 mL of ethanol. To this is added 0.3 g of mercuric oxide and 20 mg of sulphur powder and the resulting mixture is heated at reflux temperature for 2 hours. The product mixture is filtered hot through diatomaceous earth, washed with methanol and solvent is evaporated to yield an oil. The oil is purified by silica gel chromatography, utilizing a gradient of methylene chloride/methanol (95:5 to 85:15) to yield 0.062 g of 8-(5-methoxy-2-methylanilino)-2-{[2-(4-morpholinyl)ethyl]amino}imidazo[4,5-g]quinoline-7-carbonitrile as a pink solid, mp 148–150° C. (shrinks at 140° C.).

$^1$HNMR (DMSO-$d_6$+trifluoroacetic acid): δ 9.17 (s, 1H); 8.72 (s 1H); 8.04 (s, 1H); 7.34 (d, 1H, J=8.37 Hz); 7.11–7.05 (m,2H); 4.02–3.91(m, 2H); 3.91–3.81 (m, 2H); 3.80 (s, 3H); 3.76–3.71 (m, 1H); 3.57–3.53 (m, 21); 3.44–3.33 (m, 4H); 3.21–3.19 (m, 1H); 2.21 (s, 3H). MS (ES, positive mode): m/z calcd for $C_{25}H_{27}N_7O_2$: 457, found: 458 (M+H)$^+$. Analysis for $C_{25}H_{27}N_7O_2 \cdot 2H_2O$ Calcd: C:60.83; H:6.33; N:19.87 Found: C:60.56; H:6.10; N: 19.70.

EXAMPLE 32

7-Chloro-6-nitro-4-(3,4,5-trimethoxyanilino)-3-quinolinecarbonitrile

A mixture of 500 mg (1.86 mmol) of 4,7-dichloro-6-nitro-3-quinolinecarbonitrile, 342.0 mg (1.86 mmol) of 3,4,5-trimethoxyaniline and 215.5 mg (1.86 mmol) of pyridine hydrochloride in 25 mL of 2-ethoxyethanol is heated at 100–110° C. for 1.5 hours. After cooling, the mire is diluted with water and neutralized with an aqueous solution of saturated sodium carbonate. The solid is collected by filtration and is washed with water. After drying in vacuo, this yields 621.0 mg (80.5%) of the product as a deep yellow solid.

An analytical sample is obtained by column chromatography, eluting with 5:95 methanol/methylene chloride. An orange solid is obtained, mp 215–217° C.

$^1$HNMR(DMSO-$d_6$): δ 3.69 (s, 31); 3.77 (s, 6H); 6.73 (s, 2H); 8.25 (s, 1H); 8.73 (s, 1H); 9.38 (s, 1H); 10.37 (bs, 1H). MS (ES, positive ion mode): m/z calcd for $C_{19}H_{15}ClN_4O_5$:

414.1, found: 415.2 (M+H)+. Analysis for C$_{19}$H$_{15}$ClN$_4$O$_5$ Calcd: C 55.02; H 3.64; N 13.51 Found: C 54.86; H 3.65; N 13.43.

EXAMPLE 33

2-{[2-(4-Morpholinyl)ethyl]amino}-8-(3,4,5-trimethoxyanilino)imidazo[4,5-g]quinoline-7-carbonitrile A mixture of 506.1 mg (1.2 mmol) of 7-chloro-6-nitro-4-(3,4,5-trimethoxyanilino)-3-quinolinecarbonitrile and 390.0 mg (6.0 mmol) of sodium azide in 10.0 mL of DMSO is heated at 40–50° C. for 5 hours, and then at room temperature for 15 hours. The mixture is poured into ice water and extracted with ethyl acetate. The organic phase is washed with brine and dried over sodium sulfate. Removal of the solvent yields 493.4 mg (97.7%) of 7-azido-6-nitro-4-(3,4,5-trimethoxyanilino)-3-quinolinecarbonitrile as a yellow solid which is used in the next reaction without further purification.

MS (ES, positive ion mode): m/z calcd for C$_{19}$H$_{15}$N$_7$O$_5$: 421.11, found: 422.4 (M+H)+.

A solution of 493.4 mg (1.17 mmol) of 7-azido-6-nitro-4-(3,4,5-trimethoxyanilino)-3-quinolinecarbonitrile in 15 mL of THF and 5 mL of ethanol is hydrogenated at 30 psi for 1 hour in the presence of 100.0 mg of 10% palladium-on-carbon. The catalyst is removed by filtration and the solvent removed in vacuo to give 422.1 mg (98.8%) of 6,7-diamino-4-(3,4,5-trimethoxyanilino)-3-quinolinecarbonitrile as a deep yellow solid which is used directly in the next step.

MS (ES, positive ion mode): m/z calcd for C$_{19}$H$_{19}$N$_5$O$_3$: 365.16, found: 366.3 (M+H)+.

A mixture of 0.15 g (0.41 mmol) of 6,7-diamino-4-(3,4,5-trimethoxyanilino)-3-quinolinecarbonitrile and 0.14 g (0.82 mmol) of 2-(4-morpholino)ethylisothiocyanate in 0.4 mL of tetrahydrofuran is heated at 100° C. for 1.5 hours under nitrogen. The mixture is cooled and purified by silica gel chromatography, utilizing a gradient of methylene chloride/methanol (97:3 to 85:15) to yield 0.038 g of 2-{[2-(4-morpholinyl)ethyl]amino}-8-(3,4,5-trimethoxyanilino)imidazo[4,5-g]quinoline-7-carbonitrile as a yellow solid, mp 175–178° C. (shrinks at 165° C.).

$^1$HNMR (DMSO-d$_6$+trifluoroacetic acid): δ 9.17 (s, 1H); 8.63 (s 1H); 7.98 (s, 1H); 6.89 (s, 2H); 3.96–3.94(m, 2H); 3.89–3.82 (m, 2H); 3.80 (s, 6H); 3.69 (s, 3H); 3.62 (m, 2H); 3.60 (m, 3H); 3.58–3.41 (m, 2H); 3.32–3.30 (m, 1H). MS (ES, positive mode): m/z calcd for C$_{26}$H$_{29}$N$_7$O$_4$: 503, found: 504 (M+H)+. Analysis for C$_{26}$H$_{29}$N$_7$O$_4$.2.6 CH$_3$OH Calcd: C:58.52; H:6.76; N:16.71 Found: C:58.40; H:6.03; N:16.35.

EXAMPLE 34

2-Amino-8-(4-phenoxyanilino)imidazo[4,5-g]quinoline-7-carbonitrile

To a stirred mixture of 0.5 g (1.5 mmol) of 6,7-diamino-4-oxo-1-{[2-(trimethylsilyl)ethoxy]methyl}-1,4-dihydro-3-quinolinecarbonitrile in 10 mL of anhydrous methanol is added 0.174 g (1.65 mmol) of cyanogen bromide at 0° C. The ice bath is then removed and the reaction stirred at room temperature under a flow of nitrogen. The reaction is placed in an oil bath and heated to 70° C. After two hours at that temperature, the oil bath is removed and another 0.174 g (1.65 mmol) of cyanogen bromide is added. The reaction is then stirred at 70° C. for 15 hours. At that point, TLC analysis showed that no starting material remained. The reaction is cooled down to room temperature and brought to pH 10 with aqueous ammonium hydroxide. After evaporation of the mixture in vacuo, the resulting residue is suspended in methanol. The resulting precipitate is collected by filtration and dried in a vacuum oven at 50° C. to yield 0.5 g of 2-amino-8-oxo-5-([2-(trimethylsilyl)ethoxy]methyl}-5,8-dihydroimidazo[4,5-g]quinoline-7-carbonitrile as an off-white solid.

To this solid (0.5 g, 1.4 mmole) in a round bottom flask is added 5 mL of formic acid and 0.57 g (8.4 mmole) of imidazole. This mixture is stirred at reflux temperature for 2 hours. The reaction is then reduced in vacuo and then neutralized with aqueous ammonium hydroxide. The resulting solid is collected by filtration, washed with water and dried in a vacuum oven at 50° C. to yield 0.3 g of 2-amino-8-oxo-5,8-dihydroimidazo[4,5-g]quinoline-7-carbonitrile as a yellow solid. To the above solid is added 10 mL of 2M oxalyl chloride (in methylene chloride) and 1 mL of DMF. The reaction mixture is stirred at reflux until the disappearance of starting material is observed by thin layer chromatography. The reaction is cooled to room temperature, concentrated in vacuo and neutralized with cold aqueous 1N NaOH. A precipitate formed, which is collected by filtration, washed with water and dried in a vacuum oven at 50° C. to yield 0.35 g of 2-amino-8-chloroimidazo[4,5-g]quinoline-7-carbonitrile as a yellow solid.

To a stirred mixture 0.150 g (0.5 mmol) of 2-amino-8-chloroimidazo[4,5-g]quinoline-7-carbonitrile in 5 mL of ethoxyethanol and 0.063 mg (0.55 mmol) pyridine hydrochloride, is added 0.102 g (0.55 mmol) of 4-phenoxyaniline under a positive flow of nitrogen. The reaction is heated to 120° C. and stirring is continued for 2 hours. Upon cooling, a solid precipitated out of solution. The solid is collected by filtration, washed with ethanol, then stirred with a solution of saturated solution sodium bicarbonate for 30 minutes. The resulting solid is filtered, washed with water and dried in a vacuum oven at 50° C. to yield 0.128 mg of a yellow solid, mp>300° C.

$^1$HNMR(DMSO-d$_6$): δ 9.18 (s, 1H); 8.66 (s, 1H); 7.96 (s, 1H); 7.54 (d, 2H, J=8.79 Hz); 7.42 (t, 2H, J=8.43), 7.21 (m, 3H), 7.11 (d, 2H=7.71). MS (positive ion mode): m/z calcd for C$_{23}$H$_{16}$N$_6$O: 392.419, found: 393.33 (M–H)+. Analysis for C$_{23}$H$_{16}$N$_6$O.1.7H$_2$O.1 HCl Calcd: C:60.08; H:4.48; N:17.25 Found: C:60.15; H:4.67; N:17.46.

EXAMPLE 35

8-Oxo-5,8-dihydroimidazo[4,5-g]quinoline-7-carbonitrile

A mixture of 4.41 g (13.36 mmol) of 6,7-diamino-4-oxo-1-(2-trimethylsilanyl-ethoxymethyl)-1,4-dihydroquinoline-3-carbonitrile and 4.41 g (56.54 mmol) of imidazole in 50 mL of formic acid is heated at reflux temperature for 6 hours, then cooled to room temperature. The solvent is evaporated to dryness to yield a residue which is suspended in water, neutralized to pH 7 with ammonium hydroxide and stirred for 0.5 hours. The solid is collected by filtration, washed with water and dried under vacuum to yield 2.8 g of an orange-brown solid. A portion (0.17 g) of the sample is purified by silica gel chromatography utilizing a gradient of methylene chloride/methanol (93:7 to 80:20) to yield 0.11 g of 8-Oxo-5,8-dihydroimidazo[4,5-g]quinoline-7-carbonitrile as an orange solid, mp>300° C.

$^1$HNMR (DMSO-d$_6$): δ 12.80 (s, 1H); 12.78 (s, 1H); 8.76 (d, 1H, J=6.5 Hz); 8.55 (s, 1H); 8.34 (s, 1H); 7.88 (s, 1H).

MS (ES, positive mode): m/z calcd for $C_{11}H_6N_4O$: 210, found: 211 (M+H)$^+$. Analysis for $C_{11}H_6N_4O \cdot 1.0H_2O$ Calcd: C:57.89; H:3.53; N:24.55 Found: C:57.68; H:3.60; N:24.15.

EXAMPLE 36

8-Chloroimidazo[4,5-g]quinoline-7-carbonitrile

To a suspension of 2.65 g (12.61 mmol) of 8-oxo-5,8-dihydroimidazo[4,5-g]quinoline-7-carbonitrile in 60.0 mL of 2.0 M solution of oxalyl chloride in methylene chloride is added 4 drops of N,N-dimethylformamide and resulting mixture is heated at reflux temperature for 0.5 hours. While refluxing, additional 0.3 mL portions of N,N-dimethylformamide are added every hour until the reaction is complete (5 hours). After cooling the reaction mixture, the solvent is evaporated to yield a residue which is placed in an ice bath and cautiously neutralized with a solution of saturated sodium bicarbonate to pH 7. This is further stirred with cooling for 0.5 hours. The solid is collected by filtration, washed with water and dried to yield 2.9 g of a brown solid. The solid is purified by silica gel chromatography utilizing a gradient of methylene chloride/methanol (93:7 to 80:20) to yield 1.32 g of 8-chloroimidazo[4,5-g]quinoline-7-carbonitrile as a pink solid, mp>300° C.

$^1$HNMR (DMSO-d$_6$): δ 9.79 (s, 1H); 8.89 (s, 1H), 8.56 (s, 1H); 8.15 (s, 1H). MS (ES, positive mode): m/z calcd for $C_{11}H_5ClN_4$: 228, found: 229 (M+H)$^+$. Analysis for $C_{11}H_5ClN_4 \cdot 0.27H_2O$ Calcd: C:56.58; H:2.39; N:23.99 Found: C:56.95; H:2.64; N:23.59.

EXAMPLE 37

8-(3-Bromo-phenylamino)imidazo[4,5-g]quinoline-7-carbonitrile

A mixture of 0.2 g (0.87 mmol) of 8-chloroimidazo[4,5-g]quinoline-7-carbonitrile, 0.12 mL (1.1 mmol) of 3-bromoaniline, and 0.1 g (0.87 mmol) of pyridine hydrochloride in 5.0 mL of 2-ethoxyethanol is heated at reflux temperature for 45 minutes, then cooled to room temperature. The product mixture is poured into a saturated solution of sodium bicarbonate and stirred for 0.5 hour. The solid is collected by filtration, washed with water and dried. The solid is purified by silica gel chromatography, utilizing a gradient of methylene chloride/methanol (98:2 to 93:7) to yield 0.20 g of 8-(3-bromo-phenylamino)imidazo[4,5-g]quinoline-7-carbonitrile as pink solid, mp 286–288° C.

$^1$HNMR (DMSO-d$_6$+trifluoroacetic acid): δ 13.2 (bs, 2H); 9.31 (s, 1H); 9.29 (s, 1H); 9.19 (s, 1H); 8.35 (s, 1H); 7.83 (t, 1H, J=1.77 Hz); 7.69 (dt, 1H, J=7.68, 1.60 Hz); 7.56 (m, 2H). MS (ES, positive mode): m/z calcd for $C_{17}H_{10}BrN_5$: 364, found: 365 (M+H)$^+$. Analysis for $C_{17}H_{10}BrN_5 \cdot 1.2H_2O$ Calcd: C:52.92; H:3.24; N:18.15 Found: C:52.85; H:3.23; N:17.92.

EXAMPLE 38

8-(2-Bromo-4-chlorophenylamino)imidazo[4,5-g]quinoline-7-carbonitrile

A mixture of 0.25 g (1.10 mmol) of 8-chloroimidazo[4,5-g]quinoline-7-carbonitrile, 0.27 g (1.3 mmol) of 2-bromo-4-chloroaniline, and 0.13 g (1.12 mmol) of pyridine hydrochloride in 7.0 mL of 2-ethoxyethanol is heated at reflux temperature for 1 hour, cooled to room temperature, poured into a saturated solution of sodium bicarbonate and stirred for 0.5 hour. The solid is collected by filtration, washed with water and dried. The solid is purified by silica gel chromatography utilizing a gradient of methylene chloride/methanol (97:3 to 90:10) to yield 0.10 g of 8-(2-bromo-4-chlorophenylamino)imidazo[4,5-g]quinoline-7-carbonitrile as an yellow solid, mp 244–246° C. (shrinks at 200° C.).

$^1$HNMR (DMSO-d$_6$+trifluoroacetic acid): δ 9.46 (s, 1H); 9.30 (s, 1H); 9.27 (s, 1H); 8.40 (s, 1H); 8.06 (d, 1H, J=2.2 Hz); 7.77 (d, K1, J=8.5 Hz); 7.69 (dd, 1H, J=2.2, 8.5 Hz). MS (ES, positive mode): m/z calcd for $C_{17}H_9BrClN_5$: 399, found: 400 (M+H)$^+$. Analysis for $C_{17}H_9BrClN_5 \cdot 1.0H_2O$ Calcd: C:49.00; H:2.66; N:16.81 Found: C:48.96; H:2.65; N: 16.13.

EXAMPLE 39

8-(2-Bromo-4-chloro-5-methoxyphenylamino)imidazo[4,5-g]quinoline-7-carbonitrile

A mixture of 0.12 g (0.52 mmol) of 8-chloroimidazo[4,5-g]quinoline-7-carbonitrile, 0.2 g (0.63 mmol) of 2-bromo-4-chloro-5-methoxyaniline hydrobromide and 0.06 g (0.52 mmol) of pyridine hydrochloride in 5.0 mL of 2-ethoxyethanol is heated at reflux temperature for 1 hour, cooled to room temperature, poured into a saturated solution of sodium bicarbonate and stirred for 0.5 hour. The solid is collected by filtration, washed with water and dried. The solid is purified by silica gel chromatography utilizing a gradient of methylene chloride/methanol (97:3 to 90:10) to yield 0.1 g of 8-(2-bromo-4-chloro-5-methoxy-phenylamino)imidazo[4,5-g]quinoline-7-carbonitrile as a yellow solid, mp 257° C. (dec).

$^1$HNMR (DMSO-d$_6$+trifluoroacetic acid): δ 9.40 (s, 1H); 9.28 (d, 2H, J=5.3 Hz); 8.39 (s, 1H); 8.0 (s, 1H); 7.60 (s, 1H); 3.9 (s, 3H). MS (ES, positive mode): m/z calcd for $C_{18}H_{11}BrClN_5O$: 429, found: 430 (M+H)$^+$. Analysis for $C_{18}H_{11}BrClN_5O \cdot 0.4H_2O$ Calcd: C:49.60; H:2.73; N: 16.07 Found: C:49.59; H:2.93; N: 15.73.

EXAMPLE 40

8-(2-Chloro-5-methoxy-phenylamino)imidazo[4,5-g]quinoline-7-carbonitrile

A mixture of 0.2 g (0.87 mmol) of 8-chloroimidazo[4,5-g]quinoline-7-carbonitrile, 0.22 g (1.04 mmol) of 2-chloro-5-methoxyaniline hydrochloride and 0.1 g (0.87 mmol) of pyridine hydrochloride in 5.0 mL of 2-ethoxyethanol is heated at reflux temperature for 1 hour, cooled to room temperature, poured into a saturated solution of sodium bicarbonate and stirred for 0.5 hour. The solid is collected by filtration, washed with water and dried. The solid is purified by silica gel chromatography utilizing a gradient of methylene chloride/methanol (97:3 to 90:10) to yield 0.19 g of 8-(2-chloro-5-methoxy-phenylamino)imidazo[4,5-g]quinoline-7-carbonitrile as beige solid, mp 296–298° C.

$^1$HNMR (DMSO-d$_6$+trifluoroacetic acid): δ 9.42 (s, 1H); 9.29 (d, 2H, J=5.5 Hz); 8.40 (s, 1H); 7.61 (d, 1H, J=8.9 Hz); 7.37 (d, 1H, J=3.0 Hz); 7.19 (dd; 1H, J=3.0, 3.0 Hz); 3.84 (s, 3H). MS (ES, positive mode): m/z calcd for $C_{18}H_{12}ClN_5O$: 349, found: 350 (M+H)$^+$. Analysis for $C_{18}H_{12}ClN_5O \cdot 1.5H_2O$ Calcd: C:57.37; H:4.01; N:18.59 Found: C:57.31; H:3.86; N:18.21.

EXAMPLE 41

8-(3-Hydroxy-4-methylphenylamino)imidazo[4,5-g]quinoline-7-carbonitrile

A mixture of 0.15 g (0.66 mmol) of 8-chloroimidazo[4,5-g]quinoline-7-carbonitrile, 0.1 g (0.78 mmol) of 5-amino-o-cresol and 0.075 g (0.66 mmol) of pyridine hydrochloride in 5.0 mL of 2-ethoxyethanol is heated at reflux temperature for 1 hour, cooled to room temperature, poured into a saturated solution of sodium bicarbonate and stirred for 0.5 hour. The solid is collected by filtration, washed with water, diethyl ether, methylene chloride, tetrahydrofuran and dried in vacuo to yield 0.17 g of 8-(3-hydroxy-4-methyl-phenylamino)imidazo[4,5-g]quinoline-7-carbonitrile as white solid, mp 257–260° C. (dec).

$^1$HNMR (DMSO-$d_6$+trifluoroacetic acid): δ 9.38 (s, 1 H); 9.23 (d, 2H, J=3.3 Hz); 8.33 (s, 1H); 7.22 (d, 1H, J=8.0 Hz); 6.89 (m, 2H); 3.18 (s, 3H). MS (ES, positive mode): m/z calcd for $C_{18}H_{13}N_5O$: 315, found: 316 (M+H)$^+$. Analysis for $C_{18}H_{13}N_5O \cdot 0.5H_2O$ Calcd: C:66.65; H:4.35; N:21.59 Found: C:66.75; H:4.45; N:21.56.

EXAMPLE 42

8-(3,4,5-Trimethoxyanilino)imidazo[4,5-g]quinoline-7-carbonitrile

A 422.1 mg (1.16 mmol) portion of 6,7-diamino-4-(3,4,5-trimethoxyanilino)-3-quinolinecarbonitrile (intermediate from Example 33) is heated at reflux temperature in 2 mL of diethoxymethyl acetate at 120° C. for 2 hours. After cooling, the solution is diluted with water and extracted with ethyl acetate. The separated organic phase is washed with brine and dried over sodium sulfate. After filtration and removal of the solvent, the residue is flash chromatographed (elution with 93:7 methylene chloride/methanol) to give 169.9 mg (36.3%) of 7-cyanoimidazo[4,5-g]quinolin-8-yl(3,4,5-trimethoxyphenyl)formamide as a deep beige solid, mp 156° C. (dec.).

$^1$HNMR (DMSO-$d_6$): δ 3.65 (s, 3H); 3.71 (s, 6H); 6.73 (s, 2H)); 8.27 (bs, 1H); 8.41 (bs, 1H); 8.75 (s, 1H); 9.12 (s, 1H); 9.23 (s, 1H); 13.10 (bs, 1H). MS (ES, positive ion mode): m/z calcd for $C_{21}H_{17}N_5O_4$: 403.4, found: 404.2 (M+H)$^+$. HRMS m/z calcd 403.1281 for $C_{21}H_{17}N_5O_4$, found: 404.1343 (M+H)$^+$.

A suspension of 138.6 mg (0.34 mmol) of 7-cyanoimidazo[4,5-g]quinolin-8-yl(3,4,5-trimethoxyphenyl)formamide and 229.1 mg (1.66 mmol) of potassium carbonate in 10 mL of methanol is refluxed for 2 hours. After cooling, the solution is diluted with water and neutralized to pH 7 with AcOH. The precipitate is collected by filtration and washed with water, diethyl ether and ethyl acetate. After drying in vacuo, this yields a crude product. Purification of the crude product by flash chromatography (elution with 95:5 methylene chloride/methanol) yields 87.3 mg (68.5%) of the final product as a yellow solid, mp>260° C., $^1$HNMR (DMSO-$d_6$+trifluoroacetic acid): δ 3.73 (s, 3H); 3.81 (s, 6H); 6.90 (s, 2H); 8.20 (s, 1H; 8.85 (s, 1H); 9.13 (s, 1H); 9.15 (s, 1H); 11.40 (bs, 1H). MS (ES, positive ion mode): m/z calcd for $C_{20}H_{17}N_5O_3$: 375.4, found: 376.3 (M+H)$^+$. Analysis for $C_{20}H_{17}N_5O_3 \cdot 0.9H_2O$ Calcd: C 61.34; H 4.84; N 17.88 Found: C 61.03; H 4.82; N 17.76.

EXAMPLE 43

7-Chloro-6-nitro-4-(4-phenoxyanilino)-3-quinolinecarbonitrile

A mixture of 722.7 mg (2.70 mmol) of 4,7-dichloro-6-nitro-3-quinolinecarbonitrile, 100.1 mg (2.70 mmol) of 4-phenoxyaniline and 312.1 mg (2.70 mmol) of pyridine hydrochloride in 30 mL of 2-ethoxyethanol is heated at 110–120° C. for 3 hours. After cooling, the mixture is diluted with water, neutralized with an aqueous solution of saturated sodium carbonate, and extracted with ethyl acetate. The separated organic layer is washed with brine and dried over sodium sulfate. Removal of the solvent yields a solid residue which is purified by flash chromatography (elution with 99:1 methylene chloride/methanol), giving 831.0 mg (73.9%) of the product as a deep yellow solid, mp 220–222° C.

$^1$HNMR (DMSO-$d_6$): δ 7.14 (m, 5H); 7.40 (m, 4H); 8.24 (s, 1H); 8.71 (s, 1H); 9.38 (s, 1H); 10.42 (bs, 1H). MS (ES, positive ion mode): m/z calcd for $C_{22}H_{13}ClN_4O_3$: 416.8, found: 417.2 (M+H)$^+$. Analysis for $C_{22}H_{13}ClN_4O_3$ Calcd: C 63.39; H 3.14; N 13.44 Found: C 63.12; H 3.19; N 13.22.

EXAMPLE 44

8-(4-Phenoxyanilino)imidazo[4,5-g]quinoline-7-carbonitrile

Following the procedure of 7-azido-6-nitro-4-(3,4,5-trimethoxyanilino)-3-quinolinecarbonitrile (intermediate from Example 33), 728.4 mg (1.75 mmol) of 7-chloro-6-nitro-4-(4-phenoxyanilino)-3-quinolinecarbonitrile in 12 mL of DMSO is reacted with 568.1 mg (8.74 mmol) of sodium azide to yield 736.0 mg (99.5%) of 7-azido-6-nitro-4-(4-phenoxyanilino)-3-quinolinecarbonitrile.

MS (ES, positive ion mode): m/z calcd for $C_{22}H_{13}N_7O_3$: 423.1, found: 424.0 (M+H)$^+$.

Following the procedure of 6,7-diamino-4-(3,4,5-trimethoxyanilino)-3-quinolinecarbonitrile (intermediate from Example 33), hydrogenation of a suspension of 736.0 mg (1.74 mmol) of 7-azido-6-nitro-4-(4-phenoxyanilino)-3-quinolinecarbonitrile and 147.2 mg of 10% palladium-on-carbon in 21 mL of THF and 6 mL of ethanol yields 765.1 mg of crude 6,7-diamino-4-(4-phenoxyanilino)-3-quinolinecarbonitrile.

MS (ES, positive ion mode): m/z calcd for $C_{22}H_{17}N_5O$: 367.1, found: 368.3 (M+H)$^+$.

Following the procedure of 7-cyanoimidazo[4,5-g]quinolin-8-yl(3,4,5-trimethoxyphenyl)formamide (intermediate from Example 42), treatment of 765.1 mg (2.08 mmol) of the crude 6,7-diamino-4-(4-phenoxyanilino)-3-quinolinecarbonitrile with diethoxymethyl acetate at 120° C. for 3 hours, followed by the same work up yields a dark oil residue which is flash chromatographed (elution with a gradient of 99:1 to 82:18 methylene chloride/methanol), yielding 263.8 mg (31.3%) of 7-cyanoimidazo[4,5-g]quinolin-8-yl(4-phenoxyphenyl)formamide as a beige solid, mp 266° C. (dec.).

$^1$HNMR (DMSO-$d_6$): δ 7.08 (m, 5H); 7.39 (m, 4H); 8.36 (bs, 2H); 8.74 (s, 1H); 9.12 (s, 1H); 9.24 (s, 1H); 13.10 (bs, 1H). MS (ES, positive ion mode): m/z calcd for $C_{24}H_{15}N_5O_2$: 405.4, found: 406.2 (M+H)$^+$. Analysis for $C_{24}H_{15}N_5O_2 \cdot 0.3H_2O$ Calcd: C 70.16; H 3.83; N 17.05 Found: C 70.23; H 3.81; N 17.23.

A suspension of 211.8 mg (0.52 mmol) of 7-cyano-3H-imidazo[4,5-g]quinolin-8-yl(4-phenoxyphenyl)formamide and 288.9 mg (2.09 mmol) of potassium carbonate in 15 mL of methanol is refluxed for 2.5 hours. The solution is concentrated and the residue is diluted with water followed by neutralization to pH 7–8 with acetic acid. The precipitate is collected by filtration and washed with water and dried in vacuo, giving a deep yellow solid. The solid is purified by flash chromatography (elution with a gradient of 98:2 to 90:10 methylene chloride/methanol) yields 137.4 mg (70.0%) of the final product as a yellow solid, mp>270° C.

$^1$HNMR(DMSO-$d_6$): δ 7.11 (m, 5H); 7.39 (m, 4H); 8.05 (bs, 1H); 8.47 (s, 1H); 8.60 (bs, 1H); 8.89 (bs, 2H); 9.85 (bs, 1H). MS (ES, positive ion mode): m/z calcd for $C_{23}H_{15}N_5O$: 377.4, found: 378.2 (M+H)$^+$. Analysis for $C_{23}H_{15}N_5O.0.9H_2O$ Calcd: C 70.18; H 4.30; N 17.79 Found: C70.11; H 4.11; N 17.79.

EXAMPLE 45

N-[7-Amino-3-cyano-4-(3,4,5-trimethoxyanilino)-6-quinolinyl]-2-chloroacetamide and

EXAMPLE 46

N-[6-Amino-3-cyano-4-(3,4,5-trimethoxyanilino)-7-quinolinyl]-2-chloroacetamide

To an ice-cooled mixture of 0.12 g (0.33 mmol) of 6,7-diamino-4-(3,4,5-trimethoxyanilino)-3-quinolinecarbonitrile and 0.5 mL of N,N-diethylaniline in 3.0 ml of tetrahydrofuran is added dropwise 0.052 mL (0.66 mmol) of chloroacetyl chloride, which is further stirred for 15 minutes at 0° C. The mixture is diluted with water and stirred for 20 minutes, while warming to room temperature. The solid is collected by filtration and dried. Purification by silica gel chromatography, utilizing a gradient of methylene chloride/methanol (97:3 to 90:10), yields 0.11 g of a yellow solid consisting of a 1:1 mixture of N-[7-amino-3-cyano-4-(3,4,5-trimethoxyanilino)-6-quinolinyl]-2-chloroacetamide and N-[6-amino-3-cyano-4-(3,4,5-trimethoxyanilino)-7-quinolinyl]-2-chloroacetamide.

$^1$HNMR (DMSO-$d_6$): δ 9.69 (s, 0.5H); 9.42 (s, 0.5H); 8.36 (s, 0.5H); 8.23 (s, 0.5H); 7.04 (s, 1H); 6.53 (s, 2H); 6.01 (s, 2H); 4.34 (s, 2H); 3.74 (s, 6H); 3.65 (s, 3H). MS (ES, positive mode): m/z calcd for $C_{21}H_{20}ClN_5O_4$: 441, found: 442 (M+H)$^+$. Analysis for $C_{21}H_{20}ClN_5O_4.1.3H_2O$ Calcd: C:54.21; H:4.90; N:15.05 Found: C:54.23; H:4.96; N:14.94.

EXAMPLE 47

2-(Chloromethyl)-8-(3,4,5-trimethoxyanilino)imidazo[4,5-g]quinoline-7-carbonitrile A of 0.11 g (0.25 mmol) sample of product from Example 46 in 3.0 mL of glacial acetic acid is heated at 100° C. for 15 minutes, then cooled to room temperature. Following evaporation of the solvent in vacuo, the residue is suspended in water and neutralized with solid sodium carbonate. The solid is collected by filtration, washed with water and dried to yield 0.1 g of 2-(chloromethyl)-8-(3,4,5-trimethoxyanilino)imidazo[4,5-g]quinoline-7-carbonitrile as a yellow solid.

$^1$HNMR(DMSO-$d_6$+trifluoroacetic acid): δ 9.20 (s, 1H); 9.13 (s, 1H); 8.20 (s, 1H); 6.93 (s, 2 M); 5.12 (d, 2H, J=4.2 Hz); 3.83 (s, 6H); 3.76 (s, 3H). MS (ES, positive mode): m/z calcd for $C_{21}H_{18}ClN_5O_3$: 423, found: 424 (M+H)$^+$. Analysis for $C_{21}H_{18}ClN_5O_3.0.6H_2O$ Calcd: C:58.02; H:4.45; N:16.11 Found: C:57.90; H:4.30; N:15.79.

EXAMPLE 48

2-(4-Morpholinylmethyl)-8-(3,4,5-trimethoxyanilino)imidazo[4,5-g]quinoline-7-carbonitrile A mixture of 0.09 g (0.2 mmol) of 2-(chloromethyl)-8-(3,4,5-trimethoxyanilino)imidazo[4,5-g]quinoline-7-carbonitrile, 0.2 mL (2.3 mmol) of morpholine and 0.3 g (2.2 mmol) of anhydrous potassium carbonate in 5 mL of ethanol is stirred at room temperature overnight. The product mixture is filtered to remove the inorganic salts and the filtrate is evaporated to dryness to yield an oil. The oil is purified by silica gel chromatography utilizing a gradient of methylene chloride/methanol (97:3 to 90:10) to yield 0.087 g of 2-(4-morpholinylmethyl)-8-(3,4,5-trimethoxyanilino)-3H-imidazo[4,5-g]quinoline-nylmethyl)-8-(3,4,5-trimethoxyanilino)-3H-imidazo[4,5-g]quinoline-7-carbonitrile as a yellow solid, mp 258–260° C. (dec).

$^1$HNMR (DMSO-$d_6$+trifluoroacetic acid): δ 9.23 (s, 1H); 9.15 (s, 1H); 8.27 (s, 1H); 6.92 (s, 2H); 4.93 (s, 2H); 3.94 (bs, 4H); 3.82 (s, 6H); 3.75 (s, 3H); 3.56 (bs, 4H). MS (ES, positive mode): m/z calcd for $C_{25}H_{26}N_6O_4$: 474, found: 475 (M+H)$^+$. Analysis for $C_{25}H_{26}N_6O_4.1.2H_2O$ Calcd: C:60.52; H:5.77; N: 16.94 Found: C:60.20; H:5.77; N:16.80.

EXAMPLE 49

N-[7-Amino-3-cyano-4-(3,4,5-trimethoxyanilino)-6-quinolinyl]acrylamide and

EXAMPLE 50

N-[6-Amino-3-cyano-4-(3,4,5-trimethoxyanilino)-7-quinolinyl]acrylamide

To a cold mixture of 0.12 g (0.33 mmol) of 6,7-diamino-4-(3,4,5-trimethoxyanilino)-3-quinolinecarbonitrile and 0.4 mL of N,N-diethylaniline in 3.0 mL of tetrahydrofuran is added, dropwise, 0.054 mL (0.66 mmol) of acryloyl chloride and the mixture is stirred cold for 20 minutes. The mixture is diluted with water and stirred for 20 minutes. The solid is collected by filtration, dried and purified by silica gel chromatography utilizing a gradient of methylene chloride/methanol (97:3 to 90:10) to yield 0.03 g of a yellow solid as a 1:1 mixture of N-[7-amino-3-cyano-4-(3,4,5-trimethoxyanilino)-6-quinolinyl]acrylamide and N-[6-amino-3-cyano-4-(3,4,5-trimethoxyanilino)-7-quinolinyl]acrylamide.

$^1$HNMR (DMSO-$d_6$+trifluoroacetic acid): δ 8.89 (s, 1H); 8.65 (d, 1H, J=4.2 Hz); 7.03 (s, 1H); 8.23 (s, 0.5H); 6.78 (s, 2H); 6.55 (q, 1H, J=10.2 Hz); 6.30 (dd, 1H, J=2.0 Hz, J=10.0 Hz); 5.83 (dd, 1H, J=1.8 Hz, J=10.2 Hz); 3.748(s, 6H); 3.70 (s, 3H). MS (ES, positive mode): m/z calcd for $C_{22}H_{21}N_5O_4$: 419, found: 420 (M+M)$^+$. Analysis for $C_{22}H_{21}N_5O_4.1.4H_2O$ Calcd: C:59.42; H:5.40; N:15.75 Found: C:59.59; H:5.13; N:15.40.

EXAMPLE 51

N-[7-Amino-3-cyano-4-(3,4,5-trimethoxyanilino)-6-quinolinyl]-3-(4-morpholinyl)propanamide and

EXAMPLE 52

N-[6-Amino-3-cyano-4-(3,4,5-trimethoxyanilino)-7-quinolinyl]-3-(4-morpholinyl)propanamide A mixture of 0.025 g (0.06 mmol) of N-[7-amino-3-cyano-4-(3,4,5-trimethoxyanilino)-6-quinolinyl]acrylamide and N-[6-amino-3-cyano-4-(3,4,5-trimethoxyanilino)-7-quinolinyl]acrylamide and 0.05 mL (6.0 mmol) of morpholine in 0.2 mL of N,N-dimethylformamide is stirred at room temperature overnight and the solvent is evaporated to dryness to yield an oil. The oil is triturated with diethyl ether several times and dried to yield 0.03 g of N-[7-amino-3-cyano-4-(3,4,5-trimethoxyanilino)-6-quinolinyl]-3-(4-morpholinyl)propanamide and N-[6-amino-3-cyano-4-(3,4,5-trimethoxyanilino)-7-quinolinyl]-3-(4-morpholinyl)propanamide as a yellow solid.

MS (ES, positive mode): m/z calcd for $C_{26}H_{30}N_6O_5$: 506, found: 507 (M+H)$^+$. Analysis for $C_{26}H_{30}N_6O_5 \cdot 2.0H_2O$ Calcd: C 57.55; H 6.32; N 15.49 Found: C 57.91; H 6.06; N 15.40.

EXAMPLE 53

7-{[2-(4-Morpholinyl)ethyl]amino}-6-nitro-4-oxo-1-([2-(trimethylsilyl)ethoxy]methyl) 1,4-dihydro-3-quinolinecarbonitrile A mixture of 1.25 g (3.29 mmol) of 7-chloro-6-nitro-4-oxo-1-{[2-(trimethylsilyl)-ethoxy]methyl}-1,4-dihydro-3-quinolinecarbonitrile and 1.07 g (8.2 mmol) of 4-(2-aminoethyl)-morpholine in 21 mL of acetonitrile is heated at reflux temperature for 17 hours. After cooling, the mixture is concentrated under reduced pressure and the residue is partitioned between methylene chloride and brine. The separated organic layer is dried over sodium sulfate and filtered. Removal of the solvent yields a residue which is flash chromatographed (elution with methylene chloride, then a gradient of 99:1 to 98:2 methylene chloride/methanol), giving 966 mg (61.9%) of the product as a yellow solid, mp 294–216° C.

$^1$HNMR (DMSO-d$_6$): δ 0.045 (s, 9H); 0.93 (t, J=8.4 Hz, 2H); 2.51 (t, J=6 Hz, 2H); 2.72 (t, J=6 Hz, 2H); 3.53 (m, 2H); 3.66 (m, 6H); 5.66 (s, 2H); 7.01 (s, 1H); 8.59 (t, 1H); 8.87 (s, 1H); 8.97 (s, 1H). MS (ES, positive ion mode): m/z calcd for $C_{22}H_{31}N_5O_5Si$: 473.6, found: 474.3 (M+H)$^+$. Analysis for $C_{19}H_{15}ClN_4O_5$ Calcd: C 55.79; H 6.60; N 14.79 Found. C 55.84; H 6.65; N 14.96.

EXAMPLE 54

6-Amino-7-{[2-(4-morpholinyl)ethyl]amino}-4-oxo-1-{[2-(trimethylsilyl)ethoxy]methyl}-1,4-dihydro-3-quinolinecarbonitrile A suspension of 916.4 mg (1.93 mmol) of 7-{[2-(4-morpholinyl)ethyl]amino}-6-nitro-4-oxo-1-([2-(trimethylsilyl)ethoxy]methyl)-1,4-dihydro-3-quinolinecarbonitrile in 52 mL of THF and 19 mL of ethanol is hydrogenated in a Parr apparatus at 40 psi for 6 hours in the presence of 183.3 mg of 10% palladium-on-carbon. The catalyst is removed by filtration and the solvent is evaporated in vacuo to give 944.0 mg of 6-amino-7-{[2-(4-morpholinyl)ethyl]amino}-4-oxo-1-{[2-(trimethylsilyl)ethoxy]methyl}-1,4-dihydro-3-quinolinecarbonitrile as a deep yellow solid which is used directly in the next step.

For analysis, 100 mg of the crude product is purified on preparative thin layer chromatography (TLC), developing solvent: 9:1 methylene chloride/methanol, to afford 64.7 mg of the pure product as a light yellow solid, mp 236–238° C.

$^1$HNMR (DMSO-d$_6$): δ 0.06 (s, 9H); 0.92 (t, J=8.1 Hz, 2H); 2.52(t, J=4.5 Hz, 2H); 2.67(t, J=6.9 Hz, 2H); 3.36 (t, 2H); 3.65 (m, 6H); 5.26 (bs, 2H); 5.63 (s, 2H); 5.72 (t, J=3 Hz, 1H); 6.67 (s, 1H); 7.31(s, 1H); 8.67 (s, 1H). MS (ES, positive ion mode): m/z calcd for $C_{22}H_{33}N_5O_3Si$: 443.6, found: 444.2 (M+H)$^+$. Analysis for $C_{22}H_{33}N_5O_3Si$: Calcd: C 59.56; H 7.50; N 15.79 Found: C 59.17; H 7.46; N 15.63.

EXAMPLE 55

3-[2-(4-Morpholinyl)ethyl]-8-oxo-5,8-dihydro-3H-imidazo[4,5-g]quinoline-7-carbonitrile A mixture of 422 mg (0.95 mmol) of 6-amino-7-{[2-(4-morpholinyl)ethyl]amino}-4-oxo-1-{[2-(trimethylsilyl)ethoxy]methyl}-1,4-dihydro-3-quinolinecarbonitrile, 258.7 mg (3.80 mmol) of imidazole in 6 mL of 96% formic acid is refluxed for 6.5 hours. After cooling, the mixture is concentrated under reduced pressure and the residue is diluted with water. Undissolved solid is filtered off and washed with water. The combined filtrate and water washes are brought to pH 8 with 28% ammonium hydroxide aqueous solution. The precipitate is collected by filtration and washed with water. After drying in vacuo, this yields 190.0 mg of the crude product as a yellow solid. The crude product is purified by flash chromatography (elution with methylene chloride, then a gradient of 99:1 to 88:12 methylene chloride/methanol) to give 151.6 mg (49.3%) of the pure product as an off-white solid, mp>270° C.

$^1$HNMR (DMSO-d$_6$): δ 2.44 (t, J=4.4 Hz, 4H); 2.72 (t, J=6.0 Hz, 2M); 3.53 (t, J=4.45 Hz, 4H); 4.42(t, J=6 Hz, 2H); 7.74(s, 1H); 8.38 (s, 1H); 8.51(s, 1H) 8.70 (s, 1H); 12.85 (bs, 1H). MS (ES, positive ion mode): m/z calcd for $C_{17}H_{17}N_5O_2$: 323.4, found: 324.2 (M+H)$^+$. Analysis for $C_{17}H_{17}N_5O_2 \cdot 0.3H_2O$ Calcd: C 62.11; H 5.39; N 21.30 Found: C 62.23; H 5.15; N 21.47.

EXAMPLE 56

8-Chloro-3-[2-(4-morpholinyl)ethyl]-3H-imidazo[4,5-g]quinoline-7-carbonitrile

A suspension of 190.0 mg (0.59 mmol) of 3-[2-(4-morpholinyl)ethyl]-8-oxo-5,8-dihydro-3H-imidazo[4,5-g]quinoline-7-carbonitrile, 5.45 mL of 2M oxalyl chloride (in methylene chloride) and 5 drops of DMF is heated at reflux temperature for 1.5 hours. After cooling, the solvent is evaporated to dryness. The residue is cooled in an ice bath and neutralized to pH 7 by slow addition of ice-cooled, aqueous saturated sodium bicarbonate solution. The aqueous solution is extracted with methylene chloride. The organic phase is washed with cold brine and dried over sodium sulfate. Removal of the solvent in vacuo gives the crude product. Purification of the crude product by preparative TLC (developing solvent: 5:95 methanol/methylene chloride) gives 122.8 mg (61%) of the product as a yellow solid, mp 205–207° C.

¹HNMR (DMSO-d₆): δ 2.45 (t, J=4.5 Hz, 4H); 2.76 (t, J=5.9 Hz, 2H); 3.50 (t, J=4.5 Hz, 4H); 4.47 (t, J=5.9 Hz, 2H); 8.52(s, 1H); 8.60 (s, 1H); 8.76 (s, 1H); 9.11 (s, 1H). MS (ES, positive ion mode): m/z calcd for $C_{17}H_{16}ClN_5O$: 341.8, found 342.3 (M+H)⁺. Analysis for $C_{17}H_{16}ClN_5O.0.4H_2O$ Calcd: C 58.50; H 4.85; N 20.06 Found: C 58.47; H 4.76; N 19.93.

EXAMPLE 57

8-(4-Chloro-5-methoxy-2-methylanilino)-3-[2-(4-morpholinyl)ethyl]-3H-imidazo[4,5-g]quinoline-7-carbonitrile A mixture of 86.5 mg (0.25 mmol) of 8-chloro-3-[2-(4-morpholinyl)ethyl]-3H-imidazo[4,5-g]quinoline-7-carbonitrile, 67.2 mg (0.39 mmol) of 4-chloro-5-methoxy-2-methyl aniline and 28.9 mg (0.25 mmol) of pyridine hydrochloride in 3 mL of 2-ethoxyethanol is heated at 130–135° C. for 11 hours. After cooling, the mixture is diluted with water and neutralized with 2 equivalents of sodium carbonate, and then extracted with ethyl acetate. The separated organic layer is washed with brine and dried over sodium sulfate. Removal of the solvent yields a residue which is purified on preparative TLC (developing solvent: 1:9 methanol/methylene chloride), giving 83.3 mg (69.9%) of the product as a beige solid, mp 246–248° C.
¹HNMR (DMSO-d₆): δ 2.13 (s, 3H); 2.47(t, J=4.3 Hz, 4H); 2.75 (t, J=5.9 Hz, 2H); 3.52 (t, J=4.5 Hz, 4H); 3.81 (s, 3H); 4.50 (t, J=5.9 Hz, 2H); 7.13 (s, 1H); 7.42 (s, 1H); 8.16 (s, 1H); 8.45 (s, 1H); 8.57 (s, 1H); 8.94 (s, 1H); 9.70 (bs, 1H). MS (ES, positive ion mode): m/z calcd for $C_{25}H_{25}ClN_6O_2$: 476.97, found: 477.3 (M+H)⁺. Analysis for $C_{25}H_{25}ClN_6O_5.0.5H_2O$ Calcd: C 61.79; H 5.39; N 17.29 Found: C 61.91; H 5.21; N 17.06.

EXAMPLE 58

3-[2-(4-Morpholinyl)ethyl]-8-(4-phenoxyanilino)-3H-imidazo[4,5-g]quinoline-7-carbonitrile Following the procedure of Example 7, a mixture of 82.2 mg (0.24 mmol) of 8-chloro-3-[2-(4-morpholinyl)ethyl]-3H-imidazo[4,5-g]quinoline-7-carbonitrile, 53.3 mg (0.29 mmol) of 4-phenoxyaniline and 33.5 mg (0.29 mmol) of pyridine hydrochloride in 3.5 mL of 2-ethoxyethanol is heated at 130–135° C. for 1 hour to yield 81.2 mg (69%) of the product as a yellow solid, mp>260° C.
¹HNMR (DMSO-d₆): δ 2.46 (t, J=4.4 Hz, 4H); 2.76 (t, J=5.9 Hz, 2H); 3.52 (t, J=4.5 Hz, 4H); 4.50 (t, J=5.9 Hz, 2H); 7.11 (m, 5H); 7.40 (m, 4H); 8.17 (s, 1H); 8.49 (s, 1H); 8.57 (s, 1H); 8.88 (s, 1H); 9.84 (s, 1H). MS (ES, positive ion mode): m/z calcd for $C_{29}H_{26}N_6O_2$: 490.6, found: 491.3 (M+H)⁺. Analysis for $C_{29}H_{26}N_6O_2.0.3H_2O$ Calcd: C 70.23; H 5.41; N 16.94 Found: C 70.35; H 5.56; N 16.84.

EXAMPLE 59

1,4-Dihydro-7-mercapto-6-nitro-4-oxo-1-[[2-(trimethylsilyl)ethoxy[methyl]-3-quinolinecarbonitrile A solution of 100 mg (0.26 mmol) of 7-chloro-6-nitro-4-oxo-1-{[2-(trimethylsilyl)ethoxy]methyl}-1,4-dihydro-3-quinolinecarbonitrile and 63 mg (0.26 mmol) of sodium sulfide nonahydrate in 1 mL of dimethyl sulfoxide is stirred at room temperature for 17 hours and poured into 50 mL of water. To this is added 0.27 mL of 1 N HCl. The product is collected by filtration, washed with water, and dried to yield 81 mg (83%) of a tan solid, mp 200° C. (decomposed).
¹HNMR (DMSO-d₆): δ 8.86 (s, 1H), 7.91 (s, 2H), 5.47 (s, 2H), 3.51 (t, 2H), 0.77 (t, 2H), –0.09 (s, 9H).
¹HNMR (DMSO-d₆): δ 8.86 (s, 1H), 7.91 (s, 2H), 5.47 (s, 2H), 3.51 (t, 2H), 0.77 (t, 2H), –0.09 (s, 9H). MS (ES, positive ion mode): m/z calcd for $C_{16}H_{19}N_3O_4SSi$: 377.5, found: 378.4 (M+M)⁺. Analysis for $C_{16}H_{19}N_3O_4SSi.0.1DMSO.1.4H_2O$ Calcd: C 47.40; H 5.50; N 10.23 Found: C, 47.04; H, 5.02; N, 10.15.

EXAMPLE 60

8-Hydroxy[1,3]thiazolo[4,5-g]quinoline-7-carbonitrile

A mixture of 377 mg (1.0 mmol) of 1,4-dihydro-7-mercapto-6-nitro-4-oxo-1-[[2-(trimethylsilyl)ethoxy]methyl]-3-quinolinecarbonitrile and 200 mg of 20% palladium-hydroxide-on-carbon in 50 mL of tetrahydrofuran and 10 mL of methanol is hydrogenated in a Parr apparatus at 40 psi for 30 minutes. The mixture is filtered and concentrated in vacuo. The residue is dissolved in 5 mL of 98% formic acid, and 200 mg of imidazole is added to the solution. The solution is refluxed for 2 hours and cooled to room temperature. To this solution is added a mixture of 100 mL ethyl acetate and 50 mL of hexanes. The solids thus formed are filtered, washed with ethyl acetate, and dried to yield 125 mg (55%) of a tan solid, mp 200° C. (decomposed).
¹HNMR(DMSO-d₆): δ 13.1 (brs, 1H), 9.53 (s, 1H), 8.81 (s, 1H), 8.73 (s, 1H), 8.45 (s, 1H). MS (ES, positive ion mode): m/z calcd for $C_{11}H_5N_3OS$: 227.2, found: 226.3 (M–H)⁻. HRMS (ESI): Calc for $C_{11}H_5N_3OS$ (2M–H)⁻: 453.0233, found: 453.0224.

EXAMPLE 61

8-[(4-Chloro-5-methoxy-2-methylphenylamino]thiazolo[4,5-g]quinoline-7-carbonitrile To a mixture of 100 mg (0.44 mmol) of 8-hydroxy[1,3] thiazolo[4,5-g]quinoline-7-carbonitrile in 5 mL of phosphoryl chloride is added five drops of N,N-dimethylformamide. The mixture is heated at reflux temperature for 30 minutes and then concentrated in vacuo. To the residue at 0° C. is added 50 mL of water. The solids are collected, washed with water, and dried in vacuo. To a mixture of this compound in 2 mL of 2-ethoxyethanol are added 76 mg (0.44 mmol) of 4-chloro-5-methoxy-2-methylaniline and 20 mg of pyridine hydrochloride. The mixture is refluxed for one hour and concentrated. The residue is chromatographed by silica gel chromatography, eluting with 9:1 methylene chloride/methanol to yield 26 mg (16%) of product as a dark oil.
¹HNMR (DMSO-d₆): δ 9.99 (s, 1H), 9.60 (s, 1H), 9.39 (s, 1H), 8.77 (s, 1H), 8.56 (s, 1H), 7.44 (s, 1H), 7.20 (s, 1H), 3.82 (s, 3H), 2.15 (s, 3H). MS (ES, positive ion mode): m/z calcd for $C_{18}H_{13}ClN_4OS$: 380.9, found: 381.4 (M+H)⁺.
HRMS (EI): Calc for $C_{19}H_{13}N_4OSCl$: 380.0499, found: 380.0493.

EXAMPLE 62

3-(Dimethylaminomethyleneamino)benzo[b]thiophene-2-carboxylic acid methyl ester

A mixture of 3.38 g (16.32 mmol) of methyl 3-aminobenzo[b]thiophene-2-carboxylate (J. Org. Chem. 37, 3224

(1972)) in 8 mL of N,N,-dimethylformamide dimethyl acetal is heated at reflux temperature for 2 hours, then cooled to room temperature. The solid is collected by filtration, washing with hexane and ethyl acetate to provide 3.96 g (93%) of a white solid, mp 73–74° C.

$^1$HNMR (DMSO-d$_6$): δ 3.06 (s, 6H), 3.75 (s, 3H), 7.47 (t, 1H), 7.50 (t, 1H), 7.78 (d, 1H), 7.82–7.89 (m, 2H). MS (ES, positive ion mode): m/z calcd for $C_{13}H_{14}N_2O_2S$: 262.3, found: 262.9 (M+H)$^+$ Analysis for $C_{13}H_{14}N_2O_2S$ Calcd: C:59.52; H:5.38; N:10.68 Found: C:59.25; H:5.32; N: 10.58.

EXAMPLE 63

4-Hydroxybenzo[4,5]thieno[3,2-b]pyridine-3-carbonitrile

A solution of 1.6 mL (30.6 mmol) of acetonitrile in 10 mL of tetrahydrofuran is added to a –78° C. solution of 12.5 mL of 2.5 M n-butyllithium (31.2 mmol) in 40 mL of tetrahydrofuran. After stirring at –78° C. for 10 min, a solution of 4.0 g (15.2 mmol) of 3-(dimethylaminomethyleneamino) benzo[b]thiophene-2-carboxylic acid methyl ester in 40 mL of tetrahydrofuran is added dropwise over 1 hour. After stirring at –78° C. for 30 minutes, the reaction mixture is allowed to warm to room temperature and then stirred at room temperature for 1 hour. The reaction mixture is cooled to –50° C. and 2.1 mL of acetic acid is added. The solution is concentrated in vacuo and poured into water. The aqueous solution is extracted with ethyl acetate and then aqueous HCl is added to the aqueous layer. The product is extracted into ethyl acetate and the organic layer is dried over magnesium sulfate, filtered and concentrated in vacuo. Ethyl acetate and hexane are added to the residue and the resulting tan solid is collected to provide 2.20 g (64%) of product. An analytical sample is obtained by recrystallization from diethyl ether and hexane, mp>300° C.

$^1$HNMR (DMSO-d$_6$): δ 7.65 (m, 2H), 8.17 (d, 1H), 8.44 (d, 1H), 8.84 (s, 1H). MS (ES, negative ion mode): m/z calcd for $C_{12}H_6N_2OS$: 226.3, found: 224.9 (M–H)$^-$ Analysis for $C_{12}H_6N_2OS.0.25H_2O$ Calcd: C:62.46; H:2.84; N:12.14 Found: C:62.52; H:2.93; N:12.00.

EXAMPLE 64

4-Chlorobenzo[4,5]thieno[3,2-b]pyridine-3-carbonitrile

A mixture of 1.01 g (4.47 mmol) of 4-hydroxybenzo[4,5]thieno[3,2-b]pyridine-3-carbonitrile in 7 mL of phosphorous oxychloride is heated at reflux temperature for 40 minutes, then cooled to room temperature. Hexane is added and the solid is collected by filtration, dissolved in ethyl acetate and washed with saturated sodium bicarbonate. The organic layer is dried over magnesium sulfate, filtered and concentrated in vacuo to a small volume. The solids are collected by filtration to give 696 mg (64%) of product, mp 305–308° C.

$^1$HNMR (DMSO-d$_6$): δ 7.70 (t, 1H), 7.80 (t, 1H), 8.26 (d, 1H), 8.45 (d, 11), 9.20 (s, 1H). MS (ES, positive ion mode): m/z calcd for $C_{12}H_5ClN_2S$: 244.7, found: 244.6 (M+H)$^+$. Analysis for $C_{12}H_5ClN_2S.0.2H_2O$ Calcd: C:58.05; H:2.19; N:11.28 Found: C:58.29; H:2.13; N:11.27.

EXAMPLE 65

4-(3-Bromophenylamino)benzo[4,5]thieno[3,2-b]pyridine-3-carbonitrile

A solution of 150 mg (0.61 mmol) of 4-chlorobenzo[4,5]thieno[3,2-b]pyridine-3-carbonitrile in 3 mL of 2-ethoxyethanol containing 80 mg (0.74 mmol) of 3-bromoaniline and 71 mg of pyridine hydrochloride is heated at reflux temperature for 4 hours, then allowed to stir at room temperature for 3 days. The reaction mixture is partitioned between ethyl acetate and saturated sodium bicarbonate and the organic layer is dried over magnesium sulfate, filtered and concentrated in vacuo. Diethyl ether is added to the residue and the resultant solid is collected by filtration to give 139 mg (58%) of a white solid, mp 240–242° C.

$^1$HNMR (DMSO-d$_6$): δ 7.24 (d, 1H), 7.31–7.43 (m, 3H), 7.52–7.68 (m, 21), 8.06 (d, 1H), 8.37 (d, 1H), 8.83 (s, 1H), 9.84 (s, 1H). MS (ES, positive ion mode): t/z calcd for $C_{18}H_{10}BrN_3S$: 380.3, found: 379.9 (M+H)$^+$. Analysis for $C_{18}H_{10}BrN_3S.0.5H_2O$ Calcd: C:55.54; H:2.85; N:10.79 Found: C:55.84; H:2.79; N:10.73.

EXAMPLE 66

4-(4-Chloro-2-fluorophenylamino)benzo[4,5]thieno[3,2-b]pyridine-3-carbonitrile A solution of 237 mg (0.97 mmol) of 4-chlorobenzo[4,5]thieno[3,2-b]pyridine-3-carbonitrile in 6 mL of 2-ethoxyethanol containing 0.15 mL (1.36 mmol) of 4-chloro-2-fluoroaniline and 112 mg of pyridine hydrochloride is heated at reflux temperature for 30 hours. The reaction mixture is cooled to room temperature and partitioned between ethyl acetate and saturated sodium bicarbonate. The organic layer is dried over magnesium sulfate, filtered and concentrated in vacuo. Diethyl ether is added to the residue and the resultant solid is collected by filtration, washing with hexane to give 225 mg (66%) of an off-white solid, mp 250–251° C.

$^1$HNMR (DMSO-d$_6$): δ 7.40 (d, 1H), 7.50–7.69 (m, 4H), 8.08 (d, 1H), 8.37 (d, 1H), 8.80 (s, 1H), 9.68 (s, 1H). MS (ES, positive ion mode): m/z calcd for $C_{18}H_9ClFN_3S$: 353.8, found: 353.8 (M+H)$^+$. Analysis for $C_{18}H_9ClFN_3S$ Calcd: C:61.11; H:2.56; N:11.88 Found: C:61.50; H:2.58; N: 11.65.

EXAMPLE 67

4-(2,4-Dichlorophenylamino)benzo[3,2-b]pyridine-3-carbonitrile

A mixture of 250 mg (1.02 mmol) of 4-chlorobenzo[4,5]thieno[3,2-b]pyridine-3-carbonitrile, 530 mg (3.27 mmol) of 2,4-dichloroaniline and 112 mg of pyridine hydrochloride is heated until no 4-chlorobenzo[4,5]thieno[3,2-b]pyridine-3-carbonitrile remained as measured by thin layer chromatography. The reaction mire is cooled to room temperature and the solid is treated with methanol and then partitioned between ethyl acetate and saturated sodium bicarbonate. The organic layer is dried over magnesium sulfate, filtered and concentrated in vacuo. Diethyl ether is added to the residue and the solid is collected by filtration to give 225 mg (66%) of a yellow solid. An analytical sample is obtained by column chromatography, eluting with 6:1 hexane/ethyl acetate, to provide a fight yellow solid, mp 260–262° C.

$^1$HNMR (DMSO-d$_6$): δ 7.55–7.72 (m, 4H), 7.83 (s, 1H), 8.06 (d, 1H), 8.35 (d, 1H), 8.79 (s, 1H), 9.76 (s, 1H). MS (ES, positive ion mode): m/z calcd for $C_{18}H_9Cl_2N_3S$: 370.3, found: 369.8 (M+H)+. Analysis for $C_{18}H_9Cl_2N_3S \cdot 0.25H_2O$ Calcd: C:57.68; H:2.55; N:11.21 Found: C:57.64; H:2.48; N:10.94.

EXAMPLE 68

4-(2,4-Dichloro-5-methoxyphenylamino)benzo[4,5]thieno[3,2-b]pyridine-3-carbonitrile A mixture of 230 mg (1.2 mmol) of 2,4-dichloro-5-methoxyaniline (WO 8501939A1) and 48 mg (1.2 mmol) of 60% sodium hydride in mineral oil in 10 mL of tetrahydrofuran is heated at reflux temperature. The reaction mixture is cooled and 200 mg (0.82 mmol) of 4-chlorobenzo[4,5]thieno[3,2-b]pyridine-3-carbonitrile is added. The mixture is heated at reflux for 4 hours, then cooled to room temperature and partitioned between ethyl acetate and water. The organic layer is washed with water, dried over magnesium sulfate, filtered and concentrated in vacuo. Diethyl ether is added to the residue and the resultant solid is collected by filtration and purified by column chromatography, eluting with 3:1 hexane/ethyl acetate, to provide 89 mg (27%) of a white solid, mp 234–236° C.

$^1$HNMR (DMSO-$d_6$): δ 3.86 (s, 3H), 7.21 (s, 1H), 7.56–7.67 (m, 2H), 7.78 (s, 1H), 8.07 (d, 1H), 8.37 (d, 1H), 8.79 (s, 1H), 9.79 (s, 1H). MS (ES, positive ion mode): m/z calcd for $C_{19}H_{11}Cl_2N_3OS$: 400.3, found: 400.1 (M+H)+. Analysis for $C_{19}H_{11}Cl_2N_3OS \cdot 0.2\ CH_3CO_2C_2H_5$ Calcd: C:56.90; H:3.04; N:10.05 Found: C:56.99; H:3.37; N:10.07.

EXAMPLE 69

4-(4-Phenoxyphenylamino)benzo[4,5]thieno[3,2-b]pyridine-3-carbonitrile

A mixture of 250 mg (1.02 mmol) of 4-chlorobenzo[4,5]thieno[3,2-b]pyridine-3-carbonitrile and 210 mg (1.12 mmol) of 4-phenoxyaniline in 5 mL of 2-ethoxyethanol is heated at reflux temperature for 4 hours then stirred at room temperature for 3 days. The reaction mixture is then heated at reflux temperature for an additional 6 hours, then cooled to room temperature and partitioned between ethyl acetate and saturated sodium bicarbonate. The organic layer is dried over sodium sulfate, filtered and concentrated in vacuo to provide 240 mg (60%) of a beige solid, mp 230–233° C.

$^1$HNMR (DMSO-$d_6$): δ 7.06–7.19 (m, 5H), 7.32–7.47 (m, 4H), 7.55–7.86 (m, 2H), 8.05 (s, 1H), 8.34 (s, 1H), 8.75 (s, 1H), 9.65 (s, 1H). MS (ES, positive ion mode): m/z calcd for $C_{24}H_{15}N_3OS$: 393.5, found: 393.9 (M+H)+. Analysis for $C_{24}H_{15}N_3OS \cdot 0.5H_2O$ Calcd: C:71.61; H:3.98; N:10.44 Found: C:71.99; H:3.80; N:10.56.

EXAMPLE 70

4-(3-Hydroxy-4-methylphenylamino)benzo[4,5]thieno[3,2-b]pyridine-3-carbonitrile A mixture of 300 mg (1.20 mmol) of 4-chlorobenzo[4,5]thieno[3,2-b]pyridine-3-carbonitrile and 160 mg (1.32 mmol) of 5-amino-o-cresol in 5 mL of 2-ethoxyethanol is heated at reflux temperature for 8 hours, then stirred at room temperature overnight. The reaction mixture is partitioned between ethyl acetate and saturated sodium bicarbonate. The organic layer is dried over sodium sulfate, filtered and concentrated in vacuo to provide 220 mg (55%) of a light yellow solid, mp 260° C. dec.

$^1$HNMR (DMSO-$d_6$): δ 2.17 (s, 3H), 6.63 (dd, 1H), 6.69 (d, 1H), 7.09 (s, 1H), 7.52–7.67 (m, 2H), 8.01 (d, 1H), 8.33 (d, 1H), 8.76 (s, 1H), 9.55 (s, 1H). MS (ES, positive ion mode): m/z calcd for $C_{19}H_{13}N_3OS$: 331.4, found: 331.8 (M+H)+. Analysis for $C_{19}H_{13}N_3OS \cdot 0.2H_2O$ Calcd: C:68.11; H:4.03; N:12.54 Found: C:68.20; H:3.95; N: 12.31.

EXAMPLE 71

4-(4-Chloro-2-fluorophenoxy)benzo[4,5]thieno[3,2-b]pyridine-3-carbonitrile

A mixture of 0.59 mL (5.5 mmol) of 4-chloro-2-fluorophenol and 100 mg (1.78 mmol) of potassium hydroxide is heated until a homogeneous solution is formed. To this is added 245 mg (1.00 mmol) of 4-chlorobenzo[4,5]thieno[3,2-b]pyridine-3-carbonitrile and the mixture is heated for 2 hours. Ethyl acetate is added and the solution is washed with 1 N NaOH. The organic layer is dried over sodium sulfate, filtered and concentrated in vacuo. The solid is collected and recrystallized from ethyl acetate to give 195 mg (55%) of a light beige solid, mp 174–175° C.

$^1$HNMR (DMSO-$d_6$): δ 7.49 (m, 1H), 7.64–7.77 (m, 3H), 7.86 (dd, 1H), 8.15 (d, 1H), 8.46 (d, 1H), 9.19 (s, 1H). MS (ES, positive ion mode): m/z calcd for $C_{18}H_8ClFN_2OS$: 354.8, found: 354.8 (M+H)+. Analysis for $C_{18}H_8ClFN_2OS \cdot 0.3H_2O$ Calcd: C:60.02; H:2.41; N:7.78 Found: C:60.32; H:2.38; N:7.25.

EXAMPLE 72

3-Amino-5-nitrobenzo[b]thiophene

A solution of 23.00 g (91.26 mmol) of methyl 3-amino-5-nitrobenzo[b]thiophene-2-carboxylate (J. Hetero. Chem, 34(4), 1163 (1997)) in 100 mL of 1-methyl-2-pyrrolidinone and 30 mL of 1-methylpiperazine is heated at 180° C. for 2 hours. The reaction is cooled to room temperature and poured into water. The resultant solid is collected by filtration and washed with water. The solid is dissolved in a mixture of ethyl acetate and diethyl ether and the solution is washed with water twice. The organic layer is dried over magnesium sulfate, filtered and concentrated in vacuo. Diethyl ether and hexane are added to the residue and the dark red solid is collected by filtration to provide 11.17 g (63%), mp 155–158° C.

$^1$HNMR (DMSO-$d_6$): δ 5.67 (s, 2H, NH2), 6.39 (s, 1H), 8.05–8.14 (m, 2H), 8.88 (s, 1H). MS (ES, positive ion mode): m/z calcd for $C_8H_6N_2O_2S$: 194.2, found: 194.9 (M+H)+. Analysis for $C_8H_6N_2O_2S$ Calcd: C:49.48; H:3.11; N:14.42 Found: C:49.73; H:3.25; N: 14.13.

EXAMPLE 73

4-Hydroxy-8-nitrobenzo[4,5]thieno[3.2-b]pyridine-3-carbonitrile

A mixture of 9.00 g (46.34 mmol) of 3-amino-5-nitrobenzo[b]thiophene and 8.65 g (51.12 mmol) of ethyl (ethoxymethylene)cyanoacetate in 100 mL of toluene is heated at reflux for 2 hours. The reaction mixture is cooled to room temperature and the precipitate is collected by filtration washing with diethyl ether to provide 11.50 g (78%) of a bright yellow solid.

A 2.33 g portion of this solid is added to 40 mL of 1:3 biphenyl/diphenyl ether and the mixture is heated at reflux for 4 hours. The mixture is cooled slightly and the precipitate is collected by filtration, washing with diethyl ether and hexane to give 925 mg (46%) of a brown solid, mp>305° C.

$^1$HNMR (DMSO-d$_6$): δ 8.43 (s, 2H), 8.95 (s, 1H), 9.45 (s, 1H). MS (ES, negative ion mode): m/z calcd for C$_{12}$H$_5$N$_3$O$_3$S: 271.3, found: 270.2 (M–H)$^-$. Analysis for C$_{12}$H$_5$N$_3$O$_3$S Calcd: C:53.14; H:1.86; N:15.49 Found: C:52.81; H:2.07; N:15.31.

EXAMPLE 74

4-Chloro-8-nitrobenzo[4,5]thieno[3,2-b]pyridine-3-carbonitrile

A mixture of 1.22 g (4.49 mmol) of 4-hydroxy-8-nitrobenzo[4,5]thieno[3,2-b]pyridine-3-carbonitrile in 20 mL of phosphorous oxychloride is heated at reflux temperature for 3 hours, then cooled to room temperature. The solid is collected by filtration, then washed with hexane followed by water. The solid is dried to give 947 mg (73%) of a dark brown solid, mp softens at 270° C.

$^1$HNMR (DMSO-d$_6$): δ 8.59 (s, 2H, 9.09 (s, 1H), 9.34 (s, 1H). MS (ES, positive ion mode): m/z calcd for C$_{12}$H$_4$ClN$_3$O$_2$S: 289.7, found: 289.6 (M+H)$^+$. Analysis for C$_{12}$H$_4$ClN$_3$O$_2$S.1.0H$_2$O Calcd: C:46.83; H:1.97; N:13.66 Found: C:47.10; H:1.63; N:13.54.

EXAMPLE 75

4-(4-Chloro-5-methoxy-2-methylphenylamino-8-nitrobenzo[4,5]thieno[3,2-b]pyridine-3-carbonitrile A solution of 286 mg (0.99 mmol) of 4-chloro-8-nitrobenzo[4,5]thieno[3,2-b]pyridine-3-carbonitrile in 10 mL of 2-ethoxyethanol containing 131 mg (1.42 mmol) of 4-chloro-5-methoxy-2-methylaniline (WO 8501939A1) and 131 mg of pyridine hydrochloride is heated at reflux temperature overnight. The reaction mixture is cooled slightly and an additional 100 mg (0.58 mmol) of 4-chloro-5-methoxy-2-methylaniline is added and the reaction mixture is heated at reflux temperature overnight. The mixture is cooled to room temperature and the solid is collected by filtration, then suspended in methanol. Aqueous ammonium hydroxide is added and the mixture is partitioned between ethyl acetate and water. The organic layer is washed with water, then dried over magnesium sulfate, filtered and concentrated in vacuo. Diethyl ether is added to the residue and the resultant solid is collected by filtration, and washed with diethyl ether to give 110 mg (26%) of a tan solid, mp>305° C.

$^1$HNMR (DMSO-d$_6$): δ 2.10 (s, 3H), 3.78 (s, 3H), 7.23 (s, 1H), 7.49 (s, 1H), 8.33 (d, 1H), 8.39 (d, 1H), 8.83 (s, 1H), 9.00 (s, 1H), 9.70 (s, 1H). MS (ES, positive ion mode): m/z calcd for C$_{20}$H$_{13}$ClN$_4$O$_3$S: 424.9, found: 425.0 (M+H)$^+$. Analysis for C$_{20}$H$_{13}$ClN$_4$O$_3$S Calcd: C:56.54; H:3.08; N:13.19 Found: C:56.34; H:3.31; N: 12.81.

EXAMPLE 76

8-Amino-4-(4-chloro-5-methoxy-2-methylanilino)[1]benzothieno[3,2-b]pyridine-3-carbonitrile A mixture of 476 mg (1.12 mmol) of 4-(4-chloro-5-methoxy-2-methylphenylamino)-8-nitrobenzo[4,5]thieno[3,2-b]pyridine-3-carbonitrile, 180 mg (3.22 mmol) of iron powder and 180 mg (3.36 mmol) of ammonium chloride in 20 mL of 50% aqueous methanol is heated at reflux temperature for 2 hours. An additional 80 mg (1.42 mmol) of iron powder and 100 mg (1.87 mmol) of ammonium chloride are added and the reaction mixture is heated at reflux temperature for 2 hours, then stirred at room temperature overnight. The reaction mixture is heated at reflux for 4 hours then cooled slightly and filtered. The solid residue is extracted with several portions of hot ethyl acetate followed by hot methanol. All the organic layers are combined and washed with water. The organic layer is dried over magnesium sulfate, filtered and concentrated in vacuo. The residue is purified by flash chromatography eluting with a gradient of 1:1 hexane/ethyl acetate to only ethyl acetate to give 165 mg (37%) of a tan solid, mp 266–268° C. dec.

$^1$HNMR (DMSO-d$_6$): δ 2.07 (s, 3H), 3.77 (s, 3H), 5.38 (d, 2H), 6.90 (dd, 1H), 7.13 (s, 1H), 7.46 (s, 1H), 7.46 (d, 1H), 7.58 (d, 1H), 8.63 (s, 1H), 9.30 (s, 1H). MS (ES, positive ion mode): m/z calcd for C$_{20}$H$_{15}$ClN$_4$OS: 394.9, found: 395.1 (M+H)$^+$. Analysis for C$_{20}$H$_{15}$ClN$_4$OS.0.25CH$_3$CO$_2$C$_2$H$_5$ Calcd: C:60.50; H:4.11; N:13.44 Found: C:60.30; H:4.17; N:13.26.

EXAMPLE 77

7-Nitro-1-benzothiophen-3-amine

A mixture of 4.82 g (19.1 mmol) methyl 3-amino-7-nitro-1-benzothiophene-2-carboxylate (WO 9738983), 1-methyl-2-pyrrolidinone (23 mL) and 1-methylpiperazine (6.5 mL) is stirred at 185–190° C. for 4 hours, then cooled to room temperature. The precipitate is filtered, washed with diethyl ether, and dried to give 7-nitro-1-benzothiophen-3-amine (3.3 g, 89%) as a red-brown solid, m.p. 188–191° C.

$^1$HNMR (DMSO-d$_6$): δ 5.55 (s, br, 2H), 6.40 (s, 1H), 7.64 (t, 1H), 8.34 (d, 1H), 8.41 (d, 1H). MS (ES, positive ion mode): m/z calcd for C$_8$H$_6$N$_2$O$_2$S: 194.2, found: 195.1 (M+H)$^+$. Analysis for C$_8$H$_6$N$_2$O$_2$S.0.3 C$_2$H$_5$OC$_2$H$_5$. Calcd: C: 51.05; H: 4.19; N: 12.96 Found: C: 51.14; H 3.95; N: 13.21.

EXAMPLE 78

Ethyl (Z, E)-2-cyano-3-[(7-nitro-1-benzothien-3-yl)amino]-2-propenoate

A mixture of 7-nitro-1-benzothiophen-3-amine (3.3 g, 17.0 mmol) and ethyl(ethoxymethylene)cyanoacetate (3.16 g, 18.7 mmol) in toluene (30 mL) is heated at reflux temperature with stirring for two hours under nitrogen, then cooled, filtered, washed with diethyl ether, dried, and purified by column chromatography on silica gel, elution with chloroform/methanol 20:1. Ethyl (Z, E)-2-cyano-3-[(7-nitro-1-benzothien-3-yl)amino]-2-propenoate (4.5 g, 83%) is obtained as a yellow solid, m.p. 249–250° C. The ratio of Z and E isomers, determined by $^1$HNMR is 1:1.

$^1$HNMR (DMSO-d$_6$): δ 1.24 and 1.30 (t, 3H), 4.19 and 4.29 (q, 2H), 7.78 and 7.80 (t, 1H), 8.01 and 8.05 (s, 1H), 8.22 (s, 1H), 8.50 (m, 2H), 11.05 (d, 1H). MS (ES, negative ion mode): m/z calcd for C$_{14}$H$_{11}$N$_3$O$_4$S: 317.3, found: 316.2 (M–H)$^-$. Analysis for C$_{14}$H$_{11}$N$_3$O$_4$S Calcd: C: 52.99; H: 3.49; N: 13.24 Found: C: 52.85; H 3.61; N: 13.11.

EXAMPLE 79

4-Chloro-6-nitro[1]benzothieno[3,2-b]pyridine-3-carbonitrile

A suspension of ethyl (Z, E)-2-cyano-3-[(7-nitro-1-benzothien-3-yl)amino]-2-propenoate (3.17 g, 10.0 mmol) in 45 mL of 1:3 biphenyl/diphenyl ether is heated at 255° C. for 20 hours, then cooled, filtered, the precipitate thoroughly washed with diethyl ether and dried to give 1.1 g of 6-nitro-4-oxo-1,4-dihydro[1]benzothieno[3,2-b]pyridine-3-carbonitrile. This compound is dissolved in 25 mL of dichloromethane, and to the formed solution are added sequentially oxalyl chloride (4.0 mL of 2M solution in dichloromethane) and DMF (0.8 mL). The formed mixture is stirred for 4 hours at 40° C., then cooled and concentrated in vacuo. The residue is suspended in 5 mL of water, extracted with chloroform, and the extract dried over sodium sulfate. After the solvent evaporation the desired product is isolated by column chromatography on silica gel, elution with chloroform. The product is washed with diethyl ether and ethyl acetate, then dried in vacuo to provide 4-chloro-6-nitro[1]benzothieno[3,2-b]pyridine-3-carbonitrile (0.6 g, 20%) as a light-brown solid, m.p. 258–260° C.

$^1$HNMR (DMSO-$d_6$): δ 8.02 (t, 1H), 8.77 (dd, 1H), 8.96 (dd, 1H), 9.36 (s, 1H). MS (ES, positive ion mode): m/z calcd for $C_{12}H_4ClN_3O_2S$: 289.7, found: 289.0 (M+H)$^+$. Analysis for $C_{12}H_4ClN_3O_2S.0.5CH_3CO_2C_2H_5$ Calcd: C: 50.38; H: 2.42; N: 12.59 Found: C: 50.21; H: 2.33; N: 12.51.

EXAMPLE 80

4-(3-Bromoanilino)-6-nitro[1]benzothieno[3,2-b]pyridine-3-carbonitrile

A mixture of 4-chloro-6-nitro[1]benzothieno[3,2-b]pyridine-3-carbonitrile (0.27 g, 0.9 mmol), 3-bromoaniline (3.16 g, 18.4 mmol), and pyridine hydrochloride (0.06 g) in 15 mL of DMSO is stirred in the microwave (PROLABO unit) at 140° C., power range 0–10%, for one hour. The final reaction mixture is cooled, dissolved in 100 mL of chloroform, washed with 2N HCl (2×50 mL), then with saturated aqueous sodium bicarbonate (50 mL), and dried over sodium sulfate. The solvent is evaporated, and the desired compound purified by silica gel chromatography, eluting with 9:1 chloroform/methanol. After washing with diethyl ether and ethyl acetate, 4-(3-bromoanilino)-6-nitro[1]benzothieno[3,2-b]pyridine-3-carbonitrile (0.215 g, 55%) is obtained as a yellow solid, m.p. 288–290° C.

$^1$NMR (DMSO-$d_6$): δ 7.33 (d, 1H), 7.40 (t, 1H, 7.52 (m, 2H), 7.90 (t, 1H), 8.68 (d, 1H), 8.83 (d, 1H), 8.91 (s, 1H), 10.04 (s, br, 1H). MS (ES, positive ion mode): m/z calcd for $C_{18}H_9BrN_4O_2S$: 425.3, found: 427.0 (M+H)$^+$. Analysis for $C_{18}H_9BrN_4O_2S.0.5HCl.0.5CH_3CO_2C_2H_5$ Calcd: C: 49.27; H: 2.79; N: 11.49 Found: C: 49.02; H 2.42; N: 11.18.

EXAMPLE 81

6-Amino-4-(3-bromoanilino)[1]benzothieno[3,2-b]pyridine-3-carbonitrile

A mixture of 4-(3-bromoanilino)-6-nitro[1]benzothieno[3,2-b]pyridine-3-carbonitrile (0.213 g, 0.5 mmol), iron powder (0.168 g, 3.0 mmol) ammonium chloride (0.325 g, 6.0 mmol), methanol (90 mL) and water (90 mL) is heated at reflux temperature with vigorous stirring under nitrogen for 12 hours. The final mixture is concentrated, and the residue is extracted with ethyl acetate (5×20 mL). The extract is dried over sodium sulfate, evaporated, and re-dissolved in a small volume of chloroform/methanol/DMSO. Purification by silica gel chromatography, eluting with 20:1 chloroform/methanol, yields 6-amino-4-(3-bromoanilino)[1]benzothieno[3,2-b]pyridine-3-carbonitrile as a brown solid, m.p. 256–258° C.

$^1$HNMR (DMSO-$d_6$): δ 5.60 (s, br, 2H), 6.89 (d, 1H), 7.18 (d, 11), 7.32 (m, 4H), 7.65 (d, 1H), 8.83 (s, 1H), 9.76 (s, 1H). MS (ES, positive ion mode): m/z calcd for $C_{18}H_{11}BrN_4S$: 395.3, found: 397.0 (M+H)$^+$. Analysis for $C_{18}H_{11}BrN_4S.1CH_3SOCH_3$ Calcd: C: 50.74; H: 3.61; N: 11.83 Found: C: 50.90; H 3.24; N: 11.93.

EXAMPLE 82

3-(Dimethylaminomethyleneamino)benzofuran-2-carboxylic acid ethyl ester

A mixture of 4.2 g (20.0 mmol) of ethyl 3-amino-2-benzo[b]furancarboxylate (EP 187487 A1) in 10 mL of N,N-dimethylformamide dimethyl acetal is heated at reflux temperature for 1.5 hours, then cooled to room temperature and concentrated in vacuo. The residue is partitioned between ethyl acetate and water. The organic layer is washed with water, dried over sodium sulfate, passed through a pad of diatomaceous earth and concentrated in vacuo. The solid is collected by filtration to provide 3.90 g (75%) of a white solid, mp 89–90° C.;

$^1$HNMR (DMSO-$d_6$): δ 1.3 (t, 31), 3.04 (s, 3H), 3.06 (s, 31, 4.25 (t, 21), 7.38 (t, 1H), 7.49 (t, 1H), 7.57 (d, 1H), 7.68 (d, 1H), 7.99 (s, 1H). MS (ES, positive ion mode): m/z calcd for $C_{14}H_{16}N_2O_3$: 260.3, found: 260.9 (M+H)$^+$. Analysis for $C_{14}H_{16}N_2O_3$ Calcd: C:64.60; H:6.20; N:10.76 Found: C:64.45; H:6.04; N: 10.64.

EXAMPLE 83

4-Hydroxybenzo[4,5]furo[3,2-b]pyridine-3-carbonitrile

A solution of 1.5 mL (30.0 mmol) of acetonitrile in 30 mL of tetrahydrofuran is added to a −78° C. solution of 11.4 mL of 2.5 M n-butyllithium (29.00 mmol) in 35 mL of tetrahydrofuran. After stirring at −78° C. for 15 min a solution of 3.7 g (14.2 mmol) of 3-(dimethylaminomethyleneamino) benzofuran-2-carboxylic acid ethyl ester in 50 mL of tetrahydrofuran is added dropwise. After stirring at −78° C. for 30 minutes, the reaction mixture is allowed to warm to 0° C. The reaction mixture is cooled to −78° C. and 3 mL of acetic acid is added. The solution is warmed to room temperature and the resulting precipitate is collected. This solid is combined with 20 mL of acetic acid and heated at reflux temperature for 1.5 hours. The mixture is cooled to room temperature and the solid is collected by filtration washing with saturated sodium bicarbonate, water, diethyl ether and ethyl acetate to provide 2.45 g of a red solid, mp>310° C.

$^1$HNMR (DMSO-$d_6$): δ 7.53 (t, 1H), 7.72 (t, 1H), 7.86 (d, 1H), 8.13 (d, 1H), 8.80(s, 1H). MS (ES, positive ion mode): m/z calcd for $C_{12}H_6N_2O_2$: 210.2, found: 210.8 (M+H)$^+$. Analysis for $C_{12}H_6N_2O_2.0.50H_2O$ Calcd: C:65.52; H:3.21; N:12.71 Found: C:65.51; H:3.19; N:12.94.

EXAMPLE 84

4-Chlorobenzo[4,5]furo[3,2-b]pyridine-3-carbonitrile

A mixture of 2.10 g (11.0 mmol) of 4-hydroxybenzo[4,5]furo[3,2-b]pyridine-3-carbonitrile in 15 mL of phosphorous oxychloride is heated at reflux temperature for 1.5 hours, then cooled to room temperature. Hexane is added and the solid is collected by filtration, dissolved in ethyl acetate and washed with cold 1 N NaOH. The organic layer is dried over sodium sulfate, filtered through a pad of diatomaceous earth and concentrated in vacuo to give 1.55 g (65%) of a red solid, mp 229–231° C.
$^1$HNMR (DMSO-d$_6$): δ 7.64 (t, 1H), 7.87 (t, 1H), 8.00 (d, 1H), 8.28 (d, 1H), 9.14(s, 1H). MS (ES, positive ion mode): m/z calcd for C$_{12}$H$_5$ClN$_2$O: 228.6, found: 228.9 (M+)$^+$. Analysis for C$_{12}$H$_5$ClN$_2$O Calcd: C:63.04; H:2.20; N:12.25 Found: C:62.83; H:2.26; N:12.12.

EXAMPLE 85

4-(3-Bromophenylamino)benzo[4,5]furo[3,2-b]pyridine-3-carbonitrile

A solution of 300 mg (1.30 mmol) of 4-chlorobenzo[4,5]furo[3,2-b]pyridine-3-carbonitrile and 0.160 mL (1.43 mmol) of 3-bromoaniline in 8 mL of 2-ethoxyethanol is heated at reflux temperature for 24 hours. The reaction mixture is partitioned between ethyl acetate and saturated sodium bicarbonate. The organic layer is washed with saturated sodium bicarbonate, followed by brine, then dried over sodium sulfate, filtered through a pad of diatomaceous earth and concentrated in vacuo. The resultant solid is collected by filtration to give 300 mg (42%) of a beige solid, mp 242–245° C.
$^1$HNMR (DMSO-d$_6$): δ 7.21–7.57 (m, 5H), 7.70 (d, 2H), 8.18 (d, 1H), 8.74 (s 1H), 9.93 (s, 1H). MS (ES, negative ion mode): m/z calcd for C$_{18}$H$_{10}$BrN$_3$O: 362.4, found: 361.8 (M–H)$^-$. Analysis for C$_{18}$H$_{10}$BrN$_3$O Calcd: C:59.36; H:2.77; N:11.54 Found: C:59.01; H:2.97; N:11.36.

EXAMPLE 86

4-(4-Chloro-2-fluorophenylamino)benzo[4,5]furo[3,2-b]pyridine-3-carbonitrile

A mixture of 200 mg (0.88 mmol) of 4-chlorobenzo[4,5]furo[3,2-b]pyridine-3-carbonitrile and 0.11 mL (0.97 mmol) of 4-chloro-2-fluoroaniline in 6 mL of 2-ethoxyethanol is heated at reflux temperature for 4 days. A catalytic amount of pyridine hydrochloride is added and the reaction mixture is heated at reflux temperature overnight then cooled to room temperature. The reaction mixture is partitioned between ethyl acetate and water. The organic layer is dried over sodium sulfate, filtered through a pad of diatomaceous earth and concentrated in vacuo to provide 120 mg (40%) of a beige solid, mp 259–261° C.
$^1$HNMR (DMSO-d$_6$): δ 7.24–7.39 (m, 2H), 7.43–7.53 (m, 2H), 7.61 (d, 2H), 8.09 (d, 1H), 8.49 (s, 1H), 10.07 (s, 1H). MS (ES, positive ion mode): m/z calcd for C$_{18}$H$_9$ClFN$_3$O: 337.7, found: 337.8 (M+H)$^+$. Analysis for C$_{18}$H$_9$ClFN$_3$O.1.0H$_2$O Calcd: C:60.77; H:3.12; N: 11.81 Found: C:60.41; H:2.70; N:11.60.

EXAMPLE 87

4-(3-Hydroxy-4-methylphenylamino)benzo[4,5]furo[3,2-b]pyridine-3-carbonitrile

A mixture of 200 mg (0.88 mmol) of 4-chlorobenzo[4,5]furo[3,2-b]pyridine-3-carbonitrile and 120 mg (0.97 mmol) of 5-amino-o-cresol in 6 mL of 2-ethoxyethanol is heated at 80° C. for 15 hours and then at reflux temperature for 10 hours. The reaction mixture is cooled to room temperature and partitioned between ethyl acetate and saturated sodium bicarbonate. The organic layer is washed with saturated sodium bicarbonate, dried over sodium sulfate and filtered through a pad of diatomaceous earth. Concentration in vacuo yields 200 mg (72%) of a beige solid, mp 240° C. dec.
$^1$HNMR (DMSO-d$_6$): δ 2.13 (s, 3H), 6.61 (dd, 1H), 6.68 (d, 1H), 7.03 (d, 1H), 7.51 (t, 1H), 7.63–7.74 (m, 2H), 8.15 (d, 1H), 8.62 (s, 1H), 9.40 (s, 1H), 9.66 (s, 1H). MS (ES, positive ion mode): m/z calcd for C$_{19}$H$_{13}$N$_3$O$_2$: 315.3, found: 315.9 (M+H)$^+$. Analysis for C$_{19}$H$_{13}$N$_3$O$_2$.0.2H$_2$O Calcd: C:71.54; H:4.22; N:13.17 Found: C:71.39; H:4.31; N: 12.99.

EXAMPLE 88

4-(4-Phenoxyphenylamino)benzo[4,5]furo[3,2-b]pyridine-3-carbonitrile

A mixture of 200 mg (0.88 mmol) of 4-chlorobenzo[4,5]furo[3,2-b]pyridine-3-carbonitrile and 180 mg (0.96 mmol) of 4-phenoxyaniline in 5 mL of 2-ethoxyethanol is heated at reflux temperature for 3 hours. The reaction mixture is cooled to room temperature and partitioned between ethyl acetate and saturated sodium bicarbonate. The organic layer is washed with saturated sodium bicarbonate, followed by brine, then dried over sodium sulfate and filtered through a pad of diatomaceous earth. Concentration in vacuo yields 115 mg (35%) of a beige solid, mp 175–179° C.
$^1$HNMR (DMSO-d$_6$): δ 7.01–7.18 (m, 5H), 7.31–7.45 (m, 4H), 7.54 (dt, 1H), 7.65–7.73 (m, 2H), 8.15 (d, 1H), 8.62 (s, 1H), 9.83 (s, 1H). MS (ES, positive ion mode): m/z calcd for C$_{24}$H$_{15}$N$_3$O$_2$: 377.4, found: 377.9 (M+H)$^+$. Analysis for C$_{24}$H$_{15}$N$_3$O$_2$ Calcd: C:76.38; H:4.01; N:11.13 Found: C:76.13; H:3.96; N:11.14.

EXAMPLE 89

4-(4-Chloro-2-fluorophenoxy)-benzo[4,5]furo[3,2-b]pyridine-3-carbonitrile

A mixture of 0.530 mL (4.1 mmol) of 4-chloro-2-fluorophenol and 70 mg (1.25 mmol) of potassium hydroxide is heated until a homogeneous solution is formed. To this is added 170 mg (0.74 mmol) of 4-chlorobenzo[4,5]-furo[3,2-b]pyridine-3-carbonitrile and the mixture is heated for 1 hour. Ethyl acetate is added and the solution is washed with 1 N NaOH. The organic layer is dried over sodium sulfate, filtered through a pad of diatomaceous earth and concentrated in vacuo. The solid is collected to give 115 mg (46%) of a beige solid, mp 138–140° C.
$^1$HNMR (DMSO-d$_6$): δ 7.41 (d, 1H), 7.57–7.85 (m, 5H), 8.25 (d, 1H), 9.10 (s, 1H). MS (ES, positive ion mode): m/z calcd for C$_{18}$H$_8$ClFN$_2$O$_2$: 338.7, found: 338.8 (M+H)$^+$. Analysis for C$_{18}$H$_8$ClFN$_2$O$_2$.0.5H$_2$O Calcd: C:62.16; H:2.61; N:8.06 Found: C:62.00; H:2.34; N:7.71.

EXAMPLE 90

4-(2,4-Dichloroanilino)-8-nitro[1]benzothieno[3,2-b]pyridine-3-carbonitrile

A mixture of 160 mg (4.00 mmol) of sodium hydride (60% dispersion in oil) and 648 mg (4.00 mmol) of 2,4-dichloroaniline in 10 mL of dimethylformamide is stirred at room temperature for 1 hour. 4-Chloro-8-nitrobenzo[4,5]thieno[3,2-b]pyridine-3-carbonitrile, 578 mg (2.00 mmol), is added and the suspension is heated at 130° C. overnight. The reaction mixture is cooled to room temperature and partitioned between ethyl acetate and water. The organic layer is washed with water then dried over magnesium sulfate, filtered and concentrated in vacuo. Diethyl ether is added to the residue and the resultant solid is collected by filtration. The solid is suspended in diethyl ether and filtered. The filtrate is concentrated to a small volume and filtered to give 80 mg (29%) of 4-(2,4-dichloroanilino)-8-nitro[1]benzothieno[3,2-b]pyridine-3-carbonitrile as an off-white solid, mp 210–213° C.

$^1$HNMR (DMSO-d$_6$): δ 7.58 (dd, J=8 Hz, J=2 Hz, 1H), 7.65 (d, J=8 Hz, 1H), 7.85 (d, J=2 Hz, 1H), 8.36–8.45 (m, 2H), 8.87 (s, 1H) 9.01 (d, J=2 Hz, 1H), 9.97 (s, 1H). MS (ES, positive ion mode): m/z calcd for $C_{18}H_8Cl_2N_4O_2S$: 415.3, found: 415.0, 417.0 (M+H)$^+$. Analysis for $C_{18}H_8Cl_2N_4O_2S.0.2\ C_2H_5OC_2H_5$ Calcd: C, 52.50; H, 2.34; N, 13.03. Found: C, 52.27; H, 2.46; N, 13.00.

EXAMPLE 91

4-(3-Bromoanilino)-8-nitro[1]benzothieno[3,2-b]pyridine-3-carbonitrile

A solution of 400 mg (1.38 mmol) of 4-chloro-8-nitrobenzo[4,5]thieno[3,2-b]pyridine-3-carbonitrile in 8 mL of 2-ethoxyethanol containing 160 mg (1.38 mmol) of pyridine hydrochloride and 0.180 mL (1.65 mmol) of 3-bromoaniline is heated at reflux for 4 hours. The reaction mixture is filtered hot and the solid is stirred with methanol and ammonium hydroxide. The mixture is poured into water and the solid is collected, washing with ethyl acetate to give 363 mg (62%) of 4-(3-bromoanilino)-8-nitro[1]benzothieno[3,2-b]pyridine-3-carbonitrile as a brown solid, mp>300° C.

$^1$HNMR (DMSO-d$_6$): δ 7.32 (d, J=8 Hz, 1H), 7.40 (t, J=8 Hz, 1H), 7.52 (m, 2H), 8.37 (d, J=8 Hz, 1), 8.43 (dd, J=8 Hz, J=2 Hz, 1H), 8.92 (s, 1H), 9.01 (d, J=2 Hz, 1H), 10.03 (s, 1H). MS (ES, positive ion mode): m/z calcd for $C_{18}H_9BrN_4O_3S$: 425.3, found: 425.0, 427.1 (M+H)$^+$. Analysis for $C_{18}H_9BrN_4O_3S$ Calcd: C, 50.84; H, 2.13; N, 13.17. Found: C, 50.77; H, 2.47; N, 13.01.

EXAMPLE 92

8-Amino-4-(3-bromoanilino)-[1]benzothieno[3,2-b]pyridine-3-carbonitrile

A mixture of 436 mg (1.03 mmol) of 4-(3-bromoanilino)-8-nitro[1]benzothieno[3,2-b]pyridine-3-carbonitrile, 291 mg (5.19 mmol) of iron powder and 416 mg (7.77 mmol) of ammonium chloride in 160 mL of methanol and 110 mL of water is heated at reflux for 5.5 hours. The reaction mixture is filtered hot and the solid residue is extracted with several portions of hot ethyl acetate followed by hot methanol. All the organic layers are combined and washed with water. The organic layer is dried over magnesium sulfate, filtered and concentrated in vacuo. Diethyl ether and hexane are added and the solid is collected by filtration to provide 87 mg of 8-amino-4-(3-bromoanilino)-[1]benzothieno[3,2-b]pyridine-3-carbonitrile. The filtrate is concentrated and purified by flash chromatography, eluting with a gradient of 1:1 hexane/ethyl acetate to 100% ethyl acetate to give an additional 56 mg of 8-amino-4-(3-bromoanilino)-[1]benzothieno[3,2-b]pyridine-3-carbonitrile as a bright yellow solid, mp 295–300° C. dec.

$^1$HNMR (DMSO-d$_6$): δ 5.43 (s, 2H, 6.95 (dd, J=8 Hz, J=2 Hz, 1H), 7.21 (m, 1H), 7.29–7.40 (m, 3H), 7.51 (d, J=2 Hz, 1H), 7.64 (d, J=8 Hz, 1H), (8.77 (s, 1H), 9.67 (s, 1H). MS (ES, positive ion mode): m/z calcd for $C_{18}H_{11}BrN_4S$: 395.3, found: 395.2, 397.2 (M+H)$^+$. Analysis for $C_{18}H_{11}BrN_4S$ Calcd: C, 54.69; H, 2.80; N, 14.17. Found: C, 54.37; H, 2.85; N, 13.98.

EXAMPLE 93

N-[4-(3-Bromoanilino)-3-cyano[1]benzothieno[3,2-b]pyridin-8-yl]acrylamide

To a 0° C. solution of 164 mg (0.417 mmol) of 8-amino-4-(3-bromoanilino)-[1]benzothieno[3,2-b]pyridine-3-carbonitrile and 120 mg (0.626 mmol) of 1-[3-(dimethylamino)propyl]-3-ethylcarbodiimide hydrochloride in 2 mL of dimethylformamide and 2 mL of tetrahydrofuran is added 0.045 mL (0.656 mmol) of acrylic acid followed by 0.110 mL (0.633 mmol) of diisopropylethylamine. The reaction mixture is stirred at room temperature for 4 hours then partitioned between methylene chloride and water. The aqueous layer is extracted with additional methylene chloride and the organic layers are combined, dried over magnesium sulfate, filtered and concentrated in vacuo. The residue is purified by flash chromatography, eluting with a gradient of 95:5 methylene chloride/methanol to 9:1 methylene chloride/methanol, to provide 69 mg of N-[4-(3-bromoanilino)-3-cyano[1]benzothieno[3,2-b]pyridin-8-yl]acrylamide as a light tan solid, mp>300° C. dec.

$^1$HNMR (DMSO-d$_6$): δ 5.81 (dd, J=10 Hz, J=2 Hz, 1H), 6.32 (dd, J=17 Hz, J=2 Hz, 1H), 6.49 (dd, J=17 Hz, J=10 Hz, 1H), 7.25 (m, 1H), 7.30–7.47 (m, 2H), 7.80 (dd, J=9 Hz, J=2 Hz, 1H), 8.00 (d, J=9 Hz, 1H), 8.84 (s, 1H), 8.90 (d, J=2 Hz, 1H), 9.81 (s, 1H), 10.46 (s, 1H). MS (ES, positive ion mode): m/z calcd for $C_{21}H_{13}BrN_4OS$: 449.3, found: 449.1, 451.2 (M+H)$^+$. Analysis for $C_{21}H_{13}BrN_4OS$ Calcd: C, 56.13; H, 2.92; N, 12.47. Found: C, 55.91; H, 3.08; N, 12.18.

EXAMPLE 94

N-[4-(3-Bromoanilino)-3-cyano[1]benzothieno[3,2-b]pyridin-6-yl]acrylamide

A 0.138 g (0.349 mM) portion of 6-amino-4-(3-bromoanilino)[1]benzothieno[3,2-b]pyridine-3-carbonitrile is dissolved in 2 mL of tetrahydrofuran and 2 mL of dimethylformamide at 0° C. To this is added 0.042 g (0.583 mM) of acrylic acid, 0.105 g (0.575 mM) of N,N-diisopropylethylamine and 0.106 g (0.554 mM) of 1-(3-dimethylaminopropyl)-3-ethylcarbodiimide hydrochloride with stirring under nitrogen. The reaction mixture is stirred for 48 hours at room temperature, and the solvent is removed under reduced pressure. The residue is worked up with water (3 mL) and extracted with methylene chloride (10 mL), dried with sodium sulfate and evaporated. Purification of the product is carried out by silica get chromatography, eluting with 20:1 chloroform/methanol. Further purification is achieved by preparative thin layer chromatography, eluting with the same solvent system. Finally, the product is washed with ether to provide 0.068 g (43%) of N-[4-(3-bromoanilino)-3-cyano[1]benzothieno[3,2-b]pyridin-6-yl]acrylamide, m.p. 286–287° C.

$^1$H NMR (DMSO-d6): δ 5.63 (d, 1H), 6.30 (d, 1H), 6.54 (dd, 1H), 7.22 (d, 1H), 7.36 (m, 2H), 7.44 (s, 1H), 7.63 (t, 1H), 7.74 (d, 1H), 8.26 (d, 1H), 8.85 (s, 1H), 9.83 (s, 1H), 10.38 (s, 1H). MS (ES, positive ion mode): m/z calcd for $C_{21}H_{13}BrN_4OS$: 449.32, found: 451.3 (M+H)$^+$ Analysis for $C_{21}H_{13}BrN_4OS.C_4H_{10}O.0.8H_2O$ Calcd: C: 55.82; H: 4.61; N: 10.42 Found: C: 56.19; H: 4.86; N: 10.47.

EXAMPLE 95

Methyl 3-amino-6-methoxy-2-naphthoate and

EXAMPLE 96

Methyl 3-amino-7-methoxy-2-naphthoate

To 100 mL of methanol at room temperature is added 2.20 g (55 mmol) of 60% sodium hydride in mineral oil. The solution is stirred for 5 minutes, and added to a suspension of 5.0 g (21.9 mmol) 6-methoxynaphtho[2,3-c]furan-1,3-dione (Frank K. Brown, Peter J. Brown, D. Mark Bickett, C. Lynn Chambers, H. Geoff Davies, David N. Deaton, David Drewry, Michael Foley, Andrew B. McElroy, Michael Gregson, Gerald M. McGeehan, Peter L. Myers, David Norton, James M. Salovich, Frank J. Schoenen, and Peter Ward, *J. Med. Chem.*, 1994, 37, 674–688) in 100 mL of methanol. The mixture is stirred at room temperature for 10 minutes, and concentrated. The residue is partitioned between ethyl acetate and saturated sodium carbonate solution. After separation of the layers, the aqueous layer is neutralized with concentrated hydrochloric acid to pH 1. The product is extracted with ethyl acetate, dried over magnesium sulfate, and concentrated. A solution of this residue, 10 g of diphenylphosphoryl azide, and 10 mL of triethylamine in 100 mL of toluene is refluxed for 15 minutes and added dropwise to a mixture of 800 mL of acetone and 100 mL of water at 80° C. After continuing heating at 80° C. for 1 hour, the mixture is concentrated in vacuo. The residue is partitioned between ethyl acetate and saturated sodium chloride solution. Following separation of the layers, the organic layer is dried over magnesium sulfate and concentrated. The residue is chromatographed over silica gel, eluting with a gradient of 95:5 hexane/diethyl ether to 70:30 hexane/diethyl ether, providing 365 mg of (7.2%) methyl 3-amino-6-methoxy-2-naphthoate as a yellow solid, mp 152–154° C., and 466 mg of (9.2%) methyl 3-amino-7-methoxy-2-naphthoate as a yellow solid, mp 115–117° C.

Methyl 3-amino-6-methoxy-2-naphthoate: $^1$HNMR (CDCl$_3$): δ 3.89 (s, 3H); 3.93 (s, 3H); 5.59 (br s, 2H); 6.79 (d, J=1.3, 1H); 6.84 (m, 2H); 7.59 (d, J=6.6, 1H); 8.40 (s, 1H). MS (ES, positive ion mode): m/z calcd for C$_{13}$H$_{13}$O$_3$: 231.25, found: 232.2 (M+H)$^+$. Analysis for C$_{13}$H$_{13}$O$_3$ Calcd: C 67.52; H 5.67; N 6.06. Found: C 67.23; H 5.61; N 5.89.

Methyl 3-amino-7-methoxy-2-naphthoate: $^1$HNMR (CDCl$_3$): δ 3.87 (s, 3H); 3.94 (s, 3H); 5.42 (br s, 2H); 6.95 (s, 1H); 7.02 (d, J=1.8 Hz, 1H); 7.11 (dd, J=6.7 Hz, J=1.8 Hz, 1H); 7.45 (d, J=6.7 Hz, 1H); 8.40 (s, 1H). MS (ES, positive ion mode): m/z calcd for C$_{13}$H$_{13}$O$_3$: 231.25, found: 232.2 (M+H)$^+$. Analysis for C$_{13}$H$_{13}$O$_3$.0.3H$_2$O Calcd: C 65.98; H 5.79; N 5.92. Found: C 65.79; H 5.36; N 5.78.

EXAMPLE 97

Methyl 3-{[(E)-(dimethylamino)methylidene]amino}-7-methoxy-2-naphthoate

A suspension of 1.2 g (5.2 mmol) of methyl 3-amino-7-methoxy-2-naphthoate in 30 mL of dimethylformamide dimethylacetal is refluxed for 2.5 hours. The mixture is cooled to room temperature. The resulting precipitate is collected by filtration and washed with ether. After drying in vacuo, this yields 1.28 g (85.9%) of methyl 3-{[(E)-(dimethylamino)methylidene]amino}-7-methoxy-2-naphthoate as a light yellow solid, mp 160–162° C., $^1$HNMR (DMSO-d$_6$): δ 2.93 (br s, 3H); 3.00 (br s, 3H); 3.79 (s, 3H); 3.84 (s, 3H); 7.15 (dd, J=8.91 Hz, J=2.55 Hz, 1H); 7.24 (s, 1H); 7.31 (d, J=2.52 Hz, 1H); 7.68 (d, J=9.0 Hz, 1H); 7.71 (s, 1H); 7.94 (s, 1H). MS (ES, positive ion mode): m/z calcd for C$_{16}$H$_{18}$N$_2$O$_3$: 286.33, found: 287.3 (M+H)$^+$. Analysis for C$_{16}$H$_{18}$N$_2$O$_3$ Calcd: C 67.12; H 6.34; N 9.78 Found: C 67.10; H 6.35; N 9.70.

EXAMPLE 98

Methyl 3-{[(E)-(dimethylamino)methylidene]amino}-6-methoxy-2-naphthoate

According to the procedure of example 97, the reaction mixture of 1.05 g (4.54 mmol) of methyl 3-amino-6-methoxy-2-naphthoate in 20 mL of dimethylformamide dimethylacetal is refluxed for 2.5 hours to give 840.5 mg (64.6%) of methyl 3-{[(E)-(dimethylamino)methylidene]amino}-6-methoxy-2-naphthoate as a beige solid, mp 122–124° C.

$^1$HNMR (DMSO-d$_6$): δ 2.95 (br s, 3H); 3.09 (br s, 3H); 3.78 (s, 3H); 3.85 (s, 3H); 7.00 (dd, J=8.94 Hz, J=2.52 Hz, 1H); 7.14 (d, J=2.4 Hz, 1H); 7.17 (s, 1H); 7.70 (s, 1H); 7.79 (d, J=8.94 Hz, 1H); 8.01 (s, 1H). MS (ES, positive ion mode): m/z calcd for C$_{16}$H$_{18}$N$_2$O$_3$: 286.3, found: 287.3 (M+H)$^+$. Analysis for C$_{16}$H$_{18}$N$_2$O$_3$0.1H$_2$O Calcd: C 66.69; H 6.37; N 9.72 Found: C 66.68; H 6.45; N 9.42.

EXAMPLE 99

7-Methoxy-4-oxo-1,4-dihydrobenzo[g]quinoline-3-carbonitrile

To a solution of 4.75 mL (11.88 mmol) of n-butyllithium (2.5M in hexane) in 4.0 mL of tetrahydrofuran at −78° C. is added dropwise a solution of 0.68 mL (13.1 mmol) of acetonitrile in 6.8 mL of tetrahydrofuran. After completion of addition, the suspension is stirred for 10 minutes. To this is added 1.36 g (4.75 mmol) of methyl 3-{[(E)-(dimethylamino)methylidene]amino}-7-methoxy-2-naphthoate in 32 mL of tetrahydrofuran dropwise. The resulting reaction mixture is stirred at −78° C. for 1 hour, at −5° C. for 1 hour and at room temperature for 15 minutes. The reaction mixture is again cooled to −78° C. and 1.72 g (28.6 mmol) of acetic acid is added dropwise. After addition of the acetic acid, the reaction mixture is allowed to warm to room temperature. The precipitate is collected by filtration and washed sequentially with water, acetonitrile and methanol. After drying in vacuo, this yields 796.9 mg (67%) of 7-methoxy-4-oxo-1,4-dihydrobenzo[g]quinoline-3-carbonitrile as a deep yellow solid, mp>260° C.

$^1$HNMR (DMSO-d$_6$): δ 3.91 (s, 3H); 7.35 (dd, J=9.0 Hz, J=2.7 Hz, 1H); 7.62 (d, J=2.4 Hz, 1H); 8.03 (d, J=9.0 Hz, 1H); 8.23 (m, 1H); 8.09 (s, 1H); 8.71 (s, 1H); 8.75 (s, 1H). MS (ES, positive ion mode): m/z calcd for C$_{15}$H$_{10}$N$_2$O2: 250.3, found: 251.1 (M+H)$^+$. Analysis for C$_{15}$H$_{10}$N$_2$O2.0.3H$_2$O.0.3CH$_3$CN Calcd: C 69.92; H 4.33; N 12.02 Found: C 70.25; H 4.06; N 11.89.

EXAMPLE 100

8-Methoxy-4-oxo-1,4-dihydrobenzo[g]quinoline-3-carbonitrile

To a solution of 2.81 mL (7.03 mmol) of n-butyllithium (2.5M in hexane) in 2.0 mL of tetrahydrofuran at −78° C. is added dropwise a solution of 0.448 mL (8.44 mmol) of acetonitrile in 4.4 mL of tetrahydrofuran. After completion of addition, the suspension is stirred for 10 minutes. To this is added 804.5 mg (2.81 mmol) of methyl 3-{[(E)-(dimethylamino)methylidene]amino}-6-methoxy-2-naphthoate in 18 mL of tetrahydrofuran dropwise. The resulting reaction mixture is stirred at −78° C. for 1 hour and at −5° C. for 1 hour. The reaction mixture is again cooled to −78° C. and 4.0 mL (69.9 mmol) of acetic acid is added dropwise. The reaction mixture is warmed up to room temperature and stirred overnight. The precipitate is collected by filtration and washed sequentially with water, acetonitrile and methanol. After drying in vacuo, this yields 468.6 mg (67%) of 8-methoxy-4-oxo-1,4-dihydrobenzo[g]quinoline-3-carbonitrile as a yellow solid, mp>265° C.

$^1$HNMR (DMSO-$d_6$): δ 3.93 (s, 3H); 7.22 (dd, J=9.12 Hz, J=2.46 Hz, 1H); 7.45 (d, J=2.34 Hz, 1H); 7.98 (s, 1H); 8.13 (d, J=9.18 Hz, 1H); 8.74 (s, 1H); 8.75 (s, 1H). MS (ES, positive ion mode): m/z calcd for $C_{15}H_{10}N_2O_2$: 250.2567, found: 249.1 (M−H)$^-$. Analysis for $C_{15}H_{10}N_2O2.0.2H_2O$ Calcd: C 70.97; H 4.14; N 11.03 Found: C 70.74; H 3.96; N 11.14.

EXAMPLE 101

4-Chloro-7-methoxybenzo[g]quinoline-3-carbonitrile

A reaction mixture of 767.7 mg (3.1 mmol) of 7-methoxy-4-oxo-1,4-dihydrobenzo[g]quinoline-3-carbonitrile in 12 mL of phosphorus oxychloride and 5 drops of N,N-dimethylformamide (DMF) is refluxed for 2 hours. After cooling, the mixture is concentrated to dryness in vacuo to give a dark residue. The residue is partitioned between methylene chloride and ice-cooled saturated aqueous sodium carbonate solution. The organic layer is washed with ice-cooled brine and dried over sodium sulfate. The crude product is passed through a short column of silica gel, and further eluted with additional methylene chloride, followed by 95:5 methylene chloride/ethyl acetate. Removal of the solvent in vacuo yields 532.0 mg (64.7%) of 4-chloro-7-methoxybenzo[g]quinoline-3-carbonitrile as a bright yellow solid, mp 242–243° C.

$^1$HNMR (DMSO-$d_6$): δ 3.98 (s, 3H); 7.45 (dd, J=9.21 Hz, J=2.4 Hz, 1H); 7.75 (d, J=2.04 Hz, 1H); 8.24 (d, J=9.27 Hz, 1H); 8.83 (s, 1H); 8.89 (s, 1H); 9.10 (s, 1H). MS (ES, positive ion mode): m/z calcd for $C_{15}H_{10}ClN_2O$: 268.7, found: 269.1 (M+H)$^+$. Analysis for $C_{15}H_{10}N_2O2.0.1H_2O$ Calcd: C 66.60; H 3.43; N 10.35 Found: C 66.52; H 3.15; N 10.32.

EXAMPLE 102

4-Chloro-8-methoxybenzo[g]quinoline-3-carbonitrile

According to the procedure of example 101, 446.7 mg (1.8 mmol) of 8-methoxy-4-oxo-1,4-dihydrobenzo[g]quinoline-3-carbonitrile is refluxed in 102 mL of phosphorus oxychloride and 4 drops of N,N-dimethylformamide (DMF) for 1.5 hours to give 389.0 mg (81.6%) of 4-chloro-8-methoxy-benzo[g]quinoline-3-carbonitrile as a bright yellow solid, mp 258–260° C.

$^1$HNMR (DMSO-$d_6$): δ 3.99 (s, 3H); 7.41 (dd, J=9.24 Hz, J=2.43 Hz, 1H); 7.75 (d, J=2.22 Hz, 1H); 8.32 (d, J=9.3 Hz, 1H); 8.70 (s, 1H); 8.99 (s, 1H); 9.13 (s, 1H). MS (ES, positive ion mode): m/z calcd for $C_{15}H_9ClN_2O$: 268.7, found: 269.1 (M+H)$^+$. Analysis for $C_{15}H_{10}N_2O2.0.1H_2O$ Calcd: C 66.60; H 3.43; N 10.35 Found: C 66.56; H 3.22; N 10.33.

EXAMPLE 103

4-(2,4-Dichloroanilino)-7-methoxybenzo[g]quinoline-3-carbonitrile

According to the procedure of Example 14, a reaction mixture of 657.8 mg (4.06 mmol) of 2,4-dichloroaniline and 162.4 mg (4.06 mmol) of sodium hydride in 18 mL of anhydrous DMF is stirred at room temperature for 0.5 hour. To the mixture is added 494.0 mg (1.84 mmol) of 4-chloro-7-methoxybenzo[g]quinoline-3-carbonitrile. The resulting mixture is heated at 55° C. for 1 hour. After work up, 624.6 mg (86.2%) of 4-(2,4-dichloroanilino)-7-methoxybenzo[g] quinoline-3-carbonitrile is obtained as a yellow solid, mp 215–217° C.

$^1$HNMR (DMSO-$d_6$/TFA): δ 3.99 (s, 3l); 7.49 (d, J=2.28 Hz, 1H); 7.62 (dd, J=9.18 Hz, J=2.43 Hz, 1H); 7.68 (dd, J=8.55 Hz, J=2.28 Hz, 1H); 7.81 (d, J=8.55 Hz, 1H); 7.94 (d, J=2.25 Hz, 1H); 8.18 (d, J=9.27 Hz, 11); 8.59 (s, 1H); 9.28 (s, 1H); 9.40 (s, 1H). MS (ES, positive ion mode): m/z calcd for $C_{21}H_{13}Cl_2N_3O$: 394.3, found: 394.1, 396.1 (M+H)$^+$. Analysis for $C_{21}H_{13}Cl_2N_3O$ Calcd: C 63.98; H 3.32; N 10.66 Found: C 66.89; H 3.35; N 10.44.

EXAMPLE 104

4-(2,4-Dichloroanilino)-8-methoxybenzo[g]quinoline-3-carbonitrile

According to the procedure of Example 14, a reaction mixture of 487.7 mg (3.01 mmol) of 2,4-dichloroaniline and 120.6 mg (3.01 mmol) of sodium hydride in 15 mL of anhydrous DMF is stirred at room temperature for 0.5 hour. To the mixture is added 367.0 mg (1.37 mmol) of 4-chloro-8-methoxybenzo[g]quinoline-3-carbonitrile. The resulting mixture is heated at 55° C. for 0.5 hour. After work up, 443.3 mg (82.1%) of 4-(2,4-dichloroanilino)-8-methoxybenzo[g] quinoline-3-carbonitrile is obtained as a yellow solid, mp>260° C.

$^1$HNMR (DMSO-$d_6$/TFA): δ 4.02 (s, 3H); 7.47 (dd, J=9.15 Hz, J=2.28 Hz, 1H); 7.66 (m, 2H); 7.81 (d, J=8.55 Hz, 1H); 7.91 (d, J=2.28 Hz, 1H); 8.17 (d, J=9.24 Hz, 1H); 8.47 (s, 1H); 8.28 (s, 1H); 9.49 (s, 1H). MS (ES, positive ion mode): m/z calcd for $C_{21}H_{13}Cl_2N_3O$: 394.3, found: 394.1, 396.1 (M+H)$^+$. Analysis for $C_{21}H_{13}Cl_2N_3O.0.2H_2O$ Calcd: C 63.40; H 3.39 N 10.56 Found: C 63.40; H 3.43; N 10.35.

EXAMPLE 105

4-(2,4-Dichloroanilino)-7-hydroxybenzo[g]quinoline-3-carbonitrile

A reaction mixture of 566.5 mg (1.44 mmol) of 4-(2,4-dichloroanilino)-7-methoxybenzo[g]quinoline-3-carbonitrile and 10 g of pyridine hydrochloride is stirred at 215° C. for 50 min under nitrogen. After cooling, the mixture is neutralized with 40 mL of a 3% ammonium hydroxide solution and stirred for 0.5 hour. The separated solid is filtered off and washed with water and ether. After drying in vacuo, this yields 527.9 mg (96.5%) of 4-(2,4-dichloroanilino)-7-hydroxybenzo[g]quinoline-3-carbonitrile as a salmon color solid, mp>300° C.

$^1$HNMR (DMSO-$d_6$/TFA): δ 7.47 (s, 1H); 7.53(dd, J=9.06 Hz, J=2.28 Hz, 1H); 7.67 (dd, J=8.55 Hz, J=2.25 Hz, 1H); 7.81 (d, J=8.52 Hz, 1H); 7.92 (d, J=2.22 Hz, 1H); 8.23 (d, J=9.15 Hz, 1H); 8.55 (s, 1H); 9.24 (s, 1H); 9.30 (s, 1H). MS (ES, positive ion mode): m/z calcd for $C_{20}H_{11}Cl_2N_3O$:

380.2, found: 380.2, 382.1 (M+H)$^+$. Analysis for C$_{20}$H$_{11}$Cl$_2$N$_3$O.1.3H$_2$O Calcd: C 59.51; H 3.40N 10.41 Found: C 59.63; H 3.30; N 10.50

EXAMPLE 106

4-(2,4-Dichloroanilino)-8-hydroxybenzo[g]quinoline-3-carbonitrile

According to the procedure of example 105, the reaction mixture of 373.9 mg (0.954 mmol) of 4-(2,4-dichloroanilino)-8-methoxybenzo[g]quinoline-3-carbonitrile and 10 g of pyridine hydrochloride is stirred at 215° C. for 1 hour under N$_2$. After cooling, the mixture is neutralized with 40 mL of a 3% ammonium hydroxide solution and stirred for 0.5 hour. The separated solid is filtered off and washed with water and ether. After drying in vacuo, this yields 333.4 mg (92.6%) of 4-(2,4-dichloroanilino)-8-hydroxybenzo[g] quinoline-3-carbonitrile as a yellow solid, mp 267–269° C.
$^1$HNMR (DMSO-d$_6$/TFA): δ 7.44 (s, 1H); 7.47 (d, J=2.22 Hz, 1H); 7.67 (dd, J=8.49 Hz, J=2.28 Hz, 1H); 7.80 (d, J=8.52 Hz, 1H); 7.94 (d, J=2.25 Hz, 1H); 8.15 (d, J=9.78 Hz, 1H); 8.30 (s, 1H); 9.25 (s, 1H); 9.44 (s, 1H). MS (ES, positive ion mode): m/z calcd for C$_{20}$H$_{11}$Cl$_2$N$_3$O: 380.2, found: 380.2, 382.1 (M+H)$^+$. Analysis for C$_{20}$H$_{11}$Cl$_2$N$_3$O.1H$_2$O Calcd: C 60.31; H 3.29; N 10.55 Found: C 60.22; H 3.23; N 10.32

EXAMPLE 107

4-(2,4-Dichloroanilino)-7-[2-(dimethylamino) ethoxy]benzo[g]quinoline-3-carbonitrile To a suspension of 189.1 mg (0.50 mmol) of 4-(2,4-dichloroanilino)-7-hydroxybenzo[g]quinoline-3-carbonitrile, 207.2 mg (0.79 mmol) of triphenylphosphine and 66.9 mg (0.75 mmol) of 2-(dimethylamino)-ethanol in 3.0 mL of anhydrous methylene chloride at 0° C. is added dropwise diethyl azodicarboxylate. The resulting reaction mixture is stirred at room temperature under nitrogen for 2 days. The solvent is concentrated in vacuo and the residue is purified on preparative thin layer chromatography (developing solvent: 9:1 methylene chloride/methanol) to provide 46.3 mg (20.5%) of 4-(2,4-dichloroanilino)-7-[2-(dimethylamino) ethoxy]benzo[g]quinoline-3-carbonitrile as a yellow solid, mp 115–117° C.
$^1$HNMR (DMSO-d$_6$): δ 2.50 (s, 6H); 2.72(m, 2H); 4.21 (m, 1H); 4.38(m, 1H); 6.98 (d, J=8.46 Hz, 1H); 7.31 (m, 2H); 7.51 (d, J=2.01 Hz, 1H); 7.60 (s, 1H); 8.02 (d, J=9.18 Hz, 1H); 8.20 (s, 1H); 8.27 (s, 1H); 8.33 (s, 1H); 8.98 (d, J=15.72 Hz, 1H). MS (ES, positive ion mode): m/z calcd for C$_{24}$H$_{20}$Cl$_2$N$_4$O: 451.4, found: 451.2, 453.3 (M+H)$^+$. Analysis for C$_{20}$H$_{11}$Cl$_2$N$_3$O.1.3H$_2$O Calcd: C60.71; H 4.80; N 11.80 Found: C 60.62; H 4.92; N 12.20

EXAMPLE 108

1-(2-Chloroethoxy)-2-methoxybenzene

A mixture of 52.88 g (0.426 mole) of guaiacol, 100 g (0.426 mole) of chloroethyl tosylate, 88.3 g (0.639 mole) of powdered potassium carbonate and 600 mL of 2-butanone is stirred mechanically and refluxed for 2 days. The reaction is filtered and the solid is rinsed with 2-butanone. The filtrate is evaporated and the residue taken up in ether and washed with 1N NaOH to remove unreacted guaiacol. The ether layer is dried over sodium sulfate, filtered and evaporated to give an oil which slowly crystallized. The solid is isolated with cold cyclohexane to give 41.47 g (52%) of 1-(2-Chloroethoxy)-2-methoxybenzene as a white solid, m.p. 42–3° C.
$^1$HNMR (CDCl$_3$): δ 6.85–7.02 (m, 4H); 4.28 (t, J=6.3 Hz, 2H); 3.87 (s, 3H); 3.84 (t, J=6.3 Hz, 2H). MS (ES, positive ion mode): m/z calcd for C$_9$H$_{11}$ClO$_2$: 186.64, found: 187.4 (M+1)$^+$. Analysis for C$_9$H$_{11}$ClO$_2$ Calcd: C 57.92; H 5.94 Found: C 57.80; H 5.94

EXAMPLE 109

1-(2-chloroethoxy)-4,5-bis(chloromethyl)-2-methoxybenzene

To a solution of the 55.99 g (300 mmol) of 1-(2-Chloroethoxy)-2-methoxybenzene in 250 mL 1,4-dioxane is added 40 mL of concentrated hydrochloric acid while stirring at 0° C. While bubbling in HCl gas, 30 mL of 35% formalin is added. After 45 minutes, another equal volume of formalin is added. The addition of HCl gas is continued for 6 hours, the ice-bath is removed after 2 hours and allowed to warm to ambient temperature. The reaction mixture is stirred overnight at ambient temperature. The green reaction mixture is then cooled in an ice bath and the resulting solid is filtered and washed with cold dioxane/water (2.5:1). The solid is chromatographed on silica gel eluting with 2:1 hexanes/dichloromethane to give 36.35 g (42%) of 1-(2-chloroethoxy)-4,5-bis(chloromethyl)-2-methoxybenzene as a white solid, m.p. 117–8° C,
$^1$HNMR (CDCl$_3$): δ 6.92 (s, 1H); 6.91 (s, 1H); 4.70 (s, 2H); 4.69 (s, 2H); 4.29 (t, J=6.2 Hz, 2H); 3.90 (s, 31); 3.84 (t, J=6.2 Hz, 2H) MS (ES, positive ion mode): m/z calcd for C$_{11}$H$_{13}$Cl$_3$O$_2$: 282.00, found: 282.0 (M+H)$^+$. Analysis for C$_{11}$H$_{13}$Cl$_3$O$_2$ Calcd: C 46.59; H 4.62 Found: C 46.59; H 4.70

EXAMPLE 110

2-[(acetyloxy)methyl]-4-(2-chloroethoxy)-5-methoxybenzyl Acetate

To a solution of 5.67 g (0.020 mole) of 1-(2-chloroethoxy)-4,5-bis(chloromethyl)-2-methoxybenzene in 75 ml acetic acid is added a solution of 3.5 g of anhydrous sodium acetate in 100 ml acetic acid. This mixture is refluxed with stirring for 2 hours. Solids are removed by filtration and washed with acetic acid. The filtrate is evaporated to approximately 30 ml, then poured into water and extracted with ether. The organic phase is washed with aqueous sodium carbonate, water and brine. After drying over sodium sulfate, the solution is filtered and evaporated to give 5.69 g (86%) of 2-[(acetyloxy)methyl]-4-(2-chloroethoxy)-5-methoxybenzyl acetate as a white solid, m.p. 79–80° C.
$^1$HNMR (CDCl$_3$): δ 6.96 (s, 1H); 6.94 (s, 1H); 5.14 (s, 2H); 5.12 (s, 21); 4.29 (t, J=6.2 Hz, 21); 3.89 (s, 3H); 3.84 (t, =6.2 Hz, 2H); 2.09 (s, 3H); 2.08 (s, 3H). MS (EI): m/z calcd for C$_{15}$H$_{19}$ClO$_6$: 330.09, found: 329.72 (M$^+$). Analysis for C$_{15}$H$_{19}$ClO$_6$ Calcd: C 54.47; H 5.79 Found: C 54.61; H 5.59

EXAMPLE 111

[4-(2-chloroethoxy-2-(hydroxymethyl)-5-methoxyphenyl]methanol

A solution of 14.0 g of the 2-[(acetyloxy)methyl]4-(2-chloroethoxy)-5-methoxybenzyl acetate in 600 mL of methanol is stirred and cooled in an ice bath while ammonia gas is bubbled in, until the solution is saturated. The flask is stoppered and stored in the refrigerator for 15 hours. The reaction mixture is evaporated to give a white solid which is dried and chromatographed on a silica gel column eluting with 2:1 hexanes/ethyl acetate, to give 9.87 g of [4-(2-chloroethoxy)-2-(hydroxymethyl)-5-methoxyphenyl]methanol as a white solid, m.p. 934° C.

$^1$HNMR (CDCl$_3$): δ 6.94 (s, 1H); 6.93 (s, 1H); 4.68 (br s, 4H); 4.29 (t, J=6.2 Hz, 2H); 3.88 (s, 3H); 3.83 (t, J=6.2 Hz, 2H); 2.77 (br s, 1H); 2.71 (br s, 1H). MS (ES, positive ion mode): m/z calcd for C$_{11}$H$_{15}$ClO$_4$: 246.1, found: 264.10 (M+NH$_4$)$^+$. Analysis for C$_{11}$H$_{15}$ClO$_4$ Calcd: C 53.56; H 6.13 Found: C 53.86; H 6.11.

EXAMPLE 112

4-(2-chloroethoxy)-5-methoxyphthalaldehyde

To a 500 mL 3-neck round bottom flask fitted with mechanical stirrer, thermometer and addition funnel is added 100 mL dry methylene chloride and 8 mL of oxalyl chloride under nitrogen. This is cooled to −78° C. in a dry ice/acetone bath, then 13.6 mL DMSO in 25 mL dry methylene chloride is added dropwise. After complete addition it is further stirred for 5 minutes. Then 9.87 g of [4-(2-chloroethoxy)-2-(hydroxymethyl)-5-methoxyphenyl]methanol in 10 mL of dry methylene chloride (with enough DMSO added to dissolve the solid) is added dropwise. The reaction mixture is stirred for an additional 30 minutes, then 100 mL of triethylamine is added slowly at −78° C. The solution is stirred for 10 minutes, allowed to warm to room temperature and then 200 mL of ice/water is added. The aqueous layer is extracted with methylene chloride (2×100 mL). The organic layer is dried over MgSO$_4$, filtered and evaporated to give the crude product as a solid. This solid is slurried with cold methanol and filtered, washed with cold methanol, then dried to give 6.37 g of 4-(2-chloroethoxy)-5-methoxyphthalaldehyde as a yellowish solid, m.p. 113–4° C.

$^1$HNMR (CDCl$_3$): δ 7.49 (s, 1H); 7.47 (s, 1H); 4.43 (t, J=5.9 Hz, 2H); 4.03 (s, 3H); 3.91 (t, J=5.9 Hz, 2H). MS (ES, positive ion mode): m/z calcd for C$_{11}$H$_{11}$ClO$_4$: 242.03, found: 242.0 (M+H)$^+$. Analysis for C$_{11}$H$_{11}$ClO$_4$ Calcd: C 54.45; H 4.57 Found: C 54.32; H 4.21.

EXAMPLE 113

Ethyl 3-nitropropionate

A mixture of 25 g (0.21 mole) of 3-nitropropionic acid, 300 mL of absolute ethanol and 10 drops of concentrated sulfuric acid is refluxed overnight. The reaction mixture is evaporated, and the residue partitioned between water and ether. The ether layer is washed with water, aqueous sodium bicarbonate solution and brine, then dried over sodium sulfate. The ether is removed in vacuo and the product distilled as a clear liquid to provide 21.54 g (69%) of Ethyl 3-nitropropionate as a clear oil, b.p. 160–165° C. at 120 mm Hg.

$^1$HNMR (CDCl$_3$): δ 4.66 (t, J=6.1 Hz, 2H); 4.18 (q, J=7.1 Hz, 2H); 2.98 (t, J=6.1 Hz, 2H); 1.28 (t, J=7.1 Hz, 3H).

EXAMPLE 114 ethyl 7-(2-chloroethoxy)-6-methoxy-3-nitro-2-naphthoate and

EXAMPLE 115 ethyl 6-(2-chloroethoxy)-7-methoxy-3-nitro-2-naphthoate

To a solution of 2.43 g of ethyl 3-nitropropionate in 15 ml of absolute ethanol cooled using an ice bath, is added 20 mL of 1 N sodium ethoxide in ethanol dropwise over 10 minutes keeping the temperature at 0–5° C. A slurry of 4-(2-chloroethoxy)-5-methoxyphthalaldehyde in 5 mL of ethanol is added. The ice bath is removed and the reaction allowed to warm to room temperature and stirred for 16 hours. The reaction is transferred to a beaker with 300 mL of water and neutralized with acetic acid to pH 4. The solid is collected and washed first with water, then with 40 mL of cold ethanol. The solid is dried to provide 2.48 g (70%) of ethyl 7-(2-chloroethoxy)-6-methoxy-3-nitro-2-naphthoate and ethyl 6-(2-chloroethoxy)-7-methoxy-3-nitro-2-naphthoate (1:1 mixture) as a yellow solid, m.p. 119–29° C. dec.

$^1$HNMR (CDCl$_3$): δ 8.27 (s, 1H); 8.05 (s, 1H); 7.24 and 7.23 and 7.22 (3s, 2H); 4.37–4.45 (m, 4H); 4.03 (s, 3H); 3.95 (t, J=6.0 Hz, 2H); 1.38 (t, J=7.1 Hz, 3H). MS (ES, positive ion mode): m/z calcd for C$_{16}$H$_{16}$ClNO$_6$: 353.1, found: 354.2 (M+H)$^+$. Analysis for C$_{16}$H$_{16}$ClNO$_6$ Calcd: C 54.32; H 4.56; N 3.96 Found: C 53.96; H 4.43; N 3.71.

EXAMPLE 116 ethyl 3-amino-7-(2-chloroethoxy)-6-methoxy-2-naphthoate and

EXAMPLE 117 ethyl 3-amino-6-(2-chloroethoxy)-7-methoxy-2-naphthoate

A 1.60 g portion of ethyl 7-(2-chloroethoxy)-6-methoxy-3-nitro-2-naphthoate and ethyl 6-(2-chloroethoxy)-7-methoxy-3-nitro-2-naphthoate (1:1 mixture) is heated in 100 mL absolute ethanol until dissolved. The solution is allowed to cool to room temperature and 0.2 g of 10% palladium on carbon is added. Hydrogenation is carried out in a Parr apparatus at 50 psi for 2 hours. The reaction mixture is filtered through celite and the filter cake is rinsed with ethanol. The filtrate and washes are combined and evaporated to give ethyl 3-amino-7-(2-chloroethoxy)-6-methoxy-2-naphthoate and ethyl 3-amino-6-(2-chloroethoxy)-7-methoxy-2-naphthoate (1:1 mixture) as a greenish yellow solid, 1.28 g (87%), m.p. 104–8° C.

$^1$HNMR (CDCl$_3$): δ 8.34 and 8.32 (2s, 1H); 7.06 and 7.03 (2s, 1H); 6.85 and 6.84 (2s, 1H); 6.82 (s, 1H); 5.52 (br s, 2H); 4.30–4.43 (m, 4H); 3.97 and 3.93 (2s, 3H); 3.89 (t, J=6.6 Hz, 2H); 1.44 (t, J=7.1 Hz, 3H). MS (ES, positive ion mode): m/z calcd for C$_{16}$H$_{18}$ClNO$_4$: 323.1, found: 324.3 (M+H)$^+$. Analysis for C$_{16}$H$_{18}$ClNO$_4$ Calcd: C 59.35; H 5.60; N 4.33 Found: C 59.54; H 5.74; N 4.08.

EXAMPLE 118

8-(2-chloroethoxy)-7-methoxy-4-oxo-1,4-dihydrobenzo[g]quinoline-3-carbonitrile and

EXAMPLE 119

7-(2-chloroethoxy)-8-methoxy-4-oxo-1,4-dihydrobenzo[g]quinoline-3-carbonitrile

A 648 mg portion of ethyl 3-amino-7-(2-chloroethoxy)-6-methoxy-2-naphthoate and ethyl 3-amino-6-(2-chloroethoxy)-7-methoxy-2-naphthoate (1:1 mixture) and 5 mL of dimethylformamide dimethylacetal is heated to reflux using an oil bath. The reaction is kept at reflux overnight. Solvent is removed in vacuo to provide crude ethyl 6-(2-chloroethoxy)-3-{[(E)-(dimethylamino)methylidene]amino}-7-methoxy-2-naphthoate and ethyl 7-(2-chloroethoxy)-3-{[(E)-(dimethylamino)-methylidene]amino}-6-methoxy-2-naphthoate (1:1 mixture) as a dark red mixture.

To 2.5 mL of dry tetrahydrofuran at −78° C. is added 1.8 mL of 2.5 M n-butyllithium (4.4 mmol). Then 0.24 mL of dry acetonitrile in 4.5 mL of dry tetrahydrofuran is added dropwise over 10 minutes. This is stirred and additional 15 minutes at −78° C., then the ethyl 6-(2-chloroethoxy)-3-{[(E)-(dimethylamino)methylidene]-amino}-7-methoxy-2-naphthoate and ethyl 7-(2-chloroethoxy)-3-{[(E)-(dimethylamino)methylidene]amino}-6-methoxy-2-naphthoate (1:1 mixture) is dissolved in 3 mL of tetrahydrofuran and added dropwise over 15 minutes. The reaction mixture is stirred for 30 minutes at −78° C., then quenched with 0.57 mL of glacial acetic acid, and warmed to room temperature. To the yellow mixture is added 10 mL of water. The solids are filtered, washed with water and dried to give 0.502 g of 8-(2-chloroethoxy)-7-methoxy-4-oxo-1,4-dihydrobenzo]quinoline-3-carbonitrile and 7-(2-chloroethoxy)-8-methoxy-4-oxo-1,4-dihydrobenzo[g]quinoline-3-carbonitrile (1:1 mixture) as a yellow green solid (76%), m.p. 260–73° C. dec.

$^1$HNMR (DMSO-$d_6$): δ 8.68 (s, 1H); 8.62 and 8.61 (2s, 1H); 7.95 and 7.94 (2s, 1H); 7.62 and 7.61 (2s, 1H); 7.49 and 7.47 (2s, 1H); 4.37–4.47 (m, 2H); 4.00–4.11 (m, 2H); 3.96 and 3.93 (2s, 3H). MS (ES, positive ion mode): m/z calcd for $C_{17}H_{13}ClN_2O_3$: 328.1, found: 329.5 (M+H)$^+$.

EXAMPLE 120

4-chloro-7-methoxy-8-(2-chloroethoxy)benzo[g]quinoline-3-carbonitrile and

EXAMPLE 121

4-chloro-8-methoxy-7-(2-chloroethoxy)benzo[g]quinoline-3-carbonitrile

To a slurry of 1.11 g of 8-(2-chloroethoxy)-7-methoxy-4-oxo-1,4-dihydrobenzo[g]quinoline-3-carbonitrile and 7-(2-chloroethoxy)-8-methoxy-4-oxo-1,4-dihydrobenzo]quinoline-3-carbonitrile (1:1 mixture) and 5 mL of phosphorus oxychloride is added 0.15 mL of anhydrous dimethylformamide. This is stirred and heated to reflux for 20 minutes using an oil bath, followed concentration in vacuo. The dark residue is quenched with 30 mL of cold water. The solid formed is collected, washed with water and dried to give 1.02 g (87%) of 4-chloro-7-methoxy-8(2-chloroethoxy)benzo[g]quinoline-3-carbonitrile and 4-chloro-8-methoxy-7(2-chloroethoxy)benzo[g]quinoline-3-carbonitrile (1:1 mixture) as a greenish yellow solid, m.p. 195–209° C. dec.

$^1$HNMR(CDCl$_3$): δ 8.88 (s, 1H); 8.66 and 8.65 (2s, 1H); 8.52 and 8.51 (2s, 1H); 7.33 (s, 1H); 7.30 and 7.29 (2s, 1H); 4.46–4.52 (m, 2H); 4.09 and 4.08 (2s, 3H); 3.96–4.00 (m,2H). MS (ES, positive ion mode): m/z calcd for $C_{17}H_{12}Cl_2N_2O_2$: 346.0, found: 347.3 (M+H)$^+$. Analysis for $C_{17}H_{12}Cl_2N_2O_2$ Calcd: C 58.81; H 3.48; N 8.07 Found: C 58.51; H 3.19; N 7.95.

EXAMPLE 122

4-(4-chloro-5-methoxy-2-methylanilino)-7-methoxy-8-(chloroethoxy)benzo[g]quinoline-3-carbonitrile and

EXAMPLE 123

4-(4-chloro-5-methoxy-2-methylanilino)-8-methoxy-7-(chloroethoxybenzo[g]quinoline-3-carbonitrile A mixture of 248 mg (0.714 mmol) of 4-chloro-7-methoxy-8-(2-chloroethoxy)benzo[g]quinoline-3-carbonitrile and 4-chloro-8-methoxy-7-(2-chloroethoxy)benzo[g]quinoline-3-carbonitrile (1:1 mixture), 10 mg of pyridine hydrochloride, 150 mg (0.874 mmol) of 4-chloro-5-methoxy-2-methylaniline and 5 mL of 2-ethoxyethanol is stirred and heated to 135° C. After 1 hour, the reaction is cooled to room temperature, quenched with 0.2 mL of triethylamine and concentrated in vacuo. The residue is dissolved in 1:1 hexane/ethyl acetate with a little dichloromethane and chromatographed on silica gel eluting with 1:1 hexane/ethyl acetate, then ethyl acetate to provide 0.282 g of 4-(4-chloro-5-methoxy-2-methylanilino)-7-methoxy-8-(chloroethoxy)benzo[g]quinoline-3-carbonitrile and 4-(4-chloro-5-methoxy-2-methylanilino)-8-methoxy-7-(chloroethoxy)benzo[g]quinoline-3-carbonitrile (1:1 mixture) as a dull yellow solid (81%), m.p. 132–68° C. dec.

$^1$HNMR (CDCl$_3$): δ 8.66 and 8.65 (2s, 1H); 8.41 and 8.40 (2s, 1H); 8.19 and 8.17 (2s, 1H); 7.36 (s, 1H); 7.25 and 7.24 (2s, 1H); 7.12 (s, 1H); 7.02 (br s, 1H); 6.76 (s, 1H), 4.48 and 4.41 (2t, J=6.1 Hz, 2H); 4.07 and 4.01 (2s, 3H); 3.95 and 3.98 (2t, J=6.1 Hz, 2H); 3.77 (s, 3); 2.28 (s, 3H). MS (ES, positive ion mode): m/z calcd for $C_{25}H_{21}Cl_2N_3O_3$: 481.1, found: 482.0 (M+H)$^+$. Analysis for $C_{25}H_{21}Cl_2N_3O_3.H_2O$ Calcd: C 60.16; H 4.64; N 8.42 Found C 60.33; H 4.46; N 8.03

EXAMPLE 124

4-(4-chloro-5-methoxy-2-methylanilino)-7-methoxy-8-[2-(4-morpholinyl)ethoxy]benzo[g]quinoline-3-carbonitrile and

EXAMPLE 125

4-(4-chloro-5-methoxy-2-methylanilino)-8-methoxy-7-[2-(4-morpholinyl)ethoxy]benzo[g]quinoline-3-carbonitrile A mixture of 318 mg (0.66 mmol) of 4-(4-chloro-5-methoxy-2-methylanilino)-7-methoxy-8-(chloroethoxy)

benzo[g]quinoline-3-carbonitrile and 4-(4-chloro-5-methoxy-2-methylanilino)-8-methoxy-7-(chloroethoxy)benzo[g]quinoline-3-carbonitrile (1:1 mixture), 100 mg of sodium acetate and 5 mL of morpholine is stirred and heated to 130° C. using an oil bath. After 30 minutes the reaction is allowed to cool to room temperature. The reaction mixture is concentrated in vacuo and the residue purified by silica gel chromatography, eluting with 95:5 methylene chloride/methanol to yield 82 mg (23%) of 4-(4-chloro-5-methoxy-2-methylanilino)-7-methoxy-8-[2-(4-morpholinyl)ethoxy]benzo[g]quinoline-3-carbonitrile as a yellow wax and 153 mg of 4-(4-chloro-5-methoxy-2-methylanilino)-8-methoxy-7-[2-(4-morpholinyl)ethoxy]benzo[g]quinoline-3-carbonitrile as a yellow solid, mp 191–194° C. dec.

4-(4-chloro-5-methoxy-2-methylanilino)-7-methoxy-8-[2-(4-morpholinyl)ethoxy]benzo[g]quinoline-3-carbonitrile: $^1$HNMR(CDCl$_3$): δ 8.57 (s, 1H); 8.40 (s, 1H), 8.30 (s, 1H); 7.76 (br s, 1H); 7.25 (s, 1H); 7.18 (s, 1H); 7.08 (s, 1H); 6.80 (s, 1H); 4.32 (t, J=5.7 Hz, 2H); 3.92 (s, 3H); 3.75 (s, 31), 3.74–3.77 (m, 4H); 2.95 (t, J=5.7 Hz, 2H); 2.60–2.67 (br s, 4H); 2.19 (s, 3H). MS (ES, positive ion mode): m/z calcd for $C_{29}H_{29}ClN_4O_4$: 532.19, found: 533.1 (M+H)$^+$.

4-(4-chloro-5-methoxy-2-methylanilino)-8-methoxy-7-[2-(4-morpholinyl)ethoxy]benzo[g]quinoline-3-carbonitrile: $^1$HNMR (CDCl$_3$): δ 8.65 (s, 1H); 8.39 (s, 1H); 8.17 (s, 1H); 7.35 (br s, 1H); 7.27 (s, 1H); 7.22 (s, 1H); 7.10 (s, 1H); 6.75 (s, 1H); 4.28 (t, J=5.7 Hz, 2H); 4.05 (s, 3H); 3.75 (s, 3H), 3.73–3.78 (m, 4H); 2.94 (t, J=5.7 Hz, 2H); 2.62–2.67 (br s, 4H); 2.27 (s, 3H). MS (ES, positive ion mode): m/z calcd for $C_{29}H_{29}ClN_4O_4$: 532.2, found: 533.1 (M+H)$^+$. Analysis for $C_{29}H_{29}ClN_4O_4H_2O$ Calcd: C 63.21; H 5.67; N 10.17 Found C 62.90; H 5.74; N 9.99

EXAMPLE 126

4-(2,4-dichloro-5-methoxyanilino)-7-methoxy-8-(chloroethoxy)benzo[g]quinoline-3-carbonitrile and

EXAMPLE 127

4-(2,4-dichloro-5-methoxyanilino)-8-methoxy-7-(chloroethoxybenzo[g]quinoline-3-carbonitrile A mixture of 1.10 g (3.17 mmol) of 4-chloro-7-methoxy-8-(2-chloroethoxy)benzo[g]quinoline-3-carbonitrile and 4-chloro-8-methoxy-7-(2-chloroethoxy)benzo[g]quinoline-3-carbonitrile (1:1 mixture), 50 mg of pyridine hydrochloride, 742 mg (3.86 mmol) of 2,4-dichloro-5-methoxyaniline and 25 mL of 2-ethoxyethanol is stirred and heated to 135° C. After 1 hour, the reaction is cooled to room temperature, quenched with 1.0 mL of triethylamine and concentrated in vacuo. The residue is dissolved in 95:5 methylene chloride/methanol and chromatographed on silica gel, eluting with 1:1 hexane/ethyl acetate. The product is precipitated from ethyl acetate to provide 0.760 g (48%) of 4-(2,4-dichloro-5-methoxyanilino)-7-methoxy-8-(chloroethoxy)benzo[g]quinoline-3-carbonitrile and 4-(2,4-dichloro-5-methoxyanilino)-8-methoxy-7(chloroethoxy)benzo[g]quinoline-3-carbonitrile (1:1 mixture) as a dull yellow solid, m.p. 239–55° C. dec.

$^1$HNMR (CDCl$_3$+DMSO-d$_6$): δ 8.94 (br s, 1H); 8.77 (br s, 1); 8.59 (br s, 1H); 8.36 (br s, 1H), 7.54 (br s, 1H); 7.28 (br s, 1H); 7.26 (br s, 1H); 6.96 (br s, 1H); 4.40–4.49 (m, 2H); 3.94–4.07 (m, 5H); 3.86 (s, 3H). MS (ES, positive ion mode): m/z calcd for $C_{24}H_{18}Cl_3N_3O_3$: 501.0, found: 502.2 (M+H)$^+$. Analysis for $C_{24}H_{18}Cl_3N_3O_3.0.3H_2O$ Calcd: C 56.92; H 3.70; N 8.30 Found C 56.67; H 3.48; N 8.16

EXAMPLE 128

4-(2,4-dichloro-5-methoxyanilino)-8-methoxy-7-[2-(4-morpholinyl)ethoxy]benzo[g]quinoline-3-carbonitrile and

EXAMPLE 129

4-(2,4-dichloro-5-methoxyanilino)-7-methoxy-8-[2-(4-morpholinyl)ethoxy]benzo[g]quinoline-3-carbonitrile A mixture of 0.436 g (0.87 mmol) of 4-(2,4-dichloro-5-methoxyanilino)-7-methoxy-8-(chloroethoxy)benzo[g]quinoline-3-carbonitrile and 4-(2,4-dichloro-5-methoxyanilino)-8-methoxy-7-(chloroethoxy)benzo[g]quinoline-3-carbonitrile (1:1 mixture), 2.0 mL (23.0 mmol) of morpholine and 0.05 g of sodium iodide in 2.0 mL of ethylene glycol dimethyl ether is heated at 90° C. for 3.5 hours under nitrogen. The mixture is cooled, solvent is removed in vacuo and the resulting residue is stirred with a saturated solution of sodium bicarbonate. The crude solid is collected by filtration, washed with water, and dried in vacuo. Purification is carried out by silica gel chromatography, eluting with a gradient of 97:3 to 90:10 ethyl acetate/methanol to yield 0.241 g of 4-(2,4-dichloro-5-methoxyanilino)-8-methoxy-7-[2-(4-morpholinyl)ethoxy]benzo[g]quinoline-3-carbonitrile as a yellow solid, mp 210–212° C. and 0.203 g of 4-(2,4-dichloro-5-methoxyanilino)-7-methoxy-8-[2-(4-morpholinyl)ethoxy]benzo[g]quinoline-3-carbonitrile as a yellow solid, mp 207–214° C.

4-(2,4-dichloro-5-methoxyanilino)-8-methoxy-7-[2-(4-morpholinyl)ethoxy]benzo[g]quinoline-3-carbonitrile: $^1$HNMR (DMSO-d6+TFA): δ 9.35 (s, 1H); 9.25 (s 1H); 8.43 (s, 1H); 7.91 (s, 1H); 7.78 (s 1H); 7.63 (s, 1H); 7.53 (s, 1H); 4.65 (m, 2H); 4.06 (s, 3H); 4.04–3.97 (m, 21); 3.91 (s, 3H); 3.84–3.63 (m, 6H); 3.34 (t, J=10.56 Hz, 2H). MS (ES, positive mode): m/z calcd for $C_{28}H_{26}Cl_2N_4O_4$: 553, found (M+H)$^+$ 553 Analysis for $C_{28}H_{26}Cl_2N_4O_4.0.15CH_3CO_2C_2H_5$ Calcd: C 60.67; H 4.84; N 9.89 Found: C: 60.31; H: 4.97; N: 9.55

4-(2,4-dichloro-5-methoxyanilino)-7-methoxy-8-[2-(4-morpholinyl)ethoxy]benzo[g]quinoline-3-carbonitrile: $^1$HNMR (DMSO-d6+TFA): δ 9.35 (s, 1H), 9.24 (s 1H); 8.42 (s, 1H); 7.91 (s, 1H); 7.82 (s 1H); 7.61 (s, 1H); 7.48 (s, 1H); 4.66 (m, 2H); 4.07 (s, 3H); 4.04–3.97 (m, 2H); 3.90 (s, 3H); 3.83–3.63 (m, 6H); 3.34 (m, 2H). MS (ES, positive mode): m/z calcd for $C_{28}H_{26}Cl_2N_4O_4$: 553, found (M+H)$^+$ 553 Analysis for $C_{28}H_{26}Cl_2N_4O_4.2.0H_2O$ Calcd: C: 57.05; H: 5.13; N: 9.50 Found: C: 56.88; H: 4.96; N:9.10

EXAMPLE 130

4-(2,4-dichloro-5-methoxyanilino)-8-methoxy-7-[2-(4-methyl-1-piperazinyl)ethoxy]benzo[g]quinoline-3-carbonitrile and

EXAMPLE 131

4-(2,4-dichloro-5-methoxyanilino)-7-methoxy-8-[2-(4-methyl 1-piperazinyl)ethoxy]benzo[g]quinoline-3-carbonitrile A mixture of 0.4 g (0.8 mmol) of 4-(2,4-dichloro-5-methoxyanilino)-7-methoxy-8-(chloroethoxy)benzo[g]quinoline-3-carbonitrile and 4-(2,4-dichloro-5-methoxyanilino)-8-methoxy-7-(chloroethoxy)benzo[g]quinoline-3-carbonitrile (1:1 mixture), 1.25 ml (11.27 mmol) of 1-methyl piperazine and 0.05 g of sodium iodide in 2.0 mL of ethylene glycol dimethyl ether is heated at 90° C. for 2 hours under nitrogen. The mixture is cooled, the solvent is removed in vacuo and the resulting residue is stirred with saturated solution of sodium bicarbonate. The crude solid is collected by filtration, washed with water, and dried in vacuo. Purification is carried out by silica gel chromatography, eluting with a gradient of 92:8 to 85:15 methylene chloride/methanol to yield 0.149 g of 4-(2,4-dichloro-5-methoxyanilino)-8-methoxy-7-[2-(4-methyl-1-piperazinyl)ethoxy]benzo[g]quinoline-3-carbonitrile as a yellow solid, mp 141–150° C. and 0.203 g of 4-(2,4-dichloro-5-methoxyanilino)-7-methoxy-8-[2-(4-methyl-1-piperazinyl)ethoxy]benzo[g]quinoline-3-carbonitrile as a yellow solid, mp 132–135° C.

4-(2,4-dichloro-5-methoxyanilino)-8-methoxy-7-[2-(4-methyl-1-piperazinyl)ethoxy]benzo[g]quinoline-3-carbonitrile: $^1$HNMR (DMSO-d6+TFA): δ 9.34 (s, 1H); 9.23 (s 1H); 8.42 (s, 1H); 7.91 (s, 1H); 7.77 (s 1H); 7.61 (s, 1H); 7.51 (s, 1H); 4.63 (m, 2H); 4.03 (s, 3H); 3.90 (s, 3H); 3.81–3.31 (m, 10H); 2.94 (s, 3H). MS (ES, positive mode): m/z calcd for $C_{29}H_{29}Cl_2N_5O_3$: 566, found (M+H)$^+$ 566 Analysis for $C_{29}H_{29}Cl_2N_5O_3 \cdot 0.9$ $CH_2Cl_2$ Calcd: C: 55.85; H: 4.83; N: 10.89 Found: C: 55.98; H: 5.14; N: 11.17

4-(2,4-dichloro-5-methoxyanilino)-7-methoxy-8-[2-(4-methyl-1-piperazinyl)ethoxy]benzo[g]quinoline-3-carbonitrile: $^1$HNMR (DMSO-d6+TFA): δ 9.35 (s, 1H); 9.23 (s 1H); 8.42 (s, 1H); 7.91 (s, 1H); 7.80 (s 1H); 7.60 (s, 1H); 7.48 (s, 1H); 4.64 (m, 2H); 4.03 (s, 3H); 3.90 (s, 3H); 3.81–3.4 (m, 10H); 2.94 (s, 3H). MS (ES, positive mode): m/z calcd for $C_{29}H_{29}Cl_2N_5O_3$: 566, found (M+H)$^+$ 566 Analysis for $C_{29}H_{29}Cl_2N_5O_3 \cdot 0.5$ $CH_2Cl_2$ Calcd: C: 58.18; H: 4.97; N: 11.50 Found: C: 58.22; H: 5.27; N:11.69

EXAMPLE 132

4-(4-chloro-5-methoxy-2-methylanilino)-8-methoxy-7-[2-(4-methyl-1-piperazinyl)ethoxy]benzo[g]quinoline-3-carbonitrile and

EXAMPLE 133

4-(4-chloro-5-methoxy-2-methylanilino)-7-methoxy-8-[2-(4-methyl 1-piperazinyl)ethoxy]benzo[g]quinoline-3-carbonitrile A mixture of 205 mg (0.425 mmol) of 4-(4-chloro-5-methoxy-2-methylanilino)-7-methoxy-8-(chloroethoxy)benzo[g]quinoline-3-carbonitrile and 4-(4-chloro-5-methoxy-2-methylanilino)-8-methoxy-7-(chloroethoxy)benzo[g]quinoline-3-carbonitrile (1:1 mixture), 0.15 mL (1.35 mmol) of 1-methyl piperazine and 0.05 g of sodium iodide in 5 mL of ethylene glycol dimethyl ether is heated at 90° C. for 4 days under nitrogen. The mixture is cooled, the solvent is removed in vacuo and the resulting residue is stirred with saturated solution of sodium bicarbonate. The crude solid is collected by filtration, washed with water, and dried in vacuo. Purification is carried out by silica gel chromatography, eluting with a gradient of 92:8 to 85:15 methylene chloride/methanol to yield 0.10 g of 4-(4-chloro-5-methoxy-2-methylamino)-8-methoxy-7-[2-(4-methyl-1-piperazinyl)ethoxy]benzo[g]quinoline-3-carbonitrile as a yellow solid, mp 121–135° C. and 0.068 g of 4-(4-chloro-5-methoxy-2-methylanilino)-7-methoxy-8-[2-(4-methyl-1-piperazinyl)ethoxy]benzo-[g]quinoline-3-carbonitrile as a yellow solid, mp 122–137° C.

4-(4-chloro-5-methoxy-2-methylanilino)-8-methoxy-7-[2-(4-methyl-1-piperazinyl)ethoxy]benzo[g]quinoline-3-carbonitrile: $^1$HNMR (DMSO-d$_6$): δ 9.86 (s, 1H); 9.01 (s 1H); 8.42 (s, 1H); 8.32 (s, 1H); 7.57 (s, 1H); 7.43 (s 1H); 7.31 (s, 1H); 7.16 (s, 1H); 4.27 (t, J=5.6 Hz, 2H); 3.96 (s, 3H); 3.81 (s, 3H); 2.81 (t, =5.8 Hz, 2H); 2.54 (m, 4H); 2.37 (br s, 4H); 2.18 (s, 3H); 2.14 (s, 3H). MS (ES, positive mode): m/z calcd for $C_{30}H_{32}ClN_5O_3$: 546, found (M+H)$^+$ 546 Analysis for $C_{30}H_{32}ClN_5O_3 \cdot 1.6$ $CH_2Cl_2$ Calcd: C: 62.67; H: 6.17; N: 12.18 Found: C: 62.41; H: 5.96; N: 11.89

4-(4-chloro-5-methoxy-2-methylanilino)-7-methoxy-8-[2-(4-methyl-1-piperazinyl)ethoxy]benzo[g]quinoline-3-carbonitrile: $^1$HNMR (DMSO-d6): δ 9.86 (s, 1H); 9.0 (s 1H); 8.43 (s, 1H); 8.34 (s, 1H); 7.53 (s, 1H); 7.43 (s 1H); 7.33 (s, 1H); 7.16 (s, 1H); 4.27 (t, J=5.6 Hz, 2H); 3.97 (s, 3H); 3.81 (s, 3H); 2.81 (t, J=5.8 Hz, 2H); 2.55 (m, 4H); 2.36 (br s, 4H); 2.17 (s, 3H); 2.14 (s, 3H). MS (ES, positive mode): m/z calcd for $C_{30}H_{32}ClN_5O_3$: 546, found (M+H)$^+$ 546 Analysis for $C_{30}H_{32}ClN_5O_3 \cdot 1.0$ $CH_2Cl_2$ Calcd: C: 59.00; H: 5.43; N: 11.10 Found: C: 59.02; H: 5.36; N: 11.26

EXAMPLE 134

5-(Benzyloxy)-1-bromo-2-(bromomethyl)-4-methoxybenzene

4-Benzyloxy-3-methoxybenzyl alcohol (1 g, 4.1 mmol) is dissolved in acetic acid (3 ml) and cooled to 10° C. in a water/ice bath. A solution of bromine (0.25 ml, 4.92 mmol) in acetic acid (0.25 ml) is added dropwise to the reaction mixture while stirring. The reaction is allowed to warm to room temperature and stirred for 18 hours. The reaction is diluted with water and the resulting precipitate is collected by filtration. The precipitate is washed well with water and recrystallized from a small amount of methanol to yield 1.3 g of 5-(benzyloxy)-1-bromo-2-(bromomethyl)-4-methoxybenzene as a white solid, mp 103–105° C.

$^1$HNMR (d$^6$-DMSO): δ 7.5 (m, 7H); 5.09 (s, 2H); 4.69 (s, 2H); 3.77 (s, 3H) MS (ES, positive ion mode): m/z calcd for $C_{15}H_{14}Br_2O_2$: 386.08, found (M+H)$^+$ 387.1 Analysis for $C_{15}H_{14}Br_2O_2$.3CH$_3$OH Calcd: C:47.60; H:3.84 Found: C:47.44; H:3.77

EXAMPLE 135

3-(4-Benzyloxy-2-bromo-5-methoxyphenyl)-propionitrile

To a solution of n-butyllithium (1.8 mL of a 2.5 M solution in hexane, 4.5 mmol) in 5 mL of tetrahydrofuran is added a solution of acetonitrile (1.0 mL, 19.1 mmol) in 5 mL of tetrahydrofuran. The reaction mixture is stirred at −78° C. for 15 min. A solution of 5-(benzyloxy)-1-bromo-2-(bromomethyl)-4-methoxybenzene (0.7 g, 1.8 mmol) in 3 mL of tetrahydrofuran is added and stirring is continued for 1 hour at −78° C. The reaction is quenched by the addition of 15 mL of water and the mixture is allowed to warm to room temperature. The mixture is extracted with ethyl acetate and the organic layers combined, then dried with sodium sulfate. After reducing in vacuo, the crude product is purified by flash chromatography using a gradient of 95:5 to 4:1 hexanes/ethyl acetate as an eluent. The clean fractions are combined, reduced in vacuo and dried to yield 0.343 g of 3-(4-benzyloxy-2-bromo-5-methoxyphenyl)-propionitrile as a white solid, mp 52–53° C.

$^1$HNMR (d$^6$-DMSO): δ 7.39 (m, 51); 7.33 (s, 1H); 7.08 (s, 1H); 5.09 (s, 2H); 3.77 (s, 3H); 2.92 (t, 2H; J=5.49), 2.78 (t, 2H; J=5.07). MS (ES, positive ion mode): m/z calcd for $C_{17}H_{16}BrNO_2$: 346.22, found (M+H)$^+$ 347.1 Analysis for $C_{17}H_{16}BrNO_2$ Calcd: C:58.98; H:4.66; N:4.05 Found: C:58.77; H:4.71; N:3.89

EXAMPLE 136

4-Benzyloxy-3-methoxybicyclo[4.2.0]octa-1,3,5-triene-7-carbonitrile

A suspension of sodium amide is prepared from 100 mL of liquid ammonia, sodium (0.52 g, 22.8 mmol) and a catalytic amount of ferric nitrate. To this is added 3-(4-benzyloxy-2-bromo-5-methoxyphenyl)-propionitrile (2 g, 5.7 mmol) in portions and the reaction stirred at −33° C. 45 minutes. The reaction then cooled down to −78° C. and quenched with ammonium chloride. The liquid ammonia is allowed to evaporate and the resulting solid residue is washed with water. The tan solid obtained is purified by flash chromatography, using 4:1 hexanes/ethyl acetate as an eluent. The clean fractions are combined and reduced in vacuo to yield 1 g of 4-benzyloxy-3-methoxybicyclo[4.2.0]octa-1,3,5-triene-7-carbonitrile as a clear oil that solidified into a white solid upon standing, mp 85° C.

$^1$HNMR (d$^6$-DMSO): δ7.39 (, 5H); 7.04 (s,1H); 6.89 (s, 1H); 5.08 (d, 1H, J=12.15); 5.05 (d. 1H, J=12.12); 4.45 (dd, 1H, J=1.74, 3.93), 3.74 (s, 3H); 3.6 (dd, 1H, J=3.99, 10.29), 3.35 (d, 1H, J=1.77) MS (ES, positive ion mode): m/z calcd for $C_{17}H_{15}NO_2$: 265.31, found (M+H)$^+$ 266.1 Analysis for $C_{17}H_{15}NO_2$ Calcd. C:76.96; H:5.70; N:5.28 Found: C:76.87; H:5.97; N:5.01

EXAMPLE 137

4-Benzyloxy-7-(4-chlorophenylsulfanyl)-3-methoxybicyclo[4.2.0]octa-1,3,5-triene-7-carbonitrile To a solution of 4-benzyloxy-3-methoxybicyclo[4.2.0] octa-1,3,5-triene-7-carbonitrile (1.0 g, 3.7 mmol) in anhydrous tetrahydrofuran (10 mL) at −78° C. is added sodium bis(trimethylsilyl) amide (5.65 mL of a 1M solution in tetrahydrofuran, 5.6 mmol) over a period of 4 minutes, followed by the addition of 4,4'-dichlorodiphenyl disulfide in one portion. The reaction is stirred at −78° C. for 15 minutes and then at room temperature for one hour. The reaction is then diluted and extracted with ethyl acetate. The organic layer is collected and dried with sodium sulfate. After reducing in vacuo, the crude material is purified by flash chromatography using 4:1 hexanes/ethyl acetate. The clean fractions are combined, reduced and dried to yield 1.3 g of 4-benzyloxy-7-(4-chlorophenylsulfanyl)-3-methoxybicyclo[4.2.0]octa-1,3,5-triene-7-carbonitrile as an off-white solid, mp 114–115° C.

$^1$HNMR (d$^6$-DMSO): δ7.62–7.54 (m, 4H); 7.41 (m, 4H); 7.36 (m, 1H); 6.97 (s,1H); 6.83 (s, 1H); 5.08 (dd, 2H, J=9.07,10.53); 3.98 (d, 1H, J=10.47), 3.78 (s, 3H); 3.60 (d, 1H, J=10.5) MS (ES, positive ion mode): m/z calcd for $C_{23}H_{18}ClNO_2S$: 408.92, found (M+H)$^+$ 408.1 Analysis for $C_{23}H_{18}ClNO_2S$ Calcd: C:67.72; H:4.45; N:3.43 Found: C:67.99; H:4.63; N:3.33

EXAMPLE 138

4-Benzyloxy-3-methoxy-7-phenylsulfanylbicyclo[4.2.0]octa-1,3,5-triene-7-carbonitrile To a solution of 4-benzyloxy-3-methoxybicyclo[4.2.0] octa-1,3,5-triene-7-carbonitrile (7.22 g, 3.7 mmol) in anhydrous tetrahydrofuran (60 mL) at −78° C. is added sodium bis(trimethylsilyl)amide (41.0 mL of a 1M solution in tetrahydrofuran, 41.0 mmol) over a period of 4 minutes, followed by the addition of 11.9 g (54.5 mmol) of phenyl disulfide in one portion. The reaction is stirred at −78° C. for 15 minutes and then at room temperature for one hour. The reaction is quenched with water and extracted with ethyl acetate. The organic layers are combined and dried with sodium sulfate. After reducing in vacuo, the crude material is purified by flash chromatography using 4:1 hexanes/ethyl acetate. The clean fractions are combined, reduced and dried to yield 7.0 g of 4-benzyloxy-3-methoxy-7-phenylsulfanyl-bicyclo[4.2.0]octa-1,3,5-triene-7-carbonitrile as a white solid, mp 109–110° C.

$^1$HNMR (d$^6$-DMSO): δ 7.60–7.52 (m, 2H); 7.51–7.48 (m, 3H); 7.42–7.34 (m, 5H); 6.97 (s,1H); 6.80 (s, 1H); 5.03 (dd, 211, J=9.0 Hz, 11.4 Hz); 4.01 (d, 1H, =10.5 Hz); 3.78 (s, 3H); 3.60 (d, 1H, J=10.5) MS (ES, positive ion mode): m/z calcd for $C_{23}H_{19}NO_2S$: 373.5, found (M+H)$^+$ 374.0 Analysis for $C_{23}H_{19}NO_2S$ Calcd: C:73.97; H:5.13; N:3.75 Found: C:73.83; H:5.16; N:3.53

EXAMPLE 139

3-Amino-3-[4-benzyloxy-7-(4-chloro-phenylsulfanyl)-3-methoxybicyclo[4.2.0]octa-1,3,5-trien-7-yl]-acrylic acid tert-butyl ester To a stirred solution of ethylmagnesium bromide (3.26 mL of a 3M solution in diethyl ether, 9.8 mmol) in anhydrous tetrahydrofuran (10 mL) at 0° C. under nitrogen is added diisopropylamine (2.75 mL, 19.6 mmol). The mixture is stirred at 0° C. for 1 hour. 1-Butyl acetate (0.5 mL, 3.6 mmol) and a solution of 1.0 g (2.45 mmol) of 4-benzyloxy-7-(4-chloro-phenylsulfanyl)-3-methoxybicyclo[4.2.0]octa-1,3,5-triene-7-carbonitrile in anhydrous tetrahydrofuran (10 mL) are added successively, and the resulting mixture is stirred for an additional hour. The reaction is quenched with aqueous ammonium chloride and the product mixture is extracted with ethyl acetate. The ethyl acetate extract is washed with brine, dried over anhydrous sodium sulfate and passed through a plug of silica to give 3-amino-3-[4-benzyloxy-7-(4-chloro-phenylsulfanyl)-3-methoxybicyclo[4.2.0]octa-1,3,5-trien-7-yl]-acrylic acid tert-butyl ester as a clear oil, that solidified upon standing, mp 112–115° C.

$^1$HNMR (d$^6$-DMSO): δ 7.60–7.29 (m, 9H); 6.81 (s,1H); 6.72 (s, 1H); 5.08 (dd, 2H, J=9.09, 11.82 Hz); 4.15 (s, 1H); 3.73 (s, 3H); 3.48 (d, 1H, J=10.7 Hz); 3.30 (d, 1H, J=10.6 Hz); 1.36 (s, 9H) MS (ES, positive ion mode): m/z calcd for $C_{29}H_{30}ClNO_4S$: 524.1, found (M+H)$^+$ 523.9 Analysis for $C_{29}H_{30}ClNO_4S$ Calcd: C:66.46; H:5.77; N:2.67 Found: C:66.31; H:5.91; N:2.61

EXAMPLE 140

3-Amino-6-benzyloxy-7-methoxynaphthalene-2-carboxylic acid tert-butyl ester

Nitrogen gas is bubbled through a solution of 3-amino-3-[4-benzyloxy-7-(4-chloro-phenylsulfanyl)-3-methoxybicyclo[4.2.0]octa-1,3,5-trien-7-yl]-acrylic acid tert-butyl ester (0.6 g, 1.1 mmol) in 1,2-dichlorobenzene (100 mL) for 1 hour and the reaction is heated to 179° C. After one hour the reaction is cooled and reduced in vacuo. The residue is washed with ether, dissolved in methylene chloride and purified through a plug of silica eluting with methylene chloride. The filtrate is reduced and dried to afford 0.321 g of 3-amino-6-benzyloxy-7-methoxynaphthalene-2-carboxylic acid tert-butyl ester as a yellow solid, mp 179–180° C.

$^1$HNMR(d$^6$-DMSO): δ 8.18 (s, 1H); 7.4 (m, 5H); 7.18 (s, 11); 7.01 (s, 1H); 6.85 (s, 1H); 6.21(s, 2H), 5.17 (s, 2H); 3.74 (s, 3H), 1.58 (s, 9H) MS (ES, positive ion mode): m/z calcd for $C_{23}H_{25}NO_4$: 379.45, found (M+H)$^+$ 379.9 Analysis for $C_{23}H_{25}NO_4$.0.7H$_2$O Calcd: C:70.50; H:6.08; N:3.57 Found: C:70.45; H:6.24; N:3.40

EXAMPLE 141

8-Benzyloxy-7-methoxy-4-oxo-1,4-dihydrobenzo[g]quinoline-3-carbonitrile

In a round bottom flask containing 10 mL of toluene is added 3-amino-6-benzyloxy-7-methoxynaphthalene-2-carboxylic acid tert-butyl ester (3.0 g, 7.9 mmol) and dimethylformamide dimethyl acetal (5.4 mL, 31.6 mmol) under a positive nitrogen flow. The mixture is stirred at 120° C. for 1.5 hour, then cooled to room temperature. The volatiles are removed under reduced pressure and the resulting residue dried in vacuo for 15 h to yield 3.0 g of 6-benzyloxy-3-(dimethylamino-methyleneamino)-7-methoxy-naphthalene-2-carboxylic acid tert-butyl ester as a dark oil.

To a solution of n-butyllithium (7.68 mL of a 2.5 M solution in hexane, 19.2 mmol) in 30 mL of tetrahydrofuran is added a solution of acetonitrile (3.34 mL, 64.0 mmol) in 50 mL of tetrahydrofuran. The reaction mixture is stirred at −78° C. for 15 min. A solution of 6-benzyloxy-3-(dimethylamino-methyleneamino)-7-methoxy-naphthalene-2-carboxylic acid tert-butyl ester obtained in the previous step (2.8 g, 6.4 mmol) in 30 mL of tetrahydrofuran is added and stirring is continued for 1 h at −78° C. The reaction is quenched by the addition of 10 mL of glacial acetic acid and the mixture is allowed to warm up to room temperature. The volatiles are removed under reduced pressure and the resulting residue washed with water, then ethyl acetate and dried in a vacuum oven to yield 1.9 g of 8-benzyloxy-7-methoxy-4-oxo-1,4-dihydrobenzo[g]quinoline-3-carbonitrile as a yellow solid, mp>300° C.

$^1$HNMR (d$^6$-DMSO+TFA): δ 8.71 (s, 1H); 8.63 (s, 1H); 7.93 (s, 1H); 7.61 (s, 1H); 7.58 (s, 1H); 7.43 (m, 5H); 5.27 (s, 2H), 3.74 (s, 3H) MS (ES, positive ion mode): m/z calcd for $C_{22}H_{15}N_2O_2$: 356.38, found (M+H)$^+$ 357.1 Analysis for $C_{22}H_{15}N_2O_2$.0.2H$_2$O Calcd: C:73.45; H:4.54; N:7.77 Found: C:73.49; H:4.49; N:7.65

EXAMPLE 142

3-Amino-6-hydroxy-7-methoxy-naphthalene-2-carboxylic acid tert-butyl ester

A solution of 4.7 g (12.0 mmol) of 3-amino-6-benzyloxy-7-methoxynaphthalene-2-carboxylic acid tert-butyl ester and 2.0 g of 10% Pd/C in 40 mL of DMF and 100 mL of methanol is shaken on Parr shaker at 40 psi for 18 hours. The catalyst is filtered through a pad of Celite, washed with methanol and solvent is evaporated to yield a residue which is dissolved in methylene chloride. This is then filtered through a short pad of Magnesol and washed with methylene chloride and ethyl acetate. The filtrate is evaporated to yield 3.4 g of 3-amino-6-hydroxy-7-methoxy-naphthalene-2-carboxylic acid tert-butyl ester as a yellow solid, mp 262–263° C.

$^1$HNMR (d$^6$-DMSO): δ 9.61 (bs, 1H); 8.15 (s, 1H); 7.13 (s, 1H); 6.74 (d, 2H, J=2.7); 6.12 (s,2H); 3.82 (s,3H), 1.58 (s,9H) MS (ES, positive ion mode): m/z calcd for $C_{16}H_{19}NO_4$: 289.33, found (M+H)$^+$289.9 Analysis for $C_{16}H_{19}NO_4$. 0.1CH$_3$CO$_2$C$_2$H$_5$ Calcd: C:66.06; H:6.69; N:4.70 Found: C:66.30; H:6.96; N:4.30

EXAMPLE 143

3-Amino-7-methoxy-6-(2-morpholin-4-yl-ethoxy)-naphthalene-2-carboxylic acid tert-butyl ester To a solution of 0.72 g (2.49 mmol) of 3-amino-6-hydroxy-7-methoxy-naphthalene-2-carboxylic acid tert-butyl ester in 7.5 ml of tetrahydrofuran is added 0.46 mL (3.74 mmol) of 4-(2-hydroxyethyl)morpholine, followed by the addition of 1.34 g (4.98 mmol) of diphenyl-2-pyridylphosphine and 0.6 mL (3.87 mmol) of diethyl azadicarboxylate. The resulting mixture is stirred at room temperature for 1.5 hours, quenched with water, diluted with ethyl acetate and the two layers are separated. The organic layer is extracted with 0.2N hydrochloric acid. After neutralizing the aqueous layer with a saturated solution of sodium bicarbonate, it is extracted with ethyl acetate. The ethyl acetate extract is dried over anhydrous sodium sulfate, filtered and evaporated to yield a brown oil. The oil is purified by silica gel chromatography, utilizing a gradient of ethyl acetate/hexane (85:15 to 100:0), to give 0.7 g of 3-amino-7-methoxy-6-(2-morpholin-4-yl-ethoxy)-naphthalene-2-carboxylic acid tert-butyl ester as an orange solid, mp 125–127° C.

$^1$HNMR (CDCl$_3$): δ 8.24 (s, 1H); 7.00 (s, 1H); 6.81 (d, 2H, J=2.34 Hz); 5.47 (bs, 2H); 4.26 (t, 2H, J=4.5 Hz); 3.92 (s, 3H); 3.75 (t, 4H, J=3.45 z); 2.93 (t, 2H J=4.5 Hz); 2.65 (bs, 4H); 1.63 (s, 9H). MS (ES, positive ion mode): m/z calcd for $C_{22}H_{30}N_2O_5$: 402.4, found (M+H)$^+$ 403.3 Analysis for $C_{22}H_{30}N_2O_5$ Calcd: C:65.65; H:7.51; N:6.96 Found: C:65.65; H:7.30; N:6.98

EXAMPLE 144

7-Methoxy-8-(2-morpholin-4-yl-ethoxy)-4-oxo-1,4-dihydrobenzo[g]quinoline-3-carbonitrile A mixture of 0.69 g (1.7 mmol) of 3-amino-7-methoxy-6-(2-morpholin-4-yl-ethoxy)-naphthalene-2-carboxylic acid tert-butyl ester and 2.4 mL of N,N-dimethylformamide dimethyl acetal in 7.0 mL of toluene is heated under reflux for 1.5 hours. The solvent is evaporated and the residue is dried on high vacuum to yield 3-(dimethylamino-methyleneamino)-7-methoxy-6-(2-morpholin-4-yl-ethoxy)naphthalene-2-carboxylic acid tert-butyl ester as purple white foam.

To 15 mL of tetrahydrofuran at −78° C. is added 2.6 mL of n-butyllithium (1.6M in hexane) and the reaction mixture is stirred for 5 minutes. To this is added 0.36 mL (6.8 mmol) of acetonitrile dropwise, followed by stirring for 15 minutes. Finally, a solution of 3-(dimethylamino-methyleneamino)-7-methoxy-6-(2-morpholin-4-yl-ethoxy)naphthalene-2-carboxylic acid tert-butyl ester in 5 mL of tetrahydrofuran is added dropwise over a period of 15 minutes. The resulting mixture is stirred at −78° C. for 1 hour, then at room temperature for 1 hour. After cooling again to −78° C., the reaction is quenched with 0.5 mL of glacial acetic acid, the dry ice bath is removed and the resulting thick slurry is stirred for 1 hour. The solid is collected by filtration, washed with ethyl acetate and dried. Purification is carried out by silica gel chromatography, utilizing a gradient of 95:5 to 89:11 of methylene chloride/methanol to give 0.38 g of 7-methoxy-8-(2-morpholin-4-yl-ethoxy)-4-oxo-1,4-dihydrobenzo[g]quinoline-3-carbonitrile as a yellow solid, mp 275° C. (dec).

$^1$HNMR (d$^6$-DMSO+trifluoroacetic acid): δ 8.74 (s, 1H; 8.69 (s, 1H); 8.00 (s, 1H); 7.65 (s, 1H); 7.59 (s, 1H); 4.59 (t, 2H, J=3.3 Hz,); 4.05 (d, 2H, J=9.2 Hz); 3.97 (s, 3H); 3.75 (m, 4H); 3.66 (d, 2H, J=9.3 Hz); 3.34 (t, 2H, J=7.0 Hz). MS (ES, positive ion mode): m/z calcd for $C_{21}H_{21}N_3O_4$: 379.4, found (M+H)$^+$ 380.2 Analysis for $C_{21}H_{21}N_3O_4$.2.5H$_2$O Calcd: C:60.71; H:6.07; N:10.12 Found: C:60.93; H:6.11; N: 9.76

EXAMPLE 145

8-Hydroxy-7-methoxy-4-oxo-1,4-dihydrobenzo[g]quinoline-3-carbonitrile

A solution of 3.6 g (7.3 mmol) of 8-benzyloxy-7-methoxy-4-oxo-1,4-dihydrobenzo[g]quinoline-3-carbonitrile and 0.7 g of 10% Pd/C in 240 mL of dimethyl formamide is hydrogenated in a Parr shaker at 40 psi for 24 hours. The catalyst is filtered through a pad of Celite, washed with dimethyl formamide and the solvent is reduced in vacuo to yield a solid. The crude product is suspended in ether, collected by filtration, further washed with ether and dried to yield 3.0 g of 8-hydroxy-7-methoxy-4-oxo-1,4-dihydrobenzo[g]quinoline-3-carbonitrile as a yellow solid, mp>300° C.

$^1$HNMR (d$^6$-DMSO+trifluoroacetic acid): δ 8.67 (s, 1H); 8.64 (s, 1H); 7.84 (s, 1H); 7.57 (s, 1H); 7.29 (s, 1H); 3.98 (s, 3H). MS (ES, positive ion mode): m/z calcd for $C_{15}H_{10}N_2O_3$: 266.3, found (M+H)$^+$266.8 Analysis for $C_{15}H_{10}N_2O_3$.1.0 (CH$_3$)$_2$NCHO.0.8H$_2$O Calcd: C:61.11; H:5.30; N:11.88 Found: C:61.08; H:4.81; N:11.82

EXAMPLE 146

4-Chloro-8-hydroxy-7-methoxybenzo[g]quinoline-3-carbonitrile

A mixture of 3.0 g (11.3 mmol) of 8-hydroxy-7-methoxy-4-oxo-1,4-dihydrobenzo[g]quinoline-3-carbonitrile and 20.0 mL of phosphorus oxychloride is heated under reflux for 0.5 hour, then cooled to room temperature. Excess phosphorus oxychloride is evaporated to yield a residue, to which toluene is added and the resulting solution is reduced in vacuo. Toluene is added and evaporated twice more. The resulting residue is cooled with ice bath, neutralized with cold saturated solution of sodium bicarbonate and stirred. The solid is collected by filtration, washed with cold water and dried to yield 2.83 g of 4-chloro-8-hydroxy-7-methoxybenzo[g]quinoline-3-carbonitrile as a yellow solid. A sample of the material is purified by silica gel chromatography, eluting with 97:3 methylene chloride/methanol to yield a yellow solid, mp. >300° C.

$^1$HNMR (d$^6$-DMSO+trifluoroacetic acid): δ 8.68 (s,1H); 8.64 (s,1H); 7.83 (s, 1H) 7.58 (s, 1H); 7.27 (s, 1H); 3.96 (s, 3H). MS (ES, positive ion mode): m/z calcd for $C_{15}H_9ClN_2O_2$: 284.7, found (M+H)$^+$ 284.7 Analysis for $C_{15}H_9ClN_2O_2$. 0.6H$_2$O Calcd: C:61.11; H:5.30; N:11.88 Found: C:61.08; H:4.81; N:11.82

EXAMPLE 147

4-[3-Chloro-4-(1-methyl-1H-imidazol-2-ylsulfanyl phenylamino]-8-hydroxy-7-methoxybenzo[g]quinoline-3-carbonitrile A mixture of 1.0 g (3.53 mmol) of 4-chloro-8-hydroxy-7-methoxybenzo[g]quinoline-3-carbonitrile, 0.93 g (3.88 mmol) of 3-chloro-4-(1-methyl-1H-imidazol-2-ylsulfanyl)phenylamine and 0.41 g (3.52 mmol) of pyridine hydrochloride in 20 mL of 2-ethoxyethanol is heated at 120° C. for 2 hours, then cooled to room temperature. The product mixture is diluted with a saturated solution of sodium carbonate, stirred for 15 minutes and the solid is collected by filtration. The solid is washed with water and dried in vacuo. The crude product is purified by silica gel chromatography, utilizing a 95:5 to 9:1 gradient of methylene chloride/methanol to give 1.13 g of 4-[3-chloro-4-(1-methyl-1H-imidazol-2-ylsulfanyl)phenylamino]-8-hydroxy-7-methoxybenzo[g]quinoline-3-carbonitrile as a yellow solid, mp>300° C.

$^1$HNMR (d$^6$-DMSO+trifluoroacetic acid): δ 9.22 (d, 2H, J=5.1); 8.28 (s, 1H); 8.06 (d, 1H, J=1.5 Hz); 7.98(d, 1H, J=1.5 Hz); 7.92 (d, 1H, J=1.6 Hz); 7.58 (dd, 1H, J=1.7 Hz, J=8.07 Hz); 7.49 (s, 1H); 7.44 (s, 1); (d, 1H, J=6.4 Hz); 4.05 (s, 3H); 3.88 (s, 3H). MS (ES, positive ion mode): m/z calcd for $C_{25}H_{18}ClN_5O_2S$: 487.9, found (M+H)$^+$ 487.7 Analysis for $C_{25}H_{18}ClN_5O_2S$.0.3H$_2$O Calcd: C:60.86; H:3.80; N: 14.20 Found: C:60.82; H:3.66; N:14.03

EXAMPLE 148

8-(2-Chloroethoxy)-4-[3-chloro-4-(1-methyl-1H-imidazol-2-ylsulfanyl)phenylamino]-7-methoxybenzo[g]quinoline-3-carbonitrile A mixture of 0.8 g (1.64 mmol) of 4-[3-chloro-4-(1-methyl-1H-imidazol-2-ylsulfanyl)phenylamino]-8-hydroxy-7-methoxybenzo[g]quinoline-3-carbonitrile, 0.48 g (2.05 mmol) of 2-chloroethyl p-toluene sulfonate and 0.8 g (2.46 mmol) of cesium carbonate in 15 mL of dry dimethyl formamide is heated at 40° C. for 2 hours. To this is added 0.2 g (0.85 mmol) of 2-chloroethyl p-toluene sulfonate and 0.4 g (1.22 mmol) of cesium carbonate and the reaction mixture is further heated for 2 hours. After cooling to room temperature, the mixture is poured on to ice. The solid is collected by filtration, washed with water and ether, and dried to yield 1.0 g of dark yellow solid. A sample of the solid is purified by preparatory thin layer chromatography, eluting with 95:5% methylene chloride/methanol to give 8-(2-chloroethoxy)-4-[3-chloro-4-(1-methyl-1H-imidazol-2-ylsulfanyl)phenylamino]-7-methoxybenzo[g]quinoline-3-carbonitrile as a yellow solid, mp. 275–280° C.
$^1$HNMR (d$^6$-DMSO+trifluoroacetic acid): δ 9.25 (d, 2H, J=7.3 Hz); 8.41 (s, 1H); 8.06 (d, 1H, J=1.5 Hz); 7.98 (d, 1H, J=1.5 Hz); 7.93 (d, 1H, J=1.7 Hz); 7.78 (s, 1H); 7.58 (dd, 1H, J=1.7 Hz, 9.9 Hz); 7.45 (s, 1H); 7.33 (d, 1H, J=6.4 Hz); 4.55 (t, 2H, J=3.6 Hz); 4.11 (t, 2H, J=3.9 Hz); 4.04 (s, 3H); 3.85 (s, 3H). MS (ES, positive ion mode): m/z calcd for $C_{27}H_{21}Cl_2N_5O_2S$: 550.5, found (M+H)$^+$ 549.7 Analysis for $C_{27}H_{21}Cl_2N_5O_2S\cdot1.7H_2O$ Calcd: C:55.80; H:4.23; N: 12.05 Found: C:56.05; H:4.14; N: 11.70

EXAMPLE 149

4-[3-Chloro-4-(1-methyl-1H-imidazol-2-ylsulfanyl)phenylamino]-7-methoxy-8-(2-morpholin-4-yl-ethoxy benzo[g]quinoline-3 carbonitrile Procedure 1:
A mixture of 1.27 g (2.3 mmol) of 8-(2-chloroethoxy)-4-[3-chloro-4-(1-methyl-1H-imidazol-2-ylsulfanyl)phenylamino]-7-methoxybenzo[g]quinoline-3-carbonitrile, 4.0 mL of morpholine and 0.1 g of sodium iodide in 10 mL of 1,2-dimethoxyethane is heated under reflux for 16 hours. After allowing the reaction to cool, the solvent is evaporated to yield a residue, which is stirred with saturated sodium bicarbonate. The solid is collected by filtration, washed with water and dried. The crude product is purified by silica gel chromatography, utilizing a gradient of 98:2 to 90:10 of methylene chloride/methanol to give 0.53 g of 4-[3-chloro-4-(1-methyl-1H-imidazol-2-ylsulfanyl)phenylamino]-7-methoxy-8-(2-morpholin-4-yl-ethoxy)benzo[g]quinoline-3-carbonitrile as a yellow solid, mp>300° C.

Procedure 2:
A mixture of 2.32 g (6.11 mmol) of 7-methoxy-8-(2-morpholin-4-yl-ethoxy)-4-oxo-1,4-dihydrobenzo[g]quinoline-3-carbonitrile and 35 mL of phosphorus oxychloride is heated under reflux for 1 hour, then cooled to room temperature. Excess phosphorus oxychloride is evaporated to yield a residue, to which toluene is added and the resulting solution is reduced in vacuo. Toluene is added and evaporated twice more. The resulting residue is cooled with ice bath, neutralized with cold saturated solution of sodium bicarbonate and stirred. The solid is collected by filtration, washed with cold water and dried to yield 1.989 g of 4-chloro-7-methoxy-8-(2-morpholin-4-yl-ethoxy)benzo[g]quinoline-3-carbonitrile as a yellow solid.
MS (ES, positive ion mode): m/z calcd for $C_{21}H_{20}ClN_3O_4$397.9, found (M+H)$^+$ 398.2

A mixture of 1.98 g (4.98 mmol) of 4-chloro-7-methoxy-8-(2-morpholin-4-yl ethoxy)benzo[g]quinoline-3-carbonitrile, 1.31 g (5.47 mmol) of 3-chloro-4-(1-methyl-1H-imidazol-2-ylsulfanyl)phenylamine and 0.6 g (5.2 mmol) of pyridine hydrochloride in 2-ethoxyethanol is heated at 120° C. for 1.25 hours, then cooled. The crude mixture is poured into a solution of saturated sodium bicarbonate/ice and stirred for 45 minutes. The resulting solid is collected by filtration, then washed with water, ether and ethyl acetate successively. After drying in vacuo, the solid is purified by silica gel chromatography, using a 94:6 to 9:1 gradient of methylene chloride/methanol to provide a yellow solid. This solid is suspended in ether, filtered, and further washed with ether. After drying in vacuo, 1.77 g of 4-[3-chloro-4-(1-methyl-1H-imidazol-2-ylsulfanyl)phenylamino]-7-methoxy-8-(2-morpholin-4-yl-ethoxy)benzo[g]quinoline-3-carbonitrile is obtained as a yellow solid, mp. >300° C.
$^1$HNMR (d$^6$-DMSO+trifluoroacetic acid): δ 9.28 (s, 2H); 8.45 (s, 1H); 8.06 (d, 1H, J=1.5 Hz); 7.98 (d, 1H, J=1.5 Hz); 7.93 (d, 1H, J=1.7 Hz); 7.83 (s, 1H); 7.58 (dd, 1H, J=1.7 Hz, 6.4 Hz); 7.48 (s, 1H); 7.35 (d, 1H, J=6.4 Hz); 4.67 (t, 2H, J=3.6 Hz); 4.06 (m, 2H); 4.04 (s, 3H); 3.87 (s, 3H); 3.77 (m, 4H); 3.67 (d, 2H, J=9.3 Hz); 3.36 (t, 2H, J=3.6 Hz). MS (ES, positive ion mode): m/z calcd for $C_{31}H_{29}ClN_6O_3S$: 601.1, found (M+H)$^+$ 601.2 Analysis for $C_{31}H_{29}ClN_6O_3S\cdot1.7H_2O$ Calcd: C:55.80; H:4.23; N:12.05 Found: C:56.05; H:4.14; N:11.70

EXAMPLE 150

4-[3-Chloro-4-(1-methyl-1H-imidazol-2-ylsulfanyl)phenylamino]-8-(3-chloropropoxy)-7-methoxybenzo[g]quinoline-3-carbonitrile Following the procedure of Example 148, 0.3 g (0.61 mmol) of 4-[3-chloro-4-(1-methyl-1H-imidazol-2-ylsulfanyl)phenylamino]-8-hydroxy-7-methoxybenzo[g]quinoline-3-carbonitrile is reacted with 0.19 g (0.77 mmol) of 3-chloropropyl p-toluene sulfonate and 0.3 g of (0.92 mmol) of cesium carbonate, then an additional 0.05 g (0.2 mmol) of 3-chloropropyl p-toluene sulfonate and 0.07 g (0.2 mmol) of cesium carbonate in 5 mL of dry dimethyl formamide to provide 0.3 g of a beige solid. A sample of the solid is purified by silica gel chromatography, utilizing a 99:1 to 95:5 gradient of methylene chloride/methanol to give 4-[3-chloro-4-(1-methyl-1H-imidazol-2-ylsulfanyl)phenylamino]-8-(3-chloropropoxy)-7-methoxybenzo[g]quinoline-3-carbonitrile as an orange solid, mp>300° C.
$^1$HNMR (d$^6$-DMSO+trifluoroacetic acid): δ 9.25 (d, 2H, J=8.6 Hz); 8.42 (s, 1H); 8.06 (d, 1H, J=1.5 Hz); 7.98(d, 1H, J=1.5 Hz); 7.93 (d, 1H, J=1.7 Hz); 7.78 (s, 1H); 7.57 (dd, 1H, J=1.7 Hz, 6.4 Hz); 7.44 (s, 1H); 7.33 (d, 1H, J=6.4); 4.39 (t, 2H, J=4.5 Hz); 4.03 (s, 3H); 3.87(m, 2H); 3.86 (s, 3H); 2.35 (m, 2H). MS (ES, positive ion mode): m/z calcd for $C_{28}H_{23}Cl_2N_5O_2S$: 564.5, found (M+H)$^+$ 563.6 Analysis for $C_{28}H_{23}Cl_2N_5O_2S\cdot2.0H_2O$ Calcd: C:56.51; H:4.53; N:11.66 Found: C:56.51; H:4.04; N:11.37

EXAMPLE 151

4-[3-Chloro-4-(1-methyl-1H-imidazol-2-ylsulfanyl) phenylamino]-7-methoxy-8-(3-morpholin-4-yl-propoxy)benzo[g]quinoline-3-carbonitrile Following procedure 1 of Example 149, a mixture of 0.13 g (0.22 mmol) of 4-[3-chloro-4-(1-methyl-1H-imidazol-2-ylsulfanyl)phenylamino]-8-(3-chloropropoxy)-7-methoxy-benzo[g]quinoline-3-carbonitrile, 0.3 mL of morpholine and 0.01 g of sodium iodide is heated under reflux for 16 hours, to provide 0.054 g of a yellow solid. A sample of the solid is purified by silica gel chromatography, utilizing a 97:3 to 90:10 gradient of methylene chloride/methanol to give 4-[3-chloro-4-(1-methyl-1H-imidazol-2-ylsulfanyl)phenylamino]-7-methoxy-8-(3-morpholin-4-yl-propoxy)benzo[g]quinoline-3-carbonitrile as a yellow solid, mp 230–235° C.

$^1$HNMR (d$^6$-DMSO+trifluoroacetic acid): δ 9.26 (s, 2H); 8.42 (s, 1H); 8.05 (d, 1H, J=1.2 Hz); 7.97 (d, 1H, J=1.2 Hz); 7.92 (d, 1H, J=1.6 Hz); 7.73 (s, 1H); 7.57 (dd, 1H, J=1.6 Hz, 6.3 Hz); 7.46 (s, 1H); 7.33 (d, 1H, J=6.4 Hz); 4.36 (t, 2H, J=3.6 Hz); 4.07 (m, 2H); 4.02 (s, 3H); 3.85 (s, 3H); 3.71 (t, 2H, J=9.1 Hz); 3.58 (d, 2H, J=9.1 Hz); 3.38 (t, 2H, J=5.4 Hz); 3.19 (t, 2H, J=8.0 Hz); 2.33 (m, 2H). MS (ES, positive ion mode): m/z calcd for $C_{32}H_{31}ClN_6O_3S$: 615.2, found (M+H)$^+$ 614.7 Analysis for $C_{32}H_{31}ClN_6O_3S \cdot 1.5H_2O$ Calcd: C:59.85; H:5.34; N:13.09 Found: C:59.78; H:5.04; N:12.98

EXAMPLE 152

4-[3-Chloro-4-(1-methyl-1H-imidazol-2-ylsulfanyl) phenylamino]-7-methoxy-8-[2-(4-methylpiperazin-1-yl)ethoxy]-benzo[g]quinoline-3-carbonitrile Following procedure 1 of Example 149, a mixture of 0.15 g (0.3 mmol) of 8-(2-chloroethoxy)-4-[3-chloro-4-(1-methyl-1H-imidazol-2-ylsulfanyl)phenylamino]-7-methoxy-benzo[g]quinoline-3-carbonitrile, 0.5 mL of 1-methylpiperazine and 0.02 g of sodium iodide is heated under reflux for 16 hours. Purification of the material is carried out by silica gel flash chromatography, utilizing a 90:10 to 85:15 gradient of methylene chloride/methanol to give 0.052 g of 4-[3-chloro-4-(1-methyl-1H-imidazol-2-ylsulfanyl)phenylamino]-7-methoxy-8-[2-(4-methylpiperazin-1-yl)ethoxy]-benzo[g]quinoline-3-carbonitrile as a yellow solid, mp 184–186° C.

$^1$HNMR (d$^6$-DMSO+trifluoroacetic acid): δ 9.28 (d, 2H, J=1.9 Hz); 8.45 (s, 1H); 8.06 (d, 1H, J=1.4 Hz); 7.8 (d, 1H, J=1.4 Hz); 7.93 (d, 1H, J=1.7 Hz); 7.82 (s, 1H); 7.57 (dd, 1H, J=1.7 Hz, 6.4 Hz); 7.49 (s, 1H); 7.34 (d, 1H, J=6.4 Hz); 4.67 (m, 2H); 4.03 (s, 3H); 3.89 (m, 2H); 3.86(s, 3H); 3.71–3.25 (m, 6H); 3.2(m, 2H); 2.97 (s, 3H). MS (ES, positive ion mode): m/z calcd for $C_{32}H_{33}ClN_7O_2S$: 614.2, found (M+2H)$^{2+}$ 307.6 Analysis for $C_{32}H_{32}ClN_7O_2S \cdot 3.5H_2O$ Calcd: C:56.74; H:5.80; N:14.48 Found: C:56.57; H:5.46; N:14.12

EXAMPLE 153

4-[3-Chloro-4-(1-methyl-1H-imidazol-2-ylsulfanyl) phenylamino]-7-methoxy-8-(2-[1,2,3]triazol-2-yl-ethoxy)benzo[g]quinoline-3-carbonitrile and

EXAMPLE 154

4-[3-Chloro-4-(1-methyl-1H-imidazol-2-ylsulfanyl) phenylamino]-7-methoxy-8-(2-[1,2,3]triazol-1-yl-ethoxy)benzo[g]quinoline-3-carbonitrile A mixture of 0.3 g (0.55 mmol) of 8-(2-chloroethoxy)-4-[3-chloro-4-(1-methyl-1H-imidazol-2-ylsulfanyl)phenylamino]-7-methoxybenzo[g]quinoline-3-carbonitrile, 0.32 mL (5.5 mmol) of 1H-1,2,3-triazole and 0.1 g (2.5 mmol) of sodium hydroxide powder in 5 mL of N,N-dimethyl formamide is heated at 80° C. for 4.5 hours, then cooled and poured on to ice. The solid is collected by filtration, washed with water and dried. The two isomers are separated by silica gel chromatography, utilizing a 99:1 to 85:15 gradient of ethyl acetate/methanol. The less polar material, 0.062 g of 4-[3-chloro-4-(1-methyl-1H-imidazol-2-ylsulfanyl)phenylamino]-7-methoxy-8-(2-[1,2,3]triazol-2-yl-ethoxy)benzo[g]quinoline-3-carbonitrile is obtained as yellow solid, mp 235–237° C.

$^1$HNMR (d$^6$-DMSO+trifluoroacetic acid): δ 9.22 (d, 2H, J=11.5 Hz); 8.4 (s, 1H); 8.04 (d, 1H, J=1.4 Hz); 7.96 (d, 1H, J=1.4 Hz) 7.92 (d, 1H, J=1.7 Hz); 7.81 (m, 3H); 7.55 (dd, 1H, J=1.7 Hz, 6.4 Hz); 7.43 (s, 1H); 7.30 (d, 1H, J=6.4 Hz); 4.98 (t, 2H, J=3.8 Hz); 4.79 (t, 2H, J=3.8 Hz); 3.96 (s, 3H); 3.84 (s, 3H). MS (ES, positive ion mode): m/z calcd for $C_{29}H_{23}ClN_8O_2S$: 583.1, found (M+H)$^+$ 582.7 Analysis for $C_{29}H_{23}ClN_8O_2S \cdot 1H_2O$ Calcd: C:57.94; H:4.19; N:18.64 Found: C:5773; H:4.10; N:18.65

The more polar material, 0.087 g of 4-[3-chloro-4-(1-methyl-1H-imidazol-2-ylsulfanyl)phenylamino]-7-methoxy-8-(2-[1,2,3]triazol-1-yl-ethoxy)benzo[g]quinoline-3-carbonitrile, is obtained as an orange solid, mp 201–207° C.

$^1$HNMR (d$^6$-DMSO+trifluoroacetic acid): δ 9.24 (d, 2H, J=8.9 Hz); 8.4 (s, 1H); 8.24 (s, 1H); 8.06 (d, 1H, J=1.2 Hz); 7.98 (d, 1H, J=1.2 Hz); 7.93 (d, 1H, J=1.5 Hz); 7.78 (d, 2H, J=5.1 Hz); 7.57 (dd, 1H, J=1.5 Hz, 6.3 Hz); 7.43 (s,1H); 7.33 (d, 1H, J=6.4 Hz); 4.99 (t, 2H, J=4.0 Hz); 4.71 (t, 2H, J=3.6 Hz); 4.00 (s, 3H); 3.86 (s, 3H). MS (ES, positive ion mode): m/z calcd for $C_{29}H_{23}ClN_8O_2S$: 583.1, found (M+H)$^+$ 582.7 Analysis for $C_{29}H_{23}ClN_8O_2S \cdot 0.2H_2O$ Calcd: C:56.26; H:4.40; N:18.10 Found: C:56.34; H:4.19; N: 17.83

EXAMPLE 155

4-(2,4-Dichloro-5-methoxyphenylamino)-8-hydroxy-7-methoxybenzo[g]quinoline-3-carbonitrile A mixture of 0.7 g (2.46 mmol) of 4-chloro-8-hydroxy-7-methoxybenzo[g]quinoline-3-carbonitrile, 0.57 g (2.95 mmol) of 2,4-dichloro-5-methoxyaniline and 0.28 g (2.46 mmol) of pyridine hydrochloride in 7 mL of 2-ethoxyethanol is heated at 120° C. for 2 hours, then cooled to room temperature. The product mixture is diluted with saturated solution of sodium bicarbonate and stirred for 15 minutes. The resulting solid is collected by filtration, washed with water and dried. The crude product is purified by silica gel chromatography, utilizing a 98:2 to 90:10 gradient of methylene chloride/methanol to give 0.71 g of 4-(2,4-dichloro- 5-methoxyphenylamino)-8-hydroxy-7-methoxybenzo[g]
quinoline-3-carbonitrile as a yellow solid, mp, 238–240° C.

$^1$HNMR (d$^6$-DMSO+trifluoroacetic acid): δ 9.31 (s, 1H); 9.22 (s, 1H); 8.28 (s, 1H); 7.89 (s, 1H); 7.64 (s, 1H); 7.44 (s, 1H); 7.41 (s, 1H); 4.03 (s, 3H); 3.91 (s, 3H); MS (ES, positive ion mode): m/z calcd for $C_{22}H_{15}Cl_2N_3O_3$: 440.3, found (M+H)$^+$ 439.7 Analysis for $C_{22}H_{15}Cl_2N_3O_3 \cdot 1.0H_2O$ Calcd: C:57.65; H:3.74; N:9.17 Found: C:57.80; H:3.94; N:8.82

EXAMPLE 156

8-(3-Chloropropoxy)-4-(2,4-dichloro-5-methoxyphenylamino)-7-methoxybenzo[g]quinoline-3-carbonitrile Following the procedure of Example 148, 0.43 g (0.98 mmol) of L20350-72-A is reacted with 0.31 g (1.25 mmol) of 3-chloropropyl p-toluene sulfonate and 0.48 g of (1.47 mmol) of cesium carbonate, then an additional 0.05 g (0.2 mmol) of 3-chloropropyl p-toluene sulfonate and 0.07 g (0.2 mmol) of cesium carbonate in 6 mL of dry dimethyl formamide. The crude product is purified by silica gel flash chromatography, utilizing a 99.5:0.5 to 99:1 gradient of methylene chloride/methanol to give 0.71 g of 8-(3-chloropropoxy)-4-(2,4-dichloro-5-methoxyphenylamino)-7-methoxybenzo[g]quinoline-3-carbonitrile as a yellow solid, mp 220–223° C.

$^1$HNMR (d$^6$-DMSO+trifluoroacetic acid): δ 9.35 (s, 1H); 9.25 (s, 1H); 8.44 (s, 1H); 7.87 (s, 1H); 7.77 (s, 1H); 7.61 (s, 1H); 7.47 (s, 1H); 4.41 (t, 2H, J=4.5 Hz); 4.06 (s, 3H); 3.93 (s, 3H); 3.88 (t, 2H, J=4.8 Hz); 2.35 (m, 2H). MS (ES, positive ion mode): m/z calcd for $C_{25}H_{20}Cl_3N_3O_3$: 516.8, found (M+H)$^+$ 517.6 Analysis for $C_{25}H_{20}Cl_3N_3O_3 \cdot 0.5H_2O$ Calcd: C:57.10; H:4.03; N:7.99 Found: C:57.01; H:4.00; N:7.86

EXAMPLE 157

4-(2,4-Dichloro-5-methoxyphenylamino)-7-methoxy-8-(3-morpholin-4-yl-propoxy)benzo[g]quinoline-3-carbonitrile Following procedure 1 of Example 149, a mixture of 0.105 g (0.20 mmol) of 8-(3-chloropropoxy)-4-(2,4-dichloro-5-methoxyphenylamino)-7-methoxybenzo[g]quinoline-3-carbonitrile, 0.3 mL of morpholine and 0.01 g of sodium iodide in 10 mL of 1,2-dimethoxyethane is heated under reflux for 7 hours. The resulting solid is purified by silica gel chromatography, utilizing a 98:2 to 94:6 gradient of methylene chloride/methanol to give 0.089 g of 4-(2,4-dichloro-5-methoxyphenylamino)-7-methoxy-8-(3-morpholin-4-yl-propoxy)benzo[g]quinoline-3-carbonitrile as a yellow solid, mp 205–208° C.

$^1$HNMR (d$^6$-DMSO+trifluoroacetic acid): δ 9.37 (s, 1H); 9.26 (s, 1H); 8.44 (s, 1H); 7.88 (s, 1H); 7.73 (s, 1H); 7.63 (s, 1H); 7.49 (s, 1H); 4.39 (t, 2H, J=5.5 Hz); 4.09 (m, 2H); 4.05 (s, 3H); 3.93 (s, 3H); 3.75 (t, 2H, J=11.7 Hz); 3.60 (d, 2H, J=12.2 Hz); 3.42 (t, 2H, J=7.0 Hz); 3.21 (t, 2H, J=9.3 Hz); 2.35 (m, 2H). MS (ES, positive ion mode): m/z calcd for $C_{29}H_{28}Cl_2N_4O_4$: 567.5, found (M+H)$^+$ 566.7 Analysis for $C_{29}H_{28}Cl_2N_4O_4 \cdot 1.7H_2O$ Calcd: C:58.23; H:5.29; N:9.37 Found: C:57.91; H:5.15; N:9.12

EXAMPLE 158

4-(2,4-Dichloro-5-methoxyphenylamino)-7-methoxy-8-(2-[1,2,3]triazol-2-yl-ethoxy)benzo[g]quinoline-3-carbonitrile and

EXAMPLE 159

4-(2,4-Dichloro-5-methoxyphenylamino)-7-methoxy-8-(2-[1,2,3]triazol-1-yl-ethoxy)benzo[g]quinoline-3-carbonitrile Following the procedure of Example 148, 0.28 g (0:64 mmol) of 4-(2,4-dichloro-5-methoxyphenylamino)-8-hydroxy-7-methoxybenzo[g]quinoline-3-carbonitrile is reacted with 0.18 g (0.76 mmol) of 2-chloroethyl p-toluene sulfonate and 0.3 g of (0.92 mmol) of cesium carbonate, then an additional 0.05 g (0.2 mmol) of 2-chloroethyl p-toluene sulfonate and 0.07 g (0.2 mmol) of cesium carbonate in 5 mL of dry dimethyl formamide. This yields 0.31 g of 8-(2-chloroethoxy)-4-(2,4-dichloro-5-methoxyphenylamino)-7-methoxybenzo[g]quinoline-3-carbonitrile as a brown solid. MS (ES, positive ion mode): m/z calcd for $C_{28}H_{23}Cl_2N_5O_2S$: 502.8, found (M+H)$^+$ 503.7

A mixture of 0.31 g (0.62 mmol) of 8-(2-chloroethoxy)-4-(2,4-dichloro-5-methoxyphenylamino)-7-methoxybenzo[g]quinoline-3-carbonitrile, 0.36 mL (6.1 mmol) of 1H-1,2,3-triazole and 0.11 g (2.8 mmol) of sodium hydroxide powder in 5 mL of N,N-dimethyl formamide is heated at 80° C. for 4.5 hours, then cooled and poured on to ice. The solid is collected by filtration, washed with water and dried. The two isomers are separated by silica gel flash chromatography, using first 7:3 ethyl acetate/hexane, then a 100:0 to 9:1 gradient of ethyl acetate/methanol. The less polar material, 0.071 g of 4-(2,4-dichloro-5-methoxyphenylamino)-7-methoxy-8-(2-[1,2,3]triazol-2-yl-ethoxy)benzo[g]quinoline-3-carbonitrile, is obtained as yellow solid, mp 285–287° C.

$^1$HNMR (d$^6$-DMSO+trifluoroacetic acid): δ 9.34 (s, 1H; 9.22 (s, 1H) 8.44 (s, 1H); 7.84(s, 1H); 7.79 (s, 2H); 7.77 (s, 1H; 7.60(s, 1H); 7.46 (s, 1H); 5.01 (t, 2H, J=3.8 Hz); 4.84 (t, 2H J=3.7 Hz); 4.00 (s, 3H); 3.94 (s, 3H). MS (ES, positive ion mode): m/z calcd for $C_{26}H_{20}Cl_2N_6O_3$: 535.4, found (M+H)$^+$ 534.6 Analysis for $C_{26}H_{20}Cl_2N_6O_3 \cdot 0.5H_2O$ Calcd: C:57.36; H:3.89; N:15.44 Found: C:57.45; H:3.86; N:15.14

The more polar material, 0.053 g of 4-(2,4-dichloro-5-methoxyphenylamino)-7-methoxy-8-(2-[1,2,3]triazol-1-yl-ethoxy)benzo[g]quinoline-3-carbonitrile, is obtained as brown solid, mp 245° C. (dec).

$^1$HNMR (d$^6$-DMSO+trifluoroacetic acid): δ 9.35 (s, 1H); 9.27 (s, 1H); 8.42 (s, 1H); 8.25 (d, 1H, J=0.6 Hz); 7.89 (s, 1H); 7.79 (d, 2H, J=3.3 Hz); 7.64 (s, 1H); 7.44 (s, 1H); 5.0 (t, 2H, J=3.8 Hz); 4.72 (t, 2H, J=3.7 Hz); 4.03 (s, 3H); 3.91 (s, 3H). MS (ES, positive ion mode): m/z calcd for $C_{26}H_{20}Cl_2N_6O_3$: 535.4, found (M+H)$^+$ 534.6 Analysis for $C_{26}H_{20}Cl_2N_6O_3 \cdot 1.3H_2O$ Calcd: C:55.88; H:4.08; N:15.04 Found: C:55.97; H:4.05; N:14.86

EXAMPLE 160

Methyl 2-cyano-3-(4,5-dimethoxy-2-nitrophenyl-2-propenoate

To a mixture of 7.00 g (33.15 mmol) of 6-nitroveratraldehyde (80%) and 3.4 mL (38.42 mmol) of methyl cyanoacetate in 70 mL of methanol is added 0.7 mL of piperidine.

An additional 100 mL of methanol is added and the thick suspension is warmed slightly until the mixture stirred freely. After stirring at room temperature for 1 hour, the solids are collected by filtration washing with methanol followed by diethyl ether to give 7.57 g (78%) of methyl 2-cyano-3-(4,5-dimethoxy-2-nitrophenyl)-2-propenoate as a pale yellow solid, mp 162–164° C.

MS 292.1 (M+H)$^+$ Analysis for $C_{13}H_{12}N_2O_6$ Calcd: C, 53.43; H, 4.14; N, 9.59. Found: C, 53.03; H, 4.02; N, 9.59.

EXAMPLE 161

Methyl 2-amino-6,7-dimethoxy-3-quinolinecarboxylate

To methyl 2-cyano-3-(4,5-dimethoxy-2-nitrophenyl)-2-propenoate (7.00 g, 23.97 mmol) in 100 mL of acetic acid is added 5.00 g (89.6 mmol) of iron. The mixture is heated at reflux for 10 minutes, cooled slightly, filtered, and washed with ethyl acetate. The filtrate is concentrated in vacuo and partitioned between ethyl acetate and saturated sodium bicarbonate. The organic layer is dried over magnesium sulfate, filtered and concentrated in vacuo to provide 652 mg (10%) of product as a pale yellow solid. The aqueous layer is acidified with acetic acid and the resultant solid is collected by filtration, washing with water and ethyl acetate to provide 1.57 g (25%) of methyl 2-amino-6,7-dimethoxy-3-quinolinecarboxylate as a pale yellow solid, mp 227–229° C. MS 263.1 (M+H)$^+$ Analysis for $C_{13}H_{14}N_2O_4$ Calcd: C, 59.54; H, 5.38; N, 10.68. Found: C, 59.56; H, 5.46; N, 10.55.

EXAMPLE 162

Methyl 2-{[(E)-(dimethylamino)methylidene]amino}-6,7-dimethoxy-3-quinolinecarboxylate A mixture of methyl 2-amino-6,7-dimethoxy-3-quinolinecarboxylate (3.60 g, 13.04 mmol) and 4.10 g of dimethylformamide dimethylacetal in 60 mL of toluene containing 40 mg of p-toluenesulfonic acid is heated at reflux for 2 hours. Upon cooling to room temperature a solid formed and is collected by filtration to provide 736 mg of methyl 2-{[(E)-(dimethylamino)methylidene]amino}-6,7-dimethoxy-3-quinolinecarboxylate as an off-white solid, mp 166–168° C. MS 318.1, 319.0 (M+H)$^+$ Analysis for $C_{16}H_{19}N_3O_4$ Calcd: C, 60.56; H, 6.03; N, 13.24. Found: C, 60.63; H, 6.08; N, 13.32.

The filtrate is concentrated in vacuo to provide an additional 2.86 g of methyl 2-{[(E)-(dimethylamino)methylidene]amino}-6,7-dimethoxy-3-quinolinecarboxylate.

EXAMPLE 163

7,8-Dimethoxy-4-oxo-1,4-dihydrobenzo[b][1,8]naphthyridine-3-carbonitrile

Acetonitrile (1.3 mL, 24.9 mmol) is added to a −78° C. solution of 9.0 mL of 2.5 M n-butyllithium (22.5 mmol) in 40 mL of tetrahydrofuran. After stirring at −78° C. for 15 min, a solution of 2.86 g (9.02 mmol) of methyl 2-{[(E)-(dimethylamino)methylidene]amino}-6,7-dimethoxy-3-quinolinecarboxylate in 100 mL of tetrahydrofuran is added dropwise over 30 minutes. After stirring at −78° C. for 30 minutes, the reaction mixture is allowed to warm to room temperature and then stirred at room temperature for 1 hour. The reaction mixture is cooled to −78° C. and 3.0 mL of acetic acid is added. The mixture is then stirred at room temperature for 40 min. The solids are collected by filtration washing with water, methanol and ethyl acetate to provide 1.11 g (44%) of 7,8-dimethoxy-4-oxo-1,4-dihydrobenzo[b][1,8]naphthyridine-3-carbonitrile as a light yellow solid, mp>300° C. MS 281.9 (M+H)$^+$ Analysis for $C_{15}H_{11}N_3O_3.0.65H_2O$ Calcd: C, 61.49; H, 4.23; N, 14.34. Found: C, 61.40; H, 4.40; N, 14.70.

EXAMPLE 164

4-Chloro-7,8-dimethoxybenzo[b][1,8]naphthyridine-3-carbonitrile

A mixture of 7,8-dimethoxy-4-oxo-1,4-dihydrobenzo[b][1,8]naphthyridine-3-carbonitrile (500 mg, 1.78 mmol) and 5 mL of phosphorous oxychloride is heated at reflux for one hour then cooled to room temperature. Hexane (20 mL) is added and the resultant solids are collected by filtration washing with hexane, water, methanol and ethyl acetate to provide 258 mg (49%) of 4-chloro-7,8-dimethoxybenzo[b][1,8]naphthyridine-3-carbonitrile as a brown solid, mp>300° C.

MS 299.9, 302.0 (M+H)$^+$ Analysis for $C_{15}H_{10}ClN_3O_2.0.40H_2O$ Calcd: C, 58.70; H, 3.55; N, 13.69. Found: C, 58.85; H, 3.33; N, 13.97.

EXAMPLE 165

4-(2,4-Dichloro-5-methoxyanilino)-7,8-dimethoxybenzo[b][1,8]naphthyridine-3-carbonitrile A mixture of 4-chloro-7,8-dimethoxybenzo[b][1,8]naphthyridine-3-carbonitrile (150 mg, 0.50 mmol), 2,4-dichloro-5-methoxyaniline (160 mg, 0.83 mmol) and pyridine hydrochloride (70 mg, 0.60 mmol) in 15 mL of 2-ethoxyethanol is heated at reflux for 25 minutes then cooled to room temperature. The solution is partitioned between ethyl acetate and saturated sodium bicarbonate. The organic layer is dried over magnesium sulfate, filtered and concentrated in vacuo. The residue is partitioned between ethyl acetate and an aqueous solution of sodium hydroxide and sodium bicarbonate (pH 14). The organic layer is dried over magnesium sulfate, filtered and concentrated in vacuo. Diethyl ether is added to the residue and the resultant bright orange solid is collected to provide 86 mg (38%) of 4-(2,4-dichloro-5-methoxyanilino)-7,8-dimethoxybenzo[b][1,8]naphthyridine-3-carbonitrile, mp 297° C. dec.

MS 455.0, 457.00 (M+H)$^+$ Analysis for $C_{22}H_{16}Cl_2N_4O_3$ Calcd: C, 58.04; H, 3.54; N, 12.31. Found: C, 57.86; H, 3.48; N, 12.30.

EXAMPLE 166

4-(2-Chloroethoxy)-5-methoxy-2-nitrobenzaldehyde

Fuming nitric acid (10 mL) is added dropwise to a −40° C. suspension of 5.00 g (23.36 mmol) of 4-(2-chloroethoxy)-3-methoxybenzaldehyde (Milbank, J. B. J., et. al., J. Med. Chem., 42(4), 649–658, 1999) in 23 mL of 1,2-dichloroethane. The reaction mixture is slowly allowed to warm to −10° C. The mixture is poured onto 300 mL of ice water and then extracted with ethyl acetate. The organic layer is dried over magnesium sulfate, filtered and concentrated in vacuo. Diethyl ether is added to the residue and the pale yellow solid is collected by filtration to provide 2.43 g (40%) of 4-(2-chloroethoxy)-5-methoxy-2-nitrobenzaldehyde, mp 148–150° C.

MS 260.1, 262.1 (M+H)+ Analysis for $C_{10}H_{10}ClNO_5$ Calcd: C, 46.26; H, 3.88; N, 5.39. Found: C, 46.64; H, 3.60; N, 5.21.

EXAMPLE 167

Methyl (2E)-2-cyano-3-(4-[2-chloroethoxy]5-methoxy-2-nitrophenyl)-2-propenoate

To a mixture of 3.00 g (11.58 mmol) of 4-(2-chloroethoxy)-5-methoxy-2-nitrobenzaldehyde and 1.5 mL (16.95 mmol) of methyl cyanoacetate in 30 mL of methanol is added 0.3 mL of piperidine. The mixture is heated at reflux for 5 minutes then cooled slightly and the thick suspension is collected by filtration washing with ethyl acetate followed by diethyl ether to give 1.07 g (27%) of methyl (2E)-2-cyano-3-[4-(2-chloroethoxy)-5-methoxy-2-nitrophenyl]-2-propenoate as a yellow solid, mp softens at 121° C., melts at 157–160° C.

MS 340.1, 342.1 (M+H)+ Analysis for $C_{14}H_{13}ClN_2O_6$ Calcd: C, 49.35; H, 3.85; N, 8.22. Found: C, 49.56; H, 3.90; N, 8.26.

EXAMPLE 168

Methyl 2-Amino-7-[2-chloroethoxy]-6-methoxy-3-quinolinecarboxylate

To methyl (2E)-2-cyano-3-[4-(2-chloroethoxy)-5-methoxy-2-nitrophenyl]-2-propenoate (19.3 g, 56.6 mmol) in 250 mL of acetic acid is added portionwise 12.0 g (215.0 mmol) of iron. The mixture is heated at reflux for 20 minutes, cooled slightly and filtered washing with ethyl acetate. The filtrate is concentrated in vacuo and water is added to the residue. The resulting yellow solid is collected by filtration washing with water to provide 14.6 g of methyl 2-amino-7-[2-chloroethoxy]-6-methoxy-3-quinolinecarboxylate. An analytical sample is obtained by stirring a portion of the product with a mixture of methanol and aqueous ammonium hydroxide. The undissolved solids are removed by filtration. Upon standing solids appeared in the filtrate and are collected to provide methyl 2-amino-7-[2-chloroethoxy]-6-methoxy-3-quinolinecarboxylate as light yellow crystals, mp 145–157° C.

MS 311.0, 313.0 (M+H)+ Analysis for $C_{14}H_{15}ClN_2O_4$ Calcd: C, 54.11; H, 4.87; N, 9.02. Found: C, 53.88; H, 4.84; N, 8.99.

EXAMPLE 169

Methyl 7-(2-chloroethoxy)-2-{[(1E)-(dimethylamino)methylidene]amino}-6-methoxy-3-quinolinecarboxylate A mixture of methyl 2-amino-7-[2-chloroethoxy]-6-methoxy-3-quinolinecarboxylate (5.00 g, 16.09 mmol) and 5.10 g of dimethylformamide dimethylacetal in 75 mL of toluene containing 50 mg of p-toluenesulfonic acid is heated at reflux for 10 minutes then cooled to room temperature. Diethyl ether is added and the solids are collected by filtration to provide 3.81 g of methyl 7-(2-chloroethoxy)-2-{[(1E)-(dimethylamino)methylidene]amino}-6-methoxy-3-quinolinecarboxylate as a pale yellow solid, mp 108–110° F. MS 366.1, 368.1 (M+H)+ Analysis for $C_{17}H_{20}ClN_3O_4.0.5H_2O$ Calcd. C, 54.47; H, 5.65; N, 11.21. Found: C, 54.86; H, 5.62; N, 10.89.

EXAMPLE 170

8-(2-Chloroethoxy)-7-methoxy-4-oxo-1,4-dihydrobenzo[b][1,8]naphthyridine-3-carbonitrile Acetonitrile (1.4 mL, 26.8 mmol) is added to a −78° C. solution of 9.6 mL of 2.5 M n-butyllithium (24.0 mmol) in 50 mL of tetrahydrofuran. After stirring at −78° C. for 15 min. a solution of 3.50 g (9.02 mmol) of methyl 7-(2-chloroethoxy)-2-{[(1E)-(dimethylamino)methylidene]amino}-6-methoxy-3-quinolinecarboxylate in 100 mL of tetrahydrofuran is added dropwise over 35 minutes. After stirring at −78° C. for 30 minutes, the reaction mixture is allowed to warm to room temperature and then stirred at room temperature for 1 hour. The reaction mixture is cooled to −78° C. and 3.2 mL of acetic acid is added. The mixture is stirred at room temperature for 35 minutes. The solids are collected by filtration washing with water, methanol and ethyl acetate to provide 1.59 g (50%) of product. An analytical sample is obtained by heating a portion of the product with methanol and filtering the hot solution to provide 8-(2-chloroethoxy)-7-methoxy-4-oxo-1,4-dihydrobenzo[b][1,8]naphthyridine-3-carbonitrile as a tan solid, mp 280° C. dec. MS 327.6 (M+H)+ Analysis for $C_{16}H_{12}ClN_3O_3.2.0H_2O$ Calcd: C, 52.54; H, 4.41; N, 11.49. Found: C, 52.26; H, 4.47; N, 11.49.

EXAMPLE 171

4-Chloro-8-(2-chloroethoxy)-7-methoxybenzo[b][1,8]naphthyridine-3-carbonitrile

A mixture of 8-(2-chloroethoxy)-7-methoxy-4-oxo-1,4-dihydrobenzo[b][1,8]naphthyridine-3-carbonitrile (2.29 g, 6.96 mmol) and 15 mL of phosphorous oxychloride is heated at reflux for one hour then cooled to room temperature. The resultant solids are collected by filtration washing with hexane, water, methanol and ethyl acetate to provide 929 mg (38%) of product. Upon standing, an additional 155 mg of product is obtained from the filtrate. This solid is stirred in methanol, filtered and washed with methanol and ethyl acetate to provide an analytical sample of 4-chloro-8-(2-chloroethoxy)-7-methoxybenzo[b][1,8]naphthyridine-3-carbonitrile as a mustard yellow solid, mp 265° C. dec.

MS 348.0, 350.0 (M+H)+ Analysis for $C_{16}H_{11}Cl_2N_3O_2.0.50H_2O$ Calcd: C, 53.80; H, 3.39; N, 11.76. Found: C, 54.16; H, 3.19; N, 12.10.

EXAMPLE 172

8-(2-Chloroethoxy)-4-(2,4-dichloro-5-methoxyanilino)-7-methoxybenzo[b][1,8]naphthyridine-3-carbonitrile A mixture of 4-chloro-8-(2-chloroethoxy)-7-methoxybenzo[b][1,8]naphthyridine-3-carbonitrile (500 mg, 1.43 mmol) and 2,4-dichloro-5-methoxyaniline (460 mg, 2.39 mmol) in 40 mL of 2-ethoxyethanol is heated at reflux for 20 minutes then cooled to room temperature. The solution is partitioned between ethyl acetate and saturated sodium bicarbonate. The organic layer is dried over magnesium sulfate, filtered and concentrated in vacuo. The residue is partitioned between ethyl acetate and an aqueous solution of sodium hydroxide and sodium bicarbonate (pH 14). The organic layer is dried over magnesium sulfate, filtered and concentrated in vacuo. Ethyl acetate and diethyl ether are added to the residue and the resultant orange solid is collected by filtration to provide 297 mg (41%) of 8-(2-chloroethoxy)-4-(2,4-dichloro-5-methoxyanilino)-7-methoxybenzo[b][1,8]naphthyridine-3-carbonitrile, mp 227–230° C. dec.
MS 502.8, 504.6, 505.0 (M+H)+ Analysis for $C_{23}H_{17}Cl_3N_4O_3$. 0.50$H_2O$ Calcd: C, 53.87; H, 3.54; N, 10.93. Found: C, 54.09; H, 3.36 N, 10.91.

EXAMPLE 173

4-(2,4-Dichloro-5-methoxyanilino)-7-methoxy-8-[2-(4-morpholinyl)ethoxy]benzo[b][1,8]naphthyridine-3-carbonitrile A mixture of 8-(2-chloroethoxy)-4-(2,4-dichloro-5-methoxyanilino)-7-methoxybenzo[b][1,8]naphthyridine-3-carbonitrile (202 mg, 0.40 mmol) and sodium iodine (70 mg, 0.47 mmol) in 4 mL of morpholine is heated at reflux for 2 hours. The reaction mixture is concentrated in vacuo and partitioned between ethyl acetate and water. The organic layer is washed with saturated sodium bicarbonate, dried over magnesium sulfate, filtered and concentrated in vacuo. Ethyl acetate is added to the residue and the orange solid is collected by filtration to provide 105 mg (47%) of 4-(2,4-dichloro-5-methoxyanilino)-7-methoxy-8-[2-(4-morpholinyl)ethoxy]benzo[b][1,8]naphthyridine-3-carbonitrile, mp 242–244° C. dec. MS 553.8, 555.8 (M+H)+ Analysis for $C_{27}H_{25}Cl_2N_5O_4$ Calcd: C, 58.49; H, 4.54; N, 12.63. Found: C, 58.41; H, 4.23; N, 12.48.

The following compound is made by the method of example 172:

EXAMPLE 174

8-(2-Chloroethoxy)-4-{3-chloro-4-[(1-methyl-1H-imidazol-2-yl)sulfanyl]anilino}-7-methoxybenzo[b][1,8]naphthyridine-3-carbonitrile 8-(2-Chloroethoxy)-4-{3-chloro-4-[(1-methyl-1H-imidazol-2-yl)sulfanyl]anilino}-7-methoxybenzo[b][1,8]naphthyridine-3-carbonitrile is obtained as a yellow solid, mp>250° C. dec. MS 552.7 (M+H)+

The following compounds are made by the method of example 173:

EXAMPLE 175

4-(2,4-Dichloro-5-methoxyanilino)-7-methoxy-8-[2-(4-methyl-1-piperazinyl)ethoxy]benzo[b][1,8]naphthyridine-3-carbonitrile 4-(2,4-Dichloro-5-methoxyanilino)-7-methoxy-8-[2-(4-methyl-1-piperazinyl)ethoxy]benzo[b][1,8]naphthyridine-3-carbonitrile is obtained as a yellow solid, mp 240–243° C. dec MS 566.9 (M+H)+

EXAMPLE 176

4-{3-Chloro-4-[(1-methyl-1H-imidazol-2-yl)sulfanyl]anilino}-7-methoxy-8-[2-(4-morpholinyl)ethoxy]benzo[b][1,8]naphthyridine-3-carbonitrile 4-{3-Chloro-4-[(1-methyl-1H-imidazol-2-yl)sulfanyl]anilino}-7-methoxy-8-[2-(4-morpholinyl)ethoxy]benzo[b][1,8]naphthyridine-3-carbonitrile is obtained as a red solid, mp 160–162° C. dec
MS 601.7 (M+H)+

The following compounds are made by the method of example 165:

EXAMPLE 177

4-(2,4-Dichloroanilino)-7,8-dimethoxybenzo[b][1,8]naphthyridine-3-carbonitrile 4-(2,4-Dichloroanilino)-7,8-dimethoxybenzo[b][1,8]naphthyridine-3-carbonitrile is obtained as a yellow-orange solid, mp 266–270° C. dec. MS 424.7 M+H)+

EXAMPLE 178

7,8-Dimethoxy-4-(3,4,5-trimethoxyanilino)benzo[b][1,8]naphthyridine-3-carbonitrile 7,8-Dimethoxy-4-(3,4,5-trimethoxyanilino)benzo[b][1,8]naphthyridine-3-carbonitrile is obtained as an orange solid, mp 250–252° C. dec.
MS 446.7 (M+H)+

The following compounds are made by the method of examples 122 and 123:

EXAMPLE 179

8-(2-Chloroethoxy)-4-(4-chloro-5-methoxy-2-methylanilino)-7-ethoxybenzo[g]quinoline-3-carbonitrile After purification by silica gel chromatography, 8-(2-chloroethoxy)-4-(4-chloro-5-methoxy-2-methylanilino)-7-ethoxybenzo[g]quinoline-3-carbonitrile is obtained as yellow crystals, mp 129–130° C. MS 496.1 (M+H)+

EXAMPLE 180

8-(2-Chloroethoxy)-4-(2-chloro-4-fluoro-5-methoxyanilino)-7-methoxybenzo[g]quinoline-3-carbonitrile and

EXAMPLE 181

7-(2-Chloroethoxy)-4-(2-chloro-4-fluoro-5-methoxyanilino)-8-methoxybenzo[g]quinoline-3-carbonitrile The reaction of 2-chloro-4-fluoro-5-methoxyaniline (prepared by the procedure described in WO 8501939) with 4-chloro-7-methoxy-8-(2-chloroethoxy)benzo[g]quinoline-3-carbonitrile and 4-chloro-8-methoxy-7-(2-chloroethoxy)benzo[g]quinoline-3-carbonitrile (1:1 mixture), yields a 1:1 mixture of 8-(2-chloroethoxy)-4-(2-chloro-4-fluoro-5-methoxyanilino)-7-methoxybenzo[g]quinoline-3-carbonitrile and 7-(2-chloroethoxy)-4-(2-chloro-4-fluoro-5-methoxyanilino)-8-methoxybenzo[g]quinoline-3-carbonitrile as a yellow solid, mp 193–204° C.
MS (M+H)+ 486.1

EXAMPLE 182

8-(2-Chloroethoxy)-4-(2-chloro-5-methoxy-4-methylphenylamino)-7-methoxybenzo[g]quinoline-3-carbonitrile and

EXAMPLE 183

7-(2-Chloroethoxy)-4-(2-chloro-5-methoxy-4-methylphenylamino)-8-methoxybenzo[g]quinoline-3-carbonitrile The reaction of 2-chloro-5-methoxy-4-methylaniline (prepared by the procedure described in Theodoridis, G., *Pesticide Science,* 30(3), 259 (1990)) with 4-chloro-7-methoxy-8-(2-chloroethoxy)benzo[g]quinoline-3-carbonitrile and 4-chloro-8-methoxy-7-(2-chloroethoxy)benzo[g]quinoline-3-carbonitrile (1:1 mixture), yields a 1:1 mixture of 8-(2-chloroethoxy)-4-(2-chloro-5-methoxy-4-methylphenylamino)-7-methoxybenzo[g]quinoline-3-carbonitrile and 7-(2-chloroethoxy)-4-(2-chloro-5-methoxy-4-methylphenylamino)-8-methoxybenzo[g]quinoline-3-carbonitrile as a yellow solid, mp 222–236° C. MS (M+H)$^+$ 482.0

EXAMPLE 184

7-(2-Chloroethoxy)-4-(3-chloro-4-fluoroanilino)-8-methoxybenzo[g]quinoline-3-carbonitrile and

EXAMPLE 185

8-(2-Chloroethoxy)-4-(3-chloro-4-fluoroanilino)-7-methoxybenzo[g]quinoline-3-carbonitrile A 1:1 mixture of 7-(2-chloroethoxy)-4-(3-chloro-4-fluoroanilino)-8-methoxybenzo[g]quinoline-3-carbonitrile and 8-(2-chloroethoxy)-4-(3-chloro-4-fluoroanilino)-7-methoxybenzo[g]quinoline-3-carbonitrile is obtained as a yellow solid, mp 137–159° C.

MS (M+H)$^+$ 456.1

EXAMPLE 186

4-(4-Benzyloxy-3-chlorophenylamino)-7-(2-chloroethoxy)-8-methoxybenzo[g]quinoline-3-carbonitrile and

EXAMPLE 187

4-(4-Benzyloxy-3-chlorophenylamino)-8-(2-chloroethoxy)-7-methoxybenzo[g]quinoline-3-carbonitrile The reaction of 4-benzyloxy-3-chloroaniline (prepared by the procedure described in WO 9609294) with 4-chloro-7-methoxy-8-(2-chloroethoxy)benzo[g]quinoline-3-carbonitrile and 4-chloro-8-methoxy-7-(2-chloroethoxy)benzo[g]quinoline-3-carbonitrile (1:1 mixture), yields a 1:1 mixture of 4-(4-benzyloxy-3-chlorophenylamino)-7-(2-chloroethoxy)-8-methoxybenzo[g]quinoline-3-carbonitrile and 4-(4-benzyloxy-3-chlorophenylamino)-8-(2-chloroethoxy)-7-methoxybenzo[g]quinoline-3-carbonitrile as a white solid, mp 182–185° C.

Analysis for $C_{30}H_{23}Cl_2N_3O_3$ Calcd: C:66.18; H:4.26; N:7.72 Found: C:65.82; H:4.27; N:7.63

EXAMPLE 188

7-(2-Chloroethoxy)-4-(3-chloro-4-phenoxyphenylamino-8-methoxybenzo[g]quinoline-3-carbonitrile and

EXAMPLE 189

8-(2-Chloroethoxy)-4-(3-chloro-4-phenoxyphenylamino)-7-methoxybenzo[g]quinoline-3-carbonitrile The reaction of 3-chloro-4-phenoxyaniline (prepared by the procedure described in WO 9615118) with 4-chloro-7-methoxy-8-(2-chloroethoxy)benzo[g]quinoline-3-carbonitrile and 4-chloro-8-methoxy-7-(2-chloroethoxy)benzo[g]quinoline-3-carbonitrile (1:1 mixture), yields a 1:1 mixture of 7-(2-chloroethoxy)-4-(3-chloro-4-phenoxyphenylamino)-8-methoxybenzo[g]quinoline-3-carbonitrile and 8-(2-chloroethoxy)-4-(3-chloro-4-phenoxyphenylamino)-7-methoxybenzo[g]quinoline-3-carbonitrile as a white solid.

MS (M+H)$^+$ 529.9, 531.9

The following compounds (examples 190–218) are made by the method of examples 124 and 125:

EXAMPLE 190

4-(4-Chloro-5-methoxy-2-methylanilino)-8-ethoxy-7-[2-(4-morpholinyl)ethoxy]benzo[g]quinoline-3-carbonitrile 4-(4-Chloro-5-methoxy-2-methylanilino)-8-ethoxy-7-[2-(4-morpholinyl)ethoxy]benzo[g]quinoline-3-carbonitrile is obtained as yellow crystals, mp 195–196° C.

MS 547.1 (M+H)$^+$

EXAMPLE 191

4-(4-Chloro-5-methoxy-2-methylanilino)-7-ethoxy-8-[2-(4-morpholinyl)ethoxy]benzo[g]quinoline-3-carbonitrile 4-(4-Chloro-5-methoxy-2-methylanilino)-7-ethoxy-8-[2-(4-morpholinyl)ethoxy]benzo[g]quinoline-3-carbonitrile is obtained as yellow crystals, mp 201–203° C.

MS 547.1 (M+H)$^+$

EXAMPLE 192

({2[4-(4-Chloro-5-methoxy-2-methylphenylamino)-3-cyano-8-ethoxybenzo[g]quinoline-7-yloxy]-ethyl}-ethoxycarbonylmethyl-amino)-acetic acid ethyl ester ({2[4-(4-Chloro-5-methoxy-2-methylphenylamino)-3-cyano-8-ethoxybenzo[g]quinoline-7-yloxy]-ethyl}-ethoxycarbonylmethyl-amino)-acetic acid ethyl ester is obtained as yellow crystals, mp 70–71° C.

MS 649.2 (M+H)$^+$

EXAMPLE 193

({2-[4-(4-Chloro-5-methoxy-2-methylphenylamino)-3-cyano-7-ethoxybenzo[g]quinoline-8-yloxy]-ethyl}-ethoxycarbonylmethylamino)-acetic acid ethyl ester ({2-[4-(4-Chloro-5-methoxy-2-methylphenylamino)-3-cyano-7-ethoxybenzo[g]quinoline-8-yloxy]-ethyl}-ethoxycarbonylmethylamino)-acetic acid ethyl ester is obtained as yellow crystals, mp 85–86° C.
MS 649.2 (M+H)$^+$

EXAMPLE 194

2-(Carbamoylmethyl-{2-[4-(4-chloro-5-methoxy-2-methylphenylamino)-3-cyano-7-ethoxybenzo[g]quinolin-8-yloxy]-ethyl}-amino)-acetamide 2-(Carbamoylmethyl-{2-[4-(4-chloro-5-methoxy-2-methylphenylamino)-3-cyano-7-ethoxybenzo[g]quinolin-8-yloxy]-ethyl}-amino)-acetamide is obtained as yellow crystals, mp 168–170° C.
MS 591.1 (M+H)$^+$

EXAMPLE 195

4-(2,4-Dichloroanilino)-7-methoxy-8-[2-(4-morpholinyl)ethoxy]benzo[g]quinoline-3-carbonitrile 4-(2,4-Dichloroanilino)-7-methoxy-8-[2-(4-morpholinyl)ethoxy]benzo[g]quinoline-3-carbonitrile is obtained as a yellow solid, mp 250–252° C. dec.
MS 522.7 (M+H)$^+$

EXAMPLE 196

4-(2,4-Dichloroanilino)-8-methoxy-7-[2-(4-morpholinyl)ethoxy]benzo[g]quinoline-3-carbonitrile 4-(2,4-Dichloroanilino)-8-methoxy-7-[2-(4-morpholinyl)ethoxy]benzo[g]quinoline-3-carbonitrile is obtained as a yellow solid, mp 115–119° C. dec.
MS 522.7 (M+H)$^+$

EXAMPLE 197

8-Methoxy-7-[2-(4-methyl-1-piperazinyl)ethoxy]-4-(3,4,5-trimethoxyanilino)benzo[g]quinoline-3-carbonitrile 8-Methoxy-7-[2-(4-methyl-piperazinyl)ethoxy]-4-(3,4,5-trimethoxyanilino)benzo[g]quinoline-3-carbonitrile is obtained as a yellow solid, mp 115–120° C. dec.
MS 558.3 (M+H)$^+$

EXAMPLE 198

7-Methoxy-8-[2-(4-methyl-1-piperazinyl)ethoxy]-4-(3,4,5-trimethoxyanilino)benzo[g]quinoline-3-carbonitrile 7-Methoxy-8-[2-(4-methyl-1-piperazinyl)ethoxy]-4-(3,4,5-trimethoxyanilino)benzo[g]quinoline-3-carbonitrile is obtained as a yellow solid, mp 95–97° C. dec.
MS 558.2 (M+H)$^+$

EXAMPLE 199

7-Methoxy-8-[2-(4-morpholinyl)ethoxy]-4-(3,4,5-trimethoxyanilino)benzo[g]quinoline-3-carbonitrile 7-Methoxy-8-[2-(4-morpholinyl)ethoxy]-4-(3,4,5-trimethoxyanilino)benzo[g]quinoline-3-carbonitrile is obtained as a yellow solid, mp 127–130° C. dec.
MS 544.9 (M+H)$^+$

EXAMPLE 200

8-Methoxy-7-[2-(4-morpholinyl)ethoxy]-4-(3,4,5-trimethoxyanilino)benzo[g]quinoline-3-carbonitrile 8-Methoxy-7-[2-(4-morpholinyl)ethoxy]-4-(3,4,5-trimethoxyanilino)benzo[g]quinoline-3-carbonitrile is obtained as a yellow solid, mp 135–138° C. dec.
MS 544.9 (M+H)$^+$

EXAMPLE 201

4-(2-Chloro-4-fluoro-5-methoxyanilino)-8-methoxy-7-[2-(4-methyl-1-piperazinyl)ethoxy]benzo[g]quinoline-3-carbonitrile 4-(2-Chloro-4-fluoro-5-methoxyanilino)-8-methoxy-7-[2-(4-methyl-1-piperazinyl)ethoxy]benzo[g]quinoline-3-carbonitrile is obtained as a yellow solid, mp 170–173° C.
MS (M+H)$^+$ 550.2

EXAMPLE 202

4-(2-Chloro-5-methoxy-4-methylanilino)-8-methoxy-7-[2-(4-methyl 1-piperazinyl)ethoxy]benzo[g]quinoline-3-carbonitrile 4-(2-Chloro-5-methoxy-4-methylanilino)-8-methoxy-7-[2-(4-methyl-1-piperazinyl)ethoxy]benzo[g]quinoline-3-carbonitrile is obtained as a yellow solid, mp 220–227° C.
MS (M+H)$^+$ 546.2

EXAMPLE 203

4-(2-Chloro-5-methoxy-4-methylanilino)-7-methoxy-8-[2-(4-methyl 1-piperazinyl)ethoxybenzo[g]quinoline-3-carbonitrile 4-(2-Chloro-5-methoxy-4-methylanilino)-8-methoxy-7-[2-(4-methyl 1-piperazinyl)ethoxy]benzo[g]quinoline-3-carbonitrile is obtained as a yellow solid, mp 218–235° C.
MS (M+H)$^+$ 545.9

EXAMPLE 204

4-(2,4-Dichloro-5-methoxyanilino)-7-[2-(4-hydroxy-1-piperidinyl)ethoxy]-8-methoxybenzo[g]quinoline-3-carbonitrile 4-(2,4-Dichloro-5-methoxyanilino)-7-[2-(4-hydroxy-1-piperidinyl)ethoxy]-8-methoxybenzo[g]quinoline-3-carbonitrile is obtained as a yellow solid, mp 150–160° C. MS (M+H)$^+$ 566.7

EXAMPLE 205

4-(3-Chloro-4-fluoroanilino)-7-methoxy-8-[2-(4-morpholinyl)ethoxy]benzo[g]quinoline-3-carbonitrile 4-(3-Chloro-4-fluoroanilino)-7-methoxy-8-[2-(4-morpholinyl)ethoxy]benzo[g]quinoline-3-carbonitrile is obtained as a yellow solid, mp 237–242° C.
MS (M+H)$^+$ 506.8

EXAMPLE 206

4-(2,4-Dichloro-5-methoxyanilino)-8-[2-(4-hydroxy-1-piperidinyl)ethoxy]-7-methoxybenzo[g]quinoline-3-carbonitrile 4-(2,4-Dichloro-5-methoxyanilino)-8-[2-(4-hydroxy-1-piperidinyl)ethoxy]-7-methoxybenzo[g]quinoline-3-carbonitrile is obtained as a yellow solid, mp 193–198° C.
MS (M+H)$^+$ 566.8

EXAMPLE 207

4-(2-Chloro-5-methoxy-4-methylanilino)-8-methoxy-7-[2-(4-hydroxy-1-piperidinyl)ethoxy]benzo[g]quinoline-3-carbonitrile 4-(2-Chloro-5-methoxy-4-methylanilino)-8-methoxy-7-[2-(4-hydroxy 1-piperidinyl)ethoxy]benzo[g]quinoline-3-carbonitrile is obtained as a yellow solid, mp 205–235° C.
MS (M+H)$^+$ 546.8

EXAMPLE 208

4-(2-Chloro-5-methoxy-4-methylanilino)-7-methoxy-8-[2-(4-hydroxy-1-piperidinyl)ethoxy]benzo[g]quinoline-3-carbonitrile 4-(2-Chloro-5-methoxy-4-methylanilino)-7-methoxy-8-[2-(4-hydroxy-1-piperidinyl)ethoxy]benzo[g]quinoline-3-carbonitrile is obtained as a yellow solid, mp 210–215° C.
MS (M+H)$^+$ 546.8

EXAMPLE 209

4-(2-Chloro-4-fluoro-5-methoxyanilino)-8-methoxy-7-[2-(4-morpholinyl)ethoxy]benzo[g]quinoline-3-carbonitrile 4-(2-Chloro-4-fluoro-5-methoxyanilino)-8-methoxy-7-[2-(4-morpholinyl)ethoxy]benzo[g]quinoline-3-carbonitrile is obtained as a yellow solid, mp 204–214° C.
MS (M+H)$^+$ 536.8

EXAMPLE 210

4-(2-Chloro-4-fluoro-5-methoxyanilino)-7-methoxy-8-[2-(4-morpholinyl)ethoxy]benzo[g]quinoline-3-carbonitrile 4-(2-Chloro-4-fluoro-5-methoxyanilino)-7-methoxy-8-[2-(4-morpholinyl)ethoxy]benzo[g]quinoline-3-carbonitrile is obtained as a yellow solid, mp 206–222° C.
MS (M+H)$^+$ 537.1

EXAMPLE 211

4-(2-Chloro-4-fluoro-5-methoxyanilino)-7-methoxy-8-[2-(4-methyl-1-piperazinyl)ethoxy]benzo[g]quinoline-3-carbonitrile 4-(2-Chloro-4-fluoro-5-methoxyanilino)-7-methoxy-8-[2-(4-methyl-1-piperazinyl)ethoxy]benzo[g]quinoline-3-carbonitrile is obtained as a yellow solid, mp 197–205° C.
MS (M+H)$^+$ 550.2

EXAMPLE 212

4-(3-Chloro-4-fluoroanilino)-8-methoxy-7-[2-(4-morpholinyl)ethoxy]benzo[g]quinoline-3-carbonitrile 4-(3-Chloro-4-fluoroanilino)-8-methoxy-7-[2-(4-morpholinyl)ethoxy]benzo[g]quinoline-3-carbonitrile is obtained as a yellow solid, mp 205–210° C.
MS (M+H)$^+$ 506.8

EXAMPLE 213

4-(3-Chloro-4-phenoxyphenylamino)-7-methoxy-8-(2-morpholin-4-yl-ethoxy)benzo[g]quinoline-3-carbonitrile 4-(3-Chloro-4-phenoxyphenylamino)-7-methoxy-8-(2-morpholin-4-yl-ethoxy)benzo[g]quinoline-3-carbonitrile is obtained as an orange solid, mp 190–194° C. MS (M+H)$^+$ 581.2

EXAMPLE 214

4-(3-Chloro-4-phenoxyphenylamino)-8-methoxy-7-(2-morpholin-4-yl-ethoxy)benzo[g]quinoline-3-carbonitrile 4-(3-Chloro-4-phenoxyphenylamino)-8-methoxy-7-(2-morpholin-4-yl-ethoxy)benzo[g]quinoline-3-carbonitrile is obtained as a yellow solid, mp 251–253° C. MS (M+H)$^+$ 581.3

EXAMPLE 215

4-(2-Chloro-5-methoxy-4-methylphenylamino)-8-methoxy-7-(2-morpholin-4-yl-ethoxy)benzo[g]quinoline-3-carbonitrile 4-(2-Chloro-5-methoxy-4-methylphenylamino)-8-methoxy-7-(2-morpholin-4-yl-ethoxy)benzo[g]quinoline-3-carbonitrile is obtained as a yellow solid, mp 240–241° C. MS (M+H)$^+$ 533

EXAMPLE 216

4-(2-Chloro-5-methoxy-4-methylphenylamino)-7-methoxy-8-(2-morpholin-4-yl-ethoxy)benzo[g]quinoline-3-carbonitrile 4-(2-Chloro-5-methoxy-4-methylphenylamino)-7-methoxy-8-(2-morpholin-4-yl-ethoxy)benzo[g]quinoline-3-carbonitrile is obtained as a yellow solid, mp 220–222° C.
MS (M+H)$^+$ 533

EXAMPLE 217

4-(4-Benzyloxy-3-chlorophenylamino)-8-methoxy-7-(2-morpholin-yl-ethoxy)benzo[g]quinoline-3-carbonitrile 4-(4-Benzyloxy-3-chlorophenylamino)-8-methoxy-7-(2-morpholin-4-yl-ethoxy)benzo[g]quinoline-3-carbonitrile is obtained as a yellow solid.

Analysis for $C_{34}H_{31}ClN_4O_4 \cdot 0.3H_2O$ Calcd: C:68.00; H:5.30; N:9.33 Found: C:67.67; H:5.14; N:9.29 MS (M+H)$^+$ 595.1

EXAMPLE 218

4-(4-Benzyloxy-3-chlorophenylamino)-7-methoxy-8-(2-morpholin-4-yl-ethoxy)benzo[g]quinoline-3-carbonitrile 4-(4-Benzyloxy-3-chlorophenylamino)-7-methoxy-8-(2-morpholin-4-yl-ethoxy)benzo[g]quinoline-3-carbonitrile is obtained as a yellow solid.

Analysis for $C_{34}H_{31}ClN_4O_4 \cdot 1.5H_2O$ Calcd: C:65.64; H:5.51; N:9.01 Found: C:65.85; H:5.28; N:8.99 MS (M+H)$^+$ 595.1

EXAMPLE 219

8-(Benzyloxy)-4-[(2-chloro-4-fluoro-5-methoxyphenyl)amino]-7-methoxybenzo[g]quinoline-3-carbonitrile A mixture of 8-benzyloxy-7-methoxy-4-oxo-1,4-dihydrobenzo[g]quinoline-3-carbonitrile (11.4 g, 31.9 mmol) and phosphorus oxychloride (147 g, 959 mmol) is heated under reflux for one hour. After cooling to room temperature, the reaction mixture is evaporated under vacuum to remove the volatiles. The residue is carefully slurried in cold saturated aqueous sodium bicarbonate solution (500 mL). The solids are collected by filtration, washed thoroughly with saturated aqueous sodium bicarbonate solution and water and dried to give 11.7 grams of crude 8-(benzyloxy)-4-chloro-7-methoxybenzo[g]quinoline-3-carbonitrile as a light orange solid.

A mixture of 8-(benzyloxy)-4-chloro-7-methoxybenzo[g]quinoline-3-carbonitrile (1.00 g, 2.7 mmol), 2-chloro-4-fluoro-5-methoxyaniline (560 mg, 3.2 mmol), tris(dibenzylideneacetone)dipalladium(0) (240 mg, 0.26 mmol), 2-dicyclohexylphosphino-2'-(N,N-dimethylamino)biphenyl (330 mg, 0.84 mmol) and $K_3PO_4$ (860 mg, 4.1 mmol) in 15 mL of ethylene glycol dimethyl ether is heated at 80° C. for 3 hours. An additional 5% of all reagents is added and the mixture is heated at 80° C. for 2 hours then cooled to room temperature and partitioned between aqueous sodium bicarbonate and methylene chloride. The organic layer is dried over magnesium sulfate, filtered and concentrated in vacuo. Purification by column chromatography eluting with 1:1 hexane/ethyl acetate yields 500 mg (36%) of 8-(benzyloxy)-4-[(2-chloro-4-fluoro-5-methoxyphenyl)amino]-7-methoxybenzo[g]quinoline-3-carbonitrile as a yellow solid, mp 248–250° C. dec.

MS 514.2 (M+H)$^+$

EXAMPLE 220

4-[(2-Chloro-4-fluoro-5-methoxyphenyl)amino]-8-hydroxy-7-methoxybenzo[g]quinoline-3-carbonitrile A mixture of 8-(benzyloxy)-4-[(2-chloro-4-fluoro-5-methoxyphenyl)amino]-7-methoxybenzo[g]quinoline-3-carbonitrile (1.88 g, 3.70 mmol) and 280 mg of 15% Pd on carbon in a mixture of 50 mL of methylene chloride and 70 mL of N,N-dimethylformamide is hydrogenated at 50–40 psi for 15 hours. The mixture is filtered through Celite and concentrated in vacuo to a small volume. The yellow solid is collected by filtration to provide 1.50 g (95%) of 4-[(2-chloro-4-fluoro-5-methoxyphenyl)amino]-8-hydroxy-7-methoxybenzo[g]quinoline-3-carbonitrile, mp 239–242° C. dec.

MS 424.2 (M+H)$^+$

What is claimed is:

1. A compound of formula 1 having the structure:

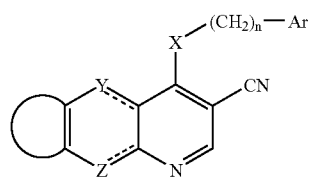

wherein:

Ar is a phenyl ring; wherein the phenyl ring may be optionally mono-, di-, or tri-substituted with substituent(s) independently selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto and benzoylamino; or Ar is the radical:

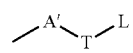

$A^1$ is a phenyl ring; wherein the phenyl ring may be optionally mono- or di-substituted with a substituent(s) independently selected from the group consisting of alkyl of 1–6 carbon atoms, alkenyl of 2–6 carbon atoms, alkynyl of 2–6 carbon atoms, azido, hydroxyalkyl of 1–6 carbon atoms, halogen, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino;

T is substituted on A' at carbon and is —NH(CH$_2$)$_m$—, —O(CH$_2$)$_m$—, —S(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S—, —SO(CH$_2$)$_m$—, —SO$_2$(CH$_2$)$_m$—, —CO(CH$_2$)$_m$—, —(CH$_2$)$_m$CO—, —(CH$_2$)$_m$SO—, —(CH$_2$)$_m$SO$_2$— or —(CH$_2$)$_m$NR—;

L is a phenyl ring that is optionally substituted with one, two, or three substituent(s) independently selected from the group consisting of alkyl of 1–6 carbon atoms, alkenyl of 2–6 carbon atoms, alkynyl of 2–6 carbon atoms, azido, hydroxyalkyl of 1–6 carbon atoms, halogen, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 3–9 carbon atoms, N,N-dialkylaminoalkoxy of 4–10 carbon atoms, mercapto, methylmercapto, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino;

m is 0–3;

n is 0–1;

X is NH or NR;

R is alkyl of 1–6 carbon atoms;

Y and Z are both carbon;

provided that when 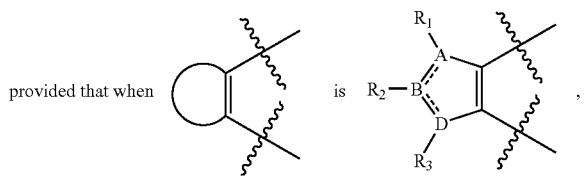

A and D are each N;

B is carbon;

the dashed line indicates an optional double bond;

R$_1$, R$_2$, and R$_3$ are each, independently, not present, hydrogen, halogen, hydroxy, amino, hydroxyamino, trifluoromethyl, trifluoromethoxy, mercapto, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, alkynyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, nitro, carboxy, alkoxycarbonyl of 2–7 carbon atoms, alkanoyl of 2–7 carbon atoms, alkenoyl of 3–7 carbon atoms, N-alkyl-N-alkenylamino of 4 to 12 carbon atoms, N,N-dialkenylamino of 6–12 carbon atoms, phenylamino, benzylamino, phenoxy, phenyl, thiophenoxy, benzyl, alkylamino of 1–6 carbon atoms, alkanoyloxy of 2–7 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, dialkylamino of 2 to 12 carbon atoms, alkanoyloxymethyl group of 2–7 carbon atoms, alkenoyloxymethyl group of 2–7 carbon atoms, alkynoyloxymethyl group of 2–7 carbon atoms, azido, benzoyl, carboxyalkyl of 2–7 carbons, carboalkoxyalkyl of 3–8 carbon atoms,

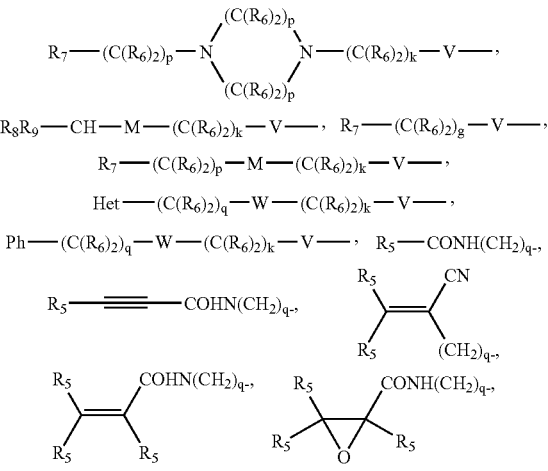

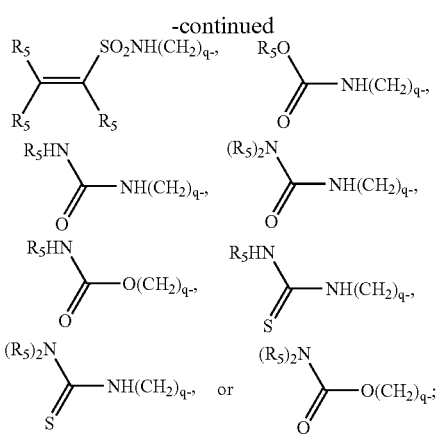

R$_5$ is independently hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperazino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, or phenyl;

V is (CH$_2$)$_m$, O, S, or NR$_6$;

R$_7$ is NR$_6$R$_6$, OR$_6$, J, N(R$_6$)$_3^+$, or NR$_6$(OR$_6$),

M is NR$_6$, O, S, N—[(C(R$_6$)$_2$)$_p$NR$_6$R$_6$], or N—[(C(R$_6$)$_2$)$_p$—OR$_6$];

W is NR$_6$, O, S, or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane pyrrole, and tetrahydropyran; wherein the heterocycle is optionally mono- or di-substituted on carbon or nitrogen with R6; optionally mono- or di-substituted on carbon with hydroxy, —N(R$_6$)$_2$, or —OR$_6$; optionally mono or di-substituted on carbon with the mono-valent radicals —(C(R$_6$)$_2$)$_s$OR$_6$ or —[(C(R$_6$)$_2$)$_s$N(R$_6$)2]; or optionally mono or di-substituted on a saturated carbon with divalent radicals =O or —O(C(R$_6$)$_2$)$_s$O—;

Ph is a phenyl ring optionally mono-, di- or tri-substituted with halogen, alkyl of 1–6 carbon atoms, trifluoromethyl, nitro, cyano, azido, halomethyl, carboxyl, alkoxycarbonyl, alkylthio, mercapto, mercaptomethyl, —N(R$_6$)$_2$, —OR$_6$, —(C(R$_6$)$_2$)$_s$OR$_6$, —[(C(R$_6$)$_2$)$_s$N(R$_6$)$_2$], or —(C(R$_6$)$_2$)$_k$Het; atoms, cycloalkyl of 1–6 carbon atoms, alkanoyl of 2–7 carbon atoms, carbamoylalkyl of 2–7 carbon atoms, hydroxyalkyl of 1–6 carbon atoms, hydroxycycloalkyl of 3–6 carbon atoms, or carboxyalkyl of 2–7 carbon atoms; or R$_6$ is phenyl optionally mono-, di-, or tri-substituted with substituent(s) independently selected from halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, alkoxycarbonyl of 2–7 carbon atoms, phenoxy, phenyl, thiophenoxy, benzoyl, benzyl, phenylamino, benzylamino; alkanoylamino of 1–6 carbon atoms or alkyl of 1–6 carbon atoms;

R$_8$ and R$_9$ are each, independently, [(C(R$_6$)$_2$)$_r$N$_6$R$_6$], and —[(C(R$_6$)$_2$)$_r$OR$_6$];

J is independently hydrogen, chlorine, fluorine, or bromine;

g=1–6;
k=0–4;
p=2–4;
q=0–4;
r=1–4;
s=1–6;

or a pharmaceutically acceptable salt thereof;

provided that at least one of the bonds between A and B or B and D must be a double bond, with the other being a single bond;

provided that when R$_5$ is bound to a nitrogen atom, the resulting structures do not include —N—C—N— or —O—C—N— radicals; and when R$_5$ is bound to an oxygen atom, the resulting structures do not include an —N—C—O— radical;

provided that when R$_6$ is alkenyl of 2–6 carbon atoms or alkynyl of 2–6 carbon atoms, the alkenyl or alkynyl moieties are bound to a nitrogen or oxygen atom through a saturated carbon atom in the alkenyl or alkynyl chain;

provided that when V is NR$_6$ and R$_7$ is NR$_6$R$_6$, N(R$_6$)$_3^+$, or NR$_6$(OR$_6$), then g=2–6;

provided that when M is O or S and R$_7$ is OR$_6$, then p=1–4;

provided that when V is NR$_6$, O, S, then k=2–4;

provided that when V is O or S and M or W is O or S, then k=1–4 provided that when W is not a bond with Het bonded through a nitrogen atom then q =2–4; and provided that when W is a bond with Het bonded through a nitrogen atom and V is O or NR$_6$ or S, then k=2–4.

2. The compound of claim 1, having the structure

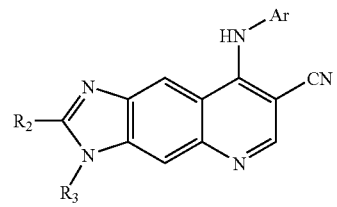

wherein

R$_2$ is hydrogen, amino, hydroxyamino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, carboxy, alkoxycarbonyl of 2–7 carbon atoms, alkanoyl of 2–7 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, N-alkyl-N-alkenylamino of 4 to 12 carbon atoms, N,N-dialkenylamino of 6–12 carbon atoms, phenylamino, benzylamino, phenoxy, phenyl, thiophenoxy, benzyl, alkylamino of 1–6 carbon atoms, dialkylamino of 2 to 12 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms,

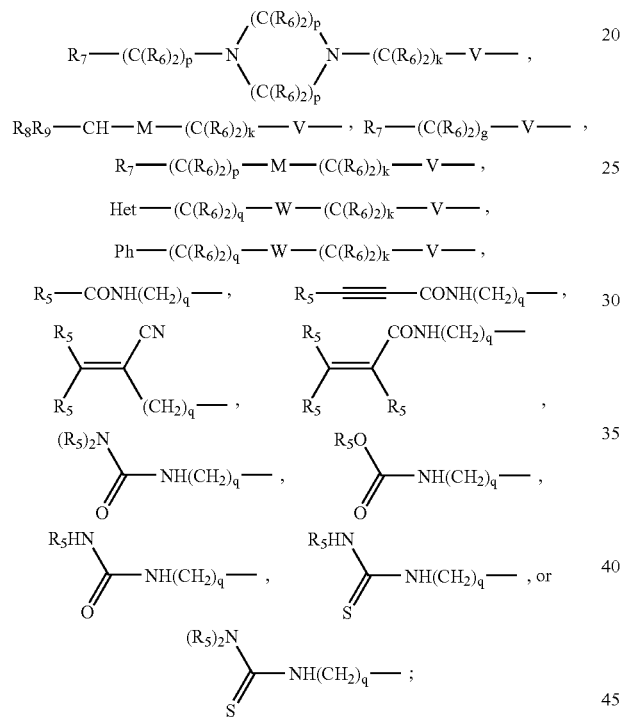

$R_3$ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

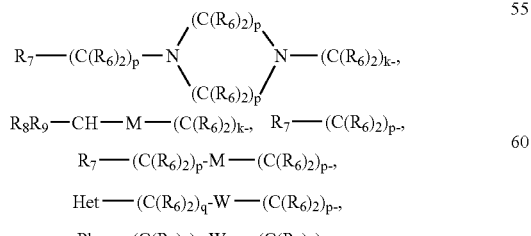

or a pharmaceutically acceptable salt thereof.

3. The compound of claim 1, having the structure

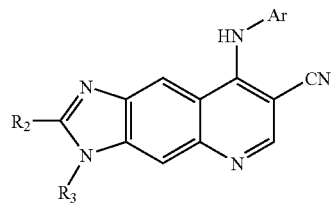

wherein

Ar is a phenyl ring which may be optionally mono-, di- or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, alkoxycarbonyl of 2–7 carbon atoms, alkanoyl of 2–7 carbon atoms, benzoyl, amino, alkylamino of 1–6 carbon atoms, dialkylamino of 2–12 carbon atoms, alkanoylamino of 1–6 carbon atoms, alkenoylamino of 3–8 carbon atoms, alkynoylamino of 3–8 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms, and benzoylamino; or Ar is the radical:

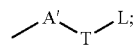

wherein A', T and I are as defined in claim 1;

$R_2$ is hydrogen, amino, hydroxyamino, trifluoromethyl, alkyl of 1–6 carbon atoms, cycloalkyl of 3–8 carbon atoms, alkenyl of 2–6 carbon atoms, alkynyl of 2–6 carbon atoms, alkenyloxy of 2–6 carbon atoms, hydroxyalkyl of 1–6 carbon atoms, mercaptoalkyl of 1–6 carbon atoms, halomethyl, alkoxymethyl of 2–7 carbon atoms, alkoxy of 1–6 carbon atoms, cycloalkoxy of 3–8 carbon atoms, alkylthio of 1–6 carbon atoms, cycloalkylthio of 3–8 carbon atoms, alkylsulphinyl of 1–6 carbon atoms, alkylsulfonyl of 1–6 carbon atoms, alkylsulfonamido of 1–6 carbon atoms, alkenylsulfonamido of 2–6 carbon atoms, alkynylsulfonamido of 2–6 carbon atoms, cyano, carboxy, alkoxycarbonyl of 2–7 carbon atoms, alkanoyl of 2–7 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms,N-alkyl-N-alkenylamino of 4 to 12 carbon atoms, N,N-dialkenylamino of 6–12 carbon atoms, phenylamino, benzylamino, phenoxy, phenyl, thiophenoxy, benzyl, alkylamino of 1–6 carbon atoms, dialkylamino of 2 to 12 carbon atoms, alkanoyloxy of 1–6 carbon atoms, alkenoyloxy of 3–8 carbon atoms, alkynoyloxy of 3–8 carbon atoms, carbamoyl, N-alkylcarbamoyl of 2–7 carbon atoms, N,N-dialkylcarbamoyl of 3–13 carbon atoms,

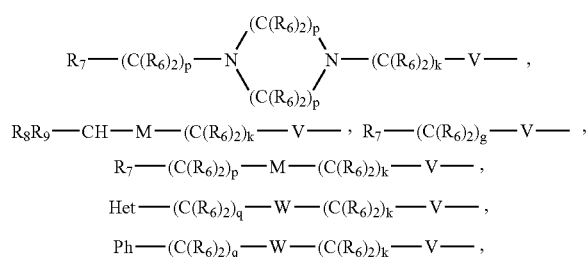

R₃ is hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms; mercaptoalkyl of 2–6 carbon atoms, phenyl, benzyl,

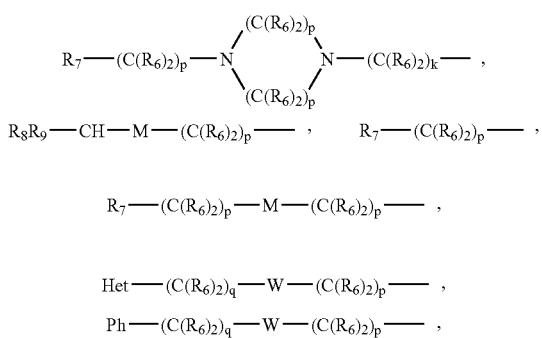

or a pharmaceutically acceptable salt thereof.

4. The compound of claim 1, which is:
a) 8-(5-methoxy-2-methylanilino)-2-{[2-(4-morpholinyl)ethyl]amino}imidazo[4,5-g]quinoline-7-carbonitrile,
b) 2-{[2-(4-morpholinyl)ethyl]amino}-8-(3,4,5-trimethoxyanilino)imidazo[4,5-g]quinoline-7-carbonitrile,
c) 2-amino-8-(4-phenoxyanilino)imidazo[4,5-g]quinoline-7-carbonitrile,
d) 8-(3-bromo-phenylamino)imidazo[4,5-g]quinoline-7-carbonitrile,
e) 8-(2-bromo-4-chlorophenylamino)imidazo[4,5-g]quinoline-7-carbonitrile,
f) 8-(2-bromo-4-chloro-5-methoxyphenylamino)imidazo[4,5-g]quinoline-7-carbonitrile,
g) 8-(2-chloro-5-methoxyphenylamino)imidazo[4,5-g]quinoline-7-carbonitrile,
h) 8-(3-hydroxy-4-methylphenylamino)imidazo[4,5-g]quinoline-7-carbonitrile,
i) 8-(3,4,5-trimethoxyanilino)imidazo[4,5-g]quinoline-7-carbonitrile,
j) 8-(4-phenoxyanilino)imidazo[4,5-g]quinoline-7-carbonitrile,
k) 2-(chloromethyl)-8-(3,4,5-trimethoxyanilino)imidazo[4,5-g]quinoline-7-carbonitrile,
l) 2-(4-morpholinylmethyl)-8-(3,4,5-trimethoxyanilino)imidazo[4,5-g]quinoline-7-carbonitrile,
m) 8-(4-chloro-5-methoxy-2-methylanilino)-3-[2-(4-morpholinyl)ethyl]-3H-imidazo[4,5-g]quinoline-7-carbonitrile,
n) 3-[2-(4-morpholinyl)ethyl]-8-(4-phenoxyanilino)-3H-imidazo[4,5-g]quinoline-7-carbonitrile, or a pharmaceutically acceptable salt thereof.

5. A method of treating, inhibiting the growth of, or eradicating a neoplasm of the breast, kidney, bladder, mouth, larynx, esophagus, stomach, colon, ovary, lung, pancreas, liver, prostate or skin in a mammal in need thereof which comprises providing to said mammal an effective amount of a compound as described in claim 1.

6. The method according to claim 5 wherein the neoplasm expresses EGFR or erbB2 (Her2).

7. The method according to claim 5 wherein the neoplasm depends, at least in part, on the MAPK pathway.

8. The method according to claim 5 wherein the neoplasm depends, at least in part, on the RAF kinase pathway.

9. The method according to claim 5 wherein the neoplasm depends, at least in part, on the SRC kinase pathway.

10. The method according to claim 5 wherein the neoplasm depends, at least in part, on the Mek-Erk pathway.

11. The method according to claim 5 wherein the neoplasm depends, at least in part, on the VEGF/KDR pathway.

12. A method of treating, inhibiting the progression of, or eradicating polycystic kidney disease in a mammal in need thereof which comprises providing to said mammal an effective amount of a compound described in claim 1.

13. A method of treating, inhibiting, or eradicating colonic polyps in a mammal in need thereof which comprises providing to said mammal an effective amount of a compound described in claim 1.

14. A method of inhibiting the biological effects of a deregulated protein kinase in a mammal which comprises providing to said mammal an effective amount of a compound described in claim 1.

15. A method of treating a disease or inhibiting a disease state whose etiology is at least in part caused by a defect in a signaling pathway upstream from a protein kinase; by overexpression of a protein kinase; or by a dysregulated protein kinase in a mammal in need thereof which comprises providing to said mammal an effective amount of a compound described in claim 1.

16. A pharmaceutical composition which comprises a pharmaceutically acceptable carrier and a compound described in claim 1.

17. A process for the preparation of a compound described in claim 1 which comprises one or more of the following steps:

A) preparing a substituted 2-amino-7-cyanoimidazo[4,5-g]quinoline of formula 23

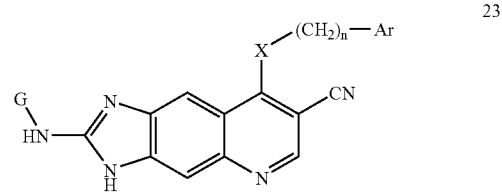

wherein Ar, X and n are as defined in claim 1 and G is selected from the group consisting of alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms, mercaptoalkyl of 2–6 carbon atoms, phenyl, benzyl,

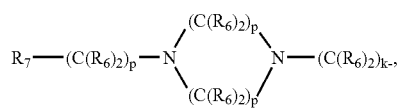

$R_8R_9$—CH—M—$(C(R_6)_2)_{k^-}$,  $R_7$—$(C(R_6)_2)_{p^-}$, $R_7$—$(C(R_6)_2)_p$-M—$(C(R_6)_2)_{p^-}$,

Het—$(C(R_6)_2)_q$-W—$(C(R_6)_2)_{p^-}$  and

Ph—$(C(R_6)_2)_q$-W—$(C(R_6)_2)_{p^-}$, wherein $R_6$, $R_7$, $R_8$, $R_9$, M, W, Het, Ph, p and q are as defined in claim 1, g=2–6 and k =2–4;
which comprises reacting a compound of formula 17

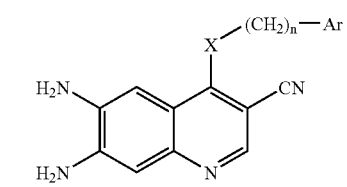

with an isothiocyanate GN=C=S in an inert solvent to produce a mixture of thiourea compounds of formulas 21 and 22

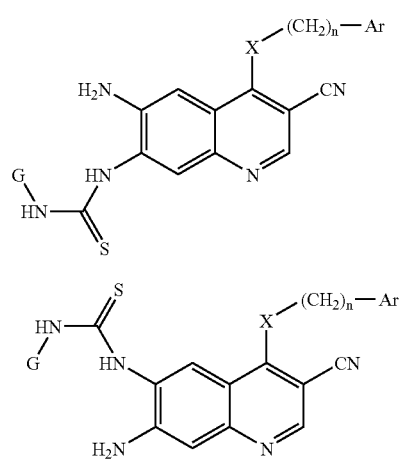

wherein Ar, X, G and n are as defined hereinabove;
heating said mixture of thiourea compounds of formulas 21 and 22 with mercury (II) oxide and a catalytic amount of sulfur in an inert solvent to provide the corresponding substituted 2-amino-7-cyanoimidazo[4,5-g]quinoline of formula 23;
B) preparing a 7-cyano imidazo[4,5-g]quinoline of formula 26

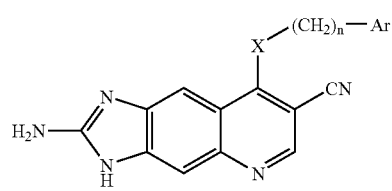

wherein Ar, X and n are as defined in claim 1;
which comprises reacting a compound of formula 12

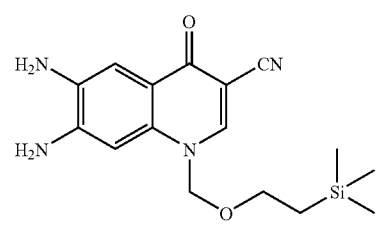

with cyanogen bromide in an inert solvent to provide a compound of formula 24

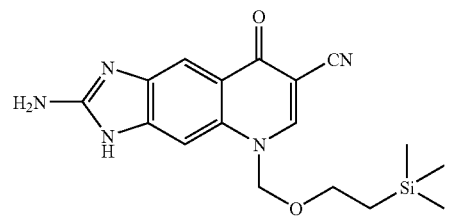

refluxing the compound of formula 24 in formic acid with four equivalents of imidazole to provide a compound of formula 25

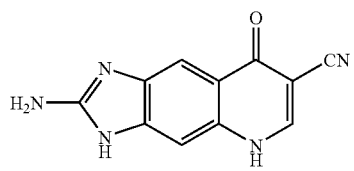

heating the compound of formula 25 with a chlorinating agent in the presence or absence of a solvent to provide the corresponding 2-amino-8-chloroimidazo[4,5-g]quinoline-7-carbonitrile;
condensing the corresponding 2-amino-8-chloroimidazo[4,5-g]quinoline-7-carbonitrile with a nucleophilic amine, aniline, mercaptan, thiophenol, phenol or alcohol reagent of formula 5

HX—$(CH_2)_n$—Ar  5 wherein Ar, X and n are as defined hereinabove; and optionally accelerating the condensation step by heating the reaction mixture together with one equivalent of pyridine hydrochloride or by using a base selected from the group consisting of trialkylamine, sodium hydride in an inert solvent, sodium alkoxide in an alcohol solvent and potassium alkoxide in an alcohol solvent, to give the 7-cyano imidazo[4,5-g]quinolines of formula 26;

C) preparing a 7-cyano imidazo[4,5-g]quinoline of formula 28

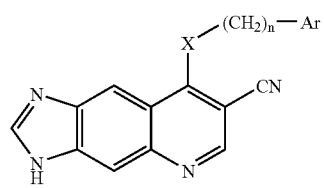

wherein Ar, X and n are as defined in claim 1;
which comprises refluxing the compound of formula 12 described hereinabove in Step B in formic acid with four equivalents of imidazole to provide a compound of formula 27

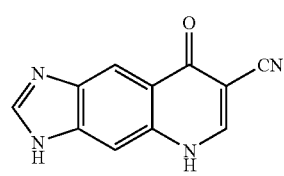

heating the compound of formula 27 with a chlorinating agent in the presence or absence of a solvent to provide the corresponding 8-chloroimidazo[4,5-g]quinoline-7-carbonitrile;
condensing the corresponding 8-chloroimidazo[4,5-g]quinoline-7-carbonitrile with a nucleophilic amine, aniline, mercaptan, thiophenol, phenol, or alcohol reagent of formula HX—(CH$_2$)$_n$—Ar 5 wherein Ar, X and n are as defined hereinabove; and optionally accelerating the condensation step by heating the reaction mixture together with one equivalent of pyridine hydrochloride or by using a base selected from the group consisting of trialkylamine, sodium hydride in an inert solvent, sodium alkoxide in an alcohol solvent and potassium alkoxide in an alcohol solvent, to give the 7-cyano-imidazo[4,5-g]quinoline of formula 28; or,
alternatively preparing the above 7-cyanoimidazo[4,5-g]quinoline compound of formula 28 described hereinabove by refluxing the compound of formula 17 described hereinabove in Step A in diethoxymethyl acetate to provide the corresponding 7-cyanoimidazo[4,5-g]quinolin-8-ylformamide; and heating the 7-cyanoimidazo[4,5-g]quinolin-8-ylformamide with potassium carbonate in methanol or ethanol to provide the 7-cyano-imidazo[4,5-g]quinoline compound of formula 28;

D) preparing a 7-cyano-imidazol[4,5-g]quinoline of formula 32

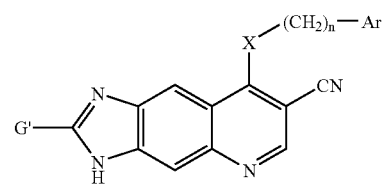

wherein Ar, X and n are as defined in claim 1 and G' is selected from the group consisting of hydrogen, alkyl of 1–6 carbon atoms, trifluoromethyl, cycloalkyl of 3–8 carbon atoms, alkenyl of 2–6 carbon atoms, alkynyl of 2–6 carbon atoms, thiol, hydroxyalkyl of 1–6 carbon atoms, mercaptoalkyl of 1–6 carbon atoms, halomethyl, alkoxycarbonyl of 2–7 carbon atoms, phenyl, benzyl, phenoxy, R$_7$—(C(R$_6$)$_2$)$_g$—V and Ph-(C(R$_6$)$_2$)$_q$—W—(C(R$_6$)$_2$)$_k$—V—, wherein g, k, q, R$_6$, R$_7$, V, W and Ph are as defined hereinabove;
which comprises reacting a compound of formula 17

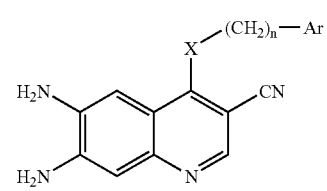

wherein Ar, X and n are as defined in claim 1;
with a carboxylic acid chloride of formula 29

G'COCL with a base selected from the group consisting of pyridine, diethylaniline and triethylamine with or without an inert solvent to provide a mixture of compounds of formulas 30 and 31

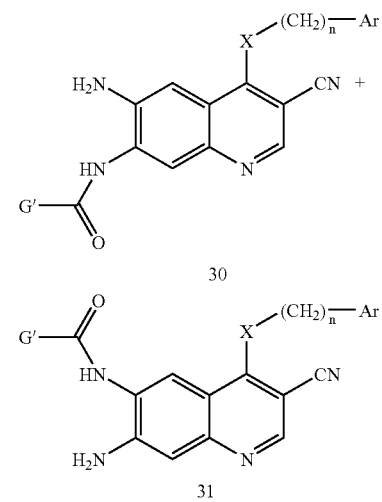

wherein Ar, X and n are as defined in claim 1 and G' is as defined hereinabove;
heating the mixture of the compounds of formulas 30 and 31 in formic acid or acetic acid to provide the corresponding substituted 7-cyano-imidazo[4,5-g]quinolines of formula 32; and, optionally, converting the G' group of formula 32 to an R₂ group of formula 1 as defined in claim 1; or, alternatively preparing the above 7-cyano-imidazo[4,5-g]quinoline of formula 32 described hereinabove by reacting the above compound of formula 17 described hereinabove in Step A with G'-C(L')₃, wherein G' is as defined hereinabove and L' is chloro, hydroxy, alkoxy, alkylthio, phenoxy, thiophenoxy or dimethylamine, or two L' groups can be taken together to form a substituent of =S, =NH, =O or =Se; by using acidic reaction conditions, basic reaction conditions, a strongly dehydrating solvent or 2-ethoxy-1-ethoxycarbonyl-1,2-dihydroquinoline or by heating in an inert solvent, to provide the corresponding substituted 7-cyano-imidazo[4,5-g]quinolines of formula 32; and optionally converting the G' group of formula 32 to an R₂ group of formula 1 as defined in claim 1;

E) preparing a 7-cyano-imidazo[4,5-g]quinoline of formula 36

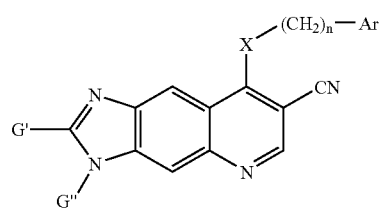

wherein Ar, X and n are as defined in claim 1, G' is as defined hereinabove and G" is selected from the group consisting of hydrogen, alkyl of 1–6 carbon atoms, cycloalkyl of 3–8 carbon atoms, alkenyl of 2–6 carbon atoms, alkynyl of 2–6 carbon atoms, hydroxyalkyl of 2–6 carbon atoms, mercaptoalkyl of 2–6 carbon atoms, phenyl, benzyl,

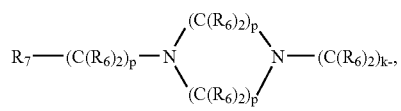

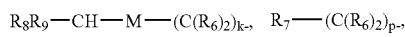

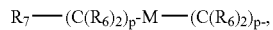

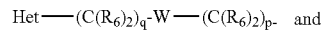

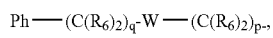

wherein R₆, R₇, R₈, R₉, M, W, Het, Ph, p and q are as hereinabove defined, g=2–6 and k=2–4;

which comprises heating a compound of formula 11

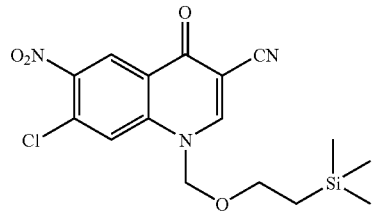

with an amine of formula 33

G"—NH₂ wherein G" is as defined hereinabove, in an inert solvent selected from the group consisting of acetonitrile and dimethyl sulfoxide (DMSO), and performing catalytic hydrogenation over palladium on carbon in tetrahydrofuran and ethanol to provide a compound of formula 34

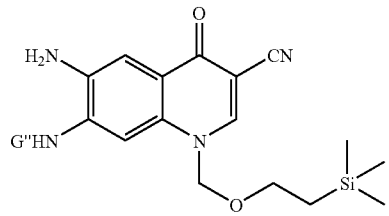

reacting the compound of formula 34 with G'-C(L')₃, wherein G' and L' are as defined hereinabove, by using acidic reaction conditions, basic reaction conditions, a strongly dehydrating solvent or 2-ethoxy-1-ethoxycarbonyl-1,2-dihydroquinoline or by heating in an inert solvent, to provide a compound of formula 35

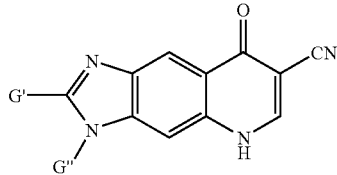

wherein G' and G" are as defined hereinabove;

heating the compound of formula 35 with a chlorinating agent in the presence or absence of a solvent to provide the corresponding 8-chloroimidazo[4,5-g]quinoline-7-carbonitrile;

condensing the corresponding 8-chloroimidazo[4,5-g]quinoline-7-carbonitrile with a nucleophilic amine, aniline, mercaptan, thiophenol, phenol, or alcohol reagent of formula HX—(CH₂)ₙ—Ar wherein Ar, X and n are as defined hereinabove; optionally accelerating the condensation step by heating the reaction mixture together with one equivalent of pyridine hydrochloride or by using a base selected from the group consisting of trialkylamine, sodium hydride in an inert solvent, sodium alkoxide in an alcohol solvent and potassium alkoxide in an alcohol solvent, to give the 7-cyano-imidazo[4,5-g]quinolines of formula 36; and optionally converting the G' group of formula 36 or formula 35 to an $R_2$ group of formula 1 as defined in claim 1 and the G" group of formula 36 or formula 35 to an $R_3$ group of formula 1 as defined in claim 1;

F) resolving a mixture containing optically active isomers and recovering a racemate or an enantiomer when Ar, G' or G" as defined in claim 1 contains an asymmetric carbon atom;

G) separating, isolating and recovering a diastereomer when Ar, G' or G" as defined in claim 1 contains more than one asymmetric carbon atoms;

H) deprotecting and removing an amine or alcohol protecting group when Ar, G' or G" as defined in claim 1 contains a primary or secondary amino group or hydroxyl group requiring protection prior to a subsequent reaction step; or I) acidifying a basic compound of formula 1 as claimed in claim 1 with a pharmaceutically acceptable acid to give a pharmaceutically acceptable salt.

* * * * *